(12) United States Patent
Tabuchi et al.

(10) Patent No.: US 6,586,617 B1
(45) Date of Patent: Jul. 1, 2003

(54) SULFONAMIDE DERIVATIVES

(75) Inventors: Takanori Tabuchi, Tsukuba (JP);
Tetsuhiro Yamamoto, Toride (JP);
Masaharu Nakayama, Tsukuba (JP)

(73) Assignee: Sumitomo Chemical Takeda Agro Company, Limited, Tokyo (JP)

( * ) Notice: Subject to any disclaimer, the term of this patent is extended or adjusted under 35 U.S.C. 154(b) by 0 days.

(21) Appl. No.: 09/958,953

(22) PCT Filed: Apr. 17, 2000

(86) PCT No.: PCT/JP00/02764

§ 371 (c)(1),
(2), (4) Date: Dec. 18, 2001

(87) PCT Pub. No.: WO00/65913

PCT Pub. Date: Nov. 9, 2000

(30) Foreign Application Priority Data

Apr. 28, 1999 (JP) ............................................. 11-123162

(51) Int. Cl.⁷ ............................................. C07C 255/50
(52) U.S. Cl. ........................ 558/394; 558/413; 568/931
(58) Field of Search ................................ 558/394, 413; 568/931

(56) References Cited

U.S. PATENT DOCUMENTS

| | | | |
|---|---|---|---|
| 3,772,320 A | 11/1973 | Zellerhoff et al. | 548/332.5 |
| 4,492,683 A | 1/1985 | Nagpal | 514/542 |
| 4,853,328 A | 8/1989 | Okazaki et al. | 435/28 |
| 4,906,650 A | 3/1990 | Beck et al. | 514/369 |
| 5,026,625 A | 6/1991 | Riediker et al. | 430/281 |
| 5,612,353 A | 3/1997 | Ewing et al. | 514/309 |
| 6,130,320 A | * 10/2000 | Lamm et al. | 534/642 |

FOREIGN PATENT DOCUMENTS

| | | |
|---|---|---|
| DE | 19725447 A1 | 12/1997 |
| EP | 0 206 581 | 12/1986 |
| EP | 0206581 A2 | 12/1986 |
| EP | 432892 | 6/1991 |
| EP | 0 570 594 | 11/1993 |
| EP | 0 621 273 | 10/1994 |
| EP | 0 778 267 | 6/1997 |
| EP | 1 044 962 | 10/2000 |
| FR | 2 000 450 | 9/1969 |
| HU | 191 074 | 1/1987 |
| HU | 198 371 | 10/1989 |
| JP | 61-286366 | 12/1986 |
| JP | 62-190104 | 8/1987 |
| JP | 63-227552 | 9/1988 |
| JP | 63-238006 | 10/1988 |
| JP | 63-307851 | 12/1988 |
| JP | 1-156952 | 6/1989 |
| WO | 96/36596 | 11/1996 |
| WO | 97/24135 | 7/1997 |
| WO | 97/31910 | 9/1997 |
| WO | 98/45255 | 10/1998 |
| WO | 99/06037 | 2/1999 |
| WO | 00/50391 | 8/2000 |

OTHER PUBLICATIONS

Derek R. Buckle et al., "Inhibition of Cyclic Nucleotide Phosphodiesterase by Derivatives of 1,3–Bis(cyclopropylmethyl)xanthine", J. Med. Chem., vol. 37, No. 4, pp. 476–485, 1994.

Francisca Lopes et al., "Acyloxymethyl as a Drug Protecting Group. Part 6: N–Acyloxymethyl– and N–[Aminocarbonyloxy)methyl]sulfonamides as Prodrugs of Agents Containing a Secondary Sulfonamide Group", Bioorganic & Medicinal Chemistry, vol. 8, No. 4, pp. 707–716, 2000.

J.S. Sukla et al., "Studies on Some Newer Possible Biologically Active Agents: Part II. Synthesis of N–(ɣ'–aminopropyl)–2–heterocyclic–p–arylidene aminobenzenesulphonamides and N'(ɣ'–aminopropyl)–2–heterocyclic sulphanalamides and their Antibacterial Activity", J. Indian Chem. Soc., vol. LVI, pp. 401–403, Apr. 1979.

D. Buckle et al., "Inhibition of Cyclic Nucleotide Phosphodiesterase by Derivatives of 1,3–Bis(cyclopropylmethyl)xanthine", J. Med. Chem., vol. 37, No. 4, pp. 476–485, 1994.

F. Lopes et al., "Acyloxymethyl as a Drug Protecting Group. Part 6: N–Acyloxymethyl– and N–[(Aminocarbonyloxy)methyl]sulfonamides as Prodrugs of Agents Containing a Secondary Sulfonamide Group", Bioorganic & Medicinal Chemistry., vol. 8, No. 4, pp. 707–716, 2000.

J. Sukla et al., "Studies on Some Newer Possible Biologically Active Agents: Part II. Synthesis of N–(γ–aminopropyl)–2–heterocyclic–p–arylidene aminobenzenesulphonamides and N'(γ–amino–propyl)–2–heterocyclic Sulphanalamides and their Antibacterial Activity", J. Indian Chem. Soc., vol. LVI, pp. 401–403, Apr. 1979.

Warner M. Linfield et al., Antibacterially Substituted Anilides of Carboxylic and Sulfonic Acids, J. Med. Chem., 26, pp. 1741–1746, 1983.

* cited by examiner

*Primary Examiner*—Ceila Chang
*Assistant Examiner*—Golam M. M. Shameem
(74) *Attorney, Agent, or Firm*—Wenderoth, Lind & Ponack, L.L.P.

(57) ABSTRACT

The present invention relates to microbicides for agricultural or horticultural use containing a sulfonamide derivative.

6 Claims, No Drawings

SULFONAMIDE DERIVATIVES

This application is a 371 of PCT/JP00/02764 Apr. 17, 2000.

TECHNICAL FIELD

This invention relates to sulfonamide derivatives useful as microbicides for agricultural or horticultural use.

BACKGROUND ART

A lot of microbicides have ever been synthesized and used as microbicides for agriculture or horticulture. They have contributed greatly to supply agricultural products constantly. However, it is well-known that frequent use of restricted number of compounds has led to outbreak of microbes which are resistant to those drugs. In addition, recent rise in demand for the safety and environmental influence of chemical substances has made it desirable to develop safer microbicides for agricultural or horticultural use. This has given an intention to the researches to explore and research novel compounds with microbicidal activity. As for sulfonamide derivatives, a lot of compounds have also been synthesized so far from the interests in their biological or chemical characteristics. A majority of them are, however, synthetic intermediates, medicines, compounds prepared for the aim of elucidating chemical reaction mechanism or reagents. As for sulfonamide derivatives related to microbicides, there may be cited those described in Japanese Patent Publication for Laid-Open 286366/1986, Japanese Patent Publication for Laid-Open 239264/1988, Japanese Patent Publication for Laid-Open 238006/1988, Japanese Patent Publication for Laid-Open 307851/1988, Japanese Patent Publication for Laid-Open 156952/1989, and in J. Med. Chem. 1983, 26, 1741, and in DE19725447, and so on.

Nevertheless, no sulfonamide derivative has been developed yet, which is safe and has little influence on human beings and firm animals, natural enemies, and the environment, and exert excellent protective effects even on drug-resistant microbes.

Disclosure of Invention

The present inventors have made intensive efforts for many years in order to find out compounds which have excellent microbicidal action and solve the problems mentioned above. As the results, they have found that the compounds represented by the formula $I^0$ or salts thereof.
Formula $I^0$:

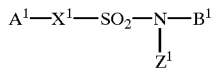

[wherein, $A^0$ is (1) an aryl group which may be substituted, or (2) a heterocyclic group which may be substituted, $X^0$ is (1) a chemical bond, (2) a methylene group which may be substituted or (3) a vinylene group which may be substituted, $B^0$ is a heterocyclic group which may be substituted or an aryl group which may be substituted, $Z^0$ is (1) a hydrocarbon group which may be substituted, (2) an acyl group which may be substituted, (3) formyl group, (4) an amino group which maybe substituted, (5) —N═CR$^1$R$^2$ (wherein R$^1$ and R$^2$is a hydrogen atom or a hydrocarbon group which may be substituted), (6) a cyclic amino group, (7) —OR$^3$(wherein R$^3$ is a hydrogen atom, a hydrocarbon group which may be substituted, an acyl group which may be substituted, formyl group or an alkylsulfonyl group which may be substituted), or (8) a —S(O)$_n$R$^4$(wherein n represents an integer from 0 to 2, and R$^4$ is a hydrogen atom or a hydrocarbon group which may be substituted)], (hereafter, they may also be mentioned as compounds ($I^0$)), or more specifically compounds (I) to (V)(as will be stated below) or salts thereof have unexpectedly a very strong microbicidal activity, while, on the contrary, they revealed only a low toxicity to human being and farm animals, fishes and natural enemies. The present inventors carried out an intensive research based on these findings and have completed the present invention. Thus, the present invention relates to:

[1] A microbicidal composition for agricultural or horticultural use comprising a compound of Formula (I):

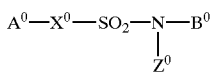

or a salt thereof

[wherein $A^1$ is (1) an aryl group which may be substituted or (2) a heterocyclic group which may be substituted, $X^1$ is (1) a chemical bond, (2) a methylene group which may be substituted, or (3) a vinylene group which may be substituted, $B^1$ is a five-membered heterocyclic group (except for an isoxazolyl group) or a condensed heterocyclic group which may be substituted, $Z^1$ is (1) a hydrocarbon group which may be substituted, (2) an acyl group which may be substituted, (3) formyl group, (4) an amino group which may be substituted, (5) a group which is represented by —N═CR$^1$R$^2$(wherein each R$^1$ and R$^2$ is respectively a hydrogen atom or a hydrocarbon group which may be substituted), (6) a cyclic amino group, (7) a group which is represented by —OR$^3$ (wherein R$^3$ is a hydrogen atom, a hydrocarbon group which may be substituted, an acyl group which may be substituted, formyl group or an alkylsulfonyl group which may be substituted) or (8) a group represented by —S(O)$_n$R$^4$ (wherein, n stands for an integer from 0 to 2, R$^4$ stands for a hydrogen atom or a hydrocarbon group which may be substituted).]

[2] A microbicidal composition for agricultural or horticultural use described in [1] above, wherein $B^1$ is a five-membered heterocyclic group which contains hetero-atoms selected from nitrogen atoms and sulfur atoms as the ring-constructing hetero atom in addition to the carbon atoms which may be substituted, or $B^1$ is a condensed heterocyclic group which may be substituted.

[3] A microbicidal composition described in [1] above, wherein $A^1$ is (1) an aryl group which may be substituted with 1 to 5 substituents selected from a group of substituents (T) which consists of (i) a $C_{1-4}$ alkyl group which may be substituted with 1 to 5 substituents selected from halogens, hydroxy, imino, hydroxyimino, $C_{1-4}$ alkoxyimino, hydrazono, mono- or di-$C_{1-4}$ alkylhydrazono and $C_{1-4}$ alkylthio, (ii) a $C_{3-6}$ cycloalkyl group which may be substituted with 1 to 5 halogens, (iii) a $C_{2-4}$ alkenyl group which may be substituted with 1 to 5 substituents selected from halogen, cyano, and nitro, (iv) a $C_{3-6}$ cycloalkenyl group which may be substituted with 1 to 5 halogens, (v) a $C_{2-4}$ alkynyl group which may be substituted with 1 to 5 halogens, (vi) hydroxyl group, (vii) a $C_{1-4}$ alkoxy group which may be substituted with 1 to 5 substituents selected from halogen and $C_{1-4}$ alkoxy group, (viii) formyloxy group, (ix) a $C_{1-4}$ alkyl-carbonyloxy group which may be substituted with 1 to 5 halogens, (x) a $C_{1-4}$ alkoxy-carbonyloxy group which may be substituted with 1 to 5 halogens, (xi) mercapto group, (xii) a $C_{1-4}$ alkylthio group which may be substituted with 1 to 5 halogens, (xiii) a $C_{1-4}$ alkyl-carbonylthio group which may be substituted with 1 to 5 halogens, (xiv) a $C_{1-4}$ alkoxy-carbonylthio group which may be substituted with 1 to 5 halogens, (xv) a $C_{1-4}$ alkylsulfinyl group which may be substituted with 1 to 5 halogens, (xvi) a $C_{1-4}$ alkylsulfonyl group which may be substituted with 1 to 5 halogens, (xvii) a sulfamoyl group, (xviii) a mono- or di-$C_{1-4}$ alkylsulfamoyl group, (xix) a group represented by

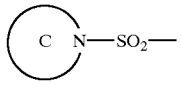

(wherein, ring C is a 3- to 6-membered heterocyclic group containing nitrogen), (xx) an amino group which may be substituted with one or two substituents selected from a $C_{1-4}$ alkyl, $C_{2-4}$ alkenyl, $C_{2-4}$ alkynyl, hydroxy, $C_{1-4}$ alkoxy, formyloxy, $C_{1-4}$ alkyl-carbonyloxy, formyl and $C_{1-4}$ alkyl-carbonyl, (xxi) a 3- to 6-membered cyclic amino group, (xxii) formyl group. (xxiii) a $C_{1-4}$ alkyl-carbonyl group which may be substituted with 1 to 5 halogens, (xxiv) a $C_{1-4}$ alkoxy-carbonyl group which may be substituted with 1 to 5 halogens, (xxv) a $C_{1-4}$ alkylthio-carbonyl group, (xxvi) a $C_{1-4}$ alkoxy-thiocarbonyl group, (xxvii) $C_{1-4}$ alkylthio-thiocarbonyl group, (xxviii) carbamoyl group, (xxix) a mono- or di-$C_{1-4}$ alkylcarbamoyl group, (xxx) a group represented by

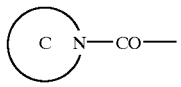

(wherein, ring C is a 3- to 6-membered heterocyclic group containing nitrogen), (xxxi) thiocarbamoyl group, (xxxii) a mono- or di-$C_{1-4}$ alkyl-thiocarbamoyl group, (xxxiii) a group represented by

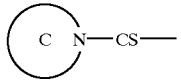

(wherein, ring C is a 3- to 6-membered heterocyclic group containing nitrogen), (xxxiv) halogen atom, (xxxv) carboxyl group, (xxxvi) thiocyanato group, (xxxvii) isothiocyanato group, (xxxviii) cyano group, (xxxix) isocyano group, (xl) azido group, (xli) nitroso group, (xlii) nitro group, (xliii) azocyano group, (xliv) azoxycyano group and (xlv) sulfo group, or (2) a heterocyclic group which may be substituted with 1 to 5 substituents selected from the group of substituents (T) mentioned above, $X^1$ is (1) a chemical bond, (2) a methylene group which may be substituted with one or two substituents selected from $C_{1-4}$ alkyl, $C_{1-4}$ alkoxy, $C_{1-4}$ alkylthio, halogen atom and cyano or (3) a vinylene group which may be substituted with one or two substituents selected from $C_{1-4}$ alkyl, $C_{1-4}$ alkoxy, $C_{1-4}$ alkylthio, halogen atom, and cyano, $B^1$ is (1) a five-membered heterocyclic group which is composed of the ring-constructing heteroatoms besides carbon atoms selected from nitrogen and sulfur atoms, and which may be substituted with 1 to 5 substituents selected from the group of substituents (T) mentioned above, or (2) a condensed heterocyclic group which is constructed either with a five- to six-membered heterocyclic ring and benzene rings or with a five- to six-membered heterocyclic ring and another (the same or different) five- to six-membered heterocyclic rings and may be substituted with substituents selected from the group of substituents (T) mentioned above, $Z^1$ is (1) a hydrocarbon group which is selected from (i) a $C_{1-6}$ alkyl group which may be substituted with 1 to 5 substituents selected from (a) halogen, (b) amino, (c) mono- or di-$C_{1-4}$ alkylamino, (d) hydroxy, (e) $C_{1-4}$ alkoxy which may be substituted with 1 to 5 halogens, (f) mercapto, (g) $C_{1-4}$ alkylthio, (h) $C_{1-4}$ alkylsulfinyl, (i) $C_{1-4}$ alkylsulfonyl, (j) cyano, (k) $C_{1-4}$ alkoxy-carbonyl, (l) carbamoyl and (m) a mono- or di-$C_{1-4}$ alkyl-carbamoyl group, (ii) a $C_{2-6}$ alkenyl group which may be substituted with 1 to 5 substituents selected from (a) halogen, (b) amino, (c) mono- or di-$C_{1-4}$ alkylamino, (d) hydroxy, (e) $C_{1-4}$ alkoxy which may be substituted with 1 to 5 halogens, (f) mercapto, (g) $C_{1-4}$ alkylthio, (h) $C_{1-4}$ alkylsulfinyl, (i) $C_{1-4}$ alkylsulfonyl, (j) cyano, (k) $C_{1-4}$ alkoxy-carbonyl, (l) carbamoyl, and (m) mono- or di-$C_{1-4}$ alkyl-carbamoyl, (iii) a $C_{2-6}$ alkynyl group which may be substituted with 1 to 5 substituents selected from (a) halogen, (b) amino, (c) mono- or di-$C_{1-4}$ alkylamino, (d) hydroxy, (e) $C_{1-4}$ alkoxy which may be substituted with 1 to 5 halogens, (f) mercapto, (g) $C_{1-4}$ alkylthio, (h) $C_{1-4}$ alkylsulfinyl, (i) $C_{1-4}$ alkylsulfonyl, (j) cyano, (k) $C_{1-4}$ alkoxy-carbonyl, (l) carbamoyl, and (m) mono- or di-$C_{1-4}$ alkyl-carbamoyl, (iv) a $C_{3-6}$ cycloalkyl group which may be substituted with 1 to 5 substituents selected from (a) $C_{1-4}$ alkyl which may be substituted with 1 to 5 halogens, (b) halogen, (c) amino, (d) mono- or di-$C_{1-4}$ alkylamino, (e) hydroxy, (f) $C_{1-4}$ alkoxy which may be substituted with 1 to 5 halogens, (g) mercapto, (h) $C_{1-4}$ alkylthio, (i) $C_{1-4}$ alkylsulfinyl, (j) $C_{1-4}$ alkylsulfonyl, (k) cyano, (l) $C_{1-4}$ alkoxy-carbonyl, (m) carbamoyl, and (n) mono- or di-$C_{1-4}$ alkyl-carbamoyl, (v) a $C_{3-6}$ alkadienyl group which may be substituted with 1 to 5 substituents selected from (a) halogen, (b) amino, (c) mono- and di-$C_{1-4}$ alkylamino, (d) hydroxy, (e) $C_{1-4}$ alkoxy which may be substituted with 1 to 5 halogens, (f) mercapto, (g) $C_{1-4}$ alkylthio, (h) $C_{1-4}$ alkylsulfinyl, (i) $C_{1-4}$ alkylsulfonyl, (j) cyano, (k) $C_{1-4}$ alkoxy-carbonyl, (l) carbamoyl and (m) mono- or di- $C_{1-4}$ alkyl-carbamoyl or (vi) $C_{6-14}$ aryl group which may be substituted with 1 to 5 substituents selected from (a) $C_{1-4}$ alkyl which may be substituted with 1 to 5 halogens, (b) halogen, (c) amino, (d) mono- or di-$C_{1-4}$ alkylamino, (e) hydroxy, (f) $C_{1-4}$ alkoxy which may be substituted with 1 to 5 halogens, (g) mercapto, (h) $C_{1-4}$ alkylthio, (i) $C_{1-4}$ alkylsulfinyl, (j) $C_{1-4}$ alkylsulfonyl, (k) cyano, (l) $C_{1-4}$ alkoxy-carbonyl, (m) carbamoyl and (n) mono- or di-$C_{1-4}$ alkyl-carbamoyl, (2) an acyl group selected from (i) $C_{1-4}$ alkyl-carbonyl, (ii) $C_{1-4}$ alkoxy-carbonyl, (iii) $C_{1-4}$ alkylthio-carbonyl, (iv) $C_{1-4}$ alkoxy-thiocarbonyl, (v) $C_{1-4}$ alkylthio-thiocarbonyl, (vi) mono- or di-$C_{1-4}$ alkyl-carbamoyl and (vii) mono- or di-$C_{1-4}$ alkyl-thiocarbamoyl, each of which may be substituted with 1 to 5 halogens, (3) formyl group, (4) an amino group which may be substituted with one or two substituents selected from (a) $C_{1-4}$ alkyl, (b) $C_{1-4}$ alkyl-carbonyl which may be substituted with 1 to 5 halogens, (c) $C_{1-4}$ alkoxy-carbonyl, (d) mono- or di-$C_{1-4}$ alkyl-carbamoyl and (e) mono- or di-$C_{1-4}$ alkyl-thiocarbamoyl, (5) a group represented by —N=$CR^1R^2$ (wherein $R^1$ and $R^2$ are the same or different, and are a hydrogen atom and a $C_{1-4}$ alkyl group), (6) a three- to six-membered cyclic amino group, (7) a group represented by —$OR^3$ (wherein $R^3$ is a hydrogen atom, a $C_{1-4}$ alkyl group which may be substituted with 1 to 5 halogens, a $C_{1-4}$ alkyl-carbonyl group which may be substituted with 1 to 5 halogens, a $C_{1-4}$ alkoxy-carbonyl group which may be substituted with 1 to 5 halogens, formyl group or a $C_{1-4}$ alkylsulfonyl group which may be substituted with 1 to 5 halogens), or (8) a group represented by —$S(O)_nR^4$ (wherein n is an integer from 0 to 2, and $R^4$ is (a) a hydrogen atom, (b) a $C_{1-4}$ alkyl group which may be substituted with 1 to 5 halogens or (c) a $C_{6-14}$ aryl group which may be substituted with 1 to 5 $C_{1-4}$ alkyl groups.

[4] A microbicidal composition for agricultural or horticultural use described in [1] above, where $A^1$ is a $C_{6-14}$ aryl group which may be substituted with 1 to 3 alkyl group, $X^1$ is a chemical bond, $B^1$ is a thienyl group, a pyrazolyl group, an isothiazolyl group, an imidazolyl group, a thiazolyl group, a thiadiazolyl group, a dioxaindanyl group or an imidazopyridyl group, each of which may be substituted with 1 to 5 substituents selected from $C_{1-4}$ alkyl which may be substituted with 1 to 5 halogens, $C_{1-4}$ alkoxy, $C_{1-4}$ alkylthio, cyano, halogens and nitro, $Z^1$ is a $C_{1-6}$ alkyl group or a $C_{1-4}$ alkoxy group.

[5] A microbicidal composition for agricultural or horticultural use comprising a compound of Formula (II):

$$A^2-X^2-SO_2-\underset{Z^2}{N}-B^2$$

or a salt thereof,

[wherein, $A^2$ is (1) an aryl group which may be substituted with 1 to 5 substituents selected from a group of substituents (T') which consists of (i) a $C_{1-4}$ alkyl group which may be substituted with 1 to 5 substituents selected from halogen, hydroxy, imino, hydroxyimino, $C_{1-4}$ alkoxyimino, hydrazono, mono- or di-$C_{1-4}$ alkylhydrazono and $C_{1-4}$ alkylthio, (ii) a $C_{3-6}$ cycloalkyl group which may be substituted with 1 to 5 halogens, (iii) a $C_{2-4}$ alkenyl group which may be substituted with substituents selected from halogens, cyano and nitro, (iv) a $C_{3-6}$ cycloalkenyl group which may be substituted with 1 to 5 halogens, (v) a $C_{2-4}$ alkynyl group which may be substituted with 1 to 5 halogens, (vi) hydroxy group, (vii) a $C_{1-4}$ alkoxy group which may be substituted with 1 to 5 substituents selected from halogens and $C_{1-4}$ alkoxy, (viii) formyloxy group, (ix) a $C_{1-4}$ alkyl-carbonyloxy group which may be substituted with 1 to 5 halogens, (x) a $C_{1-4}$ alkoxy-carbonyloxy group which may be substituted with 1 to 5 halogens, (xi) mercapto group, (xii) a $C_{1-4}$ alkylthio group which may be substituted with 1 to 5 halogens, (xiii) a $C_{1-4}$ alkyl-carbonylthio group which may be substituted with 1 to 5 halogens, (xiv) a $C_{1-4}$ alkoxy-carbonylthio group which may be substituted with 1 to 5 halogens, (xv) a $C_{1-4}$ alkylsulfinyl group which may be substituted with 1 to 5 halogens, (xvi) a $C_{1-4}$ alkylsulfonyl group which may be substituted with 1 to 5 halogens, (xvii) sulfamoyl group, (xviii) a mono- or di-$C_{1-4}$ alkylsulfamoyl group, (xix) a group represented by

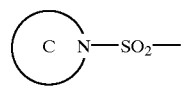

(wherein, ring C is a three- to six-membered heterocyclic group containing nitrogen), (xx) an amino group which may be mono- or disubstituted with one or two substituents selected from $C_{1-4}$ alkyl, $C_{2-4}$ alkenyl, $C_{2-4}$ alkynyl, hydroxy, $C_{1-4}$ alkoxy, formyloxy, $C_{1-4}$ alkyl-carbonyloxy, formyl and $C_{1-4}$ alkyl-carbonyl, (xxi) a three- to six-membered cyclic amino group, (xxii) formyl group, (xxiii) a $C_{1-4}$ alkyl-carbonyl group which may be substituted with 1 to 5 halogens, (xxiv) a $C_{1-4}$ alkoxy-carbonyl group which may be substituted with 1 to 5 halogens, (xxv) a $C_{1-4}$ alkylthio-carbonyl group, (xxvi) a $C_{1-4}$ alkoxy-thiocarbonyl group, (xxvii) a $C_{1-4}$ alkylthio-thiocarbonyl group, (xxviii) carbamoyl group, (xxix) a mono- or di-$C_{1-4}$ alkylcarbamoyl group, (xxx) a group represented by

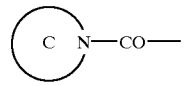

(wherein, ring C is a three- to six-membered heterocyclic group containing nitrogen), (xxxi) thiocarbamoyl group, (xxxii) a mono- or di-$C_{1-4}$ alkyl-thiocarbamoyl group, (xxxiii) a group represented by

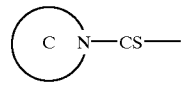

(wherein, ring C is a three- to six-membered heterocyclic group containing nitrogen), (xxxiv) halogen atom, (xxxv) carboxyl group, (xxxvi) thiocyanato group, (xxxvii) isothiocyanato group, (xxxviii) cyano group, (xxxix) isocyano group, (xl) azido group, (xli) nitroso group, (xlii) nitro group, (xliii) azocyano group and (xliv) sulfo group or (2) a heterocyclic group, which may be substituted.

$X^2$ is (1) a chemical bond, (2) a methylene group which may be substituted or (3) a vinylene group which may be substituted, $B^2$ is an aryl group which may be substituted, $Z^2$ is (1) an alkyl group which may be substituted with substituents selected from mono- or di-$C_{1-6}$ alkylamino, hydroxy, halogens, $C_{1-6}$ alkoxy, $C_{1-6}$ alkoxy-carbonyl, $C_{1-6}$ alkylthio and cyano, (2) vinyl group, (3) an allyl group, (4) a propadienyl group, (5) an alkynyl group which may be substituted, (6) a cycloalkyl group which may be substituted, (7) an aryl group which may be substituted, (8) an acyl group which may be substituted, (9) formyl group, (10) an amino group which may be substituted, (11) a group represented by —$N=CR^1R^2$ (wherein $R^1$ and $R^2$ are the same or different, and are a hydrogen atom and a hydrocarbon group which may be substituted respectively), (12) a cyclic amino group, (13) a group represented by —$OR^3$ (wherein $R^3$ is a hydrogen atom, a hydrocarbon group which may be substituted, an acyl group which may be substituted, formyl group, or an alkylsulfonyl group which may be substituted), or (14) a group represented by —$S(O)_nR^4$ (wherein, n is an integer from 0 to 2, and $R^4$ is a hydrogen atom or a hydrocarbon group which may be substituted).

[6] A microbicidal composition for agricultural or horticultural use described in [5] above, [wherein, $A^2$ is (1) a $C_{6-14}$ aryl group which may be substituted with 1 to 5 substituents selected from a group of substituents (T') which consists of (i) a $C_{1-4}$ alkyl group which may be substituted with 1 to 5 substituents selected from halogen, hydroxy, imino, hydroxyimino, $C_{1-4}$ alkoxyimino, hydrazono, mono- or di-$C_{1-4}$ alkylhydrazono and $C_{1-4}$ alkylthio, (ii) a $C_{3-6}$ cycloalkyl group which may be substituted with 1 to 5 halogens, (iii) $C_{2-4}$ alkenyl group which may be substituted with 1 to 5 substituents selected from halogens, cyano and nitro, (iv) a $C_{3-6}$ cycloalkenyl group which may be substituted with 1 to 5 halogens, (v) a $C_{2-4}$ alkynyl group which may be substituted with 1 to 5 halogens, (vi) hydroxy group, (vii) a $C_{1-4}$ alkoxy group which may be substituted with 1 to 5 substituents selected from halogens and $C_{1-4}$ alkoxy, (viii) formyloxy group, (ix) a $C_{1-4}$ alkyl-carbonyloxy group which may be substituted with 1 to 5 halogens, (x) a $C_{1-4}$ alkoxy-carbonyloxy group which may be substituted with 1 to 5 halogens, (xi) mercapto group, (xii) a $C_{1-4}$ alkylthio group which may be substituted with 1 to 5 halogens, (xiii) a $C_{1-4}$ alkyl-carbonylthio group which may be substituted with 1 to 5 halogens, (xiv) a $C_{1-4}$ alkoxy-carbonylthio group which may be substituted with 1 to 5 halogens, (xi) a $C_{1-4}$ alkylsulfinyl group which may be substituted with 1 to 5 halogens, (xvi) a $C_{1-4}$ alkylsulfonyl group which may be substituted with 1 to 5 halogens, (xvii) sulfamoyl group, (xviii) a mono- or di-$C_{1-4}$ alkylsulfamoyl group, (xix) a group represented by

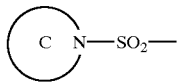

(wherein, ring C is a three- to six-membered heterocyclic group containing nitrogen), (xx) an amino group which may be substituted with one or two substituents selected from $C_{1-4}$ alkyl, $C_{2-4}$ alkenyl, $C_{2-4}$ alkynyl, hydroxy, $C_{1-4}$ alkoxy, formyloxy, $C_{1-4}$ alkyl-carbonyloxy, formyl and $C_{1-4}$ alkyl-carbonyl, (xxi) a three to six-membered cyclic amino group, (xxii) formyl group, (xxiii) a $C_{1-4}$ alkyl-carbonyl group which may be substituted with 1 to 5 halogens, (xxiv) a $C_{1-4}$ alkoxy-carbonyl group which may be substituted with 1 to 5 halogens, (xxv) a $C_{1-4}$ alkylthio-carbonyl group, (xxvi) a $C_{1-4}$ alkoxy-thiocarbonyl group, (xxvii) a $C_{1-4}$ alkylthio-thiocarbonyl group, (xxviii) carbamoyl group, (xxix) a mono- or di-$C_{1-4}$ alkylcarbamoyl group, (xxx) a group represented by

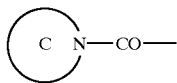

(wherein, ring C is a three- to six-membered heterocyclic group containing nitrogen), (xxxi) thiocarbamoyl group (xxxii) a mono- or di-$C_{1-4}$ alkyl-thiocarbamoyl group, (xxxiii) a group represented by

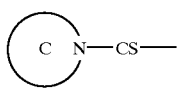

(wherein, ring C is a three- to six-membered heterocyclic group containing nitrogen), (xxxiv) halogen atom, (xxxv) carboxyl group, (xxxvi) thiocyanato group, (xxxvii) isothiocyanato group, (xxxviii) cyano group, (xxxix) isocyano group, (xl) azido group, (xli) nitroso group, (xlii) nitro group, (xliii) azocyano group and (xliv) sulfo group, or (2) heterocyclic group which may be substituted with 1 to 5 substituents selected from a group of substituents (T) which consists of (i) $C_{1-4}$ alkyl group which may be substituted with 1 to 5 substituents selected from halogens, hydroxy, imino, hydroxyimino, $C_{1-4}$ alkoxyimino, hydrazono, mono- or di-$C_{1-4}$ alkylhydrazono and $C_{1-4}$ alkylthio, (ii) a $C_{3-6}$ cycloalkyl group which may be substituted with 1 to 5 halogens, (iii) $C_{2-4}$ alkenyl group which may be substituted with 1 to 5 substituents selected from halogens, cyano and nitro, (iv) $C_{3-6}$ cycloalkenyl group which may be substituted with 1 to 5 halogens, (v) a $C_{2-4}$ alkynyl group which may be substituted with 1 to 5 halogens, (vi) hydroxy group, (vii) $C_{1-4}$ alkoxy group which may be substituted with 1 to 5 substituents selected from halogens and $C_{1-4}$ alkoxy, (viii) formyloxy group, (ix) $C_{1-4}$ alkyl-carbonyloxy group which may be substituted with 1 to 5 halogens, (x) $C_{1-4}$ alkoxy-carbonyloxy group which may be substituted with 1 to 5 halogens, (xi) mercapto group, (Xii) $C_{1-4}$ alkylthio group which may be substituted with 1 to 5 halogens, (xiii) a $C_{1-4}$ alkyl-carbonylthio group which may be substituted with 1 to 5 halogens, (xiv) a $C_{1-4}$ alkoxy-carbonylthio group which may be substituted with 1 to 5 halogens, (xv) a $C_{1-4}$ alkylsulfinyl group which may be substituted with 1 to 5 halogens, (xvi) a $C_{1-4}$ alkylsulfonyl group which may be substituted with 1 to 5 halogens, (xvii) sulfamoyl group, (xviii) a mono- or di-$C_{1-4}$ alkylsulfamoyl group, (xix) a group represented by

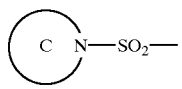

(wherein, ring C is a three- to six-membered heterocyclic group containing nitrogen), (xx) an amino group which may be substituted with one or two substituents selected from $C_{1-4}$ alkyl, $C_{2-4}$ alkenyl, $C_{2-4}$ alkynyl, hydroxy, $C_{1-4}$ alkoxy, formyloxy, $C_{1-4}$ alkyl-carbonyloxy, formyl and $C_{1-4}$ alkyl-carbonyl, (xxi) three- to six-membered cyclic amino group, (xxii) formyl group, (xxiii) $C_{1-4}$ alkyl-carbonyl group which may be substituted with 1 to 5 halogens, (xxiv) $C_{1-4}$ alkoxy-carbonyl group which may be substituted with 1 to 5 halogens, (xxv) $C_{1-4}$ alkylthio-carbonyl group, (xxvi) a $C_{1-4}$ alkoxy-thiocarbonyl group, (xxvii) $C_{1-4}$ alkylthio-thiocarbonyl group, (xxviii) a carbamoyl group, (xxix) mono- or di-$C_{1-4}$ alkylcarbamoyl group, (xxx) a group represented by

(wherein, ring C is a three- to six-membered heterocyclic group containing nitrogen), (xxxi) thiocarbamoyl group, (xxxii) mono- or di-$C_{1-4}$ alkyl-thiocarbamoyl group, (xxxiii) a group represented by

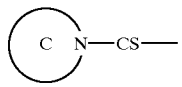

(wherein, ring C is a three- to six-membered heterocyclic group containing nitrogen), (xxxiv) halogen atom, (xxxv)

carboxyl group, (xxxvi) thiocyanato group, (xxxvii) isothiocyanato group, (xxxviii) cyano group, (xxxix) isocyano group, (xl) azido group, (xli) nitroso group, (xlii) nitro group, (xliii) azocyano group and (xliv) azoxycyano group, and (xlv) sulfo group, $X^2$ is (1) a chemical bond, (2) a methylene group which may be substituted with one or two substituents selected from $C_{1-4}$ alkyl, $C_{1-4}$ alkoxy, $C_{1-4}$ alkylthio, halogen atoms, and cyano, or (3) a vinylene group which may be substituted with one or two substituents selected from $C_{1-4}$ alkyl, $C_{1-4}$ alkoxy, $C_{1-4}$ alkylthio, halogen atoms and cyano, $B^2$ is an aryl group which may be substituted with 1 to 5 substituents selected from the group of substituents (T) described above, $Z^2$ is (1) $C_{1-6}$ alkyl group which may be substituted with 1 to 5 substituents selected from mono- or di-$C_{1-4}$ alkylamino, hydroxy, halogen, $C_{1-4}$ alkoxy, $C_{1-4}$ alkoxy-carbonyl, $C_{1-4}$ alkylthio and cyano, (2) vinyl group, (3) allyl group, (4) propadienyl group, (5) $C_{2-6}$ alkynyl group which may be substituted with 1 to 5 substituents selected from (a) halogen, (b) amino, (c) mono- or di-$C_{1-4}$ alkylamino, (d) hydroxy, (e) a $C_{1-4}$ alkoxy substituted with 1 to 5 halogens, (f) mercapto, (g) $C_{1-4}$ alkylthio, (h) $C_{1-4}$ alkylsulfinyl, (i) $C_{1-4}$ alkylsulfonyl, (j) cyano, (k) $C_{1-4}$ alkoxy- carbonyl, (l) carbamoyl and (m) mono- or di-$C_{1-4}$ alkyl-carbamoyl, (6) $C_{3-6}$ cycloalkyl group which may be substituted with 1 to 5 substituents selected from (a) $C_{1-4}$ alkyl which may be substituted with 1 to 5 halogens, (b) halogen, (c) amino, (d) mono- or di-$C_{1-4}$ alkylamino, (e) hydroxy, (f) $C_{1-4}$ alkoxy which may be substituted with 1 to 5 halogens, (g) mercapto, (h) $C_{1-4}$ alkylthio, (i) $C_{1-4}$ alkylsulfinyl, (j) $C_{1-4}$ alkylsulfonyl, (k) cyano, (l) $C_{1-4}$ alkoxy-carbonyl, (m) carbamoyl and (n) mono- or di-$C_{1-4}$ alkyl-carbamoyl, (7) $C_{6-14}$ aryl group which may be substituted with 1 to 5 substituents selected from (a) $C_{1-4}$ alkyl which may be substituted with 1 to 5 halogens, (b) halogen, (c) amino, (d) mono- or di-$C_{1-4}$ alkylamino, (e) hydroxy, (f) $C_{1-4}$ alkoxy which may be substituted with 1 to 5 halogens, (g) mercapto, (h) $C_{1-4}$ alkylthio, (i) $C_{1-4}$ alkylsulfinyl, (j) $C_{1-4}$ alkylsulfonyl, (k) cyano, (l) $C_{1-4}$ alkoxy-carbonyl, (m) carbamoyl and (n) mono- or di-$C_{1-4}$ alkyl-carbamoyl, (8) acyl group selected from (i) $C_{1-4}$ alkyl-carbonyl, (ii) $C_{1-4}$ alkoxy-carbonyl, (iii) $C_{1-4}$ alkylthio-carbonyl, (iv) $C_{1-4}$ alkoxy-thiocarbonyl, (v) $C_{1-4}$ alkylthio-thiocarbonyl, (vi) mono- or di-$C_{1-4}$ alkyl-carbamoyl and (vii) mono- or di-$C_{1-4}$ alkyl-thiocarbamoyl, each of which may be substituted with 1 to 5 halogens, (9) formyl group, (10) amino group which may be substituted with one or two substituents selected from (a) $C_{1-4}$ alkyl, (b) $C_{1-4}$ alkyl-carbonyl which may be substituted with 1 to 5 halogens, (c) $C_{1-4}$ alkoxy-carbonyl, (d) mono- or di-$C_{1-4}$ alkyl-carbamoyl and (e) mono- or di-$C_{1-4}$ alkyl-thiocarbamoyl, (11) a group represented by —N=$CR^1R^2$ (wherein $R^1$ and $R^2$ are the same or different, and are a hydrogen atom and a $C_{1-4}$ alkyl group), (12) three- to six-membered cyclic amino group, (13) a group represented by —$OR^3$ (wherein $R^3$ is a hydrogen atom, a $C_{1-4}$ alkyl group which may be substituted with 1 to 5 halogens, a $C_{1-4}$ alkoxy-carbonyl group which may be substituted with 1 to 5 halogens, formyl group, or $C_{1-4}$ alkylsulfonyl group which may be substituted with 1 to 5 halogens), or (14) a group represented by —S(O) $R^4$ (wherein n is an integer from 0 to 2, and $R^4$ is (a) hydrogen atom, (b) $C_{1-4}$ alkyl group which may be substituted with 1 to 5 halogens or (c) $C_{6-14}$ aryl group which may be substituted with 1 to 5 $C_{1-4}$ alkyl groups).

[7] A microbicidal composition for agricultural or horticultural use described in [5] above, wherein $A^2$ is (1) $C_{6-14}$ aryl group, which may be substituted with 1 to 5 substituents selected from (i) $C_{1-4}$ alkyl group which may be substituted with 1 to 5 halogens, (ii) $C_{1-4}$ alkoxy group which may be substituted with 1 to 5 halogens, (iii) amino group which may be substituted with one or two $C_{1-4}$ alkyl-carbonyl group, (iv) $C_{1-4}$ alkoxy-carbonyl group, (v) halogen atom, (vi) cyano group and (vii) nitro group, or (2) thienyl group, triazolyl group, imidazolyl group, isoxazolyl group, pyrazolyl group, pyridyl group, quinolyl group, benzothiadiazolyl group, imidazothiazolyl group or imidazopyridyl group, which may be substituted with 1 to 5 substituents selected from (i) $C_{1-4}$ alkyl group, (ii) $C_{1-4}$ alkoxy-carbonyl group, (iii) carbamoyl group, (iv) mono- or di-$C_{1-4}$ alkylcarbamoyl group, (v) $C_{1-4}$ alkylsulfonyl group, (vi) halogen atom, (vii) carboxyl group and (viii) cyano group, $X^2$ is (1) a chemical bond, (2) a methylene group which may be substituted with one or two $C_{1-4}$ alkyl group, or (3) a vinylene group which may be substituted with one or two $C_{1-4}$ alkyl, $B^2$ is a $C_{6-14}$ aryl group which may be substituted with 1 to 5 substituents selected from (1) a $C_{1-4}$ alkyl group which may be substituted with 1 to 5 substituents selected from halogen, hydroxy, imino, hydroxyimino, $C_{1-4}$ alkoxyimino, hydrazono, mono- or di-$C_{1-4}$ alkylhydrazono and $C_{1-4}$ alkylthio, (2) $C_{2-4}$ alkynyl group, (3) hydroxy group, (4) a $C_{1-4}$ alkoxy group which may be substituted with 1 to 5 substituents selected from halogens and $C_{1-4}$ alkoxy, (5) a $C_{1-4}$ alkyl-carbonyloxy group, (6) a $C_{1-4}$ alkylthio group, (7) a $C_{1-4}$ alkylsulfinyl group, (8) a $C_{1-4}$ alkylsulfonyl group, (9) mono- or di-$C_{1-4}$ alkylsulfamoyl group, (10) amino group, (11) formyl group, (12) $C_{1-4}$ alkoxy-carbonyl group, (13) carbamoyl group, (14) mono- or di-$C_{1-4}$ alkylcarbamoyl group, (15) thiocarbamoyl group, (16) halogen atom, (17) carboxyl group, (18) thiocyanato group, (19) cyano group, (20) nitroso group and (21) nitro group, $Z^2$ is (1) a $C_{1-6}$ alkyl group which may be substituted with 1 to 5 substituents selected from mono- or di-$C_{1-4}$ alkylamino, hydroxy, halogen, $C_{1-4}$ alkoxy, $C_{1-4}$ alkoxy-carbonyl, $C_{1-4}$ alkylthio and cyano, (2) vinyl group, (3) allyl group, (4) propadienyl group, (5) $C_{2-6}$ alkynyl group which may be substituted with 1 to 5 halogens, (6) $C_{3-6}$ cycloalkyl group, (7) $C_{6-14}$ aryl group, (8) $C_{1-4}$ alkyl-carbonyl which may be substituted with 1 to 5 halogens, (9) an amino group which may be substituted with one or two substituents selected from $C_{1-4}$ alkyl, $C_{1-4}$ alkyl-carbonyl and $C_{1-4}$ alkoxy-carbonyl, (10) a group represented by —N=$CR^1R^2$(wherein, both $R^1$ and $R^2$ are the same or different $C_{1-4}$ alkyl groups), (11) a group represented by —$OR^3$ (wherein $R^3$ is a $C_{1-4}$ alkyl group or a $C_{1-4}$ alkyl-carbonyl group), or (12) a group represented by —$S(O)_nR^4$ (wherein n is an integer from 0 to 2, $R^4$ is (a) a $C_{1-4}$ alkyl group which may be substituted with 1 to 5 halogens, or (b) a $C_{6-14}$ aryl group which may be substituted with 1 to 5 $C_{1-4}$ alkyl groups).

[8] A microbicidal composition for agricultural or horticultural use described in [5] above, wherein
$A^2$ is a phenyl group which may be substituted with 1 to 3 substituents selected from $C_{1-4}$ alkyl groups, halogens and cyano,
$X^2$ is a chemical bond,
$B^2$ is a phenyl group which may be substituted with 1 to 5 substituents selected from (1) a $C_{1-4}$ alkyl group which may be substituted with 1 to 3 halogens, (2) $C_{1-4}$ alkoxy group, (3) $C_{1-4}$ alkylthio group, (4) thiocarbamoyl group, (5) halogen atom, (6) cyano group and (7) nitro group, $Z^2$ is (1) a $C_{1-6}$ alkyl group which may be substituted with 1 to 3 $C_{1-4}$ alkoxy groups, (2) $C_{3-6}$ cycloalkyl group, (3) allyl group or (4) $C_{1-4}$ alkoxy group.

[9] A microbicidal composition for agricultural or horticultural use described in [5] above, wherein the compound or the salt thereof is 4'-chloro-N-ethyl-2'-nitro-p-toluenesulfonanilide, 2',4'-dinitro-N-ethyl-p-toluenesulfonanilide, 2',4'-dicyano-N-ethyl-p-toluenesulfonanilide, 4'-chloro-N-isopropyl-2'-nitro-p-toluenesulfonanilide, 4'-fluoro-N-isopropyl-2'-nitro-p-toluenesulfonanilide, 4'-cyano-N-isopropyl-2'-nitro-p-toluenesulfonanilide, 4'-chloro-N-isopropyl-2'-cyano-p-toluenesulfonanilide, 2,4'-dinitro-N-isopropyl-p-toluenesulfonanilide, 2'-cyano-N-isopropyl-4'-nitro-p-toluenesulfonanilide, 2'-cyano-N-methoxy-4'-nitro-p-toluenesulfonanilide or 2',4'- dinitro-N-methoxy-p-toluenesulfonanilide or a salt thereof.

[10] A microbicidal composition for agricultural or horticultural use comprising a compound of Formula (III):

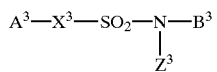

or a salt thereof, (wherein, $A^3$ is (1) an aryl group which may be substituted or (2) a heterocyclic group which may be substituted, $X^3$ is (1) a chemical bond, (2) a methylene group which may be substituted, or (3) a vinylene group which may be substituted, $B^3$ is a six-membered heterocyclic group which is substituted with substituents selected from the group of substituents (T), which consists of (i) a $C_{1-4}$ alkyl group which may be substituted with 1 to 5 substituents selected from halogen, hydroxy, imino, hydroxyimino, $C_{1-4}$ alkoxyimino, hydrazono, mono- or di-$C_{1-4}$ alkylhydrazono and $C_{1-4}$ alkylthio, (ii) a $C_{3-6}$ cycloalkyl group which may be substituted with 1 to 5 halogen, (iii) a $C_{2-4}$ alkenyl group which may be substituted with 1 to 5 substituents selected from halogens, cyano and nitro, (iv) a $C_{3-6}$ cycloalkenyl group which may be substituted with 1 to 5 halogens, (v) a $C_{2-4}$ alkynyl group which may be substituted with 1 to 5 halogens, (vi) hydroxy group, (vii) a $C_{1-4}$ alkoxy group which may be substituted with 1 to 5 substituents selected from halogen and $C_{1-4}$ alkoxy group, (viii) formyloxy group, (ix) $C_{1-4}$ alkyl-carbonyloxy group which may be substituted with 1 to 5 halogens, (x) a $C_{1-4}$ alkoxy-carbonyloxy group which may be substituted with 1 to 5 halogens, (xi) mercapto group, (xii) a $C_{1-4}$ alkylthio group which may be substituted with 1 to 5 halogens, (xiii) a $C_{1-4}$ alkyl-carbonylthio group which may be substituted with 1 to 5 halogens, (xiv) a $C_{1-4}$ alkoxy-carbonylthio group which may be substituted with 1 to 5 halogens, (xv) a $C_{1-4}$ alkylsulfinyl group which may be substituted with 1 to 5 halogens, (xvi) a $C_{1-4}$ alkylsulfonyl group which may be substituted with 1 to 5 halogens, (xvii) sulfamoyl group, (xviii) a mono- or di-$C_{1-4}$ alkylsulfamoyl group, (xix) a group represented by

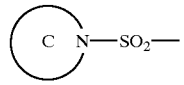

(wherein, ring C is a three- to six-membered heterocyclic group containing nitrogen), (xx) an amino group which may be substituted with one or two substituents selected from $C_{1-4}$ alkyl, $C_{2-4}$ alkenyl, $C_{2-4}$ alkynyl, hydroxy, $C_{1-4}$ alkoxy, formyloxy, $C_{1-4}$ alkyl-carbonyloxy, formyl and $C_{1-4}$ alkyl-carbonyl, (xxi) a three- to six-membered cyclic amino group, (xxii) formyl group, (xxiii) a $C_{1-4}$ alkyl-carbonyl group which may be substituted with 1 to 5 halogens, (xxiv) a $C_{1-4}$ alkoxy-carbonyl group which may be substituted with 1 to 5 halogens, (xxv) a $C_{1-4}$ alkylthio-carbonyl group, (xxvi) a $C_{1-4}$ alkoxy-thiocarbonyl group, (xxvii) a $C_{1-4}$ alkylthio-thiocarbonyl group, (xxviii) carbamoyl group, (xxix) a mono- or di-$C_{1-4}$ alkylcarbamoyl group, (xxx) a group represented by

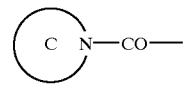

(wherein, ring C is a three- to six-membered heterocyclic group containing nitrogen), (xxxi) thiocarbamoyl group, (xxxii) mono- or di-$C_{1-4}$ alkyl-thiocarbamoyl group, (xxxiii) a group which is represented by

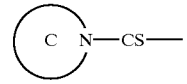

(wherein, ring C is a three- to six-membered heterocyclic group containing nitrogen), (xxxiv) halogen atom, (xxxv) carboxyl group, (xxxvi) thiocyanato group, (xxxvii) isothiocyanato group, (xxxviii) cyano group, (xxxix) isocyano group, (xl) azido group, (xli) nitroso group, (xlii) nitro group, (xliii) azocyano group (xliv) azoxycyano group, and (xlv) sulfo group, $Z^3$ is (1) a hydrocarbon group which may be substituted, (2) an acyl group which may be substituted, (3) formyl group, (4) an amino group which may be substituted, (5) a group represented by —N=CR$^1$R$^2$ (wherein, R$^1$ and R$^2$ are the same or different, and a hydrogen atom or a hydrocarbon group which may be substituted), (6) cyclic amino group, (7) a group represented by —OR$^3$ (wherein, R$^3$ stands for a hydrogen atom, a hydrocarbon group which may be substituted, an acyl group which may be substituted, formyl group or sulfonyl group which may be substituted), or (8) a group represented by —S(O)$_n$R$^4$ (wherein, n is an integer from 0 to 2, R$^4$ is a hydrogen atom or a hydrocarbon group which may be substituted)].

[11] A microbicidal composition for agricultural or horticultural use described in [10] above, wherein $A^3$ is (1) $C_{6-14}$ aryl group which may be substituted with 1 to 5 substituents selected from (i) $C_{1-4}$ alkyl group which may be substituted with 1 to 5 substituents selected from halogens, hydroxy, imino, hydroxyimino, $C_{1-4}$ alkoxyimino, hydrazono, mono- or di-$C_{1-4}$ alkylhydrazono and $C_{1-4}$ alkylthio, (ii) $C_{3-6}$ cycloalkyl group which may be substituted with 1 to 5 halogens, (iii) $C_{2-4}$ alkenyl group which may be substituted with 1 to 5 substituents selected from halogens, cyano and nitro, (iv) $C_{3-6}$ cycloalkenyl group which may be substituted with 1 to 5 halogens, (v) $C_{2-4}$ alkynyl group which may be substituted with 1 to 5 halogens, (vi) hydroxy group, (vii) $C_{1-4}$ alkoxy group which may be substituted with 1 to 5 substituents selected from halogens and $C_{1-4}$ alkoxy, (viii) formyloxy group, (ix) $C_{1-4}$ alkyl-carbonyloxy group which may be substituted with 1 to 5 halogens, (x) $C_{1-4}$ alkoxy-carbonyloxy group which may be substituted with 1 to 5 halogens, (xi) mercapto group, (xii) $C_{1-4}$ alkylthio group which may be substituted with 1 to 5 halogens, (xiii) $C_{1-4}$ alkyl-carbonylthio group which may be substituted with 1 to 5 halogens, (xiv) $C_{1-4}$ alkoxy-carbonylthio group which may be substituted with 1 to 5 halogens, (xv) $C_{1-4}$ alkylsulfinyl group which may be substituted with 1 to 5 halogens, (xvi) $C_{1-4}$ alkylsulfonyl group which may be substituted with 1 to 5 halogens, (xvii) sulfamoyl group, (xviii) mono- or di-$C_{1-4}$ alkylsulfamoyl group, (xix) a group represented by

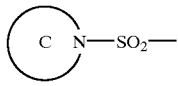

(wherein, ring C is a three- to six-membered heterocyclic group containing nitrogen), (xx) amino group which may be substituted with one or two substituents selected from $C_{1-4}$ alkyl, $C_{2-4}$ alkenyl, $C_{2-4}$ alkynyl, hydroxy, $C_{1-4}$ alkoxy, formyloxy, $C_{1-4}$ alkyl-carbonyloxy, formyl and $C_{1-4}$ alkyl-carbonyl, (xxi) three- to six-membered cyclic amino group, (xxii) formyl group, (xxiii) $C_{1-4}$ alkyl-carbonyl group which may be substituted with 1 to 5 halogens, (xxiv) $C_{1-4}$ alkoxy-carbonyl group which may be substituted with 1 to 5 halogens, (xxv) $C_{1-4}$ alkylthio-carbonyl group, (xxvi) $C_{1-4}$ alkoxy-thiocarbonyl group, (xxvii) $C_{1-4}$ alkylthio-thiocarbonyl group, (xxviii) carbamoyl group, (xxix) mono- or di-$C_{1-4}$ alkylcarbamoyl group, (xxx) a group represented by

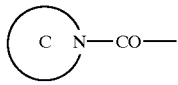

(wherein, ring C is a three- to six-membered heterocyclic group containing nitrogen), (xxxi) thiocarbamoyl group, (xxxii) mono- or di-$C_{1-4}$ alkyl-thiocarbamoyl group, (xxxiii) a group represented by

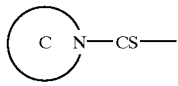

(wherein, ring C is a three- to six-membered heterocyclic group containing nitrogen), (xxxiv) halogen atom, (xxxv) carboxyl group, (xxxvi) thiocyanato group, (xxxvii) isothiocyanato group, (xxxviii) cyano group, (xxxix) isocyano group, (xl) azido group, (xli) nitroso group, (xlii) nitro group, (xliii) azocyano group (xliv) azoxycyano group, and (xlv) sulfo group, or (2) a heterocyclic group which may be substituted with 1 to 5 substituents selected from the group of substituents (T) above.

$X^3$ is (1) chemical bond, (2) methylene group which may be substituted with one or two substituents selected from $C_{1-4}$ alkyl, $C_{1-4}$ alkoxy, $C_{1-4}$ alkylthio, halogen atoms and cyano, (3) a vinylene group which may be substituted with one or two substituents selected from $C_{1-4}$ alkyl, $C_{1-4}$ alkoxy, $C_{1-4}$ alkylthio, halogen atoms and cyano, $B^3$ is a six-membered heterocyclic group which is substituted with 1 to 5 substituents selected from the group of substituents (T) mentioned above, $Z^3$ is (1) a hydrocarbon group which is selected from (i) a $C_{1-6}$ alkyl group which may be substituted with 1 to 5 substituents selected from (a) halogen, (b) amino, (c) mono- or di-$C_{1-4}$ alkylamino, (d) hydroxy, (e) $C_{1-4}$ alkoxy which may be substituted with 1 to 5 halogens, (f) mercapto, (g) $C_{1-4}$ alkylthio, (h) $C_{1-4}$ alkylsulfinyl, (i) $C_{1-4}$ alkylsulfonyl, (J) cyano, (k) $C_{1-4}$ alkoxy-carbonyl, (1) carbamoyl and (m) mono- or di-$C_{1-4}$ alkyl-carbamoyl, (ii) $C_{2-6}$ alkenyl which may be substituted with 1 to 5 substituents selected from (a) halogens, (b) amino, (c) mono- or di-$C_{1-4}$ alkylamino, (d) hydroxy, (e) $C_{1-4}$ alkoxy which may be substituted with 1 to 5 halogens, (f) mercapto, (g) $C_{1-4}$ alkylthio, (h) $C_{1-4}$ alkylsulfinyl, (i) $C_{1-4}$ alkylsulfonyl, (j) cyano, (k) $C_{1-4}$ alkoxy-carbonyl, (1) carbamoyl and (m) mono- or di-$C_{1-4}$ alkyl-carbamoyl, (iii) $C_{2-6}$ alkynyl which may be substituted with 1 to 5 substituents selected from (a) halogen, (b) amino, (c) mono- or di-$C_{1-4}$ alkylamino, (d) hydroxy, (e) $C_{1-4}$ alkoxy which may be substituted with 1 to 5 halogens, (f) mercapto, (g) $C_{1-4}$ alkylthio, (h) $C_{1-4}$ alkylsulfinyl, (i) $C_{1-4}$ alkylsulfonyl, (j) cyano, (k) $C_{1-4}$ alkoxy-carbonyl, (1) carbamoyl and (m) mono- or di-$C_{1-4}$ alkyl-carbamoyl, (iv) $C_{3-6}$ cycloalkyl groups which may be substituted with 1 to 5 substituents selected from (a) $C_{1-4}$ alkyl which may be substituted with 1 to 5 halogens, (b) halogen, (c) amino, (d) mono- or di-$C_{1-4}$ alkylamino, (e) hydroxy, (f) $C_{1-4}$ alkoxy which may be substituted with 1 to 5 halogens, (g) mercapto, (h) $C_{1-4}$ alkylthio, (i) $C_{1-4}$ alkylsulfinyl, (j) $C_{1-4}$ alkylsulfonyl, (k) cyano, (1) $C_{1-4}$ alkoxy-carbonyl, (m) carbamoyl and (n) mono- or di-$C_{1-4}$ alkyl-carbamoyl, (v) $C_{3-6}$ alkadienyl group which may be substituted with 1 to 5 substituents selected from (a) halogen, (b) amino, (c) mono- or di-$C_{1-4}$ alkylamino, (d) hydroxy, (e) $C_{1-4}$ alkoxy which may be substituted with 1 to 5 halogens, (f) mercapto, (g) $C_{1-4}$ alkylthio, (h) $C_{1-4}$ alkylsulfinyl, (i) $C_{1-4}$ alkylsulfonyl, (j) cyano, (k) $C_{1-4}$ alkoxy-carbonyl, (1) carbamoyl and (m) mono- or di-$C_{1-4}$ alkyl-carbamoyl, and (vi) $C_{6-14}$ aryl group which may be substituted with 1 to 5 substituents selected from $C_{1-4}$ alkyl which may be substituted with 1 to 5 halogens, (b) halogen, (c) amino, (d) mono- or di-$C_{1-4}$ alkylamino, (e) hydroxy, (f) $C_{1-4}$ alkoxy which may be substituted with 1 to 5 halogens, (g) mercapto, (h) $C_{1-4}$ alkylthio, (i) $C_{1-4}$ alkylsulfinyl, (j) $C_{1-4}$ alkylsulfonyl, (k) cyano, (1) $C_{1-4}$ alkoxy-carbonyl, (m) carbamoyl and (n) mono- or di-$C_{1-4}$ alkyl-carbamoyl, (2) an acyl group selected from (i) $C_{1-4}$ alkyl-carbonyl, (ii) $C_{1-4}$ alkoxy-carbonyl, (iii) $C_{1-4}$ alkylthio-carbonyl, (iv) $C_{1-4}$ alkoxy-thiocarbonyl, (v) $C_{1-4}$ alkylthio-thiocarbonyl, (vi) mono- or di-$C_{1-4}$ alkyl-carbamoyl and (vii) mono- or di-$C_{1-4}$ alkyl-thiocarbamoyl, each of these groups may be substituted with 1 to 5 halogens, (3) formyl group, (4) an amino group which may be substituted with one or two substituents selected from (a) $C_{1-4}$ alkyl, (b) $C_{1-4}$ alkyl-carbonyl which may be substituted with 1 to 5 halogens, (c) $C_{1-4}$ alkoxy-carbonyl, (d) mono- or di-$C_{1-4}$ alkyl-carbamoyl, (e) mono- or di-$C_{1-4}$ alkyl-thiocarbamoyl, (5) a group represented by —N=$CR^1R^2$ (wherein, $R^1$ and $R^2$ are the same or different, are a hydrogen atom or a $C_{1-4}$ alkyl group), (6) three-to six-membered cyclic amino group, (7) a group represented by —$OR^3$ (wherein, $R^3$ is a hydrogen atom, a $C_{1-4}$ alkyl group which may be substituted with 1 to 5 halogens, a $C_{1-4}$ alkyl-carbonyl group which may be substituted with 1 to 5 halogens, a $C_{1-4}$ alkoxy-carbonyl group which may be substituted with 1 to 5 halogens, formyl group or a $C_{1-4}$ alkylsulfonyl group which may be substituted with 1 to 5 halogens), or (8) a group represented by —$S(O)_nR^4$ (wherein n is an integer from 0 to 2, $R^4$ is (a) hydrogen atom, (b) $C_{1-4}$ alkyl group which may be substituted with 1 to 5 halogens, or (c) $C_{6-14}$ aryl group which may be substituted with 1 to 5 $C_{1-4}$ alkyl groups).

[12] A microbicidal composition for agricultural or horticultural use described in [10] above, wherein $A^3$ is phenyl group which may be substituted with 1 to 5 $C_{1-4}$ alkyl groups, or an imidazolyl group which may be substituted with one or two $C_{1-4}$ alkyl groups, $X^3$ is a chemical bond, $B^3$ is a pyridyl group, a pyridazinyl group or a pyrimidinyl group which is substituted with 1 to 5 substituents selected from $C_{1-4}$ alkyl which may be substituted with 1 to 5 halogens, $C_{1-4}$ alkoxy, halogen, nitro and cyano, $Z^3$ is a $C_{1-6}$ alkyl group, a $C_{3-6}$ cycloalkyl group or a $C_{1-4}$ alkoxy group.

[13] A microbicidal composition for agricultural or horticultural use comprising a compound of Formula (IV)

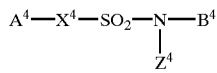

or a salt thereof, [wherein, $A^4$ is (1) an aryl group which may be substituted, or (2) a heterocyclic group which may be substituted, $X^4$ is (1) a chemical bond, (2) a methylene group which may be substituted, or (3) a vinylene group which may be substituted, $B^4$ is a pyridazinyl group or a pyrazinyl group, $Z^4$ is (1) a hydrocarbon group which may be substituted, (2) an acyl group which may be substituted, (3) formyl group, (4) an amino group which may be substituted, (5) a group represented by $—N=CR^1R^2$ (wherein $R^1$ and $R^2$ are the same or different, and hydrogen atom or hydrocarbon group which may be substituted), (6) a cyclic amino group, (7) a group represented by $—OR^3$ (wherein, $R^3$ is a hydrogen atom, a hydrocarbon group which may be substituted, an acyl group which may be substituted, formyl group or a sulfonyl group which may be substituted), or (8) a group represented by $—S(O)_nR^4$ (wherein, n is an integer from 0 to 2, $R^4$ is a hydrogen atom or a hydrocarbon group which may be substituted)].

[14] A microbicidal composition for agricultural or horticultural use comprising a compound of Formula (V)

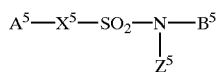

or a salt thereof,

[wherein $A^5$ is the 4-methylphenyl group, $X^5$ is a chemical bond, $B^5$ is a pyridyl or pyrimidinyl group, and $Z^5$ is a $C_{1-4}$ alkyl group].

[15] A compound of Formula (VI):

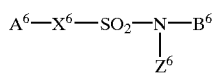

or a salt thereof,

[wherein $A^6$ is a phenyl group which may be substituted with a substituent or substituents selected from $C_{1-4}$ alkyl, halogens and cyano, $X^6$ is a chemical bond, $B^6$ is a 2-nitrophenyl group or a 2-cyanophenyl group which is substituted with a substituent or substituents selected from halogens, nitro and cyano, $Z^6$ is ethyl, isopropyl, cyclopropyl, methoxy, ethoxy or isopropoxy group].

[16] A compound or a salt thereof described in [15] above, wherein $A^6$ is a phenyl group which may be substituted with a substituent or substituents selected from $C_{1-4}$ alkyl, halogens and cyano, $X^6$ is a chemical bond, $B^6$ is a 2-nitrophenyl group which is substituted with a substituent or substituents selected from halogens, nitro and cyano, $Z^6$ is ethyl, isopropyl, or cyclopropyl group].

[17] A compound or a salt thereof described in [15] above, the compound is 4'-chloro-N-ethyl-2'-nitro-p-toluenesulfonanilide, 2',4'-dinitro-N-ethyl-p-toluenesulfonanilide, 2',4'-dicyano-N-ethyl-p-toluenesulfonanilide, 4'-chloro-N-isopropyl-2'-nitro-p-toluenesulfonanilide, 4'-fluoro-N-isopropyl-2'-nitro-p-toluenesulfonanilide, 4'-cyano-N-isopropyl-2'-nitro-p-toluenesulfonanilide, 4'-chloro-N-isopropyl-2'-cyano-p-toluenesulfonanilide, 2',4'-dinitro-N-isopropyl-p-toluenesulfonanilide, 2'-cyano-N-isopropyl-4'-nitro-p-toluenesulfonanilide, 2'-cyano-N-methoxy-4'-nitro-p-toluenesulfonanilide or 2',4'- dinitro-N-methoxy-p-toluenesulfonanilide or a salt thereof.

[18] A method for manufacturing a compound represented by a Formula:

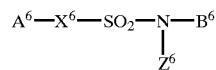

or a salt thereof (wherein each symbol has the same meaning as defined in [15] above characterized by:
(1) reacting a compound represented by a Formula:

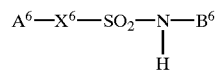

or a salt thereof
(wherein each symbol has the same meaning as defined in [15] above with an electrophile represented by Formula $Z^6—L''$ (wherein $L''$ is a leaving group, and $Z^6$ has the same meaning as defined in [15] above,
(2) reacting a compound represented by a Formula:

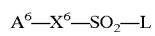

or a salt thereof,
(wherein L is a leaving group, and each of other symbols has the same meanings as those defined in [15] above, respectively) with an amine or a salt thereof represented by Formula $Z^6HN—B^6$ (wherein each symbol has the same meaning as defined in [15] above, or, by
(3) reacting a compound represented by a Formula:

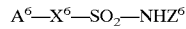

or a salt thereof
(wherein, each symbol has the same meaning as described in [15] above to react with a compound or a salt thereof represented by Formula $L'—B^6$ (wherein $L'$ is a leaving group, and the other symbol has the same meaning as defined in [15] above, respectively),or
(4) nitrating a compound represented by a Formula:

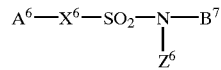

or a salt thereof
(wherein, $B^7$ is a phenyl group which is substituted with a substituent or substituents selected from halogen, nitro and cyano, provided that both 2- and 6-positions are not substituted at the same time).

Best Modes for Carrying Out the Invention

The compound (I°), belonging to sulfonamide derivatives, may have optical isomers, diastereomers and/or any geometrical isomers thereof, and the present invention contains all the isomers and mixtures of them.

As the aryl group in the "aryl group which may be substituted" regarding $A^0$, there can be mentioned $C_{6-14}$ aryl groups such as phenyl, naphthyl (for example, 1-naphthyl, 2-naphthyl) and so on.

As the substituents on the said aryl groups, there can be mentioned (i) $C_{1-4}$ alkyl groups (for example, methyl, ethyl, n-propyl, isopropyl, n-butyl, sec-butyl, isobutyl, tert-butyl) optionally substituted with 1 to 5 substituents selected from halogens, hydroxy, imino, hydroxyimino, $C_{1-4}$ alkoxyimino (for example, methoxyimino, ethoxyimino), hydrazono, mono- or di-$C_{1-4}$ alkylhydrazono (for example, methylhydrazono, ethylhydrazono, dimethylhydrazono) and $C_{1-4}$ alkylthio (for example, methylthio, ethylthio, n-propylthio, isopropylthio, n-butylthio, sec-butylthio, isobutylthio, tert-butylthio), (ii) $C_{3-6}$ cycloalkyl groups (for example, cyclopropyl, cyclobutyl, cyclopentyl, cyclohexyl) which may be substituted with 1 to 5 halogens, (iii) $C_{2-4}$ alkenyl groups (for example, vinyl, allyl, propenyl, isopropenyl, 2-methyl-1-propenyl, 1-butenyl, 2-butenyl, 3-butenyl) which may be substituted with 1 to 5 substituents selected from halogens, cyano and nitro, (iv) $C_{3-6}$ cycloalkenyl groups (for example, cyclopropenyl, cyclobutenyl, cyclopentenyl, cyclohexenyl) which may be substituted with 1 to 5 halogens, (v) $C_{2-4}$ alkynyl groups (for example, ethynyl, 1-propynyl, 2-propynyl, 1-butynyl, 2-butynyl, 3-butynyl) which may be substituted with 1 to 5 halogens, (vi) a hydroxy group, (vii) $C_{1-4}$ alkoxy groups (for example, methoxy, ethoxy, n-propoxy, isopropoxy, n-butoxy, isobutoxy, sec-butoxy, tert-butoxy) which may be substituted with 1 to 5 substituents selected from halogens and $C_{1-4}$ alkoxy (for example, methoxy and ethoxy), (viii) formyloxy group, (ix) $C_{1-4}$ alkyl-carbonyloxy group (for example, acetyloxy, propionyloxy, butyryloxy, isobutyryloxy) which may be substituted with 1 to 5 halogens, (x) $C_{1-4}$ alkoxy-carbonyloxy group (for example, methoxycarbonyloxy, ethoxycarbonyloxy, n-propoxycarbonyloxy, isopropoxycarbonyloxy) which may be substituted with 1 to 5 halogens, (xi) a mercapto group, (xii) $C_{1-4}$ alkylthio groups (for example methylthio, ethylthio, n-propylthio, isopropylthio, n-butylthio, isobutylthio, sec-butylthio, tert-butylthio) which may be substituted with 1 to 5 halogens, (xiii) $C_{1-4}$ alkyl-carbonylthio groups (for example, acetylthio, propionylthio, butyrylthio, isobutyrylthio) which may be substituted with 1 to 5 halogens, (xiv) $C_{1-4}$ alkoxy-carbonylthio groups (for example, methoxycarbonylthio, ethoxycarbonylthio, n-propoxycarbonylthio, isopropoxycarbonylthio) which may be substituted with 1 to 5 halogens, (xv) $C_{1-4}$ alkylsulfinyl groups (for example, methylsulfinyl, ethylsulfinyl, n-propylsulfinyl, isopropylsulfinyl) which may be substituted with 1 to 5 halogens, (xvi) $C_{1-4}$ alkylsulfonyl groups (for example, methylsulfonyl, ethylsulfonyl, n-propylsulfonyl, isopropylsulfonyl) which may be substituted with 1 to 5 halogens, (xvii) a sulfamoyl group, (xviii) mono- or di-$C_{1-4}$ alkylsulfamoyl groups (for example, methylsulfamoyl, ethylsulfamoyl, n-propylsulfamoyl, dimethylsulfamoyl, ethylmethylsulfamoyl, diethylsulfamoyl), (xix) groups represented by

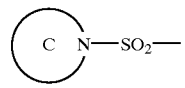

[wherein ring C is a three- to six-membered heterocyclic group containing nitrogen (for example, aziridino, azetidino, pyrrolidino, piperidino, morpholino, thiomorpholino)], (xx) an amino group which may be substituted with 1 or 2 substituents selected from $C_{1-4}$ alkyl(for example, methyl, ethyl, n-propyl, isopropyl, n-butyl, isobutyl, sec-butyl, tert-butyl), $C_{2-4}$ alkenyl (for example, vinyl, allyl, propenyl, isopropenyl, 2-methyl-1-propenyl, 1-butenyl, 2-butenyl, 3-butenyl), $C_{2-4}$ alkynyl (for example, ethynyl, 1-propynyl, 2-propynyl, 1-butynyl, 2-butynyl, 3-butynyl), hydroxy, $C_{1-4}$ alkoxy (for example, methoxy, ethoxy, n-propoxy, isopropoxy, n-butoxy, isobutoxy, sec-butoxy, tert-butoxy), formyloxy and $C_{1-4}$ alkyl-carbonyloxy (for example, acetyloxy, propionyloxy, butyryloxy, isobutyryloxy), formyl and $C_{1-4}$ alkyl-carbonyl(for example, acetyl, propionyl, butyryl, isobutyryl), (xxi) three- to six-membered cyclic amino groups (for example, azilidino, azetidino, pyrrolidino, piperidino, morpholino, thiomorpholino), (xxii) formyl group, (xxiii) $C_{1-4}$ alkyl-carbonyl groups (for example, acetyl, propionyl, butyryl, isobutyryl) which may be substituted with 1 to 5 halogens, (xxiv) $C_{1-4}$ alkoxy-carbonyl groups (for example, methoxycarbonyl, ethoxycarbonyl, n-propoxycarbonyl, isopropoxycarbonyl) which may be substituted with 1 to 5 halogens, (xxv) $C_{1-4}$ alkylthiocarbonyl groups (for example, (methylthio)carbonyl, (ethylthio)carbonyl, (n-propylthio)carbonyl, (isopropylthio)carbonyl, (n-butylthio)carbonyl, (isobutylthio)carbonyl, (sec-butylthio)carbonyl, (tert-butylthio)carbonyl, (xxvi) $C_{1-4}$ alkoxy-thiocarbonyl groups (for example, (methoxy)thiocarbonyl, (ethoxy)thiocarbonyl, (n-propoxy)thiocarbonyl, (isopropoxy)thiocarbonyl), (xxvii) $C_{1-4}$ alkylthio-thiocarbonyl groups (for example, (methylthio)thiocarbonyl, (ethylthio)thiocarbonyl, (n-propylthio)thiocarbonyl, (isopropylthio)thiocarbonyl, (n-butylthio)thiocarbonyl, (isobutylthio)thiocarbonyl, (sec-butylthio)thiocarbonyl, (tert-butylthio)thiocarbonyl), (xxviii) a carbamoyl group, (xxix) mono- or di-$C_{1-4}$ alkylcarbamoyl groups (for example, methylcarbamoyl, ethylcarbamoyl, n-propylcarbamoyl, dimethylcarbamoyl, ethylmethylcarbamoyl, diethylcarbamoyl), (xxx) groups represented by

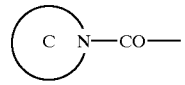

(wherein ring C is a three- to six-membered heterocyclic group containing nitrogen (for example, aziridino, azetidino, pyrrolidino, piperidino, morpholino, thiomorpholino)), (xxxi) a thiocarbamoyl group, (xxxii) mono- or di-$C_{1-4}$ alkyl-thiocarbamoyl groups (for example, (methyl) thiocarbamoyl, (ethyl) thiocarbamoyl, (n-propyl) thiocarbamoyl, (dimethyl)thiocarbamoyl, (ethylmethyl) thiocarbamoyl, (diethyl)thiocarbamoyl), (xxxiii)groups represented by

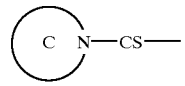

(wherein ring C is a three- to six-membered heterocyclic group containing nitrogen (for example, aziridino, azetidino, pyrrolidino, piperidino, morpholino, thiomorpholino)), (xxxiv) halogen atoms (for example, fluorine, chlorine, bromine, iodine), (xxxv) carboxyl group, (xxxvi) thiocyanato group, (xxxvii) isothiocyanato group, (xxxviii) cyano group, (xxxix) isocyano group, (xl) azido group, (xli) nitroso group, (xlii) nitro group, (xliii) azocyano group, (xliv) azoxycyano (—NO═N—CN)group, and (xlv) sulfo group.

Hereinafter, the group of the above-mentioned substituents from (i) to (xlv) may be in some cases described as the substituent group (T), and the group of the above-mentioned substituents consists of those from (i) to (xliii) and (xlv)may be in some cases described as the substituent group (T'). (In the description of the substituents above, "halogens" mean fluorine, chlorine, bromine, and iodine.)

The number of substituents in the aryl group mentioned above is from one to five (more preferably from one to three). As the heterocyclic group of the "heterocyclic group which may be substituted" regarding $A^0$, there can be mentioned, for example, a five- to six-membered heterocyclic group which contains 1 to 4 hetero atoms selected from nitrogen, oxygen and sulfur atoms, or a condensed heterocyclic group composed either of five- to six-membered heterocyclic groups which contain 1 to 4 hetero atoms selected from nitrogen, oxygen and sulfur atoms and benzene rings, or of a five- to six-membered heterocyclic groups which contain 1 to 4 heteroatoms selected from nitrogen, oxygen and sulfur atoms and, the same or different, another five- to six-membered heterocyclic groups which contain 1 to 4 heteroatoms selected from nitrogen, oxygen and sulfur atoms.

As specific examples of such heterocycles, there can be mentioned pyrrolyl (for example, 1-, 2- or 3-pyrrolyl), pyrazolyl (for example, 1-, 3-, 4- or 5-pyrazolyl), imidazolyl (for example, 1-, 2-, 4-, or 5-imidazolyl), triazolyl(for example, 1,2,3-triazol-1-, 4- or 5-yl, 1,2,4-triazol-1-, 3-, 4-, or 5-yl),tetrazolyl (for example, tetrazol-1-, 2- or 5-yl), furyl (for example, 2- or 3-furyl),thienyl (for example, 2- or 3-thienyl), oxazolyl (for example, 2-, 4- or, 5-oxazolyl), isooxazolyl (for example, 3-, 4- or 5-isooxazolyl), oxadiazolyl (for example, 1,2,3-oxadiazol-4-or 5-yl, 1,2,4-oxadiazol-3- or 5-yl, 1,2,5-oxadiazol-3-yl, 1,3,4-oxadiazol-2-yl), thiazolyl (for example, 2-, 4- or 5-thiazolyl), isothiazolyl(for example, 3-, 4- or 5-isothiazolyl), thiadiazolyl (for example, 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (for example, 1-, 2- or 3-pyrrolidinyl), pyridyl (for example, 2-, 3- or 4-pyridyl), pyridazinyl (for example, 3- or 4-pyridazinyl), pyrimidinyl (for example, 2-, 4- or 5-pyrimidinyl), pyrazinyl, piperidinyl (for example, 1-, 2-, 3- or 4-piperidinyl), piperazinyl (for example, 1- or 2-piperazinyl), indolyl (for example, 3H-indol-2-, 3-, 4-, 5-, 6- or 7-yl), pyranyl (for example, 2-, 3- or 4-pyranyl), thiopyranyl (for example, 2-, 3- or 4- thiopyranyl), morpholinyl(for example, 2-, 3- or 4-morpholinyl), thiomorpholinyl, quinolyl (for example, 2-, 3-, 4-, 5-, 6-, 7- or 8-quinolyl), isoquinolyl, pyrido[2,3-d]pyrimidinyl (for example, pyrido[2,3-d]pyrimidin-2-yl), naphthyridinyl such as 1,5-, 1,6-, 1,7-, 1,8-, 2,6- or 2,7-naphthyridinyl (for example, 1,5-naphthyridin-2- or 3-yl), thieno[2,3-d]pyridyl (for example, thieno[2,3-d]pyridin-3-yl), pyrazinoquinolyl (for example, pyrazino[2,3-d]quinolin-2-yl), chromenyl (for example, 2H-chromen-2-. 3-, 4-, 5- or 6-yl), chromanyl (for example, 1-, 2-, 3-, 4-, 5-, 6-, 7- or 8-chromanyl), isochromanyl (for example, 1-, 3-, 4-, 5-, 6-, 7- or 8-isochromanyl), benzofuryl (for example, 2-, 3-, 4-, 5-, 6- or 7-benzofuryl), benzothienyl (for example, 2-, 3-, 4-, 5-, 6-, or 7-benzothienyl), benzoimidazolyl (for example, 2-, 4-, 5-, 6- or 7-benzimidazolyl), indazolyl (for example, 1H-indazol-1-, 3-, 4-, 5-, 6- or 7-yl), benzooxazolyl (for example, 2-, 4-, 5-, 6- or 7-benzooxazolyl), benzoisooxazolyl (for example, 3-, 4-, 5-, 6-or 7-benzoisooxazolyl), benzothiazolyl (for example, 2-, 4-, 5-, 6- or 7-benzothiazolyl), benzothiadiazolyl (for example, benzo-1,2,3-thiadiazol-4-, 5-, 6- or 7-yl, benzo-1,2,4-thiadiazol-3-, 4-, 5-, 6- or 7-yl, benzo-1,2,5-thiadiazol-3-, 4-, 5-, 6- or 7-yl, benzo-1,3,4-thiadiazol-2-, 4-, 5-, 6- or 7-yl), benzoisothiazolyl (for example, 3-, 4-, 5-, 6- or 7-benzzoisothiazolyl), benzotriazolyl (for example, 4-, 5-, 6-, 7- or 8-benzo-1,2,3-triazolyl, 3-, 5-, 6-, 7- or 8-benzo-1,2,4-triazolyl), cinnolyl(for example, 3-, 4-, 5-, 6-, 7-or 8-cinnolyl), phthalazinyl (for example, 1-, 5- or 6-phthalazinyl), quinazolinyl (for example, 2-, 4-, 5-, 6-, 7- or 8-quinazolinyl), quinoxalinyl (for example, 2-, 5- or 6-quinoxalinyl), imidazopyridyl (for example, imidazo[1,2-a]pyridyl such as imidazo[1,2-a]pyridin-2-yl and imidazo[1,2-a]pyridin-3-yl), imidazothiazolyl (for example, imidazo[2,1-b]thiazolyl such as imidazo[2,1-b]thiazol-5-yl), dioxaindanyl (for example, 1,3-dioxaindanyl such as 1,3-dioxaindan-2-, 4-, 5-, 6- or 7-yl).

Among these heterocyclic groups, isoxazolyl, triazolyl, pyridyl, quinolyl, thienyl, isoxazolyl, pyrazolyl, imidazolyl, benzothiadiazolyl, imidazopyridyl, imidazothiazolyl are especially preferable.

As the substituents on the said heterocyclic groups, those which are in the substituent group (T) are preferable. The number of the said substituents is 1 to 5 (preferably 1 to 3).

As preferable substituents on the aryl group in the "aryl group which may be substituted" or on the heterocyclic group in the "heterocyclic group which may be substituted", both represented as $A^0$, there can be mentioned:

$C_{1-4}$ alkyl which may be substituted with 1 to 5 halogens, amino which may be substituted with one or two $C_{1-4}$ alkyl-carbonyl, (3) nitro,
(4) $C_{1-4}$ alkoxy which may be substituted with 1 to 5 halogens,
(5) halogens,
(6) $C_{1-4}$ alkoxy-carbonyl,
(7) cyano,
(8) mono- or di-$C_{1-4}$ alkylcarbamoyl,
(9) $C_{1-4}$ alkylsulfonyl,
(10) carbamoyl, and carboxyl.

As $A^0$ phenyl groups which may be substituted with 1 to 3 substituents selected from $C_{1-4}$ alkyl, halogens and cyano are preferable, and phenyl groups which may be substituted with 1 to 3 substituents selected from $C_{1-4}$ alkyl and halogens are more preferable. The substituent can, most preferably, be at the 4-position of the phenyl group.

As the preferable substituents on the methylene group regarding $X^0$, there may be mentioned:

$C_{1-4}$ alkyl (for example, methyl, ethyl, n-propyl, isopropyl, n-butyl, isobutyl, sec-butyl, tert-butyl), $C_{1-4}$ alkoxy (for example,methoxy, ethoxy, n-propoxy, isopropoxy, n-butoxy, isobutoxy, sec-butoxy, tert-butoxy), $C_{1-4}$ alkylthio (for example, methylthio, ethylthio, n-propylthio, isopropylthio, n-butylthio, isobutylthio, sec-butylthio, tert-butylthio),
(4) halogen atoms (for example, fluorine, chlorine, bromine, iodine) and,
(5) cyano.

The number of the substituents is preferably one or two. As the substituents on the vinylene group regarding $X^0$, there can be mentioned such substituents similar to those mentioned as the substituents on the methylene group regarding $X^0$. The number of the said substituent is preferably one or two.

As $X^0$, preferable are a chemical bond (a single bond or a bond), a methylene group which may be substituted with one or two $C_{1-4}$ alkyl or a vinylene group which may be substituted with one or two $C_{1-4}$ alkyl, a chemical bond being especially preferable.

As the "heterocyclic group which may be substituted" in $B^0$ there can be mentioned those heterocyclic groups similar to those described as the "heterocyclic group which may be substituted" in $A^0$.

The preferable heterocyclic groups is thienyl, pyrazolyl, imidazolyl, thiazolyl, isothiazolyl, thiadiazolyl, pyridyl, pyridazinyl, pyrimidinyl, imidazopyridyl, dioxaindanyl. Prefered substituents on the said heterocyclic group are nitro, halogens, cyano, $C_{1-4}$ alkyl which may be substituted with 1 to 5 halogens, $C_{1-4}$ alkoxy, and $C_{1-4}$ alkylthio.

As the "aryl group which may be substituted" in $B^0$, there can be mentioned those aryl groups similar to those described as the "aryl group which may be substituted" in $A^0$. As aryl group, phenyl group is especially preferable. As preferable substituents on the said aryl group, there can be mentioned (1) halogens, (2) $C_{1-4}$ alkyl which may be substituted with 1 to 5 substituents selected from halogens, hydroxy, imino, hydroxyimino, $C_{1-4}$ alkoxyimino, hydrazono, mono- or di-$C_{1-4}$ alkylhydrazono and $C_{1-4}$ alkylthio, (3) $C_{2-4}$ alkynyl, (4) alkoxy which may be substituted with 1 to 5 substituents selected from halogens and $C_{1-4}$ alkoxy, (5) $C_{1-4}$ alkylthio, (6) $C_{1-4}$ alkylsulfinyl, (7) $C_{1-4}$ alkylsulfonyl, (8) $C_{1-4}$ alkyl-carbonyloxy, (9) $C_{1-4}$ alkoxy-carbonyl, (10) carboxyl, (11) cyano, (12) nitro, (13) nitroso, (14) formyl, (15) carbamoyl, (16) mono- or di-$C_{1-4}$ alkylcarbamoyl, (17) thiocarbamoyl, (18) hydroxy, (19) mono- or di-$C_{1-4}$ alkylsulfamoyl, (20) thiocyanato, (21) azoxycyano, (22) amino.

As the hydrocarbon group in the "hydrocarbon group which may be substituted" in $Z^0$, there may be mentioned:
(i) a $C_{1-6}$ alkyl group (for example, methyl, ethyl, n-propyl, isopropyl, n-butyl, isobutyl, sec-butyl, tert-butyl, n-pentyl, sec-pentyl, isopentyl, neopentyl, n-hexyl, isohexyl), (ii) a $C_{2-6}$ alkenyl group (for example, a straight-chain $C_{2-6}$ alkenyl group such as vinyl, allyl, propenyl, isopropenyl, 1-butenyl, 2-butenyl or 3-butenyl; a branched $C_{2-6}$ alkenyl group such as 2-methyl-propenyl, 2-methyl-2-propenyl, 1-methyl-2-propenyl, 2-methyl-1-butenyl, 3-methyl-1-butenyl, 1,2-dimethyl-2-propenyl, 1,1-dimethyl-2-propenyl, 1-methyl-2-butenyl, 3-methyl-2-butenyl, 2-methyl-2-butenyl, 1-methyl-3-butenyl, 1-ethyl-2-propenyl, 2-methyl-3-butenyl, 3-methyl-3-butenyl, 2-methyl-1-pentenyl 3-methyl-1-pentenyl, 4-methyl-1-pentenyl, 1-methyl-2-pentenyl, 2-methyl-2-pentenyl, 3-methyl-2-pentenyl, 4-methyl-3-pentenyl, 1,1-dimethyl-2-butenyl, 1,2-dimethyl-2-butenyl, 1,3-dimethyl-2-butenyl, 2,3-dimethyl-2-butenyl, 1-methyl-3-pentenyl, 2-methyl-3-pentenyl, 3-methyl-3-pentenyl, 4-methyl-3-pentenyl, 1,1-dimethyl-3-butenyl, 1,2-dimethyl-3-butenyl, 1,3-dimethyl-3-butenyl, 2,2-dimethyl-3-butenyl, 2,3-dimethyl-3-butenyl, 1-methyl-4-pentenyl, 2-ethyl-1-butenyl, 2-ethyl-2-butenyl, 1-ethyl-1-butenyl, and 1-ethyl-2-butenyl), (iii) a $C_{2-6}$ alkynyl group (for example, ethynyl, 1-propynyl, 2-propynyl, 1-butynyl, 2-butynyl, 3-butynyl), (iv) a $C_{3-6}$ cycloalkyl group (for example, cyclopropyl, cyclobutyl, cyclopentyl, cyclohexyl), (v) a $C_{3-6}$ alkadienyl group (for example, 1,2-propadienyl, 1,2-butadienyl, 1,3-butadienyl, 3-methyl-1,2-butadienyl, 1,2-pentadienyl, 2,4-pentadienyl, 1-methyl-1,2-pentadienyl, 1-methyl-1,3-pentadienyl), and (vi) $C_{6-14}$ aryl group (for example, phenyl, and naphthyl such as 1-naphthyl, 2-naphthyl).

In cases where the said hydrocarbon group is alkyl group, alkynyl group or alkadienyl group, as preferred substituents of the said hydrocarbon group, there can be mentioned (a) halogen atoms (for example, fluorine, chlorine, bromine, iodine), (b) an amino group, (c) a mono- or di-$C_{1-4}$ alkylamino group (for example, methylamino, ethylamino, dimethylamino, methylethylamino), (d) a hydroxyl group, (e) a $C_{1-4}$ alkoxy group (for example, methoxy, ethoxy, n-propoxy, isopropoxy, n-butoxy, isobutoxy, sec-butoxy, tert-butoxy) which may be substituted with 1 to 5 (more preferably 1 to 3) halogens (for example, fluorine, chlorine, bromine, iodine), (f) mercapto, (g) $C_{1-4}$ alkylthio (for example, methylthio, ethylthio, n-propylthio, isopropylthio, n-butylthio, isobutylthio, sec-butylthio, tert-butylthio), (h) $C_{1-4}$ alkylsulfinyl (for example, methylsulfinyl, ethylsulfinyl, n-propylsulfinyl, isopropylsulfinyl), (i) $C_{1-4}$ alkylsulfonyl (for example, methylsulfonyl, ethylsulfonyl, n-propylsulfonyl, isopropylsulfonyl), (j) cyano, (k) $C_{1-4}$ alkoxy-carbonyl (for example, methoxycarbonyl, ethoxycarbonyl, n-propoxycarbonyl, isopropoxycarbonyl), (l) carbamoyl and (m) mono- or di-$C_{1-4}$ alkyl-carbamoyl (for example, methylcarbamoyl, ethylcarbamoyl, n-propylcarbamoyl, dimethylcarbamoyl, ethylmethylcarbamoyl, diethylcarbamoyl).

The number of the said substituents is 1 to 5 (more preferably 1 to 3).

In cases where the said hydrocarbon group is a cycloalkyl group or an aryl group, as the substituents on the said hydrocarbon group, there can be mentioned a $C_{1-4}$ alkyl group which may be substituted with 1 to 5 halogens (for example, fluorine, chlorine, bromine, iodine) atoms (for example, methyl, ethyl, propyl, isopropyl, tert-butyl, chloromethyl, trifluoromethyl), (b) halogen atoms (for example, fluorine, chlorine, bromine, iodine) (c) an amino group, (d) a mono- or di-$C_{1-4}$ alkylamino group (for example, methylamino, ethylamino, dimethylamino, methylethylamino), (e) a hydroxyl group, (f) a $C_{1-4}$ alkoxy (for example, fluorine, chlorine, bromine, iodine) (for example, methoxy, ethoxy, n-propoxy, isopropoxy, n-butoxy, isobutoxy, sec-butoxy, tert-butoxy) which may be substituted with 1 to 5 (more preferably 1 to 3) halogens, (g) mercapto, (h) $C_1 4$ alkylthio (for example, methylthio, ethylthio, n-propylthio, isopropylthio, n-butylthio, isobutylthio, sec-butylthio, tert-butylthio), (i) $C_{1-4}$ alkylsulfinyl (for example, methylsulfinyl, ethylsulfinyl, n-propylsulfinyl, isopropylsulfinyl), (j) $C_{1-4}$ alkylsulfonyl (for example, methylsulfonyl, ethylsulfonyl, n-propylsulfonyl, isopropylsulfonyl), (k) cyano, (l) $C_{1-4}$ alkoxy-carbonyl (for example, methoxycarbonyl, ethoxycarbonyl, n-propoxycarbonyl, isopropoxycarbonyl), (m) carbamoyl and (n) mono- or di-$C_{1-4}$ alkyl-carbamoyl (for example, methylcarbamoyl, ethylcarbamoyl, n-propylcarbamoyl, dimethylcarbamoyl, ethylmethylcarbamoyl, diethylcarbamoyl).

The number of the said substituents is 1 to 5 (more preferably 1 to 3).

As the "acyl group" in "an acyl group which may be substituted" in $Z^0$, there may be mentioned (i) a $C_{1-4}$ alkyl-carbonyl group (for example, acetyl, propionyl, butyryl, isobutyryl), (ii) a $C_{1-4}$ alkoxy-carbonyl group (for example, methoxycarbonyl, ethoxycarbonyl, n-propoxycarbonyl, isopropoxycarbonyl), (iii) a $C_{1-4}$ alkylthio-carbonyl group (for example, (methylthio)carbonyl, (ethylthio)carbonyl, (n-propylthio)carbonyl, (isopropylthio)carbonyl, (n-butylthio)carbonyl, (isobutylthio)carbonyl, (sec-butylthio)carbonyl, (tert-butylthio)carbonyl), (iv) a $C_{1-4}$ alkoxy-thiocarbonyl group (for example, (methoxy)thiocarbonyl, (ethoxy)thiocarbonyl, (n-propoxy)thiocarbonyl, (isopropoxy)thiocarbonyl), (v) a $C_{1-4}$ alkylthio-thiocarbonyl (for example, (methylthio) thiocarbonyl, (ethylthio)thiocarbonyl, (n-propylthio) thiocarbonyl, (isopropylthio)thiocarbonyl, (n-butylthio) thiocarbonyl, (isobutylthio)thiocarbonyl, (sec-butylthio) thiocarbonyl, (tert-butylthio)thiocarbonyl), (vi) a mono- or di-$C_{1-4}$ alkyl-carbamoyl group (for example, methylcarbamoyl, ethylcarbamoyl, n-propylcarbamoyl, dimethylcarbamoyl, ethylmethylcarbamoyl, diethylcarbamoyl), and (vii) a mono- or di-$C_{1-4}$ alkyl-thiocarbamoyl group (for example, (methyl)thiocarbamoyl, (ethyl)thiocarbamoyl, (n-propyl)thiocarbamoyl, (dimethyl) thiocarbamoyl, (ethylmethyl)thiocarbamoyl, (diethyl) thiocarbamoyl). As the substituents on the said acyl group, halogens (for example, fluorine, chlorine, bromine, iodine) are preferable. The number of the said substituents is 1 to 5 (more preferably 1 to 3).

As the substituents on the "amino group which may be substituted" in $Z^0$, there may be mentioned $C_{1-4}$ alkyl (for example, methyl, ethyl, n-propyl, isopropyl, n-butyl, isobutyl, sec-butyl, tert-butyl), $C_{1-4}$ alkyl-carbonyl (for example, acetyl, propionyl, butyryl, isobutyryl) which may be substituted with 1 to 5 (more preferably 1 to 3) halogens (for example, fluorine, chlorine, bromine, iodine), $C_{1-4}$ alkoxy-carbonyl (for example, methoxycarbonyl, ethoxycarbonyl, n-propoxycarbonyl, isopropoxycarbonyl), mono- or di-$C_{1-4}$ alkyl-carbamoyl (for example, methylcarbamoyl, ethylcarbamoyl, n-propylcarbamoyl, dimethylcarbamoyl, ethylmethylcarbamoyl, diethylcarbamoyl), and (e) mono- or di-$C_{1-4}$ alkyl-thiocarbamoyl (for example, (methyl)thiocarbamoyl, (ethyl)thiocarbamoyl, (n-propyl)thiocarbamoyl, (dimethyl)thiocarbamoyl, (ethylmethyl)thiocarbamoyl, (diethyl)thiocarbamoyl).

The number of the said substituents is preferably 1 or 2.

As the "hydrocarbon groups which may be substituted" in $R^1$, $R^2$, $R^3$ and $R^4$, there may be mentioned those groups similar to those mentioned as the "hydrocarbon groups which may be substituted" in $Z^0$.

Among the "hydrocarbon groups which may be substituted" in $R^1$ and $R^2$, $C_{1-4}$ alkyl group (for example, methyl, ethyl, n-propyl, isopropyl, n-butyl, isobutyl, sec-butyl, tert-butyl) are more preferable. Among the "hydrocarbon groups which may be substituted" in $R^3$, $C_{1-4}$ alkyl groups (for example, methyl, ethyl, n-propyl, isopropyl, n-butyl, isobutyl, sec-butyl, tert-butyl) which may be substituted with 1 to 5 (more preferably 1 to 3) halogens (fluorine, chlorine, bromine, iodine) are preferable.

Among the "hydrocarbon groups which may be substituted" in $R^4$, (1) $C_{1-4}$ alkyl groups (for example, methyl, ethyl, n-propyl, isopropyl, n-butyl, isobutyl, sec-butyl, tert-butyl) which may be substituted with 1 to 5 (more preferably 1 to 3) halogens (fluorine, chlorine, bromine, iodine), and (2) $C_{6-14}$ aryl groups (for example, phenyl and naphthyl such as 1-naphthyl and 2-naphthyl) which may be substituted with 1 to 5 (more preferably 1 to 3) $C_{1-4}$ alkyl (for example, methyl, ethyl, n-propyl, isopropyl, n-butyl, isobutyl, sec-butyl, tert-butyl) are preferable.

As the cyclic amino groups in $Z^0$, there may be mentioned three- to six-membered cyclic amino groups (for example, aziridino, azetidino, pyrrolidino, piperidino, morpholino, thiomorpholino).

As the "acyl group which may be substituted" in $R^3$, there may be mentioned those groups similar to those mentioned above regarding the "acyl group which may be substituted" in $Z^0$. Among them, $C_{1-4}$ alkyl-carbonyl groups (for example, acetyl, propionyl, butyryl, isobutyryl) which may be substituted with 1 to 5 (more preferably 1 to 3) halogens (for example, fluorine, chlorine, bromine, iodine), and $C_{1-4}$ alkoxy-carbonyl groups (for example, methoxycarbonyl, ethoxycarbonyl, n-propoxycarbonyl, isopropoxycarbonyl) which may be substituted with 1 to 5 (more preferably 1 to 3)halogens (for example, fluorine, chlorine, bromine, iodine) are more preferable.

As the "alkylsulfonyl" in the "alkylsulfonyl groups which may be substituted" in $R^3$ there may be mentioned $C_{1-4}$ alkylsulfonyl groups such as methylsulfonyl, ethylsulfonyl, n-propylsulfonyl, isopropylsulfonyl, and so on. As the substituents on the said alkylsulfonyl groups, halogens (for example, fluorine, chlorine, bromine, iodine) are preferable. The number of the said substituents is 1 to 5 (more preferably 1 to 3).

$Z^0$ is more preferably, among those mentioned above, $C_{1-6}$ alkyl group which may be substituted with 1 to 3 substituents selected from hydroxy, halogens, cyano, $C_{1-4}$ alkylthio, $C_{1-4}$ alkoxy, $C_{1-4}$ alkoxy-carbonyl and mono- or di-$C_{1-4}$ alkylamino, (2) $C_{2-6}$ alkenyl group, (3) $C_{2-6}$ alkynyl group which may be substituted with 1 to 3 halogens, (4) $C_{3-6}$ cycloalkyl group, (5) $C_{3-6}$ alkadienyl group, (6) phenyl group, (7) $C_{1-4}$ alkyl-carbonyl group which may be substituted with 1 to 3 halogens, (8) amino group which may be substituted with one or two substituents selected from $C_{1-4}$ alkyl, $C_{1-4}$ alkyl-carbonyl and $C_{1-4}$ alkoxy-carbonyl, (9) a group represented by —N=$CR^1R^2$ (where $R^1$ and $R^2$ are the same or different, and are a hydrogen atom or a $C_{1-4}$ alkyl group),

(10) $C_{1-4}$ alkoxy group,

(11) $C_{1-4}$ alkyl-carbonyloxy group,

(12) $C_{1-4}$ alkylthio group which may be substituted with 1 to 5 halogens,

(13) $C_{1-4}$ alkylsulfinyl group which may be substituted with 1 to 5 halogens,

(14) $C_{1-4}$ alkylsulfonyl group,

(15) phenylsulfonyl group which may be substituted with 1 to 3 $C_{1-4}$ alkyl.

As the salt of compound ($I^0$), there may be mentioned any salts which are acceptable agrochemically. In the cases where the compound ($I^0$) is of basic nature, there may be mentioned salts with inorganic acids such as hydrofluoric acid, hydrochloric acid, hydrobromic acid, phosphoric acid, sulfuric acid, nitric acid, and perchloric acid, and those with organic acids such as formic acid, acetic acid, propionic acid, tartaric acid, malic acid, citric acid, oxalic acid, succinic acid, benzoic acid, picric acid, methanesulfonic acid, p-toluenesulfonic acid and so on. In the cases where the compound ($I^0$) is of acidic nature, there may be mentioned salts, alkali metals such as lithium, sodium, potassium and so on, salts with alkaline earth metals such as magnesium, calcium and so on, ammonium salts such as ammonia, methylamine, dimethylamine, trimethylamine, triethylamine, ethylenediamine, TMEDA (tetramethylethylenediamine), aniline, N,N-dimethylaniline, pyridine, lutidine,collidine, hydrazine, and so on, and salts with, for example, urea and guanidine, and so on.

Among compound (I⁰) or salts thereof, those represented by compound (I), compound (II), compound (III), compound (IV) and compound (V) or salts thereof are more preferable.

[1] Compound (I) or salts thereof are those compounds represented by the Formula (I) or salts thereof,

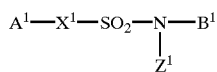
(I)

[wherein, $A^1$ is (1) an aryl group which may be substituted, or (2) a heterocyclic group which may be substituted, $X^1$ is (1) a chemical bond, (2) a methylene group which may be substituted, (3) a vinylene group which may be substituted, $B^1$ is a 5 membered heterocyclic group which may be substituted (except for an isoxazolyl group) or a condensed heterocyclic group which may be substituted, $Z^1$ is (1) a hydrocarbon group which may be substituted, (2) an acyl group which may be substituted, (3) formyl group, (4) an amino group which may be substituted, (5) a group represented by —N=CR$^1$R$^2$ (wherein R$^1$ and R$^2$ are the same or different, and are a hydrogen atom or a hydrocarbon group which may be substituted, (6) a cyclic amino group, (7) a group represented by —OR$^3$ (wherein R$^3$ is a hydrogen atom, a hydrocarbon group which may be substituted, an acyl group which may be substituted, formyl group or an alkylsulfonyl- group which may be substituted, or (8) a group represented by —S(O)$_n$R$^4$ (wherein n is an integer from 0 to 2, R$^4$ a hydrogen atom or hydrocarbon group which may be substituted).

As the substituents on $A^1$, $X^1$ and $Z^1$, there may be mentioned those on $A^0$, $X^0$ and $Z^0$, mentioned above.

As the "five-membered heterocyclic group in the "five-membered heterocyclic group which may be substituted" in $B^1$, there may be mentioned, a five-membered heterocyclic group, for example, those heterocyclic groups which contain, nitrogen and/or sulfur atoms as the ring constructing atoms besides carbon atoms,and especially those which contain 1 to 4 (more preferably 1 to 3) heteroatoms selected from nitrogen and sulfur atoms, exemplified by pyrolyl (for example, 1-, 2- or 3-pyrolyl), pyrazolyl (for example 1-. 3-, 4- or 5-pyrazolyl), imidazolyl (for example, 1-, 2-, 4- or 5-imidazolyl), triazolyl (for example, 1,2,3-triazol-1-, 4- or 5-yl, 1,2,4-triazol-1-, 3-, 4- or 5-yl), tetrazolyl (for example, tetrazol-1-, 2- or 5-yl), thienyl (for example, 2- or 3-thienyl), thiazolyl (for example, 2-, 4- or 5-thiazolyl), isothiazolyl (for example, 3-, 4- or 5-isothiazolyl), thiadiazolyl (for example, 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (for example, 1-, 2- or 3-pyrrolidinyl), and so on.

Especially preferable are thienyl, pyrazolyl, isothiazolyl, imidazolyl, thiazolyl and thiadiazolyl.

As the substituents on the said five-membered heterocyclic groups, those selected from the group of substituents (T) described above are preferable. The number of the substituents is 1 to 5 (more preferably 1 to 3). The most preferable substituents are halogens, nitro, cyano, and $C_{1-4}$ alkyl, $C_{1-4}$ alkoxy, and $C_{1-4}$ alkylthio substituted with 1 to 5 (more preferably 1 to 3) halogens.

As the "condensed heterocyclic groups" in the "condensed heterocyclic groups which may be substituted" in $B^1$, those condensed heterocylic groups which are composed of five- to six-membered heterocycles and benzene rings or five- to six-membered heterocycles and five- to six-membered heterocycles are preferable.

As specific examples of such preferable condensed heterocycles, there can be mentioned indolyl (for example, 3H-indol-2-, 3-, 4-, 5-, 6- or 7-yl), quinolyl (for example, 2-, 3-, 4-, 5-, 6-, 7- or 8-quinolyl), isoquinolyl, pyrido[2,3-d]pyrimidinyl (for example, pyrido[2,3-d]pyrimidin-2-yl), naphthyridinyl such as 1,5-, 1,6-, 1,7-, 1,8-, 2,6- or 2,7-naphthyridinyl (for example, 1,5-naphthyridin-2- or 3-yl), thieno[2,3-d]pyridyl (for example, thieno[2,3-d]pyridin-2-yl), pyrazinoquinolyl (for example, pyrazino[2,3-d]quinolin-2-yl), chromenyl (for example, 2H-chromen-2-, 3-, 4-, 5- or 6-yl), chromanyl (for example, 1-, 2-, 3-, 4-, 5-, 6-, 7- or 8-chromanyl), isochromanyl (for example, 2-, 3-, 4- ,5-, 6-, 7- or 8-isochromanyl), benzofuryl (for example, 2-, 3-, 4-, 5-, 6- or 7-benzofuryl), benzothienyl (for example, 2-, 3-, 4-, 5-, 6- or 7-benzothienyl), benzoimidazolyl (for example, 2-, 4-, 5-, 6- or 7-benzimidazolyl), indazolyl (for example, 1H-indazol-1-, 3-, 4-, 5-, 6- or 7-yl), benzooxazolyl (for example, 2-, 4-, 5-, 6- or 7-benzooxazolyl), benzoisooxazolyl (for example, 3-, 4-, 5-, 6- or 7-benzoisooxazolyl), benzothiazolyl (for example, 2-, 4-, 5-, 6- or 7-benzothiazolyl), benzothiadiazolyl (for example, benzo-1,2,3-thiadiazol-4-, 5-, 6- or 7-yl, benzo-1,2,4-thiadiazol-3-, 4-, 5-, 6- or 7-yl), benzo-1,2,5-thiadiazol-3-, 4-, 5-, 6- or 7-yl, benzo-1,3,4-thiadiazol-2-, 4-, 5-, 6- or 7-yl), benzoisothiazolyl (for example, 3-, 4-, 5-,6- or 7-benzoisothiazolyl), benzotriazolyl (for example, 4-, 5-, 6-, 7- or 8-benzo-1,2,3-triazolyl, 3-, 5-, 6-, 7- or 8-benzo-1,2,4-triazolyl), cinnolyl (for example, 3-, 4-, 5-, 6-, 7- or 8-cinnolyl), phthalazinyl (for example, 1-, 5- or 6-phthalazinyl), quinazolynyl (for example, 2-, 4-, 5-, 6-, 7- or 8-quinazolynyl), quinoxalinyl (for example, 2-, 5- or 6-quinoxalinyl), imidazopyridyl (for example, imidazo[1,2-a]pyridyl such as imidazo[1,2-a]pyridin-2-yl, imidazo[1,2-a]pyridin-3-yl, and so on) imidazothiazolyl (for example, imidazo[2,1-b]thiazolyl such as imidazo[2,1-b]thiazol-5-yl), dioxaindanyl (for example, 1,3-dioxaindanyl such as 1,3-dioxaindan-2-, 4-, 5-, 6- or 7-yl, and so on). Among these, imidazopyridyl and dioxaindanyl are more preferable.

As the substituents on the "condensed heterocyclic groups",those selected from the group of substituents (T) described above are preferable. The number of the substituents is 1 to 5 (more preferably 1 to 3). Among those substituents, nitro is especially preferable.

Among compounds included in compound (I), preferable are the compounds represented by the Formula (I) above or salts thereof. In the Formula(I), $A^1$ is a $C_{6-14}$ aryl group which may be substituted with 1 to 3 $C_{1-4}$ alkyl groups, $X^1$ is a chemical bond, $B^1$ is a thienyl group, pyrazolyl group, isothiazolyl group, imidazolyl group, thiazolyl group, thiadiazolyl group, dioxaindanyl group or imidazopyridyl group, each of which may be substituted with 1 to 5 substituents selected from $C_{1-4}$ alkyl which may be substituted with 1 to 5 halogens, $C_{1-4}$ alkyl, $C_{1-4}$ alkoxy, $C_{1-4}$ alkylthio, cyano, halogens and nitro, $Z^1$ is a $C_{1-6}$ alkyl group or $C_{1-4}$ alkoxy group.

Hereinafter, the more preferable embodiments of the compound (I) and the salts thereof are described:

As $A^1$, a phenyl which may be substituted with 1 to 3 $C_{1-4}$ alkyl is preferable, and the 4-methylphenyl group is especially preferable.

(2) As $B^1$, either (i) a thienyl group, a pyrazolyl group, an isothiazolyl group, an imidazolyl group, a thiazolyl group or a thiadiazolyl group, each of which may be substituted with 1 to 5 substitutents selected from $C_{1-4}$ alkyl substituted with 1 to 5 halogens, $C_{1-4}$ alkoxy, $C_{1-4}$ alkylthio, cyano, halogens and nitro, or (ii) a dioxaindanyl group or an imidazopyridyl group which may be substituted with 1 to 3 nitros are preferable.

The more preferable $B^1$ are:
(i) the thienyl group which may be substituted with 1 to 3 substituents selected from halogens and nitro, (ii) the pyrazolyl group which may be substituted with 1 to 3 substituents selected from $C_{1-4}$ alkyl, nitro and cyano, (iii) the imidazolyl group which may be substituted with 1 to 3 substituents selected from $C_{1-4}$ alkyl and nitro, (iv) the thiazolyl group which may be substituted with 1 to 3 substituents selected from $C_{1-4}$ alkyl which may be substituted with 1 to 5 halogens, $C_{1-4}$ alkylthio, halogens, nitro and cyano, (v) the thiadiazolyl group (more preferably a 1,3,4-thiadiazolyl group) which may be substituted with $C_{1-4}$ alkyl which may be substituted with 1 to 5 halogens, (vi) the isothiazolyl group which may be substituted with 1 to 3 substituents selected from $C_{1-4}$ alkyl which may be substituted with 1 to 5 halogens, $C_{1-4}$ alkoxy, nitro and cyano, (vii) the 1,3-dioxaindanyl group which may be substituted with 1 to 3 nitro, and (viii) the imidazo[1,2-a]pyridyl group which may be substituted with 1 to 3 nitro,
(3) As $Z^1$, a $C_{1-6}$ alkyl group or a $C_{1-4}$ alkoxy group is preferable.
(4) As $X^1$, a chemical bond (a single bond or a bond) is preferable.

The preferable embodiments regarding $A^1$, $B^1$, $Z^1$ and $X^1$ described in (1) to (4) above can be combined together arbitrarily.

[2] Compound (II) or salts thereof are the compounds represented by the Formula (II)

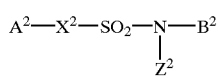
(II)

or salts thereof,
[where $A^2$ is (1) an aryl group or a heterocyclic group or (2) heterocyclic group, which may be substituted with 1 to 5 (more preferably 1 to 3) substituents selected from the substituent group (T') described above,
$X^2$ (1) a chemical bond, (2) a methylene group which may be substituted, or (3) a vinylene group which may be substituted,
$B^2$ is an aryl group which may be substituted,
$Z^2$ is (1) an alkyl group which may be substituted with substituents selected from mono- or di-$C_{1-6}$ alkylamino, hydroxy, halogens, $C_{1-6}$ alkoxy, $C_{1-6}$ alkoxy-carbonyl, $C_{1-6}$ alkylthio and cyano, (2) the vinyl group, (3) the allyl group, (4) the propadienyl group, (5) the alkynyl group which may be substituted, (6) the cycloalkyl group which may be substituted, (7) the aryl group which may be substituted, (8) the acyl group which may be substituted, (9) the formyl group, (10) the amino group which may be substituted, (11) the group represented by —N=$CR^1R^2$ (wherein $R^1$ and $R^2$ are the same or different, and are a hydrogen or a hydrocarbon group which may be substituted), (12) the cyclic amino group, (13) the group represented by —$OR^3$ (wherein $R^3$ is a hydrogen atom, a hydrocarbon group which may be substituted, an acyl group which may be substituted, formyl group, or a alkylsulfonyl group which may be substituted), or the group represented by —$S(O)_nR^4$ (where n is an integer from 0 to 2, $R^4$ a hydrogen atom or hydrocarbon group which may be substituted).

As an aryl group in $A^2$, there may be mentioned a $C_{6-14}$ aryl groups such as phenyl, and naphthyl (for example, 1-naphthyl, 2-naphthyl).

A phenyl group is especially preferable.

As a heterocyclic group which may be substituted in $A^2$, there may be mentioned the same heterocyclic groups as those which may be substituted in $A^0$.

As the substituents on $X^2$, there can be mentioned the same ones as those on $X^0$.

As the aryl group which may be substituted in $B^2$, there can be mentioned the same ones as those in $B^0$. As the aryl group, a phenyl group is especially preferable.

As the alkyl group in "an alkyl group which may be substituted with substituents selected from mono- or di-$C_{1-6}$ alkylamino, hydroxy, halogens, $C_{1-6}$ alkoxy, $C_{1-6}$ alkoxy-carbonyl, $C_{1-6}$ alkylthio and cyano" in $Z^2$, there may be mentioned $C_{1-6}$ alkyl groups such as methyl, ethyl, n-propyl, isopropyl, n-butyl, isobutyl, sec-butyl, tert-butyl, n-pentyl, sec-pentyl, isopentyl, neopentyl, n-hexyl, isohexyl and soon. The number of substituents on the said alkyl groups is 1 to 5, or more preferably 1 to 3. As the mono- or di-$C^{1-6}$ alkylamino groups as the said substituent, there may be mentioned methylamino, ethylamino, n-propylamino, dimethylamino, ethylmethylamino, diethylamino, and mono- or di-$C_{1-4}$ alkylamino groups are especially preferable. As halogens, there may be mentioned fluorine, chlorine, bromine, and iodine. As $C_{1-6}$ alkoxy, there may be mentioned methoxy, ethoxy, n-propoxy, isopropoxy, n-butoxy, isobutoxy, sec-butoxy, tert-butoxy, and so on, the $C_{1-4}$ alkoxy groups being especially preferable. As $C_{1-6}$ alkoxy-carbonyl, there may be mentioned methoxycarbonyl, ethoxycarbonyl, n-propoxycarbonyl, isopropoxycarbonyl, and so on, the $C_{1-4}$ alkoxy-carbonyl groups being especially preferable. As $C_{1-6}$ alkylthio, there may be mentioned methylthio, ethylthio, n-propylthio, isopropylthio, n-butylthio, isobutylthio, sec-butylthio, tert-butylthio, and so on, the $C_{1-4}$ alkylthio groups being especially preferable.

As alkynyl in "alkynyl which may be substituted" in $Z^2$, there may be mentioned $C_{2-6}$ alkynyl group such as ethynyl, 1-propynyl, 2-propynyl, 1-butynyl, 2-butynyl, 3-butynyl and so on. As cycloalkyl in "cycloalkyl which may be substituted", there may be mentioned $C_{3-6}$ cycloalkyl such as cyclopropyl, cyclobutyl, cyclopentyl, cyclohexyl and so on. As aryl in "the aryl group which may be substituted", there may be mentioned $C_{6-14}$ aryl such as phenyl, naphthyl, (for example, 1-naphthyl, 2-naphthyl) and so on. As the substituents on alkynyl group, cycloalkyl group or aryl group described above, there may be mentioned the same substituents as those on alkynyl group, cycloalkyl group or aryl group exemplified in hydrocarbon group in "hydrocarbon group which may be substituted" regarding $Z^0$ mentioned above, Each of "an acyl group which may be substituted", "an amino group which may be substituted", "a group represented by —N=$CR^1R^2$", "a cyclic amino group", "a group represented by —$OR^3$" and "a group represented by —$S(O)_nR^4$" in $Z^2$ has the same meaning as that of "an acyl group which may be substituted", "an amino group which may be substituted", "a group represented by —N=$CR^1R^2$", "a cyclic amino group", "a group represented by —OR 3 and "a group represented by —$S(O)_nR^4$ in $Z^0$ mentioned above.

Among compounds included in compound (II), preferable are the compounds represented by the Formula (II) above or salts thereof.

In the Formula, [where $A^2$ is (1) a $C_{6-14}$ aryl group which may be substituted with 1 to 5 substituents selected from (i) a $C_{1-4}$ alkyl group which may be substituted with 1 to 5 halogens, (ii) the $C_{1-4}$ alkoxy group which may be substituted with 1 to 5 halogens, (iii) the amino group which may be substituted with 1 or 2 $C_{1-4}$ alkylcarbonyl, (iv) the $C_{1-4}$ alkoxy-carbonyl group, (v) halogen atoms, (vi) the cyano group, and (vii) the nitro group, or the thienyl group, the triazolyl group, the imidazolyl group, the isooxazolyl group, the pyrazolyl group, the pyridyl group, the quinolyl group, the benzothiadiazolyl group, the imidazothiazolyl group or the imidazopyridyl group, each of which may be substituted with 1 to 5-substitutents selected from (i) the $C_{1-4}$ alkyl group, (ii) the $C_{1-4}$ alkoxy-carbonyl group, (iii) the carbamoyl group, (iv) the mono- or di-$C_{1-4}$ alkylcarbamoyl group, (v) $C_{1-4}$ alkylsulfonyl group, (vi) halogen atoms, (vii) the carboxyl group and (viii) the cyano group, $X^2$ is (1) the chemical bond, (2) the methylene group which may be substituted with 1 or 2 $C_{1-4}$ alkyl, (3) the vinylene group which may be substituted with 1 or 2 $C_{1-4}$ alkyl, $B^2$ is a $C_{6-14}$ aryl group which may be substituted with 1 to 5 substituents selected from (1) a $C_{1-4}$ alkyl group which may be substituted with 1 to 5 substituents selected from halogens, hydroxy, imino, hydroxyimino, $C_{1-4}$ alkoxyimino, hydrazono, mono- or di-$C_{1-4}$ alkylhydrazono and $C_{1-4}$ alkylthio, (2) a $C_{2-4}$ alkynyl group, (3) the hydroxy group, (4) the $C_{1-4}$ alkoxy group which may be substituted with 1 to 5 substituents selected from halogens and $C_{1-4}$ alkoxy groups, (5) a $C_{1-4}$ alkyl-carbonyloxy group, (6) the $C_{1-4}$ alkylthio group, (7) the $C_{1-4}$ alkylsulfinyl group, (8) the $C_{1-4}$ alkylsulfonyl group, (9) the mono or di-$C_{1-4}$ alkylsulfamoyl group, (10) the amino group, (11) the formyl group, (12) the $C_{1-4}$ alkoxy-carbonyl group, the carbamoyl group, the mono- or di-$C_{1-4}$ alkylcarbamoyl group, the thiocarbamoyl group, halogen atoms, the carboxyl group, the thiocyanato group, the cyano group, the nitroso group, and the nitro group, $Z^2$ is (1) the $C_{1-6}$ alkyl group which may be substituted with 1 to 5 substituents selected from mono- or di-$C_{1-4}$ alkylamino, hydroxy, halogens, $C_{1-4}$ alkoxy, $C_{1-4}$ alkoxycarbonyl, $C_{1-4}$ alkylthio and cyano, (2) the vinyl group, (3) the allyl group, (4) the propadienyl group, (5) the $C_{2-6}$ alkynyl group which may be substituted with 1 to 5 halogens, (6) the $C_{3-6}$ cycloalkyl group, (7) the $C_{6-14}$ aryl group, (8) the $C_{1-4}$ alkyl-carbonyl which may be substituted with 1 to 5 halogens, (9) the amino group which may be substituted with 1 or 2 substituents selected from $C_{1-4}$ alkyl, $C_{1-4}$ alkyl-carbonyl and $C_{14}$ alkoxy-carbonyl, (10) the group represented by —N=$CR^1R^2$ (where $R^1$ and $R^2$ are a $C_{1-4}$ alkyl group, respectively), (11) the group represented by —$OR^3$ (where $R^3$ is a $C_{1-4}$ alkyl group or a $C_{1-4}$ alkyl-carbonyl group) or (12) the group represented by —$S(O)_nR^4$ (wherein, n is an integer from 0 to 2, $R^4$ is (a) the $C_{1-4}$ alkyl group which may be substituted with 1 to 5 halogens, or (b) the $C_{6-14}$ aryl group which may be substituted with 1 to 5 $C_{1-4}$ alkyl groups).

Hereinafter, the more preferable embodiments of the compound (II) and the salts thereof are described:

$A^2$ is (a) the phenyl group which may be substituted with 1 to 3 substituents selected from $C_{1-4}$ alkyl which may be substituted with 1 to 3 halogens, halogens, nitro, cyano, acetylamino, $C_{1-4}$ alkoxy which may be substituted with 1 to 3 halogens and $C_{1-4}$ alkoxy-carbonyl, (b) the naphthyl group, (c) the isoxazolyl group which may be substituted with 1 to 3 $C_{1-4}$ alkyl groups, (d) the triazolyl group which may be substituted with 1 to 3 mono-or di-$C_{1-4}$ carbamoyl, (e) the pyridyl group, (f) the quinolyl group, (g) the thienyl group which may be substituted with 1 to 3 substituents selected from $C_{1-4}$ alkyl and halogens, (h) the pyrazolyl group which may be substituted with 1 to 3 substituents selected from $C_{1-4}$ alkyl, $C_{1-4}$ alkoxy-carbonyl, carboxyl, carbamoyl, cyano and halogens, (i) the imidazolyl group which may be substituted with 1 to 3 $C_{1-4}$ alkyl, (j) the benzothiadiazolyl group (preferably a 2,1,3-benzothiadiazolyl group), (k) the imidazothiazolyl group (preferably an imidazo[2,1-b]thiazolyl group) which may be substituted with 1 to 3 halogens, (1) the imidazopyridyl group (preferably an imidazo[1,2-a] pyridyl group) which may be substituted with 1 to 3 substituents selected from halogens and $C_{1-4}$ alkylsufonyl. More preferable is a phenyl or a thienyl group which may be substituted with 1 to 3 substituents such as $C_{1-4}$ alkyl groups, $C_{1-4}$ alkoxy groups, halogens or cyano group is more preferable. Among these, a phenyl group which may be substituted with 1 to 3 substituents selected from $C_{1-4}$ alkyl and halogens is much more preferable. And the phenyl group which is substituted at the 4-position with a methyl group or a chlorine atom is the most preferable.

(2) As $B^2$, preferable is a phenyl group which is substituted at the 2- or 4-position with substituent selected from (a) the $C_{1-4}$ alkyl group which may be substituted with 1 to 5 substituents selected from halogens, hydroxy, imino, hydroxyimino, $C_{1-4}$ alkoxyimino, hydrazono, mono- or di-$C_{1-4}$ alkylhydrazono and $C_{1-4}$ alkylthio, (b) the $C_{2-4}$ alkynyl group, (c) the hydroxy group, (d) the $C_{1-4}$ alkoxy group which may be substituted with 1 to 5 substituents selected from halogens and $C_{1-4}$ alkoxy, (e) a $C_{1-4}$ alkyl-carbonyloxy group, (f) a $C_{1-4}$ alkylthio group, (g) a $C_{1-4}$ alkylsulfinyl group, (h) a $C_{1-4}$ alkylsulfonyl group, (i) a mono- or di-$C_{1-4}$ alkylsulfamoyl group, (j) formyl group, (k) a $C_{1-4}$ alkoxy-carbonyl group, (1) a carbamoyl group, (m) a mono- or di-$C_{1-4}$ alkylcarbamoyl group, (n) a thiocarbamoyl group, (o) halogen atoms, (p) a carboxyl group, (q) a thicyanato group, (r) a cyano group, s a nitroso group, and (t) a nitro group.

As $B^2_1$, a group represented by

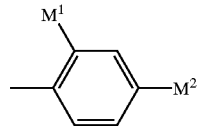

(wherein, $M^1$ is a nitro group, a cyano group, a trifluoromethyl group or a thiocarbamoyl group, and $M^2$ is halogen atoms, a cyano group, a nitro group or a trifluoromethyl group) is especially preferable.

(3) As $Z^2$, preferable are (a) a $C_{1-6}$ alkyl group which may be substituted with 1 to 5 substituents selected from mono- or di-$C_{1-4}$ alkylamino, hydroxy, halogens, $C_{1-4}$ alkoxy, $C_{1-4}$ alkoxy-carbony, $C_{1-4}$ alkylthio and cyano, (b) a vinyl group, (c) an allyl group, (d) a propadienyl group, (e) a $C_{2-6}$ alkynyl group which may be substituted with 1 to 5 halogens, or (f) a $C_{3-6}$ cycloalkyl group, or (g) a $C_{1-4}$ alkoxy group. Among these, a $C_{1-6}$ alkyl group, a $C_{3-6}$ cycloalkyl group, a vinyl group, an allyl group, a $C_{2-6}$ alkynyl group or a $C_{1-4}$ alkoxy group is especially preferable.

(4) $X^2$ is preferably a chemical bond (a single bond or a bond).

The preferable embodiments of $A^2$, $B^2$, $Z^2$ and $X^2$ described in (1) to (4) above, can be combined arbitrarily.

Another preferable embodiments of compounds (II) or salts thereof are preferably the compounds or salts thereof described the following:

A² is a phenyl group which may be substituted with 1 to 3 substituents selected from $C_{1-4}$ alkyl groups, halogens and cyano, X² is a chemical bond, B² is a phenyl group which may be substituted with 1 to 5 substituents selected from (1) a $C_{1-4}$ alkyl group which may be substituted with 1 to 3 halogens, (2) a $C_{1-4}$ alkoxy group, (3) a $C_{1-4}$ alkylthio group, (4) a thiocarbamoyl, (5) halogen atoms, (6) a cyano group, and (7) a nitro group, Z² is (1) a $C_{1-6}$ alkyl group which may be substituted with 1 to 3 $C_{1-4}$ alkoxy, (2) a $C_{3-6}$ cycloalkyl group, (3) an allyl group or (4) a $C_{1-4}$ alkoxy group.

[3] Compound (III) or salts thereof are preferably the compounds represented by the Formula (III):

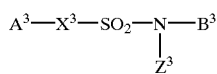

(III)

or a salt thereof,

[where A³ is (1) an aryl group which may be substituted or (2) a heterocyclic group which may be substituted, X³ is (1) a chemical bond, (2) a methylene group which may be substituted or (3) a vinylene group which may be substituted, B³ is a six-membered heterocyclic group containing sucstituents, Z³ is (1) a hydrocarbon group which may be substituted, (2) an acyl group which may be substituted, (3) formyl group, (4) an amino group which may be substituted, (5) a group represented by $-N=CR^1R^2$ (wherein, R¹ and R² are the same or different, and are a hydrogen atom or hydrocarbon group which may be substituted), (6) a cyclic amino group, (7) a group represented by $-OR^3$ (wherein R³ is a hydrogen atom, a hydrocarbon group which may be substituted, an acyl group which may be substituted, formyl group or a sulfonyl group which may be substituted), or (8) a group represented by $-S(O)_nR^4$ (wherein n is an integer from 0 to 2, R⁴ is a hydrogen atom or a hydrocarbon group which may be substituted)].

The substituents on A³, X³ and Z³ are the same as those on A⁰, X⁰ and Z⁰, respectively.

As the "six-membered heterocyclic group" in the "six-membered heterocyclic group with substituents" in B³, there can be mentioned six-membered heterocyclic groups comprising 1 to 4 heteroatoms selected from nitrogen, oxygen and sulfur atoms. As the specific examples, there can be mentioned pyridyl (for example, 2-, 3- or 4-pyridyl), pyridazinyl (for example, 3- or 4-pyridazinyl), pyrimidinyl (for example, 2-, 4-, or 5-pyrimidinyl), pyrazinyl, piperidinyl (for example, 1-, 2-, 3- or 4-piperidinyl), piperazinyl (for example, 1- or 2-piperazinyl), and so on. Among these six-membered heterocyclic groups, pyridyl, pyridazinyl and pyrimidinyl are especially preferable.

As substituents on the said six-membered heterocyclic groups, those included in the substituents group (T) mentioned above are preferable. The number of the said substituents is 1 to 5 (more preferably 1 to 3).

Among the compounds included in compound (III), preferable are those represented by the Formula (III)or salts thereof. In the Formula(III), wherein A³ is a phenyl group which may be substituted with 1 to 5 $C_{1-4}$ alkyl or an imidazolyl group which may be substituted with one or two $C_{1-4}$ alkyl, X³ is a chemical bond, B³ is a pyridyl group, a pyridazinyl group or a pyrimidinyl group which may be substituted with 1 to 5 substituents selected from $C_{1-4}$ alkyl, $C_{1-4}$ alkoxy, halogens and nitro, Z³ is a $C_{1-6}$ alkyl group or $C_{3-6}$ cycloalkyl group or salts thereof. As for A³ above, a phenyl group which may be substituted with 1 to 5 $C_{1-4}$ alkyl is more preferable, and furthermore a 4-methylphenyl group is the most preferable.

[4] Compounds(IV) or salts thereof are the compounds represented by the Formula (IV):

(IV)

or salts thereof,

[wherein A⁴ is (1) an aryl group which may be substituted or (2) a heterocyclic group which may be substituted, X⁴ is (1) a chemical bond, (2) a methylene group which may be substituted or (3) a vinylene group which may be substituted, B⁴ is a pyridazinyl group or a pyradinyl group, Z⁴ is (1) a hydrocarbon group which may be substituted, (2) an acyl group which may be substituted, (3) formyl group, (4) an amino group which may be substituted, (5) a group represented by $-N=CR^1R^2$ (wherein R¹ and R² are the same or different, and are a hydrogen atom or a hydrocarbon group which may be substituted), (6) a cyclic amino group, (7) a group represented by $-OR^3$ (wherein R³ is a hydrogen atom, a hydrocarbon group which may be substituted an acyl group which may be substituted with hormyl group or sulfonyl group which may be substituted), (8) a group represented by $-S(O)_nR^4$ (wherein n is an integer from 0 to 2, R⁴ is a hydrogen atom or a hydrocarbon group which may be substituted].

Substituents on A⁴, X⁴ and Z⁴ are the same as those on A⁰, X⁰ and Z⁰ described above, respectively.

[5] Compounds (V) or salts thereof are the compounds represented by the Formula (V):

(V)

or salts thereof,

[wherein A⁵ is a 4-methylphenyl group, X⁵ is a chemical bond (a single bond or a bond), B⁵ is a pyridyl group or a pyrimidinyl group, Z⁵ is a $C_{1-4}$ alkyl group (for example, methyl, ethyl, n-propyl, isopropyl)].

Among the compound (1) to (V) stated above, compound (I) to (III) or salts thereof are more preferable, and compound (II) or salts thereof are especially preferable.

Among the compound (I⁰) or salts thereof, the compound (VI) shown below or salts thereof are novel compounds and can be used especially preferably. The said comound (VI) or salts thereof are compounds included in the compound (II) or salts thereof mentioned above. Compounds represented by the Formul(VI) and saltys thereof,

(VI)

[wherein, A⁶ is a phenyl group which may be substituted with substituents selected from $C_{1-4}$ alkyl (for example, methyl, ethyl, n-propyl, isopropyl), halogens (for example, fluorine, chlorine, bromine, iodine) and cyano, X⁶ is a chemical bond (a single bond or a bond), B⁶ is a 2-nitrophenyl group (or 6-nitrophenyl group) or 2-cyanophenyl group (or 6-cyanophenyl group) which may be substituted with substituents selected from halogen atoms (for example, fluorine, chlorine, bromine, iodine), nitro and cyano, $Z^6$ is an ethyl group, an isopropyl group, a cyclopropyl group, a methoxy group, an ethoxy group or an isopropoxy group].

Especially preferable are the compounds or salts thereof which have as $A^6$ a phenyl group which may be substituted with substituents selected from $C_{1-4}$ alkyl, halogens and cyano, as $X^6$ a chemical bond, as $B^6$ a 2-nitrophenyl group which may be substituted with substituents selected from halogen atoms, nitro and cyano, and as $Z^6$ an ethyl group, an isopropyl group or a cyclopropyl group.

The number of the substituents on the phenyl group as $A^6$ is 1 to 3. As the said substituent, methyl and chlorine atom are especially preferable. The substitutent of the said phenyl group is preferably at position 4 of the said phenyl group.

The number of substituents on the 2-nitrophenyl group (or 6-nitrophenyl group) or the 2-cyanophenyl group (or 6-cyanophenyl group) as $B^6$ is 1 to 3. As the said substituent, halogens and cyano are especially preferable. The said substituents are preferably at the 4 position of the 2-nitrophenyl (or 6-nitrophneyl) group or 2-cyanophenyl (or 6-cyanophenyl) group.

When compound ($I^0$), (I), (II), (III), (IV), (V) or (VI) or salts thereof mentioned above (hereinafter, they may be called as "compound ($I^0$) or the salts thereof" for short) are used as microbicidal compositions, they can be applied in the per se known forms for general use of agrochemical compositions. Namely, depending on the objects one or more than two kinds (preferably not less than one nor more than three) of compound ($I^0$) or salts thereof are taken as the effective constituents and mixed with or dispersed in some appropriate liquid carrier, or mixed with or adsorbed on some appropriate solid carrier to get various forms of compositions, for example, emulsions, oils, aqueous suspensions, liquids, ULV preparations, hydrates, powders, DL (driftless) powders, granules, fine granules, fine granules F, flowable preparations, dry-flowable preparations, tablets, Jumbo preparations, sprays, ointments, pastes, foams, aerosols, micocapsules, seed coating agents, fumigants, and stick preparations for infusing the crops. These preparations may be further admixtured, if necessary, for example, with emulsifiers, suspending agents, spreading agents, permeating agents, moistening agents, dispersing agents, mucilage, stabilizers, binders, fluidization auxiliaries, hardening preventives, flocculants, antioxidants, floating agents, antifoaming agents, antifreeze agents, antiseptics, moisture removers, ultraviolet absorbers, ultraviolet scattering agents, coloring agents and suspension-stabilizers, to prepare microbicidal compositions of the present invention by the per se known methods. Namely, by mixing comound ($I^0$) or salts thereof, liquid carriers or solid carriers, if necessary, various additives mentioned above, and other active ingredients of pesticides uniformly.

Emulsions of the present invention, for example, can be prepared by mixing and dissolving uniformly compound ($I^0$) or salts thereof, emulsifiers, organic solvents, and so on. Granules and wettable granules of the present invention, for example, can be manufactured by mixing uniformly compound ($I^0$) or salts thereof, dispersing agents (surfactants), binders, fillers (or solid carriers) and so on, uniformly, and then granulating.

Powders (DL powders and so on) of the present invention, for example, can be manufactured by mixing compound ($I^0$) or salts thereof with fillers (or solid carriers) uniformly and pulverizing the resulting mixture. Flowable preparations of the present invention can be manufactured by mixing, dispersing compound ($I^0$) or salts thereof, dispersing agents and so on with a mixer, and then by wet-pulverizing the resulting mixture by means of dynomill, and so on. Jumbo preparations, for example, can be manufactured by mixing compound ($I^0$) or salts thereof with dispersing agents (surfactants), binders, floating agents, fillers (or solid carriers) uniformly, and by granulating the resulting mixture. Jambo formulations, powders, granules, wettable granules, hydrates and so on can be packed into water-soluble film-packages of 20 to 200 g each, for the sake of convenience in spraying. As the water-soluble films, there may be mentioned those of polyvinyl alcohol, carboxymethyl cellulose, starch, gelatin, polyvinylpyrrolidone, polyacrylic acid or salts thereof, pullulan (trade name: polysaccharide of a kind of starch), PAOGEN (Trade Name: a thermoelastic water soluble polymer), and so on.

As liquid carriers (solvents) appropriate for use, there may be mentioned, for example, water, alcohols such as methanol, ethanol, propanol, isopropanol, ethylene glycol, and so on, ketones such as acetone and methyl ethyl ketone, and so on, ethers such as 1,4-dioxane, tetrahydrofuran, ethylene glycol monomethyl ether, diethylene glycol monomethyl ether, propylene glycol monomethyl ether, and soon, aliphatic hydrocarobons such as kerosene, paraffin, fuel oil, machine oil, and edible oil, and so on, aromatic hydrocarbons such as benzene, toluene, xylene, solvent naphtha, methylnaphthalene, and so on, halogenated hydrocarbons such as dichloromethane, chloroform, carbon tetrachloride, and so on, acid amides such as N,N-dimethylformamide, N,N-dimethylacetamide, and so on, esters such as ethyl acetate, butyl acetate, fatty acid glycerol esters, and so on, and nitrites such as acetonitrile, propionitrile,and so on. These solvents can be used by mixing one or more than two (preferably not less than one nor more than three) of them in appropriate ratios. As solid carriers (diluents, fillers), there may be mentioned, for example, vegetable powders such as soybean powder, tobacco powder, wheat flour, wood flour, and so on, mineral powder, for example, clays such as kaolin, bentonite, acid clay, and so on, talcs such as talcum powder, agalmatolite powder, and so on, silicate minerals such as diatomaceous earth, mica, and so on, calcium carbonate, alumina, sulfur powder, activated carbon, and so on. These fillers can be used by mixing one or more than two (preferably not less than one nor more than three) of them in appropriate ratios. Further, as the ointment bases, there may be used, for example, one or more than two (preferably not less than one nor more than three) of polyethylene glycol, pectin, polyol higher fatty acid esters such as glycerol mono-stearic acid ester, and so on, cellulose derivatives such as methyl cellulose, and so on, sodium alginate, bentonite, higher alcohols, polyols such as glycerol, and so on, vaseline, white Vaseline, liquid paraffin, lard, various vegetable oils, lanoline, dehydrated lanoline, hydrogenated oil, resins, or mixtures of these substances with various surfactants described below appropriately.

As surfactants which may be used as emulsifiers, spreading agents, penetrants, moistening agents, dispersing agents, there may be mentioned nonionic surfactants such as soaps, polyoxyethylene alkylethers (NEWKALGEN FS4™ (TM means trademark.), NOIGEN EA-177™, NOIGEN ET83™, NOIGEN ET157™ and so on), polyoxyethylene alkylphenyl ethers, polyoxyethylene nonylphenyl ethers (NONIPOL20™, NONIPOL100™ and so on), polyoxyethylene alkylaryl ethers [for example, NOIGEN EA142™, NOIGEN EA92™; manufacured by Dai-ichi Kogyo Seiyaku Co., Ltd., NONAL™; manufactured by Toho Chemical Industry Co., Ltd.], polyethyleneglycol ethers [for example, NONIPOL85™, NONIPOL160™; manufactured by Sanyo Chemical Industries Ltd.], polyol esters [for example, Tween 20™, Tween80™; manufactured by KAO Corp.], polyoxyethylene polyoxypropylene ethers, polyoxyethylene distylenated phenylether (NOIGEN EA87™, NOIGEN EA177™ and so on), polyoxyethylene alkylesters (ionetMO20™, ionetMO600™, and so on), sorbitan fatty acid esters (LEODOL SP-S10™, LEODOL TW-S20™ and so on), polyoxyethylene sorbitan fatty acid esters, block copolymer of ethylene oxide with propylene oxide (NEWPOL PE64™), higher fatty acid alkanol amides, alkylmaleic acid copolymer (DEMOL EP™ and so on); cationic surfactants such as alkylamine salts and tert-ammonium salts, and so on; anionic surfactants such as alkylsulfuric acid salts [for example, EMAL10™, EMAL40™; manufactured by KAO Corp.], alkylsulfonic acid salts such as [for example, NEOGEN™, NEOGEN T™ manufactured by Dai-ichi Kogyo Seiyaku Co.,Ltd., NEOPEREX; manufactured by KAO Corp.], polymeric compounds such as naphtahlenesulfonic acid polycondensation product metal salts, formalin condensate of naphthalenesulfonic acid salts (NEWKALGEN FS4™ and so on), alkylnaphthalene sulfonic acid salts (SOLPOL5115™ and so on), ligninsulfonic acid metal salts, alkyl aryl sulfonic acid salts, alkyl arylsulfonate sulfate, and so on, anionic surfactant such as polynaphthylmethanesulfonic acid salts, polystyrenesulfonic acid sodium salt, polycarboxylic acid metal salts, polyoxyethylen histhylyl phenylether sulfate ammonium, higher alcohol sulfonic acid salts, higher alcohol ether sulfonic acid salts, dialkylsulfosuccinate (NEWKALGEN EP70P™ and so on), and higher fatty acid alkali metal salts, and so on.

As salts, sodium salts, potassium salts, ammonium salts, diethanolamine salts, triethanolamine salts, monoisopropanolamine salts, diisopropanolamine salts, triisopropanolamine salts, other tertiary amine salts such as dialkyldimethylammonium salts, and so on can be used (applied, employed), in an extent where the function of the surfactants is not influenced.

As spreading agents, anionic surfactants, among surfactants mentioned above, which contain tert-amines as cationic part [for example, dialkyl dimethyl ammonium salts of polynaphthylmethanesulfonic acid such as Needs™ (marketed by KUMIAI Chemical, The material is manufactured by KAO Corp.)] can be used preferable.

As stabilizers, compounds having epoxy groups, antioxidants [for example, dibutylhydroxytoluene (BHT), butylhydroxy anisole (BHA), tetrakis[3-(3,5-di-tert-butyl-4-hydroxyphenyl)propionyloxymeth yl]methane (Irganox 1010), DL-tocopherol, propyl gallate, erythorbic acid, sodium erythorbate, isopropyl citrate, and so on], phosphoric acid, PAP auxiliary agents (isopropyl acid phosphate), cyclodextrin (TOYODELLINE P), tall oil (Hartall fatty acids), and so on, can be used. One or more than two (preferably not less than one nor more than three) of these compounds can be admixed in appropriate ratios when used.

As binders, dextrin, pregelatinized starch, polyvinyl alcohol, Arabic gum, sodium alginate, polyvinylpyrrolidone, glucose, saccharose, mannitol, sorbitol, and so on, can be used. One or more than two (preferably not less than one nor more than three) of these compounds can be admixed in appropriate ratios when used.

As fluidization auxiliaries, PAP auxiliaries (for example, isopropyl acidphosphate) and talc, and so on can be used. One or more than two (preferably not less than one nor more than three) of these compounds can be admixed in appropriateratios when used.

As hardening preventives, white carbon, diatomaceous earth, magnecium stearate, aluminum oxide, titanium dioxide, and so on, can be used. One or more than two (preferably not less than one nor more than three) of these compounds can be admixed in appropriate ratios when used.

As flocculants, liquid paraffin, ethylene glycol, diethylene glycol, triethylene glycol, isobutylene polymers (for example, IP Solvent), and so on,be used. One or more than two (preferably not less than one nor more than three) of these compounds can be admixed in appropriate ratios when used.

As antioxidants, dibutylhydroxytoluene, 4,4-thiobis-6-tert-butyl-3-methylphenol, butylhydroxyanisole, paraoctylphenol, mono- (or di- or tri-)(α-methylbenzyl) phenol, 2,6-di-tert-butyl-4-methylphenol, tetrakis[3-(3,5-di-tert-butyl-4-hydroxyphenyl)propionyloxymethyl]methane, and so on, can be used. One or more than two (preferably not less than one nor more than three) of these compounds can be admixed in appropriate ratios when used.

As floating agents, used especially for manufactureing jambo formulation, powder bases which have the specific gravity of 1 or less than 1 (preferably 1 to 0.5) and the particle diameter of 600 μm or less, more preferably from 600 m to 10 μm, are preferably used. As inorganic floating agents, there can be mentioned those which can be obtained by calcinating natural glass-like materials and consist of glass particles with one or several air bubbles, in them, for example perlite made from pearlite and orobsidian, Shirasu-balloon (Trade Name) made from Shirasu, vermiculite made from Hiru-ishi and phyllite (Trade Name)which is one of aluminosilicates and can be obtained by calcination, and so on, and as organic floating agents, there can be mentioned such substances called in general wax-like materials, for example, higher fatty acids such as stearic acid and palmitic acid which are solid at room temperatures, higher alcohols such as stearyl alcohols, and paraffin wax, and so on. However, as these wax-like materials are water-repellant, they have tendency to prevent water from penetrating into them and to prevent the agrochemical active constituents which are confined in them from leaking and spreading into surrounding water, thus making it reasonable to make use of such wax-like organic floating agents in a mixture with the glass hollow bodies mentioned above.

As antifoaming agents, silicone antifoaming agents (for example, Antifoam E20), and so on, can be preferably used. One or more than two (preferably not less than one nor more than three) of these compounds can be admixed in appropriate ratios when used.

As antifreezing agents, ethylene glycol, diethylene glycol, polyethylene glycol, glycerol, and so on, can be used. One or more than two (preferably not less than one nor more than three) of these compounds can be admixed in appropriate ratios when used.

As antiseptic agents, butylparaben and potassium sorbate, and so on, can be used. One or more than two (preferably not less than one nor more than three) of these compounds can be admixed in appropriate ratios when used.

As moisture removers, anhydrous gypsum and silica gel powder, and so on, can be used. One or more than two (preferably not less than one nor more than three) of these compounds can be admixed in appropriate ratios when used.

As ultraviolet absorbers, 2-(2'-hydroxy-5'-methylphenyl) benzotriazole, 2-ethoxy-2'-methyloxalic acid bisanilide, dimethyl succinate-1-(2-hydroxyethyl)-4-hydroxy-2',2,6,6-tetramethylpiperidine polycondensates and so on, can be used preferably. One or more than two (preferably not less than one nor more than three) of these compounds can be admixed in appropriate ratios when used.

As ultraviolet scattering agents, titanium dioxide, and so on, can be used. One or more than two (preferably not less than one nor more than three) of these compounds can be admixed in appropriate ratios when used.

As coloring agents, CYANINEGREEN G, ERIOGREEN B400, and so on, can be used. One or more than two (preferably not less than one nor more than three) of these compounds can be admixed in appropriate ratios when used.

As suspension stabilizers, polyvinyl alcohol (GOHSENOL GH17 and so on), clay minerals (Kunipia F, VEEGUM R, and so on), silicone dioxide (AEROSIL COK84, and so on), and so on, can be used. One or more than two (preferably not less than one nor more than three) of these compounds can be admixed in appropriate ratios when used. Jumbo preparations, powders, granules wettable granules, hydrates and so on can be packed into water-soluble film-packages of 20 to 200 g each, for convenience in spraying. As the said water-soluble film, there may be mentioned polyvinyl alcohol, carboxymethyl cellulose, starch, gelatin, polyvinylpyrrolidone, polyacrylic acid or salts thereof, Pullulan (Trade Name: polysaccharide of a kind of starch), PAOGEN (trade name: a thermoelastic water soluble polymer), and so on.

Furthermore, compound ($I^o$) or salts thereof can be combined and used with, for example, insecticides, acaricide, nematocides, herbicides, plant hormones, plant growth regulators, antimicrobials, synergists, attractants, repellants, pigments, fertilizers, and so on.

Thus, the present invention includes also microbiocides for agricultural or horticultural use which contain both the compound ($I^o$) or salts thereof and other active agrochmical constituents.

The said other agrochemical constituents may be contained in the same preparation with compound ($I^o$) or salts thereof or may be formulated into separate preparations which can be mixed just before use.

Representative insecticides, acaricide and nematocides which can be used by admixing with compound ($I^o$) or salts thereof are as follows: acephate, acetamiprid, acrinathrin, alanycarb, aldrin, allethrin, Aluminium phosphide, amitraz, Arsenic acid, avermectin-B, bendiocarb,benfuracarb, bensultap, benzoximate, bifenthrin, bromopropylate, buprofezin, Calcium cyanamide, Calcium polysulfide, carbaryl:NAC, carbofuran, carbosulfan, cartap, chlordane, chlorfenvinphos:CVP, chlorfluazuron, chlorphenapyr, chlorpyrifos-methyl, chromafenozide, clofentezine, clothianidin, cyanophos:CYAP, cycloprothrin, cyfluthrin, cyhalothrin, cypermethrin, cyromazine, dichlorodiisopropyl ether, D—D(1,3-Dichloropropene), DDT, deltamethrin, diafenthiuron, diazinon, dichlofenthion, dichlorvos:DDVP, dicofol, dieldrin, dienochlor, diflubenzuron, dimethoate, dimethylvinphos, disulfoton, DSP, endosulfan, EPN, esfenvalerate, ethion, ethofenprox, ethoprophos, etoxazole, fenbutatin oxide, fenitrothion:MEP, fenobucarb, fenothiocarb, fenoxycarb, fenpropathrin, fenpyroximate, fenvalerate, fipronil, fluazinam, flucythrinate, flufenoxuron, flupyrazofos, fluvalinate, formetanate, formothion, fosthiazate, furathiocarb, halfenprox, hexaflumuron, hexythiazox, Hydrogen phosphide, imidacloprid, isofenphos, isoprocarb, isoxathion, malathion, mesulfenfos, metam-ammonium, metam-sodium, methidathion, methiocarb, methomyl, methoxychlor, methoxyfenozide, Methyl bromide, metolcarb:MTMC, milbemycin-A, monocrotophos, naled:BRP, nicotine-sulfate, nidinotefuran, nitenpyram, oxamyl, oxydeprofos:ESP, parathion, permethrin, phenthoate:PAP, phosalone, phosmet:PMP, pirimicarb, pirimiphos-methyl, Potassium oleate, profenofos, propaphos, propargite:BPPS, propoxur, prothiofos, protrifenbute, pymetrozine, pyraclofos, pyrethrins, pyridaben, pyridafenthion, pyrimidifen, pyriproxyfen, quinalphos, resmethrin, salithion, silafluofen, Sulfur, sulprofos, tebufenozide, tebufenpyrad, teflubenzuron, tefluthrin, temephos, tetrachlorvinphos, tetradifon, thiacloprid, thiamethoxam, thiocyclam, thiodicarb, thiometon, tolfenpyrad, tralomethrin, trichlorfon:DEP, triflumuron, vamidothion, XMC.

Representative antimicrobials which can be used by admixing with compound ($I^o$) or salts thereof are as follows: for example, acetic acid, acibenzolar-S-methyl, amobam, anilazine, azoxystrobin, benomyl, benthiazole, bitertanol, blasticidin-S, Bordeaux mixture, bromuconazole, buthiobate, Calcium hypochlorite, Calcium polysulfide, captan, carbendazol, carpropamid, IKF-916 (4-chloro-2-cyano-N,N-dimethyl-5-p-tolylimidazole-1-sulfonamide), chloroneb, chloropicrin, chlorothalonil:TPN, Cinnamaldehyde, RH-7281 (3,5-dichloro-N-(3-chloro-1-ethyl-1-methyl-2-oxopropyl)4-methylbenzamide), CNA (2,6-Dichloro-4-nitroaniline), Copper hydroxide, Copper sulfate, AC382042 (N-(1-cyano-1,2-dimethylpropyl)-2-(2,4-dichlorophenoxy) propionamide(R,S)-and(R,R)-and(S,R)-and(S,S)), cymoxanil, cyproconazole, cyprodinil, dazomet, dichlofluanid, D—D (1,3-Dichloropropene), diclocymet, diclomezine, diethofencarb, difenoconazole, diflumetorim, dimethirimol, dimethomorph, diniconazole-M, dinocap, Nickel dimethyldithiocarbamate, etridiazole, famoxadone, fenarimol, fenbuconazole, Fendazosulam, fenhexamid, NNF-9425:fenoxanil, fenpiclonil, fentiazon, fentin hydroxide, ferimzone, fluazinam, fludioxonil,RPA-403397:flumetover, fluoroimide, fluquinconazole, flusulfamide, flutolanil, fosetyl-Al, fthalide, furametpyr, hexaconazole, hymexazol, imazalil, imibenconazole, iminoctadine-albesilate, iminoctadinetriacetate, iodocarb, ipconazole, iprodione, isoprothiolane, kasugamycin, kresoxim-methyl, mancozeb, maneb, mepanipyrim, mepronil, metalaxyl, metalaxyl-M, metam-sodium, methasulfocarb, Methyl bromide, RPA407213 (s-5-methyl-2-methylthio-5-phenyl-3-phenylamino-3,5-dihydroimidazol-4-one), metominostrobin, mildiomycin, milneb, myclobutanil, nabam, oxadixyl, oxolinic acid, oxpoconazole, oxycarboxin, oxytetracycline, pefurazoate, penconazole, pencycuron, picoxystrobin, polycarbamate, polyoxin, Potassium hydrogen carbonate, probenazole, prochloraz, procymidone, propamocarb-hydrochloride, propiconaole, propineb, pyrazophos, pyributicarb, pyrifenox, pyrimethanil, pyroquilon, quinoxyfen, quintozene:PCNB, MON65500:silthiopham, sipconazole, Sodium bicarbonate, sodium hypochlorite, SSF-129 ((E)-2[2-(2,5-dimethylphenoxymethyl)phenyl]-2-methoxyimino-N-methylacetamide), streptomycin, Sulfur, tebuconazole, tecloftalam, tetraconazole, thiabendazole, thiram:TMTD, thifluzamide, thiophanate-methyl, triadimefon, triadimenol, tricyclazole, tridemorph, triflumizole, trifloxystrobin, triforine, validamycin, vinclozolin, zineb, ziram.

Representative herbicides, plant hormones, and plant growth regulators which can be used by admixing with compound ($I^o$) or salts thereof are as follows: Abscisic acid, acetochlor, acifluorfen-sodium, alachlor, alloxydim, ametryn, amidosulfuron, amiprofos-methyl, ancymidol, asulam, atrazine, azimsulfuron, benfluralin, benfuresate, bensulfuron-methyl, bensulide:SAP, bentazone, benthiocarb, benzamizole, benzfendizone, benzofenap, Benzyl adenine, bialaphos, bifenox, Brassinolide, bromacil, bromobutide, butachlor, butafenacil, butamifos, butylate, cafenstrole, Calcium carbonate, Calcium peroxide, carbaryl, chlomethoxynil, chloridazon, chlorimuron-ethyl, chlorphthlim, chlorpropham, chlorsulfuron, chlorthaldimethyl, chlorthiamid:DCBN, choline chloride, cinmethylin, cinosulfuron, clethodim, clomeprop, cloxyfonac-sodium, 4-CPA (4-chlorophenoxyacetic acid), cumyluron,cyanazine, cyclosulfamron, cyhalofop-butyl, 2,4-D salts (2,4-Dichlorophenoxyacetic acid salts), dichlorprop:2,4-DP, daimuron, dalapon:DPA, daminozide, dazomet, n-Decyl alcohol, dicamba sodium:MDBA, dichlobenil:DBN, diflufenican, dimepiperate, dimethametryn, dimethenamid, diquat, dithiopyr, diuron, endothal, esprocarb, ethephon, ethidimuron, ethoxysulfuron, ethychlozate, etobenzanid, fenarimol, fenoxaprop-ethyl, fentrazamide, flazasulfuron, florasulam, fluazifop-butyl, flumioxazin, flupropanate-sodium, flurprimidol, fluthiacetmethyl, forchlorfenuron, formesafen, gibberellin, glufosinate, glyphosate, halosulfuron-methyl, hexazinone, imazamox, imazapyr, imazaquin, imazosulfuron, inabenfide, Indole acetic acid:IAA, Indole butyric acid, ioxyniloctanoate, isouron, karbutilate, lactofen, lenacil, linuron, Maleic hydrazide, mecoprop:MCPP, MCP salts (2-Methyl-4-chlorophenoxyacetic acid salts), MCPA.thioethyl (MCPA-thioethyl), MCPB (2-Methyl-4-chlorophenoxybutanoic acid ethyl ester), mefenacet, mefluidide, mepiquat, methyl daimuron, metolachlor, metribuzin, metsulfuron-methyl, molinate, AND (1-naphthaleneacetamide), naproanilide, napropamide, nicosulfuron, orbencarb, oxadiazon, oxaziclomefone, oxine-sulfate, paclobutrazol, paraquat, Pelargonic acid, pendimethalin, pentoxazone, pethoxamide, phenmedipham, picloram, piperonyl butoxide, piperophos, pretilachlor, primisulfuronmethyl, procarbazone, prodiamine, prohexadione-calcium, prometryn, propanil, propyzamide, pyraflufen-ethyl, pyrazolate, pyrazosulfuronethyl, pyrazoxyfen, pyributicarb, pyridate, pyriminobacmethyl, pyrithiobac, quiclorac, quinoclamine, quizalofopethy, rimsulfuron, sethoxydim, siduron, simazine, simetryn, Sodium chlorate, sulfosulfuron, swep:MCC, tebuthiuron, terbacil, terbucarb:MBPMC, thenylchlor, thiazafluron, thifensulfuron-methyl, triaziflam, triclopyr, tridiphane, trifluralin, trinexapac-ethyl, tritosulfuron, uniconazole-P, vemolate:PPTC.

Among "other active agrochemical constituents" mentioned above, antimicrobial active constituents and insecticidal active constituents are especially preferable.

Furthermore, as the said antimicrobial active constituents, in addition to azoxystrobin, chlorothalonil, hexaconazole, iminoctadine, mepanipyrim, kresoxim-methyl and iprodione, there may be mentioned carpropamid, diclocymet, probenazole, tricyclazole, pyroquilon, isoprothiolane, acibenzolar-S-methyl, as agents for treating the soil, seed of rice and for spraying on the water surface of the rice cultivation. And as agents for spraying on the leaves and stems of the rice plant, carpropamid, diclocymet, probenazole, tricyclazole, pyroquilon, isoprothiolane, acibenzolar-S-methyl, validamycin A, ferimzone, fthalide and so on, can be used more preferably, and among said agents, validamycin A, ferimzone and fthalide can be used most preferably.

Futhermore, as the said inscticidal active constituents, clothianidin [1-(2-chlorothiazol-5-ylmethyl)-3-methyl-2-nitroguanidine], nitenpyram [(E)-N-(6-chloro-3-pyridylmethyl)-N-ethyl-N'-methyl-2-nitrovinylydeneamine], cartap hydrochloride [1,3-bis(carbamoylthio)-2-(N,N-di-methylamino)propane hydrochloride], bensultap [S,S'-2-dimethyl-amminotrimethylene=di(benzenethiosulfonate)], pyraclofos [(RS)-[O-1-(4-chlorophenyl)pyrazol-4-yl]=O-ethyl=S-propyl=phosphorothioate], and so on, can be used especially preferably.

Thus, the present invention includes

[1] A microbicide for agricultural or horticultural use which contains compound (I) or salts thereof and other agrochemically active constituents,

[2] A microbicide for agricultural or horticultural use which contains compound (II) or salts thereof and other agrochemically active constituents,

[3] A microbicide for agricultural or horticultural use which contains compound (III) or salts thereof and other agrochemical active constituents,

[4] A microbicide for agricultural or horticultural use which contains compound (IV) or salts thereof and other agrochemical active constituents,

[5] A microbicide for agricultural or horticultural use which contains compound (V) or salts thereof and other agrochemical active constituents,

[6] A microbicide for agricultural or horticultural use which contains compound (VI) or salts thereof and other agrochemical active constituents,

[7] A microbicide for agricultural or horticultural use which contains compound (II') which will be described below or salts thereof and other agrochemically active constituents,

[8] A microbicide for agricultural or horticultural use described in [1] to [7] above, wherein the other agrochemical active constituents are insecticides,

[9] A microbicide for agricultural or horticultural use described in [8], wherein the other agrochemical active constituents are more than one of those selected from bensultap, cartap, clothianidin, nitenpyram and pyraclofos,

[10] A microbicide described in [1] to [7] above, wherein the other agrochemical active constituents are antimicrobial active constituents,

[11] A microbicide for agricultural or horticultural use described in [10] above, wherein the other agrochemical active constituents are more than one of those selected from azoxystrobin, chlorothalonil, hexaconazole, iminoctadine, mepanipyrim, kresoxim-methyl, iprodione, ferimzone, fthalide and validamycin, and

[12] A method to increment the microbicidal action of compound (I), (II), (III), (IV), (V), (VI) or (II') described below, or salts thereof which comprises using them in combination with other agrochemically active constituents.

Among the said compound (I), (II), (III), (IV), (V), (VI) which may be used in combination with other agrochemical active constituents or (II') which will be described below, or salts thereof, compound (I), (II), (III), (VI) or (II') or salts thereof are more preferable, and compound (II), (VI) or (II') or salts thereof are especially preferable.

Specific examples of the more preferable compound are 4'-chloro-N-ethyl-2'-nitro-p-toluenesulfonanilide, 2',4'-dinitro-N-ethyl-p-toluenesulfonanilide, 2',4'-dicyano-N-ethyl-p-toluensulfonanilide, 4'-chloro-N-isopropyl-2'-nitro-p-toluenesulfonanilide, 4'-fluoro-N-isopropyl-2'-nitro-p-toluene-sulfonanilide, 4'-cyano-N-isopropyl-2'-nitro-p-toluenesulfonanilide, 4'-chloro-N-isopropyl-2'-cyano-p-toluenesulfonanilide, 2',4'-dinitro-N-iso-propyl-p-toluenesulfoanilide, 4'-nitro-N-isopropyl-2'-cyano-p-toluenesulfonanilide, 2'-cyano-N-methoxy-4'-nitro-p-toluenesulfonanilide, or 2',4'-dinitro-N-methoxy-p-toluenesufonanilide or salts thereof.

In those compositions which contain compound (I°) [for example, compound (I), (II), (III), (IV), (V), (VI) or (II') which will be described below] or salts thereof and nitenpyram, it may be advantageous to make first an inclusion compound of nitenpyram with cyclodextrin, for example, TOYODERIN (commercial product name), and then the resulting inclusion compound come into the composition in order to enhance stability of the composition.

These compositions may further contain not less than one kind (more preferably not less than one nor more than three kinds) of other agrochemical active constituents,(for example, insecticidal, acaricidal, antimicrobial active components, and so on). As such compositions, there can be mentioned compositions which contain compound (I°) [for example, compound (I), (II), (III), (IV), (V), (VI) or (II') which will be described below] or salts thereof, ferimzone and fthalide, and compositions which contain compound (I°) [compound (I), (II), (III), (IV), (V), (VI) or (II') which will be described below] or salts thereof, validamycin, ferimzone and fthalide and so on.

More preferable embodiments of composition which contain other agrochemically active constituents are as follows:

(i) A microbicide for agricultural or horticultural use which contains 4'-chloro-N-ethyl-2'-nitro-p-toluenesulfonanilide or salts thereof and ferimzone.
(ii) A microbicide for agricultural or horticultural use which contains 4'-chloro-N-ethyl-2'-nitro-p-toluenesulfonanilide or salts thereof and fthalide.
(iii) A microbicide for agricultural or horticultural use which contains 4'-chloro-N-ethyl-2'-nitro-p-toluenesulfonanilide or salts thereof and validamycin.
(iv) An insecticide/microbicide for agricultural or horticultural use which contains 4'-chloro-N-ethyl-2'-nitro-p-toluenesulfonanilide or salts thereof and bensultap.
(v) An insecticide/microbicide for agricultural or horticultural use which contains 4'-chloro-N-ethyl-2'-nitro-p-toluenesulfonanilide or salts thereof and cartap,
(vi) An insecticide/microbicide for agricultural or horticultural use which contains 4'-chloro-N-ethyl-2'-nitro-p-toluenesulfonanilide or salts thereof and clothianidin.
(vii) An insecticide/microbicide for agricultural or horticultural use which contains 4'-chloro-N-ethyl-2'-nitro-p-toluenesulfonanilide or salts thereof and nitenpyram.
(viii) An insecticide/microbicide for agricultural or horticultural use which contains 4'-chloro-N-ethyl-2'-nitro-p-toluenesulfonanilide or salts thereof and pyraclofos.
(ix) A microbicide for agricultural or horticultural use which contains 2',4'-dinitro-N-methoxy-p-toluenesulfonanilide or salts thereof and ferimzone.
(x) A microbicide for agricultural or horticultural use which contains 2',4'-dinitro-N-methoxy-p-toluenesulfonanilide or salts thereof and fthalide.
(xi) A microbicide for agricultural or horticultural use which contains 2',4'-dinitro-N-methoxy-p-toluenesulfonanilide or salts thereof and validamycin.
(xii) An insecticide/microbicide for agricultural or horticultural use which contains 2',4'-dinitro-N-methoxy-p-toluenesulfonanilide or salts thereof and bensultap.
(xiii) An insecticide/microbicide for agricultural or horticultural use which contains 2',4'-dinitro-N-methoxy-p-toluenesulfonanilide or salts thereof and cartap.
(xiv) An insecticide/microbicide for agricultural or horticultural use which contains 2',4'-dinitro-N-methoxy-p-toluenesulfonanilide or salts thereof and chlothianidin.
(xv) An insecticide/microbicide for agricultural or horticultural use which contains 2',4'-dinitro-N-methoxy-p-toluenesulfonanilide or salts thereof and nitenpyram.
(xvi) An insecticide/microbicide for agricultural or horticultural use which contains 2',4'-dinitro-N-methoxy-p-toluenesulfonanilide or salts thereof and pyraclofos.

Regarding [12] mentioned above, the present inventors have found that using the compound (I), (II), (III), (IV), (V), (VI) or (II') which will be described below, or salts thereof of the present invention in combination with other agrochemical active constituents may give an increased effectiveness in their microbicidal action over that which may be obtained when each of those agents is used singly.

Those microbicides obtained by combining the sulfonamide derivatives of the present invention described above [for example, compound (I), (II), (III), (IV), (V), (VI) or compound (II') which will be described below] and other agrochemical active constituents can exert excellent effectiveness in that (1) the antimicrobial/insecticidal/acaricidal/nematocidal effectiveness may be increased relative to the cases where each agent is used separately, (2) an immediate antimicrobial/insecticidal/acaricidal/nematocidal effect is gained, (3) a wide antimicrobial/insecticidal/acaricidal/nematocidal spectrum and a sustained effectiveness are gained, which has not been realized with known antimicrobicide/insecticide/acaricide/nematocide, (4) the amounts of agents needed can be decreased compared to the cases where each agents is used singly, and (5) a more reliable protective effect can be expected compared to the cases where each agent is used singly against each harmful organism.

As the diseases protected using compound (I°) or salts are, there may be mentioned, for example, diseases of rice plant such as rice blast (*Pyricularia oryzae*), Helminthosporium leaf blight (*Helminthosporium oryzae, Cochliobolus miyabeanus*), Bakanae disease (*Gibberella fujikuroi*), seedling blight (*Rhizopus oryzae*), sheath blight (*Rhizoctonia solani*), and so on, those of oat such as crown rust (*Puccinia coronata*), and so on, those of barley such as powdery mildew (*Erysiphe graminis*), scald (*Rhynchsporium secalis*), spot-blotch (*Cochliobolus sativus*), yellow mottleleaf (*Helminthosporium gramineum, Pyrenophora gramineum*), net blotch (*Pyrenophra teres*), stinking smut (*Tilletia caries*), loose smut (*Ustilago nuda*), and so on, those of wheat such as powdery mildew (*Erysiphe graminis*), glume-blotch (*Leptosphaeria nodorum, Septoria nodorum*), stripe rust (*Puccinia striiformis*), Typhula snow blight (*Typhula incarnate*), eye spot (*Pseudocercosporella herpotrichoides*), snow mold (*Calonectria graminicola, Fusarium nivale*), stem rust (*Puccinia graminis*), black snow blight (*Typhula ishikariensis*), scab (*Gibberella zeae*), leaf rust (*Puccinia recondita, Puccinia triticina*), stripe (*Helminthosporium gramineum*), stinking smut (*Tilletia caries*), speckled leaf blight (*Septoria tritici*), loose smut (*Ustilago tritici*), and so on, those of corn such as damping-off (*Pythium debaryanum*), and so on, those of rye such as purple snow mold (*Fusarium nivale*), and so on, those of potato such as foot rot (*Phytophthora infestans*), and so on, those of tabacco plant such as downy mildew (*Peronospora tabacina*), foot rot (*Phytophthora parasitica* var), septoria blight (*Cercospora nicotianae*), mosaic disease (tobacco mosaic virus), and so on, those of sugar beet such as leaf spot (*Cercospora beticola*), damping-off (*Pythium debaryanum, Rhizoctonia solani*), take-all (*Pythium aphanidermatum*), and so on, those of paprika such as gray mold (*Botrytis cinerea*), and so on, those of kidney bean such as gray mold (*Botrytis cinerea*), sclerotinia seed rot (sclerotial rot) (*Sclerotinia sclerotiorum*), southern blight (*Corticium rolfsii*), and so on, those of broad bean such as powdery mildew (*Erysiphe polygoni, Sphaerotheca fuliginea*), rust (*Uromyces fabae, Uromyces phaseoli*), gray mold (*Botrytis cinerea*), and so on, those of peanut such as Ascochyta spot (*Mycosphaerella arachidicola*), and so on, those of cabbage such as damping blight (*Rhizoctonia solani*), and so on, those of cucumber such as powdery mildew (*Sphaerotheca fuliginea*), stem rot (*Fusarium oxysporum*), gummy stem blight (*Mycosphaerella melonis*), downy mildew (*Pseudoperonospora cubensis*), gray mold (*Botrytis cinerea*), sclerotial seed rot (*Sclerotinia sclerotiorum*), anthracnose (*Colletotrichum lagenarium*), damping blight (*Fusarium oxysporum, Pythium aphanidermatum, Rhizoctonia solani*), mosaic disease (Cucumber mosaic virus), and so on, those of KOMATSUNA such as Alternaria sooty spot (*Alternaria brassicicola*), club root (*Plasmodiophora brassicae*), and so on, those of celery such as speckled leaf blotch (*Septoria apii*), and soon, those of radish such as yellows (*Fusarium oxysporum*), and so on, those of tomato such as Fusarium wilt (*Fusarium oxysporum*), foot rot (*Phytophthora infestans*), ring leaf-spot (*Alternaria solani*), gray mold (*Botrytis cinerea*), leaf blight (*Phytophthora capsici*), black rot (*Alternaria tomato*), and so on, those of eggplant such as brown rot (*Phytophthora capsici*), Verticillium wilt (*Verticillium albo-atrum*), and so on, those of Chinese cabbage such as black rot (*Alternaria japonica*), club root (*Plasmodiophora brassicae*), and so on, those of sweet pepper such as foot rot (*Phytophthora capsici*), gray mold (*Botrytis cinerea*), and so on, those of lettuce such as gray mold (*Botrytis cinerea*), and so on, those of citrus fruits such as pod and stem blight (*Diaporthe citri*), and so on, those of pear such as scab (*Venturia nashicola*), black rot (*Alternaria kikuchiana*), brown-spot (*Gymnosporangium haraeanum*), and so on, those of grape such as downy mildew (*Plasmopara viticola*), gray mold (*Botrytis cinerea*), Sphaceloma scab (*Elsinoe ampelina*), and so on, those of peach such as leaf curl (*Taphrina deformans*), shot hole (*Mycosphaerella cerasella*), and so on, those of apple such as powdery mildew (*Podosphaera leucotria*), scab (*Cladsporium carpophilum*), gray mold (*Botrytis cinerea*), black rot (*Venturia inaequalis*), brown spot (*Gymnosporangium yamadae*), white root rot (*Rosellinia nectrix*), Alternaria leaf spot (*Alternaria mali*), and so on, and other deseases of grains, fruits and vegetables such as oil-seed rape, sunflower, carrot, pepper, strawberry, melon, kiwi fruit, onion, leek, sweet potato, fig, ume, asparagus, persimmon, soybean, adzukibean, watermelon, crown daisy, spinach, tea and so on. Thus, compound ($I^0$) or salts thereof show high activities against deseases caused by microorganisms of, especially the genus Pyricularia, Cochliobolus, Curvularia, Pyrenophora, Alternaria, and others akin to them. As for examples of deseases caused by those microbes, there may be mentioned rice blast, Helminthosporium leaf spot, and discolored rice grains of rice plant, spot-blotch, stripe, and net blotch of barley, stripe and spot-blotch of wheat, Helminthosporium leaf spot of corn, early blight of potato, Alternaria sooty spot of HAKUSAI, ring leaf-spot and black rot of tomato, black rot of Chinese cabbage, black rot of pear, and Alternaria leaf spot of apple, and so on.

Among compound ($I^0$) or salts thereof mentioned above, those which have, as $Z^0$, a group represented by —$OR^3$ or salts thereof show excellent protective effectiveness against clubroot disease in the plants of Brassica family (for example, canola, turnip, cauliflower, cabbage, KOMATSUNA, rape seed, and Chinese cabbage.

Among them, compound (I), (II) and (III) mentioned-above or salts thereof, which have, as $Z^1$, $Z^2$ and $Z^3$, a group represented by —$OR^3$, respectively, are more preferable, especially preferable being compound (II') below or salts thereof.

Compound (II') are compounds represented by the Formula (II'):

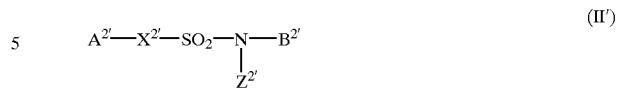

or salts thereof,

[where $A^{2'}$, $X^{2'}$ and $B^{2'}$ have the same meanings as $A^2$, $X^2$ and $B^2$ mentioned above, respectively, $Z^{2'}$ is a group represented by —$OR^3$ ($R^3$ has the same meaning as that mentioned above)].

Among the compounds included in compound (II'), preferable compounds or salts thereof are those which have, as $A^{2'}$, either (1) a $C_{6-14}$ aryl group which may substituted with 1 to 5 substituents selected from (i) a $C_{1-4}$ alkyl group which may be substituted with 1 to 5 halogens, (ii) a $C_{1-4}$ alkoxy group which may be substituted with 1 to 5 halogens,(iii) an amino group which may be substituted with 1 or 2 $C_{1-4}$ alkyl-carbonyl, (iv) the $C_{1-4}$ alkoxy-carbonyl group, (v) halogen atoms, (vi) the cyano group, and (vii) the nitro group, or (2) the thenyl group, the triazolyl group, the imidazolyl group, the isooxazolyl group, the pyrazolyl group, the pyridyl group, the quinolyl group, the benzothiadiazolyl group, the imidazothiazolyl group or the imidazopyridyl group, each of which may be substituted with 1 to 5 substituents selected from (i) the $C_{1-4}$ alkyl group, (ii) the $C_{1-4}$ alkoxy-carbonyl group, (iii) the carbamoyl group, (iv) mono- or di-$C_{1-4}$ alkylcarbamoyl group, (v) the $C_{1-4}$ alkylsulfonyl group, (vi) halogen atoms, (vii) the carboxyl group and (viii) the cyano group, as $X^2$ is (1) the chemical bond, (2) the methylene group which may be substituted with 1 or 2 $C_{1-4}$ alkyl, or (3) the vinylene group which may be substituted with 1 or 2 $C_{1-4}$ alkyl, $B^2$ is a $C_{6-14}$ aryl group which may be substituted with 1 to 5 Substituents selected from (1) a $C_{1-4}$ alkyl group which may be substituted with 1 to 5 substituents such as halogen, hydroxy, imino, hydroxyimino, $C_{1-4}$ alkoxyimino, hydrazono, mono- or di-$C_{1-4}$ alkyl-hydrazono and $C_{1-4}$ alkylthio, (2) the $C_{2-4}$ alkynyl group, (3) the hydroxy group, (4) the $C_{1-4}$ alkoxy group which may be substituted with 1 to 5 substituents selected from halogens and $C_{1-4}$ alkoxy, (5) the $C_{1-4}$ alkyl-carbonyloxy group, (6) the $C_{1-4}$ alkylthio group, (7) the $C_{1-4}$ alkylsulfinyl group, (8) the $C_{1-4}$ alkylsulfonyl group, (9) mono- or di-$C_{1-4}$ alkylsulfamoyl group, (10) the amino group, (11) the formyl group, (12) the $C_{1-4}$ alkoxy-carbonyl group, (13) the carbamoyl group, (14) mono- or di-$C_{1-4}$ alkylcarbamoyl group, (15) the thiocarbamoyl group, (16) halogen atoms, (17) the carboxyl group, (18) the thiocyanato group, (19) the cyano group, (20) the nitroso group and (21) the nitro group, $Z^2$ is a group which is represented by —$OR^3$ (wherein $R^3$ is a $C_{1-4}$ alkyl group or a $C_{1-4}$ alkyl-carbonyl group) or salts thereof.

More preferable embodiments of compound (II') or salts thereof are as follows:

Preferably, $A^{2'}$ is (a) a phenyl group which may be substituted with 1 to 3 substituents selected from $C_{1-4}$ alkyl which may be substituted with 1 to 3 halogens, halogens and nitro, (b) a thienyl group which may be substituted with 1 to 3 halogens, or (c) a pyrazolyl group which may be substituted with 1 to 3 substituents selected from $C_{1-4}$ alkyl and halogens, a phenyl group substituted with a methyl group at 4-position being especially preferable.

Preferably, $B^{2'}$ is a phenyl group which may be substituted with substituents selected from (a) the $C_{1-4}$ alkyl group which may be substituted with 1 to 5 (preferably with 1 to 3) halogen atoms, (b) halogen atoms (c) the cyano group and (d) the nitro group, especially preferable being phenyl groups which have substituents at the 2- or 4- position.

$Z^2$ should preferably be a $C_{1-4}$ alkoxy group or a $C_{1-4}$ alkyl-carbonyloxy group, especially preferable being methoxy and ethoxy groups.

Preferably, $X^2$ is a chemical bond (a single bond or a bond).

Those preferable features of $A^{2'}$, $B^{2'}$, $Z^{2'}$ and $X^{2'}$ mentioned in (1) to (4) above, may be combined together arbitrarily.

Since compound ($I^0$) or salts thereof have microbicidal action and are of very low toxicity and safe to handle, they can be used as excellent microbicidal compositions. The compositions of the present invention can be used in a manner similar to the known microbicidal compositions, and can exert superior effect to the previously known compositions. The compositions of the present invention can be used by spraying them on the irrigated rice field, a field, an orchard, and non-cultivated land, and so on, by the per se known method. More specifically, they can be used, for example, by treating a seed bed with them, spraying them on the stem/leaves of the plants, spraying them in the water of the irrigated field, by treating seeds or the soil with them, and applying them directly on the stem of fluit trees. And, the amount used may be, in general, 0.3 g to 3000 g effective constituents per 1 hectare, or more preferably 50 g to 1000 g effective constituents(compound($I^0$) or salts thereof) per 1 hectare, although it can be altered within a wide range according to the time, place, and method of applying. Furthermore, in cases where the compositions of the present invention are wettable powders, they can be used by diluting them to adjust the final concentration of the effective constituents to a range of 0.1 to 1000 ppm, or more preferably to 10 to 500 ppm.

The contents of compound ($I^0$) or salts thereof to the whole amount of the composition can usually be about 0.1 to 80 wt %, or more preferably about 1 to 20 wt % or so. More specifically, when they re used as an emulsion, liquids, wettable powders (for example wettable granules), aqueous suspensions, microemulsions and so on, they can be used in a ratio, in general, of about 1 to 80wt % or so, or more preferably of about 1 to 20 wt % or so, and when they are used as ointments or powders and so on, they can be used usually in a ratio of about 0.1 to 50 wt % or so, or more preferably in that of about 1 to 20 wt % or so. When they are used as granules, tablets, Jumbo agents and so on, they can be used usually in a ratio of about 5 to 50 wt % or so, or more preferably of about 1 to 20 wt % or so. The other agrochemical active constituents (for example, insecticides, acgaricides, herbicides and (or) microbicides) which may be mixed to prepare compositions of the present invention, can be used usually in a ratio of about 1 to 80 wt % or so, or more preferably in that of about 1 to 20 wt % or so to the whole amount of the compositions. The contents of the additives other than the active constituents mentioned above are in general about 0.001 to 99.9 wt % or so, or more preferably about 1 to 99 wt % or so, although they vary depending upon the kinds, contents or preparation form of the agrochemical active.

More specifically, it is preferable to add, to the total amount of the compositions, usually about 1–20 wt % or so, or more preferably about 1–15 wt % of surfactants, about 1–20 wt % or so fluidization auxiliaries, about 1–90 wt % or so, or more preferably about 1–70 wt % or so of carriers. To give more specific examples, in the cases where liquids are to be prepared, it is usually preferable to add about 1–20 wt % or so , or more preferably 1–10 wt % or so of surfactants, and 20–90 wt % or so of water. It is preferable to dilute emulsions or wettable powders (for example wettable granules) and so on to an appropriate volume (for example, to about 100 to 5000 times of volume), for example, with water and so on before use, and to spray it (them).

Compound ($I^0$) or salts thereof can be manufactured, for example, according to the reaction equations (A), (B), (C) or by means of the synthetic method (D) given below:

Reaction Equations (A)

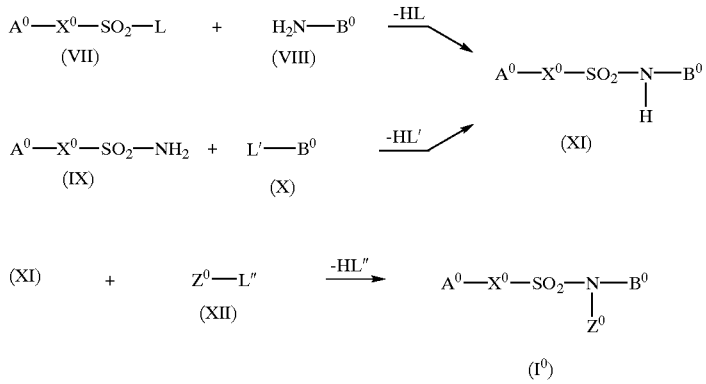

Compound ($I^0$) or salts thereof can be manufactured by making compounds XI which are obtainable by the reaction of sulfonylating agents represented by Formula (VII)

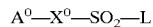

(wherein $A^0$ and $X^0$ have the same meanings as those mentioned above, and L is a leaving group) with amines represented by Formula (VIII)

(wherein $B^0$ has the same meaning as mentioned above), or salts thereof or by the reaction of sulfonamides represented by Formula (IX)

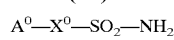

(wherein the symbols have the same meanings as those mentioned above) or salts thereof, with the compounds represented by Formula (X)

(wherein L' is a leaving group and $B^0$ has the same meaning as mentioned above) or salts thereof to give the compounds represented y Formula (XI), (wherein each symbol has the same meaning as mentioned above) and Formula(XI):

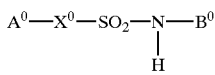

react with electrophiles of Formula (XII)

(wherein L" is a leaving group, and $Z^0$ has the same meaning as mentioned above).

As the sulfonylating agent represented by Formula (VII), there can be mentioned, for example, sulfonyl chloride, sulfonyl bromide, and sulfonic anhydride, and so on.

As the leaving group represented by L, L' or L", there can be mentioned, for example, halogen atoms such as fluorine, chlorine, bromine, and iodine, a lower alkoxy (preferably a $C_{1-4}$ alkoxy) group such as methoxy, ethoxy, propoxy, and so on, a phenoxy group, a lower alkylthio (preferably a $C_{1-4}$ alkylthio) group such as methylthio, ethylthio, propylthio, and so on, a lower alkylsulfinyl (preferably a $C_{1-4}$ alkylsulfinyl) group such as methylsulfinyl, ethylsulfinyl, propylsulfinyl, a lower alkylsulfonyl (preferably a $C_{1-4}$ alkylsulfonyl) group such as methylsulfonyl, ethylsulfonyl, propylsulfonyl, and so on, a lower alkylsulfonyloxy (preferably a $C_{1-4}$ alkylsulfonyloxy) group such as methylsulfonyloxy, ethylsulfonyloxy, propylsulfonyloxy group, and so on, a trifluoromethylsulfonyloxy group, a benzenesulfonyloxy group, a p-toluenesulfonyloxy group, and so on.

① The reaction of sulfonylating agents (VII) with amines (VIII) can be carried out according to the method described in, for example, The Journal of Pesticide Science Society of Japan 21,p31(1996), Japanese Patent Publication for Opposition 6836/1970, and so on. Japanese Publication Patent for Opposition 19199/1965, Japanese Patent for Laid-Open 31655/1982, Japanese Patent Application Laid-Open 219159/1983, Japanese Patent Application Laid-Open 197553/1986, Japanese Patent Application Laid-Open 271270/1986, Japanese Patent Application Laid-Open 57565/1988, Japanese Patent Application Laid-Open 272566/1989, Japanese Patent for Laid-Open 156953/1989, Japanese Patent Application Laid-Open 72151/1990, Japanese Patent Application Laid-Open 96560/1990, Japanese Patent Application Laid-Open 231465/1990, Japanese Patent Application Laid-Open 212467/1990, Japanese Patent Application Laid-Open 54161/1992, Japanese Patent Application Laid-Open 145060/1992, The reaction of sulfonamide bodies (IX) with compounds (X) are usually carried out both with or without solvent.

As the solvent, in cases where it is used, there can be mentioned, for example, hydrocarobons such as petrol ether, pentane, hexane, cyclohexane, benzene, toluene, xylene, and so on, halogenated hydrocarbons such as dichloromethane, chloroform, carbon tetrachloride, 1,2-dichloroethane, 1,2-dichloroethylene, trichloroethylene, chlorobenzene, and so on, ethers such as diethyl ether, diisopropyl ether, tetrahydrofuran, 1,4-dioxane, dimethoxyethane, ethyleneglycol monomethylether, diethyleneglycol dimethylether, and so on, esters such as ethyl acetate, butyl acetate, and so on, ketones such as acetone, methyl ethyl ketone, and so on, nitrites such as acetonitrile, propionitrile, and so on, amides such as N,N-dimethylformamide, N,N-dimethylacetamide, N-methylpyrrolidone, and so on, sulfoxides such as dimethylsulfoxide, and so on, sulfones such as sulfolan, and so on, nitro compounds such as nitromethane, nitrobenzene, and so on, alcohols such as methanol, ethanol, isopropanol, 1-butanol, ethylene glycol, and so on, carbon disulfide, water, and so on.

The reaction can be carried out at temperatures selected from −100 to 300° C., or more preferably from −50 to 200° C. The reaction time is 1 minute to 1 week, or more preferably 5 minutes to 24 hours.

Acids or bases may be added to promote the reaction. As the acids employable for that purpose, there can be mentioned, for example, hydrofluoric acid, hydrochloric acid, hydrobromic acid, hydroiodic acid, phosphoric acid, sulfuric acid, nitric acid, perchloric acid, and organic acids such as formic acid, acetic acid, propionic acid, trifluoroacetic acid, tartaric acid, malic acid, oxalic acid, succinic acid, benzoic acid, picric acid, methanesulfonic acid, p-toluenesulfonic acid, trifluoromethanesulfonic acid, and so on.

As the bases employable, there can be mentioned, for example, metal hydroxides such as lithium hydroxide, sodium hydroxide, potassium hydroxide, calcium hydroxide, and so on, metal carbonates such as sodium carbonate, potassium carbonate, sodium bicarbonate, potassium bicarbonate, and so on, metal hydrides such as sodium hydride, potassium hydride, carcium hydride, and so on, metal amides such as lithium diisopropylamide, sodium amide, potassium amide, and so on, organolithium reagents such as methyllithium, n-butyllithium, sec-butyllithium, tert-butyllithium, phenyllithium, and so on, organomagnesium reagents (Grignard reagent) such as methylmagnesium bromide, ethylmagnesium chloride, and so on, metals such as lithium metal, sodium metal, potassium methal, and so on, organic bases such as trimethylamine, triethylamine, diisopropylamine, N,N-dimethyaniline, pyridine, lutidine, collidine, DMAP (4-dimethylaminopyridine), TMEDA (tetramethylethylenediamine), DBU (1,8-diazacyclo[5.4.0] undec-7-ene), and so on.

Further, in order to promote the reaction, metal salts (for example, oxides, fluorides, chlorides, bromides, iodides, sulfides, sulfates, nitrates, phosphates, perchlorate, and so on) or metal elements of titanium, vanadium, chromium, manganum, iron, cobalt, nickel,copper, zinc, zilconium, niobium, molybdenum, ruthenium, rhodium, palladium, silver, cadmium, tungsten , platinum, gold, mercury, and so on, can be used as catalyst in an amount of 0.000001 to 1000 equivalents, or more preferably 0.001 to 10 equivalents.

The reactions of sulfonamide bodies (XI) with electrophiles are usually carried out with or without solvent.

As the solvent, in cases where it is employed, there can be mentioned those solvents which can be employed in reaction ② above. The reactions can be carried out at temperatures of −100 to 300° C., or more preferably at −50 to 200° C. And the reaction time is from 1 minutes to 1 week, or more preferably from 5 minutes to 24 hours. Acids and bases may be added to promote the reaction, and as such acids and bases, there can be mentioned the same ones as mentioned in reaction ② above also here.

Further, in order to promote the reaction, metal salts (for example, oxides, fluorides, chlorides, bromides, iodides, sulfides, sulfates, nitrates, phosphates, perchlorate, and so on) or metal elements of titanium, vanadium, chromium, manganum, iron, cobalt, nickel,copper,zinc, zilconium, niobium, molybdenum, ruthenium, rhodium, palladium, silver, cadmium, tungsten (wolfram), platinum, gold, mercury, and so on, can be used as catalyst in an amount of 0.000001 to 1000 equivalents, or more preferably 0.001 to 10 equivalents. The electrophiles (XII) can be used even in a large excess, unless they have an effect wrongly on the reaction of sulfonamides (XI). However, it is usually preferable to use 1.0 to 10 equivalents of them. As such electrophiles, there can be mentioned, for example, halogenides such as methyl iodide, ethyl iodide, propyl bromide, propyl iodide, isopropyl idodide, cyclopropyl bromide, butyl bromide, isobutyl bromide, allyl chloride, allyl bromide, propargyl bromide, 1,2-dibromoethane, acetyl chloride, propargyl chloride, methyl chloro-formate, ethyl chloroformate, methanesulfonyl chloride, benzene-sulfonyl chloride, p-toluenesulfonyl chloride, and so on, sulfuric acid esters such as dimethyl sulfate, diethyl sulfate, and so on, sulfuric acid esters such as dimethyl sulfate, diethyl sulfate, and so on, sulfonates such as methyl methanesulfonate, ethyl benzenesulfonate, isopropyl p-toluenesulfonate, and so on, and acid anhydrides such as acetic anhydride, trifluoroacetic acid anhydride, trifluoromethane-sulfonic acid anhydride, mixed anhydride of acetic acid-formic acid, and so on.

Reaction Equation (B)

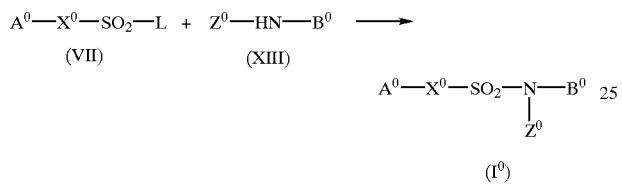

Compound ($I^0$) or salts thereof can be obtained by reacting sulfonylating agents represented by Formula (VII) mentioned above, with amines represented by the Formula (XIII) (wherein symbols have the same meanings as mentioned above) or salts thereof.

The reactions of this type are usually carried out with or without solvent. As the solvent which is employable in reactions with solvent, there can be mentioned those mentioned in (A) ② above. The reaction temperature is −100 to 300° C., or more preferably −50 to 200° C., and the reaction time is from 1 minutes to 1 week, or, more preferably from 5 minutes to 24 hours. Acids and bases may be added to promote the reaction, and as those acids and bases, there can be mentioned the same ones as those mentioned above regarding the reaction equation (A) ② described above. Furthermore, in order to promote the reaction, metal salts (for example, oxides, fluorides, chlorides, bromides, iodides, sulfides, sulfates, nitrates, phosphates, perchlorate, and so on) or metal elements of titanium. vanadium. chromium, manganum, iron, cobalt, nickel,copper, zinc, zilconium, niobium, molybdenum, ruthenium, rhodium, palladium, silver, cadmium, tungsten, platinum, gold, mercury, and so on, can be added as catalyst in an amount of 0.000001 to 1000 equivalents, or more preferably 0.001 to 10 equivalents.

Reaction Equation (C)

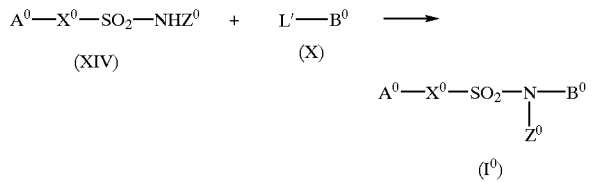

Compound ($I^0$) or salts thereof can be obtained by reacting sulfonamides represented by Formula XIV (wherein each symbol has the same meaning as mentioned before) or salts thereof, with compounds represented by the Formula (X) above or salts thereof.

$$A^0\!-\!X^0\!-\!SO_2\!-\!NHZ^0 \qquad (XIV):$$

This kind of reaction is carried out usually with or without solvent. As the solvent which is employable in reactions using solvent, there can be mentioned those described in (A) ② above. The reaction temperature is −100 to 300° C., or more preferably at −50 to 200° C., and the reaction time is from 1 minutes to 1 week, or more preferably from 5 minutes to 24 hours. Acids and bases may be added to promote the reaction, and as for those acids and bases, there may be mentioned the same ones as those mentioned above regarding the reaction equation (A) ②. Further, in order to promote the reaction, metal salts (for example, oxides, fluorides, chlorides, bromides, iodides, sulfides, sulfates, nitrates, phosphates, perchlorate, and so on) or metal elements of titanium. vanadium. chromium, manganum, iron, cobalt, nickel,copper, zinc, zilconium, niobium, molybdenum, ruthenium, rhodium, palladium, silver, cadmium, tungsten, platinum, gold, mercury, and so on, can be added as catalyst in an amount of 0.000001 to 1000 equivalents, or more preferably 0.001 to 10 equivalents.

When compounds (VII) to (XIV) are in the forms of salts, they can be in the types of the salt similar to those mentioned concerning compound ($I^0$)

Synthetic Method (D)

When compound ($I^0$) or salts thereof have nitro groups as the substituent in $B^0$, they can be obtained by nitrating the corresponding raw-material (compounds which have no substituents at the positions where the nitro substitution will be introduced) with nitrating agents [synthetic method (D)]. As nitrating agents, 30 to 100% nitric acids and fuming nitric acids are commonly used. However, other nitrating agents such as alkali metal nitrates, for example, sodium nitrate, potassium nitrate, and so on, alkyl ester nitrates such as ethyl nitrate, amyl nitrate, and so on, nitronium tetrafluoroborate ($NO_2BF_4$), nitronium trifluoromethanesulfonate ($NO_2CF_3SO_3$), nitrogen oxides (for example, $NO_2$, $N_2O_3$, $N_2O_4$, $N_2O_5$), and so on. Fifty to 100% nitric acids are especially preferable. The nitrating agents may be used about in 1.0 to 20 equivalents to the raw-material which is not substituted at positions where nitro substitution will occur. More preferably, the ratio of nitrating agent to the raw material is 1.0 to 10 equivalents, or about 1.0 to 3.0 equivalents in cases where nitric acid of 90% or so is used.

Although the nitration reaction may be carried out in the absence of solvent, it is usually done in the presence of acidic solvents such as sulfuric acid, acetic acid, acetic anhydride, trifluoroacetic acid anhydride, trifluoromethane sulfonic acid, and so on. If it is desirable, any solvents or mixtures of solvents which do not affect wrongly to the reaction can be used. As such solvents, there can be mentioned, in addition to the acidic solvents mentioned above, those solvents described regarding the reaction (A) ② above. Those solvents can either be used singly, or, if necessary, as mixtures of two or more (preferably 2 to 3) species of them together, in appropriate ratios of, for example, about 1:1 to 1:10 (v/v ratios).

In the cases where the reaction solvent is not homogeneous, the reaction may be made in the presence of phase-transfer-catalysts, for example, quaternary ammonium salts such as triethylbenzyl-ammonium chloride, tri-n-octylmethylammonium chloride, trimethyldecylammonium chloride, tetramethylammonium bromide, cetyl-pyridinium bromide, and so on, and crown ethers, and so on.

The most preferable solvents are acetic acid and acetic anhydride. The reaction temperature is usually about −50 to 200° C., more preferably about −20 to 130° C., and the reaction time is from about 1 mimute to 24 hours, more preferably from about 15 minutes to 3 hours.

Here, the compound (VI) or salts thereof can be prepared according to the method (D) above, thus, for example, by nitrating the compounds which may be represented by the Formula

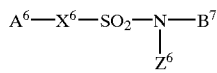

(where B7 is a phenyl group which is substituted with substituents selected from halogen atoms (for example, fluorine, chlorine, bromine, iodine), nitro, and cyano, but at least one of the 2- and 6-positions is remained unsubstituted), and other symbols have the same meanings as mentioned above) or satls thereof.

The "phenyl group of which at least one of the 2- and 6-positions is remained unsubstituted" in $B^6$ can be substituted with substituents selected from halogen atoms, nitro, and cyano, and the number of substituents can be 1 to 3.

In the cases where compound ($I^0$) or salts thereof have substituents, those substituents can either be introduced in advance at the stage of the raw material or the intermediates (VII) to (XIV), or necessary sabstituents can be introduced or converted into afterward, after synthesizing compound ($I^0$) or salts thereof, by means of known methods for converting functional groups following the methods describedin, for example, Organic Reactions, Organic Syntheses, Synthetic Methods of Organic Chemistry, Compendium of Organic Synthetic Methods), and so on.

As such substituent convertion reactions, there may be mentioned, for example, the synthetic methods of (E) to (T) which will be followed, but these are only examples and the methods applicable, and should not be considered to be restricted to them.

Synthetic Method (E)

Those compounds which have alkylthio groups and can be prepared from known raw materials according to the reaction equations (A), (B) or (C), may be converted into compounds which have alkylsulfinyl groups by reacting them with 0.5 to 2.0 equivalents, or more preferably with 0.8 to 1.5 equivalents of appropriate oxidating agent (for example, hydrogen peroxide, peracetic acid, perbenzoic acid, meta-chloroperbenzoic acid, potassium permanganate). Similarly, but with 1.5 or more equivalents, or more preferably, with 2.0 to 3.0 equivalents of oxidating agents, the compounds which have alkylthio groups which have alkylsulfonyl groups can be converted into the corresponding alkylsulfonyl compounds.

Synthetic Method (F)

Those compounds which have alkoxycarbonyl groups and can be prepared from known raw materials according to the reaction equations (A), (B) or (C), may be converted into compounds having carboxyl groups by subjecting them to hydrolysis reaction in the presence of bases (for example, sodium hydroxide, potassium hydroxide, and so on) or acids (for example, sulfuric acid, hydrochloric acid, and so on).

Synthetic Method (G)

Those compounds which have carboxyl groups, can be esterified by reacting them with alcohols (for example, methanol, ethanol, and so on), in the presence of appropriate acids (for example, sulfuric acid, p-toluenesulfonic acid, and so on). Further, the carboxyl groups can be converted into compounds which have esters or amides by first activating the carboxyl groups (for example, by converting it (them) into acid chloride with thionyl chloride or phosphorus oxychloride, by converting it (them) into acid anhydride with carboxylic chloride,chlorofolmic ester by activating it (them) with dicyclohexylcarbodiimide, methylpyridinium chloride, and so on), and then by reacting the products with alcohols or amines, respectively.

Synthetic Method (H)

Compounds having amide ($CONH_2$) groups can be converted into compounds having cyano groups by reacting the former compounds with dehydrating agents (for example, acetic anhydride, trifluoroacetic acid anhydride, thionyl chloride, phosphorus oxychloride, phosphorus pentoxide, and so on) in the presence or absence of bases (for example, pyridine, triethylamine, and so on).

Synthetic Method (I)

Compounds having amide groups can be converted into compounds with thioamide groups by reacting the amide compounds with Lawesson's Reagent (2,4-bis(4-methoxyphenyl)-1,3-dithia-2,4-di-phosphetane-2,4-di sulfide) or with phosphorus pentasulfide, those compounds having cayno groups can be converted into compounds having thioamide groups by adding hydrogen sulfide to the cyano groups.

Synthetic Method (J)

Compounds with carboxyl groups prepared by the synthetic method (F), and so on, compounds with ester groups or amide groups prepared by the synthetic method (G), and so on, or compounds with cyano groups prepared by the synthetic method (H), and so on, can be converted to compounds with formyl groups by subjecting them to reduction reaction with appropriate reducing agents (for example, catalytic hydrogenation, diborane, silanes, sodium borohydride, lithium aluminum hydride, diisobutyl aluminum, and so on), or compounds with methyl groups or hydroxymethyl groups prepared by the synthetic methods of (A) to (C) can be converted into compounds with formyl groups by oxidizing them with oxidizing agents (for example, chromic acids, dichromates, manganum dioxide, potassium permanganate, selenium dioxide, dimethylsulfoxide-oxalyl chloride-triethylamine [Swern oxidation], and so on).

Synthetic Method (K)

Compounds (compounds unsubstituted at positions where formyl group can be Introduced) which can be prepared from known raw material accoding to the methods shown by the reaction equations (A), (B) or (C) can be converted into compounds with formyl groups by formulating them with formylating agents (for example, phosphorus oxychloride-N,N-dimethylformamide [Vilsmeier reaction], zinc chloride-hydrogen cyanide-hydrogen chloride [Gattermann reaction], chloroform-sodium hydroxide [Reimer-Tiemann reaction] and dichloromethoxyethane-aluminum chloride, and so on).

Synthetic Method (L)

Oximes and hydrazones can be prepared from compounds with formyl groups which can be prepared by the synthetic methods (J) or (K), by reacting them with hydroxylamines or hydrazines, respectively.

Synthetic Method (M)

Compounds with haloalkyl groups can be converted to compounds with various functional group by making them to react with appropriate nucleophiles (for example, mercaptanes such as methyl mercaptane, ethyl mercaptane, and so on, amines such as ammonia, methylamine, dimethylamine, and so on, alcohols such as methanol, ethanol, and so on) in the presence of appropriate bases (for example, sodium hydroxide sodium hydride, sodium carbonate, potassium carbonate, and so on).

Synthetic Method (N)

Compounds with haloethyl group which can be prepared from known raw material accoding to the methods shown by the reaction equations (A), (B) or (C) can be converted into compounds with vinyl groups by subjecting them to dehydrohalogenation reaction with bases.

Synthetic Method (O)

Compounds with terminal acetylene group which can be prepared from known raw material accoding to the methods shown by the reaction equations (A), (B) or (C) can be converted into compounds with haloacetylene groups by making them to react with halogen sorces (for example, N-chlorosuccinimide, N-bromosuccinimide, N-iodosuccinimide, chlorine, bromine,iodine, and so on) in the presence of appropriate bases (for example, sodium hydroxide, sodium hydride, sodium carbonate, potassium carbonate, n-butyllithium, and so on).

Synthetic Method (P)

Compounds with nitro groups which can be obtained according to the reaction equation (A), (B), or (C), or the synthetic method (D), can be converted into compounds with amino groups by making them to react with reducing agents (for example, catalytic hydrogenation, iron, tin, zinc, ferrous chloride, stannous chloride, and so on).

Synthetic Method (Q)

Compounds with amino groups which can be synthesized by the synthetic method (P), and so on, may be converted to compounds with nitroso groups by making them to react with oxidizing agents (for example, hydrogen peroxide, peracetic acid, perbenzoic acid, meta-chloro-perbenzoic acid, potassium permanganate, and so on).

Synthetic Method (R)

Compounds with nitroso groups which can be prepared by the synthetic method (Q), and so on, may be converted to compounds with azoxycyano groups by making them to react first with N-oxidizing agents (for example, N-chlorosuccinimide, N-bromosuccinimide, iodobenzene diacetate, and so on), and then with cyanamide in the presence of bases (for example, sodium carbonate, potassium carbonate, sodium hydroxide, and so on).

Synthetic Method s

Compounds with hydroxy groups protected with a protecting group (for example, methoxymethyl group, dihydropyranyl group, acetyl group, methoxycarbonyl group, benzyl group, tert-butylmethylsilyl group, and so on) which can be produced from known raw materials according to the reaction equation (A), (B), or (C), can be converted into compounds with hydroxyl groups by subjecting them to deprotection reactions according to the method described in, for example, "Protective Groups in Organic Synthesis", and so on.

Synthetic Method (T)

Compounds with hydroxy groups which can be prepared by the synthetic method s, and so on, may be converted to compounds with various substituents by making them to react with electrophiles (for example, methyl iodide, dimethyl sulfate, ethyl iodide, isopropyl iodide, propyl bromide, 1,2-dibromo ethane, acetic anhydride, acetyl chloride, methyl chloroformate, trifluoroacetic anhydride, methanesulfonyl chloride, p-toluenesulfonyl chloride, and so on), e.g., by means of substitution reactions, in the presence of appropriate bases (for example, sodium hydroxide, sodium hydride, sodium carbonate, potassium carbonate, and so on).

Hereunder, the present invention is illustrated in more detail by reference to the following Examples, Formulation Examples, and Test Examples. However, the scope of the compound ($I^0$) or salts thereof is not to be considered to be restricted to the present embodiment.

In the synthesis examples, elution in silica gel column chromatography was carried out under observation by means of TLC (Thin Layer Chromatography). In the TLC-observation, the Kieselgel 60F$_{254}$ (70–230 mesh) plates manufactured by Merck & Co., were used as the TLC-plate, and as the eluents used were the same solvent as that used in the column chromatography as eluent, and as the detection method, either the UV-detector or coloration method with iodine was adopted. As silica gel for the column chromatography, Kieselgel 60 (70–230 mesh) manufactured by Merck & Co. was used.

When a mixed solvent was used as eluent, the ratio shown in the ( ) indicates the volume to volume ratio of the solvents mixed. NMR (Nuclear Magnetic Resonance) spectrum means the proton NMR, and was measured by a Bruker AC-200P type (200 MHz) spectrometer, using tetramethylsilane as internal standard. All δ values are in ppm. Abbreviations used in the Reference Examples, Examples and Tables below have the meanings which follow, s: singlet, d: doublet, t: triplet, q: quartet, m: multiplet, dd: double doublet, dt: double triplet, dq: double quartet, septet: septet(a set of seven lines), br: broad, brs: broad singlet, ddd: double double doublet, ddt: double double triplet, brd: broad doublet, brq: broad quartet, J: coupling constant, $J_{HF}$: coupling constant of the coupling between hydrogen atom and fluorine atom, Hz: Heltz, CDCl$_3$: deutero-chloroform (chloroform-d), DMSO-d$_6$: dimethyl sulfoxide-d$_6$, DMF: N,N-dimethylformamide, %: wt %, and mp: melting point. In addition, room temperature means a temperature or temperatures within 15–25° C.

EXAMPLES

Example 1

Synthesis of 2',4'-Dichloro-N-methyl-p-toluenesulfonanilide (Compound No. 51)

To a suspension of sodium hydride (60%, 0.07 g (1.75 mmol)) in DMF (2.0 ml), 2',4'-dichloro-p-toluenesulfonanilide (0.50 g (1.58 mmol)) was added with stirring at room temperature. To the resulting mixture, after 15 minutes' stirring at room temperature, dimethyl sulfate (0.17 ml (1.80 mmol)) was added dropwise. After 15 hours' stirring at room temperature, the reaction mixture was poured into water and extracted with ethyl acetate. The extract was washed with water and saturated sodium chloride solution, successively, dried over anhydrous magnesium sulfate, and then concentrated under reduced pressure. The crystals separated were filtered and washed with diisopropyl ether to give 0.38 g (73%) of the title compound.

mp: 86.0–87.0° C.; NMR (CDCl$_3$) δ: 2.44 (3H, s), 3.17 (3H, s), 7.13 (1H, d, J=8.6 Hz), 7.22 (1H, dd, J=8.6 & 2.3 Hz), 7.30 (2H, d, J=8.4 Hz), 7.42 (1H, d, J=2.3 Hz), 7.65 (2H, d, J=8.4 Hz).

Example 2

Synthesis of N,4'-Dimethyl-3'-nitro-p-toluenesulfonanilide (Compound No. 126)

To a suspension of sodium hydride (60%, 0.14 g (3.50 mmol)) in DMF (3.0 ml), 4'-methyl-3'-nitro-p-toluenesulfonanilide (1.00 g (3.26 mmol)) was added with stirring at room temperature. To the resulting mixture, after 15 minutes' stirring at room temperature, dimethyl sulfate (0.34 ml (3.56 mmol)) was added dropwise. After one hours' stirring at room temperature, the reaction mixture was poured into water and extracted with ethyl acetate. The extract was washed with water and saturated sodium chloride solution, successively, dried over anhydrous magnesium sulfate, and then concentrated under reduced pressure. Diethyl ether was added to the residue, and the solid separated was filtered and washed to give 0.79 g (76%) of the title compound as pale yellow crystals.

mp: 103.5–106.0° C.; NMR (CDCl$_3$) δ: 2.43 (3H, s), 2.59 (3H, s), 3.17 (3H, s), 7.27 (2H, d, J=8.3 Hz), 7.31 (1H, d, J=8.2 Hz), 7.43 (2H, d, J=8.3 Hz), 7.45 (1H, dd, J=8.2 & 2.3 Hz), 7.58 (1H, d, J=2.3 Hz).

Example 3

Synthesis of N-Ethyl-4'-fluoro-2'-nitro-p-toluenesulfonanilide (Compound No. 263)

To a suspension of sodium hydride (60%, 0.05 g (1.25 mmol)) in DMF (2.0 ml), 4'-fluoro-2'-nitro-p-toluenesulfonanilide (0.31 g (1.00 mmol)) was added with stirring at room temperature. To the resulting mixture, after 15 minutes' stirring at room temperature, ethyl iodide (0.30 ml (3.75 mmol)) was added dropwise. After 30 minutes' heating at 100° C. with stirring, the reaction mixture was poured into water and extracted with ethyl acetate. The extract was washed with water and saturated sodium chloride solution, successively, dried over anhydrous magnesium sulfate, and then concentrated under reduced pressure. Diisopropyl ether was added to the residue and the solid separated was filtered and washed to give 0.25 g (74%) of the title compound as pale yellow crystals.

mp: 93.0–94.5° C.; NMR (CDCl$_3$) δ: 1.18 (3H, s), 2.44 (3H, s), 3.67 (2H, brq, J=7.2 Hz), 7.10 (1H, dd, J=8.9 Hz, J$_{HF}$=5.1 Hz), 7.23 (1H, ddd, J=8.9 & 2.9 Hz, J$_{HF}$=7.2 Hz), 7.27 (2H, d, J=8.4 Hz), 7.53 (2H, d, J=8.4 Hz), 7.60 (1H, dd, J=2.9 Hz, J$_{HF}$=7.7 Hz).

Example 4

Synthesis of 4'-Chloro-N-ethyl-2'-nitro-p-toluenesulfonanilide (Compound No. 289)

To a suspension of sodium hydride (60%, 0.05 g (1.25 mmol)) in DMF (2.0 ml), 4'-chloro-2'-nitro-p-toluenesulfonanilide (0.30 g (0.92 mmol)) was added with stirring at room temperature. To the resulting mixture, after 15 minutes' stirring at room temperature, ethyl iodide (0.50 ml (6.25 mmol)) was added dropwise. After one hour's heating at 100° C. with stirring, the reaction mixture was poured into water and extracted with ethyl acetate. The extract was washed with water and saturated sodium chloride solution, successively, dried over anhydrous magnesium sulfate, and then concentrated under reduced pressure. The residue was subjected to silica gel column chromatography with ethyl acetate-hexane (1:3) as eluent, giving 0.24 g (74%) of the title compound as pale yellow crystals.

mp: 132.5–134.0° C.; NMR (CDCl$_3$) δ: 1.18 (3H, t, J=7.2 Hz), 2.44 (3H, s), 3.66 (2H, q, J=7.2 Hz), 7.05 (1H, d, J=8.6 Hz), 7.28 (2H, d, J=8.2 Hz), 7.50 (1H, dd, J=8.6 & 2.5 Hz), 7.53 (2H, d, J=8.2 Hz), 7.86 (1H, d, J=2.5 Hz).

Example 5

Synthesis of 4'-Methoxy-2'-nitro-N-isopropyl-p-toluenesulfonanilide (Compound No. 207)

To a suspension of sodium hydride (60%, 0.10 g (2.50 mmol)) in DMF (2.0 ml), 4'-methoxy-2'-nitro-p-toluenesulfonanilide (0.65 g (2.02 mmol)) was added with stirring at room temperature. To the resulting mixture, after 15 minutes' stirring at room temperature, isopropyl iodide (1.00 g (5.88 mmol)) was added dropwise. After five hours' heating at 130° C. with stirring, the reaction mixture was poured into water and extracted with ethyl acetate. The extract was washed with water and saturated sodium chloride solution, successively, dried over anhydrous magnesium sulfate, and then concentrated under reduced pressure. The residue was subjected to silica gel column chromatography with ethyl acetate-hexane (1:2) as eluent, giving 0.21 g (28.5%) of the title compound as pale brown crystals.

mp: 148.0–149.5° C.; NMR (CDCl$_3$) δ: 1.04 (3H, d, J=6.7 Hz), 1.11 (3H, d, J=6.7 Hz), 2.43 (3H, s), 3.89 (3H, s), 4.36 (1H, septet, J=6.7 Hz), 7.06 (1H, dd, J=8.8 & 2.8 Hz), 7.16 (1H, d, J=8.8 Hz), 7.28 (2H, d, J=8.3 Hz), 7.38 (1H, d, J=2.8 Hz), 7.67 (2H, d, J=8.3 Hz).

Example 6

Synthesis of 4-Chloro-4'-cyano-2'-nitro-N-(isopropyl)-benzenesulfonanilide (Compound No. 413)

(1) To a solution of 4-aminobenzonitrile (2.36 g (20.0 mmol))in pyridine (10 ml), 4-chlorobenzenesulfonyl chloride (4.35 g (20.6 mmol)) was added under cooling in a water bath (15° C.). After 18 hours' stirring at room temperature, water (100 ml) was added to the reaction mixture and the stirring was continued to bring about separation of crystals, which were then collected by filtration and washed with water to give 4.45 g (76%) of 4-chloro-4'-cyanobenzenesulfonanilide as pale orange crystals.

mp: 182.5–184.0° C.; NMR (CDCl$_3$) δ: 7.11 (1H, s), 7.18 (2H, d, J=8.8 Hz), 7.47 (2H, d, J=8.8 Hz), 7.56 (2H, d, J=8.8 Hz), 7.78 (2H, d, J=8.8 Hz).

(2) To a suspension of 4-chloro-4'-cyanobenzenesulfonanilide (4.03 g (13.8 mmol)) in 15 ml of acetic anhydride, 97% fuming nitric acid (0.61 ml (14.3 mmol)) was added dropwise with stirring at room temperature. After one hour's stirring at 50° C. the reaction mixture was poured into water to give crystals, which were then collected by filtration and washed with water to give 4.30 g (93%) of 4-chloro-4'-cyano-2'-nitrobenzenesulfonanilide as pale yellow crystals.

mp: 193.0–195.0° C.; NMR (CDCl$_3$) δ: 7.53 (2H, d, J=8.8 Hz), 7.81 (1H, dd, J=8.8 & 1.9 Hz), 7.88 (2H, d, J=8.8 Hz), 7.95 (1H, d, J=8.8 Hz), 8.50 (1H, d, J=1.9 Hz), 10.28 (1H, brs).

(3) To a suspension of sodium hydride (60%, 0.10 g (2.50 mmol)) in 4.0 ml of DMF, 4-chloro-4'-cyano-2'-nitrobenzenesulfonanilide (0.70 g (2.07 mmol)) was added with stirring at room temperature.

To the resulting mixture, after 15 minutes' stirring at room temperature, isopropyl iodide (0.50 ml (5.01 mmol)) was added dropwise. After three hours' heating at 130° C. with stirring, the reaction mixture was poured into water and extracted with ethyl acetate. The extract was washed with water and saturated sodium chloride solution, successively, dried over anhydrous magnesium sulfate, and then concentrated under reduced pressure. The residue was subjected to silica gel column chromatography with ethyl acetate-hexane (1:2) as eluent, giving 0.11 g (14%) of the title compound as pale yellow crystals.

mp: 167.5–168.5° C.; NMR (CDCl$_3$) δ: 1.07 (3H, d, J=6.7 Hz), 1.19 (3H, d, J=6.7 Hz), 4.39 (1H, septet, J=6.7 Hz), 7.46 (1H, d, J=8.3 Hz), 7.50 (2H, d, J=8.8 Hz), 7.72 (2H, d, J=8.8 Hz), 7.89 (1H, dd, J=8.3 & 2.0 Hz), 8.20 (1H, d, J=2.0 Hz).

Example 7

Synthesis of N-Allyl-4'-chloro-2'-nitro-p-toluenesulfonanilide (Compound No.299)

To a suspension of sodium hydride (60%, 0.05 g (1.25 mmol)) in DMF (2.0 ml), 4'-chloro-2'-nitro-p-toluenesulfonanilide (0.30 g (0.92 mmol)) was added with stirring at room temperature. To the resulting mixture, after 15 minutes' stirring at room temperature, allyl bromide (0.50 ml (5.78 mmol)) was added dropwise. After being stirred for 30 minutes' at 50° C. and for 15 hours at room temperature, the reaction mixture was poured into water and extracted with ethyl acetate. The extract was washed with water and saturated sodium chloride solution, successively, dried over anhydrous magnesium sulfate, and then concentrated under reduced pressure. Diisopropyl ether was added to the residue, and the crystals separated was filtered and washed to give 0.21 g (62%) of the title compound as pale yellow crystals.

mp: 77.0–78.0° C.; NMR (CDCl$_3$) δ: 2.44 (3H, s), 4.22 (2H, dt, J=6.9 & 1.2 Hz), 5.05 (1H, ddt, J=17.0 & 2.5 & 1.2 Hz), 5.11 (1H, ddt, J=10.1 & 2.5 & 1.2 Hz), 5.89 (2H, ddt, J=17.0 & 10.1 & 6.9 Hz), 7.05 (1H, d, J=8.5 Hz), 7.28 (2H, d, J=8.4 Hz), 7.48 (1H, dd, J=8.5 & 2.4 Hz), 7.54 (2H, d, J=8.4 Hz), 7.84 (1H, d, J=2.4 Hz).

Example 8

Synthesis of N-Acetyl-4'-methoxy-2'-nitro-p-toluenesulfonanilide (Compound No.213)

To a suspension of sodium hydride (60%, 0.08 g (2.00 mmol)) in DMF (3.0 ml), 4'-methoxy-2'-nitro-p-toluenesulfonanilide (0.50 g (1.55 mmol)) was added with stirring at room temperature. To the resulting mixture, after 15 minutes' stirring at room temperature, acetic anhydride (0.20 ml (2.12 mmol)) was added dropwise. After one hour's stirring at room temperature, water was poured into the reaction mixture and extracted with ethyl acetate. The extract was washed with water and saturated sodium chloride solution, successively, dried over anhydrous magnesium sulfate, and then concentrated under reduced pressure. Crystals separated was added to diethyl ether, filtered and washed to give 0.51 g (90%) of the title compound as pale yellow crystals.

mp: 172.5–174.0° C.; NMR (CDCl$_3$) δ: 2.08 (3H, s), 2.45 (3H, s), 3.94 (3H, s), 7.22 (1H, dd, J=8.8 & 2.9 Hz), 7.32 (2H, d, J=8.5 Hz), 7.37 (1H, d, J=8.8 Hz), 7.56 (1H, d, J=2.9 Hz), 7.82 (2H, d, J=8.5 Hz).

Example 9

Synthesis of N,N-bis(p-Toluenesulfonyl)-4-methoxy-2-nitroaniline (Compound No. 214)

To a solution of 4'-Methoxy-2'-nitro-p-toluenesulfonanilide (0.32 g (1.00 mmol)) in pyridine (1,0 ml), p-toluenesulfonyl chloride (0.20 g (1.05 mmol)) was added with stirring at room temperature. After 15 hours' stirring at room temperature, the reaction mixture was poured into water and crystals separated was filtered and washed to give 0.34 g (83%) of the title compound as pale yellow crystals.

mp: 180.5–182.0° C.; NMR (CDCl$_3$) δ: 2.46 (6H, s), 3.90 (3H, s), 6.95–7.15 (2H, m), 7.33 (4H, d, J=8.4 Hz), 7.45–7.55 (1H, m), 7.83 (4H, d, J=8.4 Hz).

Example 10

Synthesis of 4-Chloro-2-nitro-N-methyl-N-[(trans)-β-styrenesulfonyl]aniline (Compound No. 282)

To a suspension of sodium hydride (60%, 0.13 g (3.25 mmol)) in DMF (7.0 ml), 4-chloro-2-nitro-N-[(trans)-β-styrenesulfonyl]aniline (1.00 g (2,95 mmol)) was added with stirring at room temperature. To the resulting mixture, after 15 minutes' stirring at room temperature, dimethyl sulfate (0.32 ml (3.38 mmol)) was added. The resulting mixture was stirred at 80° C. for 3 hours, and then poured into water, extracted with diethyl ether. The extract was washed with 1% sodium hydroxide solution, water and saturated sodium chloride solution, successively, dried over anhydrous magnesium sulfate, and then concentrated under reduced pressure. Small amount of diethyl ether was added to the residue and crystals separated was filtered and washed to give 0.99 g (95%) of the title compound as pale yellow crystals.

mp: 162.0–164.0° C.; NMR (CDCl$_3$) δ: 3.28 (3H, s), 6.74 (1H, d, J=15.4 Hz), 7.35–7.60 (7H, m), 7.60 (1H, dd, J=8.6 & 2.3 Hz), 7.87 (1H, d, J=2.3 Hz).

Example 11

Synthesis of 2',4'-Dinitro-N-methylbenzenesulfonanilide (Compound No. 425)

To a suspension of sodium hydride (60%, 0.12 g (3.00 mmol)) in DMF (4.0 ml), N-methyl-2,4-dinitroaniline (0.39 g (1.98 mmol)) was added with stirring at room temperature. To the resulting mixture, after 15 minutes' stirring at room temperature, benzenesulfonyl chloride (0.38 ml (2.98 mmol)) was added dropwise. After two hours' stirring at room temperature, the reaction mixture was poured into water and extracted with diethyl ether. The extract was washed with water and saturated sodium chloride solution, successively, dried over anhydrous magnesium sulfate, and then concentrated under reduced pressure. The residue was subjected to silica gel chromatography with ethyl acetate-hexane (1:2) as eluent, to give 0.52 g (78%) of the title compound as pale yellow crystals.

mp: 151.5–153.0° C.; NMR (CDCl$_3$) δ: 3.28 (3H, s), 7.38 (1H, d, J=8.8 Hz), 7.45–7.75 (5H, m), 8.39 (1H, dd, J=8.8 & 2.6 Hz), 8.73 (1H, d, J=2.6 Hz).

Example 12

Synthesis of 2',4'-Dinitro-N-ethyl-p-toluenesulfonanilide (Compound No. 435)

To a suspension of sodium hydride (60%, 0.12 g (3.00 mmol)) in DMF (4.0 ml), 2,4-dinitro-N-ethylaniline (0.42 g (1.99 mmol)) was added with stirring at room temperature. To the resulting mixture, after 15 minutes' stirring at room temperature, p-toluenesulfonyl chloride (0.57 g (2.99 mmol)) was added. After two hours' stirring at room temperature, the reaction mixture was poured into water and extracted with ethyl acetate. The extract was washed with water and saturated sodium chloride solution, successively, dried over anhydrous magnesium sulfate, and then concentrated under reduced pressure. The residue was subjected to silica gel chromatography with ethyl acetate-hexane (1:2) as eluent, to give 0.47 g (65%) of the title compound as pale yellow crystals.

mp: 135.0–136.5° C.; NMR (CDCl$_3$) δ: 1.21 (3H, t, J=7.2 Hz), 2.45 (3H, s), 3.69 (2H, q, J=7.2 Hz), 7.30 (2H, d, J=8.4 Hz), 7.30 (1H, d, J=8.8 Hz), 7.52 (2H, d, J=8.4 Hz), 8.38 (1H, dd, J=8.8 & 2.6 Hz), 8.74 (1H, d, J=2.6 Hz).

Example 13

Synthesis of 4'-Chloro-N-cyclopropyl-2'-nitro-p-toluenesulfonanilide (Compound No. 292)

(1) A mixture of 2,5-dichloronitrobenzene (2.00 g (10.4 mmol)) and cyclopropylamine (2.0 ml) was heated under reflux for 60 hours, and the excess cyclopropylamine was removed by concentration under reduced pressure. The residue was dissolved in ethyl acetate and the resulting solution was washed with aqueous 1% sodium hydroxide, saturated sodium chloride solution. The organic layer was dried over anhydrous magnesium sulfate and then concentrated under reduced pressure. The residue was subjected to silica gel column chromatography with ethyl acetate-hexane (1:10) as eluent to give 1.30 g (59%) of 4-chloro-N-cyclopropyl-2-nitroaniline as orange crystals.

mp: 65.0–66.0° C.; NMR (CDCl$_3$) δ: 0.60–0.75 (2H, m), 0.85–1.00 (2H, m), 2.50–2.65 (1H, m), 7.29 (1H, d, J=9.5 Hz), 7.42 (1H, dd, J=9.5 & 2.4 Hz), 8.05 (1H, brs), 8.15 (1H, d, J=2.4 Hz).

(2) To a suspension of sodium hydride (60%, 0.10 g (2.50 mmol)) in DMF (3.0 ml), 4-chloro-N-cyclopropyl-2-nitroaniline (0.40 g (1.88 mmol)) was added with stirring at room temperature. To the resulting mixture, after 15 minutes' stirring at room temperature, p-toluenesulfonyl chloride (0.38 g (1.99 mmol)) was added. After one hour's stirring at room temperature, the reaction mixture was poured into water and extracted with ethyl acetate. The extract was washed with water and saturated sodium chloride solution, successively, dried over anhydrous magnesium sulfate, and then concentrated under reduced pressure. The residue was subjected to silica gel chromatography with ethyl acetate-hexane (1:3) as eluent, to give 0.42 g (61%) of the title compound as yellow crystals mp: 98.5–100.0° C.; NMR (CDCl$_3$) δ: 0.55–0.85 (2H, m), 0.85–1.20 (2H, m), 2.45 (3H, s), 2.60–2.80 (1H, m), 7.02 (1H, d, J=8.6 Hz), 7.32 (2H, d, J=8.2 Hz), 7.48 (1H, dd, J=8.6 & 2.4 Hz), 7.60 (2H, d, J=8.2 Hz), 7.81 (1H, d, J=2.4 Hz).

Example 14

Synthesis of 2',4'-Dinitro-N-methoxy-p-toluenesulfonanilide (Compound No. 545)

(1) 2,4-Dinitrochlorobenzene (4.05 g (20.0 mmol)) and methoxylamine hydrochloride (2.00 g (23.9 mmol)) were dissolved in 15 ml of acetonitrile. To this mixture, under ice cooling and with stirring, triethylamine (7.00 ml (50.2 mmol)) was added. After being stirred for 24 hours at room temperature, the resulting black solution was concentrated under reduced pressure. Water and dilute hydrochloric acid were added to the residue and the mixture was extracted with ethyl acetate. The extract was dried over anhydrous magnesium sulfate and then concentrated under reduced pressure. The residue was then subjected to silica gel column chromatography with ethyl acetate-hexane (1:5) as eluent, to give 2.26 g (53%) of N-(2,4-dinitrophenyl)-O-methylhydroxylamine as yellow crystals.

mp: 109.5–111.5° C.; NMR (CDCl$_3$) δ: 3.92 (3H, s), 7.47 (1H, d, J=9.5 Hz), 8.38 (1H, dd, J=9.5 & 2.6 Hz), 9.11 (1H, d, J=2.6 Hz), 10.23 (1H, brs).

(2) To a suspension of sodium hydride (60%, 0.24 g (6.00 mmol)) in DMF (8.0 ml), N-(2,4-dinitrophenyl)-O-methylhydroxylamine (0.85 g (3.99 mmol)) was added under ice-cooling with stirring. After 15 minutes' stirring under ice-cooling, p-toluenesulfonyl chloride (1.15 g (6.03 mmol)) was added. Then, the temperature of the reaction mixture was brought to room temperature and stirred at the same temperature for 18 hours. The reaction mixture was then poured into water and extracted with ethyl acetate. The extract was washed with water and saturated sodium chloride solution, successively, dried over anhydrous magnesium sulfate, and then concentrated under reduced pressure. The residue was subjected to silica gel chromatography with ethyl acetate-hexane (1:3) as eluent, to give 0.30 g (21%) of the title compound as orange crystals.

mp: 146.0–148.0° C.; NMR (CDCl$_3$) δ: 2.47 (3H, s), 3.90 (3H, s), 7.31 (1H, d, J=9.0 Hz), 7.32 (2H, d, J=8.3 Hz), 7.54 (2H, d, J=8.3 Hz), 8.28 (1H, dd, J=9.0 & 2.5 Hz), 8.71 (1H, d, J=2.5 Hz).

Example 15

Synthesis of N-(5-Chloro-3-nitropyridin-2-yl)-N-methyl-p-toluenesulfonamide (Compound No. 494)

To a suspension of sodium hydride (60%, 0.05 g (1.25 mmol)) in 2.0 ml of DMF, 5-chloro-2-methylamino-3-nitropyridine (0.20 g (1.07 mmol)) was added under cooling with ice and with stirring. To the resulting mixture, after 15 minutes' stirring under cooling with ice, p-toluenesulfonyl chloride (0.23 g (1.21 mmol)) was added. The reaction mixture was stirred under cooling with ice for 30 minutes and then at room temperature for 30 minutes, poured into water and extracted with ethyl acetate. The extract was washed with water and saturated sodium chloride solution, successively, dried over anhydrous magnesium sulfate, and then concentrated under reduced pressure. The residue was then subjected to silica gel column chromatography with ethyl acetate-hexane (1:3) as eluent, to give 0.16 g (44%) of the title compound as pale yellow crystals.

mp: 141.0–143.0° C.; NMR (CDCl$_3$) δ: 2.44 (3H, s), 3.22 (3H, s), 7.29 (2H, d, J=8.3 Hz), 7.48 (2H, d, J=8.3 Hz), 8.28 (1H, d, J=2.4 Hz), 8.48 (1H, d, J=2.4 Hz).

Example 16

Synthesis of 4',5-Dichloro-N-methyl-2'-nitro-2-thiophenesulfonanilide (Compound No. 370)

To a suspension of sodium hydride (60%, 0.15 g (3.75 mmol)) in DMF (5.0 ml), 4-chloro-N-methyl-2-nitroaniline (0.34 g (1.82 mmol)) was added with stirring at room temperature. To the resulting mixture, after 30 minutes' stirring at room temperature, 5-chloro-2-thiophenesulfonyl chloride (0.67 g (3.11 mmol)) was added. The reaction mixture was stirred at room temperature for 24 hours and then poured into water and extracted with chloroform. The extract was washed with water and saturated sodium chloride solution, successively, dried over anhydrous magnesium sulfate, and then concentrated under reduced pressure. The residue was then subjected to silica gel column chromatography with acetone-hexane (1:4) as eluent, to give 0.11 g (16%) of the title compound as pale yellow crystals.

mp: 85.0–86.0° C.; NMR (CDCl$_3$) δ: 3.31 (3H, s), 6.96 (1H, d, J=4.0 Hz), 7.17 (1H, d, J=8.5 Hz), 7.26 (1H, d, J=4.0 Hz), 7.56 (1H, dd, J=8.5 & 2.5 Hz), 7.90 (1H, d, J=2.5 Hz).

Example 17

Synthesis of N-(6-Chloro-3-pyridazinyl)-N-methyl-p-toluenesulfonamide (Compound No. 420)

To a suspension of sodium hydride (60%, 0.42 g (10.5 mmol)) in 10.0 ml of DMF, N-methyl-p-toluenesulfonamide (1.85 g (9.99 mmol)) was added under ice-cooling and with stirring. To the resulting mixture, after 15 minutes' stirring under cooling with ice, 3,6-dichloropyridazine (1.49 g (10.0 mmol)) was added. The reaction mixture was stirred at room temperature for one hour, poured into water and extracted with ethyl acetate. The extract was washed with water and saturated sodium chloride solution, successively, dried over anhydrous magnesium sulfate, and then concentrated under reduced pressure. The residue was then subjected to silica gel column chromatography with ethyl acetate-hexane (1:3) as eluent, to give 1.41 g (47%) of the title compound as white crystals.

mp: 80.0–81.0° C.; NMR (CDCl$_3$) δ: 2.41 (3H, s), 3.38 (3H, s), 7.27 (2H, d, J=8.4 Hz), 7.47 (2H, d, J=8.4 Hz), 7.48 (1H, d, J=9.3 Hz), 8.02 (1H, d, J=9.3 Hz).

Example 18

Synthesis of N,2'-Dimethyl-4'-nitro-p-toluenesulfonanilide (Compound No. 125)

To a suspension of sodium hydride (60%, 0.08 g (2.00 mmol)) in 2.0 ml of DMF, N-methyl-p-toluenesulfonamide (0.37 g (2.00 mmol)) was added at room temperature with stirring. To the resulting mixture, after 15 minutes' stirring at room temperature, 2-fluoro-5-nitrotoluene (0.31 g (2.00 mmol)) was added. The reaction mixture was stirred at room temperature for 2 hours, poured into water and extracted with ethyl acetate. The extract was washed with water and saturated sodium chloride solution, successively, dried over anhydrous magnesium sulfate, and then concentrated under reduced pressure. Diisopropyl ether was added to the residue and crystals separated was filtered and washed to give 0.22 g (36%) of the title compound as pale yellow crystals.

mp: 103.0–104.0° C.; NMR (CDCl$_3$) δ: 2.47 (3H, s), 2.51 (3H, s), 3.13 (3H, s), 6.77 (1H, d, J=8.7 Hz), 7.34 (2H, d, J=8.3 Hz), 7.58 (2H, d, J=8.3 Hz), 7.92 (1H, dd, J=8.7 & 2.6 Hz), 8.17 (1H, d, J=2.6 Hz).

Example 19

Synthesis of 5-Chloro-N-methyl-N-(p-toluenesulfonyl) Anthranilic Acid (Compound No. 71)

(1) To a solution of methyl 5-chloroanthranilate (10.50 g (56.6 mmol) in pyridine (30 ml), p-toluenesulfonyl chloride (12.00 g (62.9 mmol)) was added with stirring at 5° C. The mixture was stirred at room temperature for 18 hours, and then, 200 ml of water was added to the resulting mixture. The crystals separated were filtered and washed to give 18.20 g (95%) of 4'-chloro-2'-methoxycarbonyl-p-toluenesulfonanilide as white crystals.

mp: 112.5–113.5° C.; NMR (CDCl$_3$) δ: 2.37 (3H, s), 3.88 (3H, s), 7.23 (2H, d, J=8.4 Hz), 7.40 (1H, dd, J=9.0 & 2.6 Hz), 7.67 (1H, d, J=9.0 Hz), 7.72 (2H, d, J=8.4 Hz), 7.88 (1H, d, J=2.6 Hz), 10.48 (1H, s).

(2) To a suspension of sodium hydride (60%, 0.43 g (10.8 mmol)) in DMF (10.0 ml), 4'-chloro-2'-methoxycarbonyl-p-toluenesulfonanilide (3.33 g (9.80 mmol)) was added under cooling with ice and with stirring. After 15 minutes' stirring under cooling with ice, dimethyl sulfate (1.02 g (10.8 mmol)) was added dropwise, and the reaction mixture was stirred at room temperature for 16 hours. Then, resulting reaction mixture was poured into water and extracted with ethyl acetate, and the extract was washed with water, dried over anhydrous magnesium sulfate, and then concentrated under reduced pressure. The residue was subjected to silica gel column chromatography with ethyl acetate-hexane (1:3) as eluent, to give 2.95 g (85%) of 4'-chloro-2'-methoxycarbonyl-N-methyl-p-toluenesulfonanilide as white crystals.

mp: 65.5–67.0° C.; NMR (CDCl$_3$) δ: 2.43 (3H, s), 3.23 (3H, s), 3.85 (3H, s), 6.85 (1H, d, J=8.5 Hz), 7.27 (2H, d, J=8.3 Hz), 7.37 (1H, dd, J=8.5 & 2.6 Hz), 7.52 (2H, d, J=8.3 Hz), 7.82 (1H, d, J=2.6 Hz).

(3) To a suspension of 4'-chloro-2'-methoxycarbonyl-N-methyl-p-toluenesulfonanilide (13.3 g (37.5 mmol)) in methanol (30.0 ml), 10% aqueous sodium hydroxide solution (30.0 ml) was added dropwise with stirring at room temperature. The mixture was stirred at room temperature for 48 hours, and then concentrated under reduced pressure. Water was added to the residue to get a homogeneous solution, followed by addition of concentrated hydrochloric acid (10.0 ml) to bring about precipitation of crystals. To this, ethyl acetate was added to extract the product. The extract was then washed with water, dried over anhydrous magnesium sulfate, and concentrated under reduced pressure. Diethyl ether was added to the crystals. The crystals were collected by filtration and washed to give 10.4 g (82%) of the title compound as white crystals.

mp: 175.0–177.0° C.; NMR (CDCl$_3$) δ: 2.44 (3H, s), 3.25 (3H, s), 5.70–6.60 (1H, br), 6.86 (1H, d, J=8.5 Hz), 7.31 (2H, d, J=8.3 Hz), 7.42 (1H, dd, J=8.5 & 2.6 Hz), 7.55 (2H, d, J=8.3 Hz), 7.98 (1H, d, J=2.6 Hz).

Example 20

Synthesis of 4'-Chloro-2'-Carbamoyl-N-methyl-p-toluenesulfonanilide (Compound No. 79)

5-Chloro-N-methyl-N-(p-toluenesulfonyl)anthranilic acid (5.00 g (14.7 mmol)) and pyridine (1.33 ml (16.4 mmol)) were dissolved in 70.0 ml of acetonitrile. To this, under cooling with ice and with stirring, isopropyl chloroformate (2.00 g (16.3 mmol)) was added dropwise. After 30 minutes' stirring under ice-cooling, ammonia gas (ca. 1.25 g (73.4 mmol)) was bubbled into the reaction mixture. The resulting mixture was stirred under cooling with ice for 30 minutes and at room temperature for 20 hours, and then concentrated under reduced pressure. Water was added to the residue, and the mixture was extracted with ethyl acetate. The extract was washed with water, dilute sodium hydroxide solution and water, successively, dried over anhydrous magnesium sulfate, and then concentrated under reduced pressure to give crude crystals. Diethyl ether was added to these crystals, followed by filtration and washing, to give 1.70 g (34%) of the title compound.

mp: 176.5–178.0° C.; NMR (CDCl$_3$) δ: 2.49 (3H, s), 3.17 (3H, s), 5.92 (1H, brs), 6.44 (1H, d, J=8.5 Hz), 7.24 (1H, dd, J=8.5 & 2.6 Hz), 7.37 (2H, d, J=8.4 Hz), 7.44 (1H, br), 7.61 (2H, d, J=8.4 Hz), 7.84 (1H, d, J=2.6 Hz).

Example 21

Synthesis of 4'-Chloro-2'-cyano-N-methyl-p-toluenesulfonanilide (Compound No.94)

To a solution of 4'-chloro-2'-carbamoyl-N-methyl-p-toluenesulfonanilide (0.70 g (2.07 mmol)) in pyridine (3.0 ml), under cooling with ice and with stirring, trifluoroacetic anhydride (0.40 ml (2.83 mmol)) was added dropwise. The temperature of the reaction mixture was brought to room temperature and the mixture was stirred at the same temperature for 2 hours. Then, the mixture was poured into water and extracted with ethyl acetate. The extract was washed with dilute hydrochloric acid, water and saturated sodium chloride solution, successively, dried over anhydrous magnesium sulfate and concentrated under reduced pressure. Diisopropyl ether was added to the residue and crystals separated was filtered and washed to give 0.63 g (95%) of the title compound as white crystals.

mp: 145.0–147.0° C.; NMR (CDCl$_3$) δ: 2.46 (3H, s), 3.22 (3H, s), 7.24 (1H, d, J=8.7 Hz), 7.33 (2H, d, J=8.3 Hz), 7.54 (1H, dd, J=8.7 & 2.5 Hz), 7.63 (1H, d, J=2.5 Hz), 7.64 (2H, d, J=8.3 Hz).

Example 22

Synthesis of 4'-Chloro-N-methyl-2'-thiocarbamoyl-p-toluenesulfonanilide (Compound No. 83)

4'-Chloro-2'-carbamoyl-N-methyl-p-toluenesulfonanilide (1.05 g (3.10 mmol)) and 95% Lawsone reagent (2,4-bis(4-methoxyphenyl)-1,3-dithia-2,4-diphosphetane-2,4-disulfide) (1.70 g (3.99 mmol)) were heated in 1,4-dioxane (10.0 ml) at 100° C. for one hour with stirring. The reaction mixture was then concentrated under reduced pressure and the residue was subjected to silica gel column chromatography with chloroform as eluent to give 0.51 g (46%) of the title compound as pale yellow crystals.

mp: 180.5–182.5° C.; NMR (CDCl$_3$) δ: 2.50 (3H, s), 3.17 (3H, s), 6.34 (1H, d, J=8.5 Hz), 7.16 (1H, dd, J=8.5 & 2.5 Hz), 7.38 (2H, d, J=8.3 Hz), 7.64 (2H, d, J=8.3 Hz), 7.74 (1H, d, J=2.5 Hz), 8.04 (1H, brs), 8.68 (1H, brs).

Example 23

Synthesis of 4'-Chloro-N-methyl-2'-methanesulfinyl-p-toluenesulfonanilide (Compound No. 63)

To a suspension of 4'-chloro-N-methyl-2'-methylthio-p-toluenesulfonanilide (0.35 g (1.02 mmol)) in acetic acid (2.0 ml), 30% hydrogen peroxide water (0.12 g (1.06 mmol)) was added dropwise with stirring at room temperature. The mixture was stirred at 50° C. for 15 minutes to get a homogeneous solution, and then stirring was continued at room temperature for 18 hours. Then, the resulting solution was dissolved in ethyl acetate, washed with aqueous sodium hydroxide solution, and water, dried over anhydrous magnesium sulfate and concentrated under reduced pressure to give a crude crystals. Disopropyl ether was added to these crystals. The crystals were filtered and washed to give 0.27 g (74%) of the title compound as white crystals.

mp: 142.0–143.5° C.; NMR (CDCl$_3$) δ: 2.49 (3H, s), 2.98 (3H, s), 3.12 (3H, s), 6.59 (1H, d, J=8.5 Hz), 7.33 (1H, dd, J=8.5 & 2.3 Hz), 7.37 (2H, d, J=8.3 Hz), 7.60 (2H, d, J=8.3 Hz), 8.06 (1H, d, J=2.3 Hz).

Example 24

Synthesis of 4'-Fluoro-N-methyl-2'-nitro-p-toluenesulfonanilide (Compound No.262)

(1) To a suspension of sodium hydride (60%, 0.31 g (7.75 mmol)) in DMF (10.0 ml), 4'-fluoro-p-toluenesulfonanilide (2.00 g (7.54 mmol)) was added with stirring at room temperature. To the mixture, after 15 minutes' stirring at room temperature, dimethyl sulfate (0.75 ml (7.93 mmol)) was added dropwise and stirring was continued at room temperature for another one hour. Then, the reaction mixture was poured into water, extracted with ethyl acetate. The extract was washed with water, saturated sodium chloride solution successively, dried over anhydrous magnesium sulfate and concentrated under reduced pressure. Diisopropyl ether was added to the residue and the crystals separated were filtered and washed to 1.96 g (93%) of 4'-fluoro-N-methyl-p-toluenesulfonanilide as pale yellowish gray crystals.

mp: 92.0–94.5° C.; NMR (CDCl$_3$) δ: 2.43 (3H, s), 3.14 (3H, s), 6.90–7.15 (4H, m), 7.25 (2H, dt, J=8.3 & 0.6 Hz), 7.43 (2H, dt, J=8.3 & 1.8 Hz).

(2) 4'-Fluoro-N-methyl-p-toluenesulfonanilide (1.00 g (3.58 mmol) was dissolved in 5.0 ml of acetic acid. To this, was added with stirring at room temperature, 97% fuming nitric acid (0.35 ml (8.19 mmol)) dropwise, and the mixture was stirred at 100° C. for one hour, poured into water and extracted with ethyl acetate. The extract was washed with saturated aqueous solution of sodium bicarbonate, dried over anhydrous magnesium sulfate and concentrated under reduced pressure to give crude crystals. Diethyl ether was added to these crystals. The crystals were filtered and washed to give 0.81 g (70%) of the title compound as yellow crystals.

mp: 93.5–94.5° C.; NMR (CDCl$_3$) δ: 2.45 (3H, s), 3.25 (3H, s), 7.11 (1H, dd, J=8.8 Hz, J$_{HF}$=4.9 Hz), 7.15–7.40 (3H, m), 7.50–7.65 (3H, m).

Example 25

Synthesis of N-(2-Bromoethyl)-4'-chloro-2'-nitro-p-toluenesulfonanilide (Compound No. 305)

To a suspension of sodium hydride (60%, 0.20 g (5.00 mmol)) in DMF (7.0 ml), 4'-chloro-2'-nitro-p-toluenesulfonanilide (1.20 g (3.67 mmol)) was added with stirring at room temperature. To the resulting mixture, after 15 minutes' stirring at room temperature, 1,2-dibromoethane (2.00 ml (23.2 mmol)) was added and the mixture was heated at 130° C. for one hour with stirring. The reaction mixture was cooled to room temperature, poured into water and extracted with diethyl ether. The extract was washed with 1% aqueous sodium hydroxide solution, a saturated sodium chloride solution successively, dried over anhydrous magnesium sulfate, and then concentrated under reduced pressure to make the residue crystalline. Hexane was added to the crystals and the crystals were collected while washing to give 1.12 g (70%) of the title compound as pale yellow crystals.

mp: 70.0–72.0° C.; NMR (CDCl$_3$) δ: 2.44 (3H, s), 3.61 (2H, t, J=8.1 Hz), 3.97 (2H, t, J=8.1 Hz), 7.15 (1H, d, J=8.6

Hz), 7.28 (2H, d, J=8.4 Hz), 7.50 (2H, d, J=8.4 Hz), 7.54 (1H, dd, J=8.6 & 2.5 Hz), 7.89 (1H, d, J=2.5 Hz).

Example 26

Synthesis of 4'-Chloro-N-(2-methylthioethyl)-2'-nitro-p-toluenesulfonanilide (Compound No. 307)

N-(2-Bromoethyl)-4'-chloro-2'-nitro-p-toluenesulfonanilide (0.30 g (0.69 mmol) was dissolved in 3.0 ml of acetonitrile. To this, 15% aqueous methylmercaptane sodium salt solution (0.50 g (1.07 mmol)) was added dropwise with stirring at room temperature. The mixture was stirred at room temperature for 15 hours and concentrated under reduced pressure. Water was added to the residue and the resulting mixture was extracted with ethyl acetate. The extract was washed with water and saturated sodium chloride solution, dried over anhydrous magnesium sulfate and concentrated under reduced pressure. Diisopropyl ether was added to the residue to bring about separation of crystals. These crystals were filtered and washed to give 0.22 g (79%) of the title compound as pale yellow crystals.

mp: 94.5–95.5° C.; NMR (CDCl$_3$) δ: 2.09 (3H, s), 2.44 (3H, s), 2.77 (2H, dd, J=7.9 & 5.9 Hz), 3.78 (2H, dd, J=7.9 & 7.5 Hz), 7.13 (1H, d, J=8.6 Hz), 7.28 (2H, d, J=8.3 Hz), 7.51 (2H, d, J=8.3 Hz), 7.52 (1H, dd, J=8.6 & 2.5 Hz), 7.87 (1H, d, J=2.5 Hz).

Example 27

Synthesis of 4'-Chloro-2'-nitro-N-vinyl-p-toluenesulfonanilide (Compound No. 298)

To a suspension of sodium hydride (60%, 0.04 g (1.00 mmol)) in DMF (5.0 ml), 1,2,4-triazole (0.08 g (1.16 mmol)) was added with stirring at room temperature. To the resulting mixture, after 15 minutes' stirring at room temperature, N-(2-bromoethyl)-4'-chloro-2'-nitro-p-toluenesulfonanilide (0.35 g (0.81 mmol)) was added and the mixture was stirred at room temperature for 18 hours. The reaction mixture was poured into water and extracted with ethyl acetate. The extract was washed with water and saturated sodium chloride solution, dried over anhydrous magnesium sulfate, and then concentrated under reduced pressure. The residue was subjected to silica gel column chromatography with ethyl acetate-hexane (1:3) as eluent, to give 0.052 g (18%) of the title compound as pale yellow crystals.

mp:>108.0° C. (dec.); NMR (CDCl$_3$) δ: 2.45 (3H, s), 3.88 (1H, dd, J=15.5 & 1.7 Hz), 4.40 (1H, dd, J=8.9 & 1.7 Hz), 6.96 (1H, d, J=8.5 Hz), 7.12 (1H, dd, J=15.5 & 8.9 Hz), 7.30 (2H, d, J=8.3 Hz), 7.54 (1H, dd, J=8.5 & 2.4 Hz), 7.57 (2H, d, J=8.3 Hz), 7.99 (1H, d, J=2.4 Hz).

Example 28

Synthesis of 4'-Methoxymethoxy-N-methyl-2'-nitro-p-toluenesulfonanilide (Compound No. 219)

(1) To a suspension of sodium hydride (60%, 2.70 g (67.5 mmol)) in THF (100.0 ml), under cooling with ice and with stirring, 4-amino-3-nitrophenol (10.0 g (64.9 mmol)) was added. To the resulting mixture, after 10 minutes' stirring under cooling with ice, chloromethyl methyl ether (5.50 g (68.3 mmol)) was added dropwise and the mixture was stirred at 5° C. for one hour and at room temperature for one hour, and then concentrated under reduced pressure. The residue was dissolved in ethyl acetate, washed with water and saturated aqueous solution of sodium bicarbonate successively, dried over anhydrous magnesium sulfate, and then concentrated under reduced pressure. Then the residue was subjected to silica gel column chromatography with chloroform-ethanol (100:1) as eluent to give 7.69 g (60%) of 4-methoxymethoxy-2-nitroaniline as red oil.

NMR (CDCl$_3$) δ: 3.48 (3H, s), 5.12 (2H, s), 5.92 (2H, brs), 6.77 (1H, d, J=9.0 Hz), 7.15 (1H, dd, J=9.0 & 2.9 Hz), 7.78 (1H, d, J=2.9 Hz).

(2) 4-Methoxymethoxy-2-nitroaniline (7.69 g (38.8 mmol)) was dissolved in 19.0 ml of pyridine. To this, p-toluenesulfonyl chloride (8.14 g (42.7 mmol)) was added with stirring at room temperature and the mixture was stirred at room temperature for 18 hours. Then, water (200.0 ml) was added to the reaction mixture, and the resulting mixture was extracted with chloroform. The extract was washed with water, dried over anhydrous magnesium sulfate, and concentrated under reduced pressure. The residue was then subjected to silica gel column chromatography with chloroform-ethanol (100:1) as eluent, to give 9.46 g (63%) of 4'-methoxymethoxy-2'-nitro-p-toluenesulfonanilide as a yellow oil.

NMR (CDCl$_3$) δ: 2.38 (3H, s), 3.46 (3H, s), 5.16 (2H, s), 7.23 (2H, d, J=8.4 Hz), 7.29 (1H, dd, J=9.1 Hz & 2.7 Hz), 7.64 (2H, dt, J=8.4 & 2.0 Hz), 7.70 (1H, d, J=2.7 Hz), 7.79 (1H, d, J=9.1 Hz), 9.34 (1H, brs).

(3) To a suspension of sodium hydride (60%, 0.40 g (10.0 mmol)) in 15.0 ml of DMF, 4'-methoxymethoxy-2'-nitro-p-toluenesulfonanilide (3.00 g (8.51 mmol)) was added with stirring at room temperature. To the resulting mixture, after 15 minutes' stirring at room temperature, dimethyl sulfate (1.0 ml (10.6 mmol)) was added and the mixture was stirred for 15 hours at room temperature. The reaction mixture was poured into water and extracted with ethyl acetate. The extract was washed with water and dried over anhydrous magnesium sulfate, and then concentrated under reduced pressure. The residue was then subjected to silica gel column chromatography with ethyl acetate-hexane (1:2) to give 2.91 g (93%) of the title compound as yellow crystals.

mp: 110.5–112.0° C.; NMR (CDCl$_3$) δ: 2.44 (3H, s), 3.24 (3H, s), 3.49 (3H, s), 5.21 (2H, s), 7.01 (1H, d, J=8.8 Hz), 7.15 (1H, dd, J=8.8 & 2.8 Hz), 7.29 (2H, d, J=8.3 Hz), 7.50 (1H, d, J=2.8 Hz), 7.57 (2H, d, J=8.3 Hz).

Example 29

Synthesis of 4'-Hydroxy-N-methyl-2-nitro-p-toluenesulfonanilide (Compound No. 156)

4'-Methoxymethoxy-N-methyl-2'-nitro-p-toluenesulfonanilide (2.70 g (7.37 mmol) was suspended in 20.0 ml of methanol. To this, 35% hydrochloric acid (5.0 ml) was added with stirring at room temperature. The mixture was stirred at room temperature for 15 hours and then concentrated under reduced pressure. Diethyl ether was added to the residual solid. The solid was filtered and washed to give 2.30 g (97%) of the title compound as pale red crystals.

mp: 173.0–174.0° C.; NMR (CDCl$_3$) δ: 2.45 (3H, s), 3.22 (3H, s), 6.37 (1H, brs), 6.90–7.05 (2H, m), 7.25 (1H, d, J=2.3 Hz), 7.31 (2H, d, J=8.4 Hz), 7.59 (2H, d, J=8.4 Hz).

Example 30

Synthesis of N-Methyl-2'-nitro-4'-(n-propoxy)-p-toluenesulfonanilide (Compound No. 216)

To a suspension of sodium hydride (60%, 0.05 g (1.25 mmol)) in 1.0 ml of DMF, 4'-hydroxy-N-methyl-2'-nitro-p- toluenesulfonanilide (0.32 g (0.99 mmol)) was added with stirring at room temperature. To the resulting mixture, after 15 minutes' stirring at room temperature, n-propyl bromide (0.20 g (2.20 mmol)) was added dropwise and the mixture was stirred at room temperature for 15 hours. The reaction mixture was poured into water and extracted with ethyl acetate. The extract was washed with water and saturated sodium chloride solution, dried over anhydrous magnesium sulfate, and then concentrated under reduced pressure. Diisopropyl ether was added to the residue and crystals separated were filtered and washed to give 0.15 g (42%) of the title compound as pale yellow crystals.

mp: 93.0–94.0° C.; NMR (CDCl$_3$) δ: 1.05 (3H, t, J=7.3 Hz), 1.83 (2H, tq, J=6.5 & 7.3 Hz), 2.44 (3H, s), 3.24 (3H, s), 3.96 (2H, t, J=6.5 Hz), 6.90–7.10 (2H, m), 7.20–7.35 (3H, m), 7.56 (2H, d, J=8.3 Hz).

Example 31

Synthesis of 4'-Bromo-N-methyl-2'-nitro-p-toluenesulfonanilide (Compound No. 398)

(1) To a suspension of sodium hydride (60%, 0.18 g (4.50 mmol)) in 5.0 ml of DMF, 4'-bromo-p-toluenesulfonanilide (1.30 g (3.99 mmol)) was added with stirring at room temperature. To the resulting mixture, after 15 minutes' stirring at room temperature, dimethyl sulfate (0.40 g (4.23 mmol)) was added dropwise and the mixture was stirred at room temperature for 24 hours. The reaction mixture was then poured into water and extracted with ethyl acetate. The extract was washed with water, dried over anhydrous magnesium sulfate, and then concentrated under reduced pressure to make the residue crystalline. The crystals were collected by filtration, while washing them with diisopropyl ether, giving 1.17 g (86%) of the title compound as white crystals.

mp: 82.5–83.5° C.; NMR (CDCl$_3$) δ: 2.42 (3H, s), 3.13 (3H, s), 6.98 (2H, d, J=8.9 Hz), 7.25 (2H, d, J=8.4 Hz), 7.42 (2H, d, J=8.9 Hz), 7.42 (2H, d, J=8.4 Hz).

(2) 4'-Bromo-N-methyl-p-toluenesulfonanilide (0.90 g (2.65 mmol)) was dissolved in 5.0 ml of acetic acid. To this, 97% fuming nitric acid (0.64 ml (15.0 mmol)) was added dropwise, and the mixture was heated at 100° C. for 1.5 hours with stirring, followed by cooling to room temperature. Then, the reaction mixture was poured into water and extracted with ethyl acetate. The extract was washed with saturated aqueous solution of sodium bicarbonate, dried over anhydrous magnesium sulfate, and concentrated under reduced pressure. The residue was subjected to silica gel column chromatography with ethyl acetate-hexane (1:3) as eluent, to give 0.64 g (63%) of the title compound as pale yellow crystals.

mp: 108.0–110.5° C.; NMR (CDCl$_3$) δ: 2.45 (3H, s), 3.24 (3H, s), 7.00 (1H, d, J=8.5 Hz), 7.31 (2H, d, J=8.4 Hz), 7.56 (2H, d, J=8.4 Hz), 7.65 (1H, dd, J=8.5 & 2.3 Hz), 7.99 (1H, d, J=2.3 Hz).

Example 32

Synthesis of 4'-Chloro-N-ethyl-2'-methoxycarbonyl-p-toluenesulfnanilide (Compound No.76)

In a manner similar to that in Example 19-(2), but diethyl sulfate was used instead of dimethyl sulfate and the reaction was carried out at 80 for one hour, the title compound was obtained as white crystals in a yield of 72%.

mp: 105.0–107.0° C.; NMR (CDCl$_3$) δ: 1.15 (3H, t, J=7.1 Hz), 2.42 (3H, s), 3.67 (2H, q, J=7.1 Hz), 3.81 (3H, s), 6.86 (1H, d, J=8.5 Hz), 7.25 (2H, d, J=8.4 Hz), 7.38 (1H, dd, J=8.5 & 2.6 Hz), 7.50 (2H, d, J=8.4 Hz), 7.84 (1H, d, J=2.6 Hz).

Example 33

Synthesis of 4'-Chloro-N-isopropyl-2'-methoxycarbonyl-p-toluenesulfonanilide (Compound No. 77)

In a manner similar to that in Example 19-(2), but isopropyl iodide was used instead of dimethyl sulfate and the reaction was carried out at 130° C. for one hour, the title compound was obtained as white crystals in a yield of 19%.

mp: 113.5–115.5° C.; NMR (CDCl$_3$): 1.04 (3H, d, J=6.7 Hz), 1.06 (3H, d, J=6.7 Hz), 2.42 (3H, s), 3.87 (3H, s), 4.49 (1H, septet, J=6.7 Hz), 6.94 (1H, d, J=8.5 Hz), 7.26 (2H, d, J=8.4 Hz), 7.41 (1H, dd, J=8.5 & 2.6 Hz), 7.60 (2H, d, J=8.4 Hz), 7.89 (1H, d, J=2.6 Hz).

Example 34

Synthesis of 5-Chloro-N-ethyl-N-(p-toluenesulfonyl)-anthranilic Acid (Compound No. 72)

In a manner similar to that in Example 19-(3), but 4'-chloro-N-ethyl-2'-methoxycarbonyl-p-toluenesulfonanilide was used instead of 4'-chloro-2'-methoxycarbonyl-N-methyl-p-toluenesulfonanilide, the title compound was obtained as white crystals in a yield of 68%.

mp: 163.0–165.0° C.; NMR (CDCl$_3$) δ: 1.12 (3H, t, J=7.2 Hz), 2.44 (3H, s), 3.20–3.80 (1H, br), 3.50–4.10 (1H, br), 4.00–5.20 (1H, br), 6.77 (1H, d, J=8.6 Hz), 7.30 (2H, d, J=8.3 Hz), 7.41 (1H, dd, J=8.6 & 2.6 Hz), 7.55 (2H, d, J=8.3 Hz), 7.99 (1H, d, J=2.6 Hz).

Example 35

Synthesis of 5-Chloro-N-isopropyl-N-(p-toluenesulfonyl)-anthranilic Acid (Compound No. 73)

In a manner similar to that in Example 19-(3), but 4'-chloro-N-isopropyl-2'-methoxycarbonyl-p-toluenesulfonanilide was used instead of 4'-chloro-2'-methoxycarbonyl-N-methyl-p-toluenesulfonanilide, the title compound was obtained as white crystals in a yield of 90%.

mp: 175.0–176.5° C.; NMR (CDCl$_3$) δ: 1.02 (3H, d, J=6.7 Hz), 1.10 (3H, d, J=6.7 Hz), 2.46 (3H, s), 4.67 (1H, septet, J=6.7 Hz), 6.61 (1H, d, J=8.6 Hz), 7.32 (2H, d, J=8.3 Hz), 7.36 (1H, dd, J=8.6 & 2.6 Hz), 7.61 (2H, d, J=8.3 Hz), 7.91 (1H, d, J=2.6 Hz).

Example 36

Synthesis of 4'-Chloro-2'-carbamoyl-N-ethyl-p-toluenesulfonanilide (Compound No. 80)

5-Chloro-N-ethyl-N-(p-toluenesulfonyl)anthranilic acid (3.40 g (9.61 mmol)), thionyl chloride (5.00 ml (68.5 mmol)) and chloroform (50.0 ml) were mixed and heated at 70° C. for one hour with stirring. The reaction mixture was left to cool to room temperature, followed by concentration under reduced pressure, to give crude crystals of the corresponding acid chloride. The whole product(acid chloride) was dissolved in 25.0 ml of acetonitrile. To this, under cooling with ice, a solution made by dissolving 5.00 g (73.4 mmol) of 25% aqueous ammonia in 25.0 ml of acetonitrile was added dropwise. After 30 minutes' stirring under cooling with ice, the reaction mixture was concentrated under reduced pressure. Water was added to the residue to bring about separation of crystals, which were filtered and washed to give 3.14 g (93%) of the title compound as white crystals.

mp: 148.5–150.0° C.; NMR (CDCl$_3$) δ: 1.05 (3H, t, J=7.2 Hz), 2.49 (3H, s), 2.90–3.70 (1H, br), 3.60–4.40 (1H, br), 5.93 (1H, brs), 6.37 (1H, d, J=8.5 Hz), 7.24 (1H, dd, J=8.5 & 2.6 Hz), 7.36 (2H, d, J=8.3 Hz), 7.61 (2H, d, J=8.3 Hz), 7.63 (1H, brs), 7.82 (1H, d, J=2.6 Hz).

Example 37

Synthesis of 4'-Chloro-2'-carbamoyl-N-isopropyl-p-toluenesulfonanilide (Compound No. 81)

In a manner similar to that in Example 36, but 5-chloro-N-isopropyl-N-(p-toluenesulfonyl)anthranilic acid was used instead of 5-chloro-N-ethyl-N-(p-toluenesulfonyl) anthranilic acid, the title compound was obtained as white crystals in a yield of 94%.

mp: 177.0–178.5° C.; NMR (CDCl$_3$) δ: 0.84 (3H, d, J=6.7 Hz), 1.14 (3H, d, J=6.7 Hz), 2.48 (3H, s), 4.65 (1H, septet, J=6.7 Hz), 5.87 (1H, brs), 6.43 (1H, d, J=8.6 Hz), 7.25 (1H, dd, J=8.6 & 2.6 Hz), 7.35 (2H, d, J=8.3 Hz), 7.67 (2H, d, J=8.3 Hz), 7.78 (1H, d, J=2.6 Hz), 7.82 (1H, brs).

Example 38

Synthesis of 4'-Chloro-2'-cyano-N-ethyl-p-toluenesulfonanilide (Compound No. 95)

In a manner similar to that in Example 21, but 4'-chloro-2'-carbamoyl-N-ethyl-p-toluenesulfonanilide was used instead of 4'-chloro-2'-carbamoyl-N-methyl-p-toluenesulfonanilide, the title compound was obtained as white crystals in a yield of 84%.

mp: 138.5–140.5° C.; NMR (CDCl$_3$) δ: 1.10 (3H, t, J=7.2 Hz), 2.45 (3H, s), 3.64 (2H, q, J=7.2 Hz), 7.20 (1H, d, J=8.6 Hz), 7.32 (2H, d, J=8.4 Hz), 7.55 (1H, dd, J=8.6 & 2.5 Hz), 7.60–7.75 (3H, m).

Example 39

Synthesis of 4'-Chloro-2'-cyano-N-isopropyl-p-toluenesulfonanilide (Compound No.97)

In a manner similar to that in Example 21, but 4'-chloro-2'-carbamoyl-N-isopropyl-p-toluenesulfonanilide was used instead of 4'-chloro-2'-carbamoyl-N-methyl-p-toluenesulfonanilide, the title compound was obtained as white crystals in a yield of 90%.

mp: 129.5–130.5° C.; NMR (CDCl$_3$) δ: 1.14 (6H, d, J=6.7 Hz), 2.44 (3H, s), 4.49 (1H, septet, J=6.7 Hz), 7.26 (1H, d, J=8.6 Hz), 7.31 (2H, d, J=8.5 Hz), 7.57 (1H, dd, J=8.6 & 2.5 Hz), 7.68 (1H, d, J=2.5 Hz), 7.74 (2H, d, J=8.5 Hz).

Example 40

Synthesis of 4'-Chloro-N-ethyl-2'-thiocarbamoyl-p-toluenesulfonanilide (Compound No. 84)

In a manner similar to that in Example 22, but 4'-chloro-2'-carbamoyl-N-ethyl-p-toluenesulfonanilide was used instead of 4'-chloro-2'-carbamoyl-N-methyl-p-toluenesulfonanilide, the title compound was obtained as pale yellow crystals in a yield of 91%.

mp: 180.0–182.0° C.; NMR (CDCl$_3$) δ: 1.06 (3H, t, J=7.2 Hz), 2.49 (3H, s), 3.21 (1H, dq, J=7.0 & 7.2 Hz), 3.88 (1H, dq, J=7.0 & 7.2 Hz), 6.29 (1H, d, J=8.6 Hz), 7.17 (1H, dd, J=8.6 & 2.5 Hz), 7.37 (2H, d, J=8.4 Hz), 7.63 (2H, d, J=8.4 Hz), 7.84 (1H, d, J=2.5 Hz), 8.01 (1H, brs), 9.04 (1H, brs).

Example 41

Synthesis of 4'-Chloro-N-isopropyl-2'-thiocarbamoyl-p-toluenesulfonanilide (Compound No. 85)

In a manner similar to that in Example 22, but 4'-chloro-2'-carbamoyl-N-isopropyl-p-toluenesulfonanilide was used instead of 4'-chloro-2'-carbamoyl-N-methyl-p-toluenesulfonanilide, the title compound was obtained as pale yellow crystals in a yield of 34%.

mp: 189.0–191.0° C.; NMR (CDCl$_3$) δ: 0.85 (3H, d, J=6.8 Hz), 1.23 (3H, d, J=6.8 Hz), 2.48 (3H, s), 4.59 (1H, septet, J=6.8 Hz), 6.36 (1H, d, J=8.6 Hz), 7.19 (1H, dd, J=8.6 & 2.6 Hz), 7.35 (2H, d, J=8.4 Hz), 7.65 (2H, d, J=8.4 Hz), 7.98 (1H, d, J=2.6 Hz), 7.99 (1H, brs), 9.29 (1H, brs).

Example 42

Synthesis of 2'-Cyano-N-methoxy-4'-nitro-p-toluenesulfonanilide (Compound No. 535)

(1) Methoxylamine (9.00 g (108 mmol) was suspended in pyridine (30.0 ml). To this, under cooling with ice and with stirring, p-toluenesulfonyl chloride (19.07 g (100 mmol)) was added and the mixture was stirred under cooling with ice for 30 minutes and at room temperature for 2 hours. Water (200.0 ml) was added to the reaction mixture to bring about separation of crystals. After 30 minutes' stirring, the crystals were filtered and washed to give 20.26 g (99%) of N-methoxy-p-toluenesulfonamide as white crystals.

mp: 116.0–117.0° C.; NMR (CDCl$_3$) δ: 2.45 (3H, s), 3.79 (3H, s), 7.14 (1H, s), 7.35 (2H, d, J=8.3 Hz), 7.84 (2H, d, J=8.3 Hz).

(2) To a suspension of sodium hydride (60%, 0.09 g (2.25 mmol)) in 3.0 ml of DMF, N-methoxy-p-toluenesulfonamide (0.45 g (2.20 mmol)) was added under cooling with ice and with stirring. To the resulting mixture, after 15 minutes' stirring under cooling with ice, 2-chloro-5-nitrobenzonitrile (0.37 g (2.03 mmol)) was added and the mixture was stirred under cooling with ice for one hour and at room temperature for 18 hours. The reaction mixture was then poured into water and extracted with diethyl ether. The extract was washed twice with water, dried over anhydrous sodium sulfate, and then concentrated under reduced pressure. The residue was subjected to silica gel column chromatography with ethyl acetate-hexane (1:5) as eluent to give 0.48 g (68%) of the title compound as pale yellow crystals.

mp: 148.0–149.5° C.; NMR (CDCl$_3$) δ: 2.48 (3H, s), 3.84 (3H, s), 7.32 (1H, d, J=9.0 Hz), 7.35 (2H, d, J=8.3 Hz), 7.62 (2H, d, J=8.3 Hz), 8.32 (1H, dd, J=9.0 & 2.5 Hz), 8.54 (1H, d, J=2.5 Hz).

Example 43

Synthesis of 2'-Chloro-N-ethoxy-4'-nitro-p-toluenesulfonanilide (Compound No. 533)

(1) In a manner similar to that in Example 42-(1), except for that ethoxylamine hydrochloride was used instead of methoxylamine hydrochloride, N-ethoxy-p-toluenesulfonamide was obtained as white crystals in a yield of 91%.

mp: 94.0–95.0° C.; NMR (CDCl$_3$) δ: 1.20 (3H, t, J=7.0 Hz), 2.45 (3H, s), 4.03 (2H, q, J=7.0 Hz), 6.89 (1H, s), 7.35 (2H, d, J=8.3 Hz), 7.82 (2H, d, J=8.3 Hz).

(2) To a suspension of sodium hydride (60%, 0.18 g (4.50 mmol)) in 6.0 ml of DMF, N-ethoxy-p-toluenesulfonamide (0.90 g (4.18 mmol)) was added under cooling with ice and with stirring. To the resulting mixture, after 15 minutes' stirring under cooling with ice, 3-chloro-4-fluoronitrobenzene (0.70 g (3.99 mmol)) was added and the mixture was stirred under cooling with ice for one hour and at room temperature for 18 hours. The reaction mixture was then poured into water and extracted with diethyl ether. The extract was washed twice with water, dried over anhydrous magnesium sulfate, and then concentrated under reduced pressure to give crude crystals. These crystals were filtered while washing with diisopropyl ether to give 1.06 g (72%) of the title compound as pale yellow crystals.

mp: 133.5–135.0° C.; NMR (CDCl$_3$) δ: 1.15 (3H, t, J=7.0 Hz), 2.49 (3H, s), 4.10 (2H, q, J=7.0 Hz), 6.89 (1H, d, J=8.9 Hz), 7.34 (2H, d, J=8.4 Hz), 7.62 (2H, d, J=8.4 Hz), 7.95 (1H, dd, J=8.9 & 2.5 Hz), 8.35 (1H, d, J=2.5 Hz).

Example 44

Synthesis of 2'-Chloro-N-isopropoxy-4'-nitro-p-toluenesulfonanilide (Compound No. 534)

(1) In a manner similar to that in Example 42-(1), except for that isopropoxylamine hydrochloride was used instead of methoxylamine hydrochloride, N-isopropoxy-p-toluenesulfonamide was obtained as pale yellow crystals in a yield of 96%.

mp: 103.5–104.5° C.; NMR (CDCl$_3$) δ: 1.18 (6H, d, J=6.2 Hz), 2.45 (3H, s), 4.24 (1H, septet, J=6.2 Hz), 6.75 (1H, s), 7.34 (2H, d, J=8.3 Hz), 7.81 (2H, d, J=8.3 Hz).

(2) In a manner similar to that in Example 43-(2), except for that N-isopropoxy-p-toluenesulfonamide was used instead of N-ethoxy-p-toluenesulfonamide was used to give the title compound as pale yellow crystals in a yield of 80%.

mp: 160.5–162.0° C.; NMR (CDCl$_3$) δ: 1.14 (6H, d, J=6.2 Hz), 2.49 (3H, s), 4.42 (1H, septet, J=6.2 Hz), 6.86 (1H, d, J=9.0 Hz), 7.34 (2H, d, J=8.3 Hz), 7.59 (2H, d, J=8.3 Hz), 7.94 (1H, dd, J=9.0 & 2.5 Hz), 8.35 (1H, d, J=2.5 Hz).

Example 45

Synthesis of 2',4-Dichloro-N-methoxy-4'-nitrobenzenesulfonamide (Compound No. 526)

(1) In a manner similar to that in Example 42-(1), but 4-chlorobenzenesulfonyl chloride was used instead of p-toluenesulfonyl chloride to give 4-chloro-N-methoxybenzenesulfonamide as pale yellow crystals in a yield of 97%.

mp: 81.0–82.5° C.; NMR (CDCl$_3$) δ: 3.81 (3H, s), 7.23 (1H, s), 7.53 (2H, dt, J=8.7 & 2.5 Hz), 7.87 (2H, dt, J=8.7 & 2.5 Hz).

(2) In a manner similar to that in Example 43-(2), except for that 4-chloro-N-methoxybenzenesulfonamide was used instead of N-ethoxy-p-toluenesulfonamide to give the title compound as pale yellow crystals in a yield of 49%.

mp: 150.0–151.0° C.; NMR (CDCl$_3$) δ: 3.84 (3H, s), 6.91 (1H, d, J=8.9 Hz), 7.54 (2H, d, J=8.5 Hz), 7.70 (2H, d, J=8.5 Hz), 8.00 (1H, dd, J=8.9 & 2.5 Hz), 8.37 (1H, d, J=2.5 Hz).

Example 46

Synthesis of 2',4'-Dicyano-N-isopropyl-p-toluenesulfonanilide (Compound No. 114)

(1) To a solution of potassium permanganate (47.5 g (0.30 mol) in 500.0 ml of water, 3-methyl-4-nitrobenzoic acid (20.0 g (0.13 mol) was added and the resulting mixture was stirred at 70° C. overnight. Then, porassium permanganate (24.5 g (0.16 mol) was further added and the mixture was stirred at 70° C. for another two days. The insolubles were removed by filtrering while hot, and the filtrate was made, after being cooled, acidic with concentrated hydrochloric acid to have crystals separated. The resulting crystals were filtered and washed with water to give 11.9 g (51%) of 4-nitroisophthalic acid as white crystals.

mp: 256.8–258.5° C.; NMR (DMSO-d$_6$) δ: 8.07 (1H, dd, J=8.3 & 0.3 Hz), 8.27 (1H, dd, J=8.3 & 1.9 Hz), 8.34 (1H, dd, J=1.9 & 0.3 Hz), 13.80 (2H, brs).

(2) A mixture of 4-nitroisophthalic acid (11.9 g (56.4 mmol) and thionyl chloride (20.0 ml) was heated at 70° C. for two days with stirring, and then concentrated under reduced pressure. The residue was diluted with 30.0 ml of acetonitrile and, to this, ice-cooled 25% aqueous ammonia (30.0 ml) was added dropwise. The crystals separated were filtered and washed with water to give 11.9 g (100%) of 4-nitroisophthalamide as white crystals.

mp: 287.0–289.0° C.; NMR (DMSO-d$_6$) δ: 7.77 (2H, br), 8.00–8.20(3H, m), 8.25 (2H, br).

(3) To a solution of 4-nitroisophthalamide (6.0 g (28.7 mmol) in ethanol (150.0 ml), stannous chloride (20.02 g (86.1 mmol) was added and the mixture was stirred at 70° C. overnight. After cooling, the reaction mixture was neutralized with a saturated aqueous sodium bicarbonate solution, and insolubles formed were removed by filtration. The filtrate was extracted with ethyl acetate and the extract was dried over anhydrous magnesium sulfate and concentrated under reduced pressure to give 2.59 g (50%) of 4-aminoisophthalamide as pale yellow crystals.

mp: 177.0–197.5° C.; NMR (DMSO-d$_6$) δ: 6.68 (1H, d, J=8.6 Hz), 6.90–7.30 (4H, m), 7.40–7.80 (2H, m), 7.65 (1H, dd, J=8.6 & 1.9 Hz), 8.11 (1H, d, J=1.9 Hz).

(4) To a solution of 4-aminoisophthalamide (1.00 g (5.58 mmol) in pyridine (10.0 ml), p-toluenesulfonyl chloride (1.06 g (5.58 mmol) was added with stirring at room temperature. After 3 hours' stirring at room temperature, water was added to the reaction mixture to separate crystals. The crystals were filtered and washed with water and ethyl acetate to give 0.94 g (51%) of 2',4'-dicarbamoyl-p-toluenesulfonanilide as white crystals.

mp: 212.0–215.0° C.; NMR (DMSO-d$_6$) δ: 2.33 (3H, s), 7.35 (2H, d, J=8.3 Hz), 7.40 (1H, brs), 7.53 (1H, d, J=8.6 Hz), 7.70 (2H, d, J=8.3 Hz), 7.79 (1H, brs), 7.90 (1H, dd, J=8.6 & 1.8 Hz), 7.97 (1H, brs), 8.26 (1H, d, J=1.8 Hz), 8.38 (1H, brs), 12.30 (1H, s).

(5) Phosphorus oxychloride (5.00 g) was added to 2',4'-dicarbamoyl-p-toluenesulfonanilide (0.30 g (0.90 mmol), and the mixture was heated at 50° C. for 4 hours with stirring. After cooling, addition of water, and stirring brought about precipitation of an insoluble solid. These crystals were filtered, washed with water and recrystallized from ethyl acetate-hexane to give 0.16 g (60%) of 2',4'-dicyano-p-toluenesulfonanilide as pale brown crystals.

mp: 200.0–206.0° C.; NMR (DMSO-d$_6$) δ: 2.38 (3H, s), 7.31 (1H, d, J=8.7 Hz), 7.41 (2H, d, J=8.3 Hz), 7.73 (2H, d, J=8.3 Hz), 8.01 (1H, dd, J=8.7 & 2.0 Hz), 8.40 (1H, d, J=2.0 Hz).

(6) To a suspension of sodium hydride (65%, 0.12 g (3.30 mmol)) in 6.0 ml of DMF, 2',4'-dicyano-p-toluenesulfonanilide (0.49 g (1.65 mmol)) was added with stirring at room temperature. To the resulting mixture, after 10 minutes' stirring at room temperature, isopropyl iodide (0.50 ml (4.94 mmol)) was added and the mixture was heated at 130° C. for 6 hours with stirring. The reaction mixture was then cooled to room temperature, poured into water and extracted with diethyl ether. The extract was washed with 1% aqueous sodium hydroxide solution and with a saturated aqueous solution of sodium chloride, dried over anhydrous magnesium sulfate, and concentrated under reduced pressure. The residue was subjected to silica gel column chromatography with ethyl acetate-hexane (3:7) as eluent, to give 0.07 g (13%) of the title compound as white crystals.

mp: 157.2–157.7° C.; NMR (CDCl$_3$) δ: 1.16 (6H, d, J=6.7 Hz), 2.45 (3H, s), 4.48 (1H, q, J=6.7 Hz), 7.33 (2H, d, J=8.4 Hz), 7.49 (1H, d, J=8.3 Hz), 7.74 (2H, d, J=8.4 Hz), 7.89 (1H, dd, J=8.3 & 2.0 Hz), 8.01 (1H, d, J=2.0 Hz).

Example 47

Synthesis of 2'-Cyano-N-ethyl-4'-nitro-p-toluenesulfonanilide (Compound No. 420)

(1) To a solution of 2-aminobenzonitrile (2.36 g (20.0 mmol in pyridine (10.0 ml), p-toluenesulfonyl chloride (4.20 g (22.0 mmol) was added with stirring at room temperature. After 15 hours' stirring at room temperature, water (100 ml) was added to the reaction mixture and stirring was continued for another 30 minutes. The crystals separated were filtered, washed with water and re-dissolved in chloroform. The soluble part in 1% aqueous sodium hydroxide solution was extracted from the chloroform solution. The extract was made acidic with hydrochloric acid and re-extracted with chloroform. The chloroform extract was dried over anhydrous magnesium sulfate and concentrated under reduced pressure to give a product which then crystallized. The crystals were washed with diisopropyl ether and filtered to give 4.83 g (89%) of 2'-cyano-p-toluenesulfonanilide as white crystals.

mp: 134.5–136.5° C.; NMR (CDCl$_3$) δ: 2.39 (3H, s), 7.06 (1H, brs), 7.10–7.35 (3H, m), 7.40–7.60 (2H, m), 7.60–7.80 (3H, m).

(2) To a suspension of 2'-cyano-p-toluenesulfonanilide (2.67g (9.80 mmol)) in acetic anhydride (7.0 ml), 97% fuming nitric acid (0.45 ml (10.5 mmol) was added with stirring at room temperature. After stirring for one hour at 50° C., crystals began to separate. Water was added to decompose excess acetic anhydride, and the crystals were filtered, washed with water, dried in the air and then, washed with diethyl ether and collected by filtration to give 3.05 g (98%) of 2'-cyano-4'-nitro-p-toluenesulfonanilide as pale yellow crystals.

mp: 165.5–167.0° C.; NMR (CDCl$_3$) δ: 2.43 (3H, s), 7.34 (2H, d, J=8.4 Hz), 7.62 (1H, s), 7.81 (2H, d, J=8.4 Hz), 7.80–7.95 (1H, m), 8.25–8.45 (2H, m).

(3) To a suspension of sodium hydride (60%, 0.12 g (3.00 mmol)) in 3.0 ml of DMF, 2'-cyano-4'-nitro-p-toluenesulfonanilide (0.80 g (2.52 mmol)) was added with'stirring at room temperature. To the resulting mixture, after 15 minutes' stirring at room temperature, diethyl sulfate (0.40 ml (3.05 mmol)) was added dropwise and the mixture was heated at 80° C. for 2 hours and at 100° C. for 2 hours with stirring. The reaction mixture was then cooled to room temperature, poured into water and extracted with diethyl ether. The extract was washed three times with 1% aqueous sodium hydroxide solution, dried over anhydrous magnesium sulfate, and concentrated under reduced pressure. The residue was subjected to silica gel column chromatography with ethyl acetate-hexane (1:2) as eluent, to give 0.23 g (26%) of the title compound as white crystals.

mp: 135.0–136.5° C.; NMR (CDCl$_3$) δ: 1.13 (3H, t, J=7.2 Hz), 2.46 (3H, s), 3.72 (2H, q, J=7.2 Hz), 7.34 (2H, d, J=8.4 Hz), 7.50 (1H, d, J=8.8 Hz), 7.65 (2H, d, J=8.4 Hz), 8.43 (1H, dd, J=8.8 & 2.2 Hz), 8.54 (1H, d, J=2.2 Hz).

Example 48

Synthesis of 4'-Chloro-N-ethyl-2'-nitro-p-toluenesulfonanilide (Compound No. 289)

(1) To a solution of 4-chloroaniline (98%, 500 g (3.84 mol) in pyridine (338 ml) and acetonitrile (800 ml), p-toluenesulfonyl chloride (807.8 g (4.11 mol)) was added with stirring at temperature below 15° C. After stirring for 16 hours at room temperature, water (4000 ml) was added to the reaction mixture and stirring was continued for 3 hours to have crystals separated. The crystals were then filtered and washed with water to give 1100 g (102%) of 4'-chloro-p-toluenesulfonanilide as pale red crude crystals.

mp: 122.0–123.0° C.; NMR (CDCl$_3$) δ: 2.39 (3H, s), 6.73 (1H, brs), 7.00 (2H, d, J=8.8 Hz), 7.20 (2H, d, J=8.8 Hz), 7.24 (2H, d, J=8.3 Hz), 7.64 (2H, d, J=8.3 Hz).

(2) To a suspension of 4'-chloro-p-toluenesulfonanilide (1100 g (3.90 mol) in acetic acid (2200 ml), fuming nitric acid (273.9 g (4.22 mol) was added dropwise over a period of 40 minutes with stirring at 50° C. After completion of the addition, the reaction mixture was stirred at the same temperature to complete the reaction. After being left to cool to room temperature, the reaction mixture was treated with 7000 ml of water to bring about precipitation of crystals. The crystals were filtered and washed with water to give 1261 g (99%) of 4'-chloro-2'-nitro-p-toluenesulfonanilide as yellow crystals.

mp: 110.0–111.0° C.; NMR (CDCl$_3$) δ: 2.40 (3H, s), 7.27 (2H, d, J=8.4 Hz), 7.54 (1H, dd, J=9.0 & 2.4 Hz), 7.71 (2H, d, J=8.4 Hz), 7.83 (1H, d, J=9.0 Hz), 8.09 (1H, d, J=2.4 Hz), 9.72 (1H, s).

(3) Sodium hydroxide (96%, 164.0 g (3.94 mol)) was dissolved in a mixed solvent of water (390 ml) and ethanol (1600 ml). To this, 4'-chloro-2'-nitro-p-toluenesulfonanilide (1261 g (3.86 mol)) was added, while being stirred at temperatures of 10 to 25° C. After being stirred at room temperature for 4 hours, the reaction mixture was cooled and crystals formed were filtered and washed with ethanol to give 1253 g (93%) of 4'-chloro-2'-nitro-p-toluenesulfonanilide sodium salt as orange crystals.

mp: 267.0–284.0° C.; NMR (DMSO-d$_6$) δ: 2.29 (3H, s), 7.06 (1H, dd, J=9.1 & 2.7 Hz), 7.17 (2H, d, J=8.3 Hz), 7.25 (1H, d, J=9.1 Hz), 7.42 (1H, d, J=2.7 Hz), 7.59 (2H, d, J=8.3 Hz).

(4) To a mixture of 4'-chloro-2'-nitro-p-toluenesulfonanilide sodium salt (1046 g (3.00 mol)) and DMF (1100 ml), heated in an oil bath kept at 100° C., was added diethyl sulfate (733.8 g (4.50 mol)) over a period of one hour. The resulting mixture was further stirred for 1.5 hours at the same temperature to complete the reaction, and then left to cool to room temperature. A 1.5% aqueous sodium hydroxide solution was added and the mixture was stirred for one hour. The resulting solid was then filtered, washed with water, dried and recrystallized from 1450 ml of ethyl acetate to give 858 g (81%) of the title compound as pale yellow crystals.

mp: 132.5–134.0° C.; NMR (CDCl$_3$) δ: 1.18 (3H, t, J=7.2 Hz), 2.44 (3H, s), 3.66 (2H, q, J=7.2 Hz), 7.05 (1H, d, J=8.6 Hz), 7.28 (2H, d, J=8.2 Hz), 7.50 (1H, dd, J=8.6 & 2.5 Hz), 7.53 (2H, d, J=8.2 Hz), 7.86 (1H, d, J=2.5 Hz).

Example 49

Synthesis of 4'-Chloro-N-isopropyl-2'-nitro-p-toluenesulfonanilide (Compound No. 291)

In a manner similar to that of Example 48-(4), but isopropyl iodide was used instead of diethyl sulfate, and the reaction was carried out by heating for three hours in an oil bath kept at the temperature of 120° C. to give the title compound as pale yellow crystals in a yield of 48%.

mp: 112.0–114.0° C.; NMR (CDCl$_3$) δ: 1.06 (3H, d, J=6.7 Hz), 1.13 (3H, d, J=6.7 Hz), 2.44 (3H, s), 4.38 (1H, septet, J=6.7 Hz), 7.22 (1H, d, J=8.5 Hz), 7.29 (2H, d, J=8.4 Hz), 7.54 (1H, dd, J=8.5 & 2.5 Hz), 7.66 (2H, d, J=8.4 Hz), 7.88 (1H, d, J=2.5 Hz).

Example 50

Synthesis of 4'-Fluoro-N-isopropyl-2'-nitro-p-toluenesulfonanilide (Compound No. 265)

(1) To a solution of 4-fluoroaniline (200.0 g (1.80 mol) in pyridine (155.0 g (1.96 mol)) and acetonitrile (155 ml), under cooling with ice and with stirring, p-toluenesulfonyl chloride (360.3 g (1.89 mol)) was added. After stirring for 20 hours at room temperature, water (1500 ml) was added to the reaction mixture to bring about separation of crystals. The crystals were filtered and washed with water to give 486.6 g (102%) of 4'-fluoro-p-toluenesulfonanilide as pale red crude crystals.

mp: 78.0–79.5° C.; NMR (CDCl$_3$) δ: 2.39 (3H, s), 6.61 (1H, brs), 6.85–7.10 (4H, m), 7.23 (2H, dt, J=8.3 & 0.6 Hz), 7.60 (2H, dt, J=8.3 & 1.8 Hz).

(2) To a suspension of 4'-fluoro-p-toluenesulfonanilide (486.6 g (1.80 mol) in acetic acid (955 ml), 97% fuming nitric acid (128.6 g (1.98 mol) was added dropwise, keeping the inner temperature at 45° C., over a period of 40 minutes. After completion of the addition, the reaction mixture was stirred at 50° C. for 2 hours and left to cool to room temperature. Water (2000 ml) was then added and the mixture was stirred for 30 minutes. The crystals separated were filtered and washed with water to give 543.5 g (97%) of 4'-fluoro-2'-nitro-p-toluenesulfonanilide as yellow crystals.

mp: 117.5–118.5° C.; NMR (CDCl$_3$) δ: 2.39 (3H, s), 7.25 (2H, d, J=8.4 Hz), 7.35 (1H, ddd, J=9.3 & 3.0 Hz, J$_{HF}$=6.9 Hz), 7.66 (2H, d, J=8.4 Hz), 7.79 (1H, dd, J=3.0 Hz, J$_{HF}$=8.2 Hz), 7.89 (1H, dd, J=9.3 Hz, J$_{HF}$=4.9 Hz), 9.51 (1H, s).

(3) Sodium hydroxide (97%, 12.0 g (291 mmol)) was dissolved in a mixed solvent of water (24 ml) and methanol (89 ml). To this, 4'-fluoro-2'-nitro-p-toluenesulfonanilide (89.16 g (287 mmol)) was added with stirring at room temperature. After being stirred at room temperature for 30 minutes, the mixed suspension obtained was cooled with ice, and crystals formed were filtered and washed with methanol to give 79.31 g (83%) of 4'-fluoro-2'-nitro-p-toluenesulfonanilide sodium salt as orange crystals.

mp: 276.0–278.0° C.; NMR (DMSO-d$_6$) δ: 2.29 (3H, s), 6.97 (1H, ddd, J=9.3 & 3.2 Hz, J$_{HF}$=8.3 Hz), 7.16 (2H, d, J=8.3 Hz), 7.20–7.40 (2H, m), 7.58 (2H, d, J=8.3 Hz).

(4) 4'-Fluoro-2'-nitro-p-toluenesulfonanilide sodium salt (66.46 g (200 mmol)) was dissolved in DMF (66 ml). To this, under heating in an oil bath kept at 120° C., isopropyl iodide (102.0 g (600 mmol)) was added over a period of 20 minutes. The resulting mixture was left to cool to room temperature, mixed with 1% aqueous sodium hydroxide solution and stirred. The resulting crystals were filtered, washed with water and ethanol, successively. The crude crystals thus obtained were recrystallized from ethyl acetate to give 30.58 g (43%) of the title compound as pale yellow crystals.

mp: 129.0–130° C.; NMR (CDCl$_3$) δ: 1.05 (3H, d, J=6.7 Hz), 1.13 (3H, d, J=6.7 Hz), 2.44 (3H, s), 4.38 (1H, septet, J=6.7 Hz), 7.20–7.40 (4H, m), 7.55–7.75 (3H, m).

Example 51

Synthesis of 4'-Cyano-N-isopropyl-2'-nitro-p-toluenesulfonanilide (Compound No. 409)

(1) 4-Aminobenzonitrile (98%, 500.0 g (4.15 mol) was dissolved in a mixed solvent of pyridine (360 ml) and acetonitrile (900 ml). To this, p-toluenesulfonyl chloride (872.3 g (4.44 mol)) was added with stirring at room temperature. After stirring for 16 hours at room temperature, water (4000 ml) was added to the reaction mixture to bring about separation of crystals. The crystals were filtered and washed with water to give 1153 g (98%) of 4'-cyano-p-toluenesulfonanilide as pale red crude crystals.

mp : 182.0–184.0° C. NMR (CDCl$_3$) δ: 2.40 (3H, s), 7.18 (2H, dt, J=8.8 & 2.3 Hz), 7.28 (2H, d, J=8.4 Hz), 7.52 (2H, dt, J=8.8 & 2.0 Hz), 7.59 (1H, s), 7.75 (2H, dt, J=8.4 & 1.7 Hz).

(2) To a suspension of 4'-cyano-p-toluenesulfonanilide (1153 g (4.23 mol) in acetic anhydride (2306 ml), fuming nitric acid (294.3 g (4.53 mol) was added dropwise, keeping the temperature at 50° C. with stirring, over a period of 100 minutes. After completion of the addition, the reaction mixture was stirred at 50° C. for 1.5 hours. Then, 1.75 ml (0.042 mol) of fuming nitric acid was further added and stirring was continued for another one hour at 50° C. To the resulting mixture, after being left to cool to room temperature, water (7000 ml) was then added to make crystals to deposite. After stirring under cooling with ice for one hour, the crystals were filtered and washed with water to give 1305 g (97%) of 4'-cyano-2'-nitro-p-toluenesulfonanilide as yellow crystals.

mp: 150.0–152.0° C.; NMR (CDCl$_3$) δ: 2.42 (3H, s), 7.33 (2H, d, J=8.5 Hz), 7.78 (1H, dd, J=8.8 & 2.3 Hz), 7.82 (2H, d, J=8.5 Hz), 7.95 (1H, d, J=8.8 Hz), 8.46 (1H, d, J=2.3 Hz), 10.60 (1H, brs).

(3) Sodium hydroxide (96%, 174.8 g (4.20 mol)) was dissolved in a mixed solvent of water (420 ml) and methanol (1950 ml). To this, under cooling with ice and with stirring, 4'-cyano-2'-nitro-p-toluenesulfonanilide (1305 g (4.11 mol)) was added. After stirring at 5 to 12° C. for 75 minutes, crystals formed were filtered and washed with methanol to give 1330 g (95%) of 4'-cyano-2'-nitro-p-toluenesulfonanilide sodium salt as yellow crystals.

mp: higher than 300° C.; NMR (DMSO-d$_6$) δ: 2.31 (3H, s), 7.22 (2H, d, J=8.1 Hz), 7.29 (1H, d, J=8.9 Hz), 7.39 (1H, dd, J=8.9 & 2.0 Hz), 7.61 (2H, d, J=8.1 Hz), 7.85 (1H, d, J=2.0 Hz).

(4) To a mixture of 4'-cyano-2'-nitro-p-toluenesulfonanilide sodium salt (1330 g (3.92 mol)) and DMF (3000 ml), under heating in an oil bath kept at 110° C., isopropyl iodide (2019 g (11.8 mol)) was added over a period of 1.5 hours. After completion of the addition, the mixture was further heated at the same temperature with stirring for 3 hours, and then left to cool to room temperature. Water (1500 ml) was added to bring about separation of crystals. The crystals were filtered, washed with water, dried, and then suspended in diethyl ether. The suspension was stirred for 4 hours, and the insolubles were removed by filtration, the diethyl ether solution was washed with 0.1% aqueous sodium hydroxide solution to remove the remaining starting material, 4'-cyano-2'-nitro-p-toluenesulfonanilide. The diethyl ether layer was dried over anhydrous magnesium sulfate, filtered, and concentrated under reduced pressure to give crude crystals which were, after washing with ethanol, recrystallized from ethyl acetate to give 124 g (8.8%) of the title compound as pale yellow crystals.

mp: 125.0–126.0° C.; NMR (CDCl$_3$) δ: 1.07 (3H, d, J=6.7 Hz), 1.15 (3H, d, J=6.7 Hz), 2.45 (3H, s), 4.40 (1H, septet, J=6.7 Hz), 7.31 (2H, d, J=8.4 Hz), 7.44 (1H, d, J=8.3 Hz), 7.66 (2H, d, J=8.4 Hz), 7.86 (1H, dd, J=8.3 & 1.9 Hz), 8.19 (1H, d, J=1.9 Hz).

Example 52

Synthesis of N-Methyl-2'-nitro-p-toluenesulfonanilide (Compound No. 38) and N,N-bis(p-toluenesulfonyl)-2'-nitroaniline (Compound No. 39)

(1) 2-Nitroaniline (2.15 g (15.6 mmol)) was dissolved in 10.0 ml of pyridine. To this, p-toluenesulfonyl chloride (3.55 g (18.6 mmol)) was added with stirring at room temperature. After stirring for 15 hours at room temperature, water (100 ml) was added to the reaction mixture to bring about separation of crystals. The crystals were filtered, washed with water, dried and then subjected to silica gel column chromatography with ethyl acetate-hexane (2:3) as eluent to give 2.88 g (53%) of 2'-nitro-p-toluenesulfonanilide as yellow crystals, and 1.17 g (17%) of N,N-bis(p-toluenesulfonyl)-2'-nitroaniline (Compound No. 39) as pale yellow crystals. Physical Constants of 2'-nitro-p-toluenesulfonanilide mp: 115.0–116.5° C.; NMR (CDCl$_3$) δ: 2.39 (3H, s), 7.15 (1H, dt, J=1.3 & 8.5 Hz), 7.26 (2H, d, J=8.3 Hz), 7.58 (1H, dt, J=1.5 & 8.5 Hz), 7.73 (2H, d, J=8.3 Hz), 7.85 (1H, dd, J=8.5 & 1.3 Hz), 8.11 (1H, dd, J=8.5 & 1.5 Hz), 9.85 (1H, s). Physical Constants of Compound No. 39 mp: 184.5–186.5° C.; NMR (CDCl$_3$) δ: 2.47 (6H, s), 7.15 (1H, dd, J=7.6 & 2.0 Hz), 7.33 (4H, d, J=8.5 Hz), 7.56 (1H, dt, J=2.0 & 7.5 Hz), 7.62 (1H, dt, J=1.9 & 7.6 Hz), 7.84 (4H, dt, J=8.5 & 1.9 Hz), 8.02 (1H, dd, J=7.5 & 1.9 Hz).

(2) To a suspension of sodium hydride (60%, 0.15 g (3.75 mmol)) in 3.0 ml of DMF, 2'-nitro-p-toluenesulfonanilide (1.00 g (3.42 mmol)) was added with stirring at room temperature. To the resulting mixture, after 15 minutes' stirring at room temperature, dimethyl sulfate (0.4 ml (4.22 mmol)) was added dropwise. After 2 hour's stirring, water was added to bring about separation of crystals. The resulting crystals were filtered, washed with water, dried and subjected to silica gel column chromatography with ethyl acetate-hexane (1:2 to 1:1) as eluent to give 0.93 g (89%) of N-methyl-2'-nitro-p-toluenesulfonanilide (Compound No.38) as pale yellow crystals.

mp: 131.5–132.5° C.; NMR (CDCl$_3$) δ: 2.44 (3H, s), 3.26 (3H, s), 7.11 (1H, dd, J=7.1 & 2.2 Hz), 7.29 (2H, d, J=8.5 Hz), 7.40–7.60 (2H, m), 7.55 (2H, d, J=8.5 Hz), 7.85 (1H, dd, J=7.5 & 2.3 Hz).

Example 53

Synthesis of 2'-Chloro-N-ethyl-4'-nitro-p-toluenesulfonanilide (Compound No. 275)

(1) 2-Chloro-4-nitroaniline (1.73 g (10.0 mmol)) was dissolved in 5.0 ml of pyridine. To this, p-toluenesulfonyl chloride (1.91 g (10.0 mmol)) was added with stirring at room temperature. After stirring for 18 hours at room temperature, water (50 ml) was added to the reaction mixture to bring about separation of crystals. The crystals were filtered, washed with water and then dissolved in an aqueous solution of sodium hydroxide. The resulting solution was washed with diethyl ether, and the water layer was made acidic again with hydrochloric acid and extracted with ethyl acetate. The extract was dried over anhydrous magnesium sulfate and concentrated under reduced pressure to give 2.61 g (80%) of 2'-chloro-4'-nitro-p-toluenesulfonanilide as pale yellow crystals.

mp: 167.0–168.5° C.; NMR (CDCl$_3$) δ: 2.41 (3H, s), 7.30 (2H, d, J=8.4 Hz), 7.41 (1H, s), 7.77 (1H, d, J=9.0 Hz), 7.77 (2H, d, J=8.4 Hz), 8.09 (1H, dd, J=9.0 & 2.5 Hz), 8.21 (1H, d, J=2.5 Hz).

(2) To a suspension of sodium hydride (60%, 0.07 g (1.75 mmol)) in 3.0 ml of DMF, 2'-chloro-4'-nitro-p-toluenesulfonanilide (0.50 g (1.53 mmol)) was added under cooling with ice and with stirring. To the resulting mixture, after 15 minutes' stirring under cooling with ice, dimethyl sulfate (0.23 ml (1.76 mmol)) was added dropwise and the mixture heated at 100° C. for 2 hours with stirring. Then, after being left to cool to room temperature, water was added and the mixture was extracted with diethyl ether. The extract was washed with water and 1% aqueous solution of sodium hydroxide, dried over anhydrous magnesium sulfate, filtered and concentrated under reduced pressure. The residue was purified by subjecting it to silica gel column chromatography with ethyl acetate-hexane (1:3) as eluent and the crystals obtained were recrystallized from ethyl acetate to give 0.31 g (57%) of the title compound as pale yellow crystals.

mp: 118.0–119.0° C.; NMR (CDCl$_3$) δ: 1.10 (3H, t, J=7.2 Hz), 2.45 (3H, s), 3.67 (2H, q, J=7.2 Hz), 7.30 (2H, d, J=8.3 Hz), 7.39 (1H, d, J=8.7 Hz), 7.64 (2H, d, J=8.3 Hz), 8.11 (1H, dd, J=8.7 & 2.6 Hz), 8.31 (1H, d, J=2.6 Hz).

Example 54

Synthesis of 2'-Chloro-N-isopropyl-4'nitro-p-toluenesulfonanilide (Compound No. 272)

In a manner similar to that of Example 53-(2), but isopropyl iodide was used instead of dimethyl sulfate, and the reaction was carried out by heating at 130° C. for 2 hours, to give the title compound as pale yellow crystals in a yield of 24%.

mp: 154.0–157.0° C.; NMR (CDCl$_3$) δ: 1.09 (3H, d, J=6.7 Hz), 1.14 (3H, d, J=6.7 Hz), 2.45 (3H, s), 4.46 (1H, septet, J=6.7 Hz), 7.31 (2H, d, J=8.4 Hz), 7.33 (1H, d, J=8.7 Hz), 7.69 (2H, d, J=8.4 Hz), 8.11 (1H, dd, J=8.7 & 2.6 Hz), 8.38 (1H, d, J=2.6 Hz).

Example 55

Synthesis of 2'-Chloro-4'-cyano-N-ethyl-p-toluenesulfonanilide (Compound No. 92)

(1) 4-Amino-3-chlorobenzonitrile (1.50 g (9.83 mmol)) was dissolved in 5.0 ml of pyridine. To this, p-toluenesulfonyl chloride (1.90 g (9.97 mmol)) was added under cooling with ice and with stirring. After stirring for 18 hours at room temperature, water (100 ml) was added to the reaction mixture to bring about separation of crystals. The crystals were filtered, washed with water and then dissolved in an aqueous solution of sodium hydroxide. The resulting solution was washed with diethyl ether, and the water layer was made acidic again with hydrochloric acid and extracted with chloroform. The extract was dried over anhydrous magnesium sulfate and concentrated under reduced pressure to give 1.65 g (55%) of 2'-chloro-4'-cyano-p-toluenesulfonanilide as white crystals.

mp: 186.0–187.0° C.; NMR (CDCl$_3$) δ: 2.41 (3H, s), 7.20–7.40 (1H, br), 7.29 (2H, d, J=8.4 Hz), 7.49 (1H, dd, J=8.7 & 1.7 Hz), 7.58 (1H, d, J=1.7 Hz), 7.72 (1H, d, J=8.7 Hz), 7.75 (2H, d, J=8.4 Hz).

(2) To a suspension of sodium hydride (60%, 0.07 g (1.75 mmol)) in 3.0 ml of DMF, 2'-chloro-4'-cyano-p- toluenesulfonanilide (0.50 g (1.63 mmol)) was added under cooling with ice and with stirring. To the resulting mixture, after 15 minutes' stirring under cooling with ice, diethyl sulfate (0.25 ml (1.91 mmol)) was added dropwise and the mixture heated at 100° C. for 2 hours with stirring. Then, after being left to cool to room temperature, water was added and the mixture was extracted with diethyl ether. The extract was washed with water and 1% aqueous solution of sodium hydroxide, dried over anhydrous magnesium sulfate, filtered and concentrated under reduced pressure. The resulting crystals were recrystallized from diethyl ether to give 0.33 g (61%) of the title compound as white crystals.

mp: 112.0–114.0° C.; NMR (CDCl$_3$) δ: 1.08 (3H, t, J=7.1 Hz), 2.44 (3H, s), 3.64 (2H, q, J=7.1 Hz), 7.29 (2H, d, J=8.4 Hz), 7.31 (1H, d, J=8.3 Hz), 7.55 (1H, dd, J=8.3 & 1.9 Hz), 7.63 (2H, d, J=8.4 Hz), 7.73 (1H, d, J=1.9 Hz).

Example 56

Synthesis of 2'-Chloro-4'-cyano-N-isopropyl-p-toluenesulfonanilide (Compound No. 93)

In a manner similar to that of Example 55-(2), but isopropyl iodide was used instead of diethyl sulfate, and the reaction was carried out by heating at 130° C. for 2 hours, to give the title compound as pale yellow crystals in a yield of 19%.

mp: 118.0–119.0° C.; NMR (CDCl$_3$) δ: 1.06 (3H, d, J=6.7 Hz), 1.12 (3H, d, J=6.7 Hz), 2.45 (3H, s), 4.45 (1H, septet, J=6.7 Hz), 7.26 (1H, d, J=8.3 Hz), 7.30 (2H, d, J=8.4 Hz), 7.56 (1H, dd, J=8.3 & 1.9 Hz), 7.68 (2H, d, J=8.4 Hz), 7.81 (1H, d, J=1.9 Hz).

Example 57

Synthesis of Methyl 5-Chloro-2-(N-ethyl-N-p-toluenesulfonyl)aminobenzthioimidate Hydroiodic Acid Salt (Compound No. 87)

A mixture of 4'-chloro-N-ethyl-2'-thiocarbamoyl-p-toluenesulfonanilide (0.30 g (0.81 mmol)), methyl iodide (1.0 ml (16.1 mmol)) and chloroform (3.0 ml) was heated under reflux for 5 hours. After being left to cool to room temperature, the reaction mixture was concentrated under reduced pressure to give crude crystals. Diethyl ether was added to the crystals and stirred, and then the crystals were filtered and washed with diethyl ether to give 0.41 g (99%) of the title compound as pale yellow crystals.

mp:>160° C. (dec.); NMR (CDCl$_3$) δ: 1.03 (3H, t, J=7.2 Hz), 2.47 (3H, s), 3.30 (3H, s), 3.00–3.50 (1H, br), 3.50–4.10 (1H, br), 6.72 (1H, d, J=8.6 Hz), 7.38 (2H, d, J=8.3 Hz), 7.49 (1H, dd, J=8.6 & 2.4 Hz), 7.62 (2H, d, J=8.3 Hz), 7.82 (1H, d, J=2.4 Hz), 10.50–12.50 (2H, br).

Example 58

Synthesis of Ethyl 5-Chloro-2-(N-ethyl-N-p-toluenesulfonyl)aminobenzthioimidate Hydroiodic Acid Salt (Compound No. 88)

In a manner similar to that of Example 57, but ethyl iodide was used instead of methyl iodide, and the reaction was carried out by heating under reflux for 6 hours, to give the title compound as pale yellow crystals in a yield of 94%.

mp:>161° C. (dec.); NMR (CDCl$_3$) δ: 1.03 (3H, t, J=7.1 Hz), 1.56 (3H, t, J=7.5 Hz), 2.47 (3H, s), 2.90–3.50 (1H, br), 3.50–4.00 (1H, br), 3.93 (2H, q, J=7.5 Hz), 6.74 (1H, d, J=8.6 Hz), 7.38 (2H, q, J=8.4 Hz), 7.49 (1H, dd, J=8.6 & 2.4 Hz), 7.63 (2H, d, J=8.4 Hz), 7.79 (1H, d, J=2.4 Hz), 10.50–12.50 (2H, br).

Example 59

Synthesis of N-Ethyl-4'-methylthio-2'-nitro-p-toluenesulfonanilide (Compound No. 227)

(1) To a solution of 4-Aminophenyl thiocyanate (10.0 g (66.6 mmol)) in pyridine (70 ml), p-toluenesulfonyl chloride (12.7 g (66.6 mmol)) was added with stirring at room temperature, and the mixture was stirred at room temperature for 16 hours. Then, water was added to the reaction mixture and the resulting mixture was extracted with ethyl acetate. The extract was washed with dilute hydrochloric acid and a saturated aqueous solution of sodium chloride, dried over magnesium sulfate, filtered and concentrated under reduced pressure to give 19.4 g (98%) of 4'-thiocyano-p-toluenesulfonanilide as pale yellow crystals.

mp: 122.0–123.5° C.; NMR (CDCl$_3$) δ: 2.40 (3H, s), 7.16 (2H, dt, J=8.7 & 2.0 Hz), 7.20–7.30 (2H, m), 7.37 (1H, brs), 7.40(2H, dt, J=8.7 & 2.0 Hz), 7.71 (2H, d, J=8.3 Hz).

(2) 4'-Thiocyano-p-toluenesulfonanilide (19.2 g (63.2 mmol)) was dissolved in acetic acid (60 ml). To this, fuming nitric acid (3.04 ml (75.9 mmol)) was added dropwise with stirring at room temperature. Then, the mixture was stirred at 50° C. for 4 hours, poured into water, and the crystals separated were filtered and washed with water. The resulting crystals were dissolved in ethyl acetate, and the solution was dried over anhydrous magnesium sulfate and then concentrated under reduced pressure to give 21.8 g (99%) of 2'-nitro-4'-thiocyano-p-toluenesulfonanilide as pale yellow crystals.

mp: 121.0–122.5° C.; NMR (CDCl$_3$) δ: 2.42 (3H, s), 7.32 (2H, d, J=8.6 Hz), 7.73 (1H, dd, J=9.0 & 2.3 Hz), 7.78 (2H, d, J=8.6 Hz), 7.95 (1H, d, J=9.0 Hz), 8.33 (1H, d, J=2.3 Hz).

(3) To a solution of 2'-Nitro-4'-thiocyano-p-toluenesulfonanilide (5.0 g (14.3 mmol) in methanol (20 ml), sodium borohydride (2.80 g (66.7 mmol)) was added under cooling with ice and with stirring. After 30 minutes' stirring, to the resulting mixture, methyl iodide (3.67 ml (59.0 mmol)) was added dropwise under cooling with ice and the mixture was then stirred at room temperature for 20 hours. Then, water was added to the reaction mixture and the resulting mixture was extracted with ethyl acetate. The extract was washed with a saturated aqueous solution of sodium chloride, dried over anhydrous magnesium sulfate, filtered and concentrated. The residue was then subjected to silica gel column chromatography with ethyl acetate-hexane (1:4) as eluent. The resulting crystals were recrystallized from ethyl acetate to give 2.27 g (47%) of 2'-nitro-4'-methylthio-p-toluenesulfonanilide as orange crystals.

mp: 116.0–117.0° C.; NMR (CDCl$_3$) δ: 2.39 (3H, s), 2.48 (3H, s), 7.25 (2H, d, J=8.4 Hz), 7.44 (1H, dd, J=8.8 & 2.3 Hz), 7.68 (2H, d, J=8.4 Hz), 7.78 (1H, d, J=8.8 Hz), 7.88 (1H, d, J=2.3 Hz).

(4) To a suspension of sodium hydride (65%, 0.21 g (5.76 mmol)) in 4.0 ml of DMF, 2'-nitro-4'-methylthio-p-toluenesulfonanilide (1.50 g (4.43 mmol)) was added with stirring at room temperature. To the resulting mixture, after 30 minutes' stirring at room temperature, ethyl iodide (0.52 ml (6.21 mmol)) was added dropwise and the mixture was stirred at room temperature for 16 hours. Then, the reaction mixture was poured into water and extracted with ethyl acetate. The extract was washed with a saturated aqueous solution of sodium bicarbonate, dilute hydrochloric acid, and saturated aqueous solution of sodium chloride successively. The ethyl acetate layer was dried over anhydrous magnesium sulfate, filtered and concentrated under reduced pressure. The resulting residue was then subjected to silica gel column chromatography with chloroform as eluent to give 1.04 g (64%) of the title compound as pale yellow crystals.

mp: 135.0–136.5° C.; NMR (CDCl$_3$) δ: 1.18 (3H, t, J=7.2 Hz), 2.43 (3H, s), 2.53 (3H, s), 3.50–3.80 (2H, m), 6.96 (1H, d, J=8.5 Hz), 7.20–7.40 (3H, m), 7.53 (2H, d, J=8.3 Hz), 7.62 (1H, d, J=2.3 Hz).

Example 60

Synthesis of N-Isopropyl-4'-methylthio-2'-nitro-p-toluenesulfonanilide (Compound No. 229)

In a manner similar to that of Example 59-(4), but isopropyl iodide was used instead of ethyl iodide, and the reaction was carried out by heating at 80° C. for 7 hours with stirring, to give the title compound as pale yellow crystals in a yield of 31%.

mp: 124.5–126.0° C.; NMR (CDCl$_3$) δ: 1.05 (3H, d, J=6.7 Hz), 1.11 (3H, d, J=6.7 Hz), 2.43 (3H, s), 2.54 (3H, s), 4.37 (1H, septet, J=6.7 Hz), 7.14 (1H, d, J=8.5 Hz), 7.28 (2H, d, J=8.2 Hz), 7.36 (1H, dd, J=8.5 & 2.3 Hz), 7.60–7.70 (3H, m).

Example 61

Synthesis of 2'-Cyano-N-methyl-4'-methylthio-p-toluenesulfonanilide (Compound No. 99)

(1) To a solution of 2-aminobenzonitrile (4.00 g (33.9 mmol)) and sodium thiocyanate (3.00 g (37.0 mmol)) in methanol (20 ml), a solution of bromine (5.50 g (34.4 mmol)) in methanol (5.0 ml) was added dropwise over a period of 40 minutes under cooling with ice and with stirring. The mixture was then stirred under cooling with ice for 30 mitutes, and then neutralized with a saturated aqueous solution of sodium bicarbonate and extracted with ethyl acetate. The extract was washed with water, dried over anhydrous magnesium sulfate, and concentrated under reduced pressure. The resulting residue was subjected to silica gel column chromatography with chloroform as eluent to give 4.21 g (71%) of 2-amino-5-thiocyanobenzonitrile as pale yellow-white crystals.

mp: 123.5–125.0° C.; NMR (CDCl$_3$) δ: 4.77 (2H, br), 6.81 (1H, d, J=8.8 Hz), 7.54 (1H, dd, J=8.8 & 2.2 Hz), 7.64 (1H, d, J=2.2 Hz).

(2) Sodium hydroxide (97%, 1.20 g (29.1 mmol)) was dissolved in a mixed solvent of water (4.0 ml) and methanol (20.0 ml). To this, 2-amino-5-thiocyanobenzonitrile (5.03 g (28.7 mmol)) was added with stirring. To the resulting mixture, after 30 minutes' stirring under cooling with ice, sodium borohydride (90%, 0.60 g (14.3 mmol)) was added and further stirred for 30 minutes under cooling with ice. Then, dimethyl sulfate (95%, 3.0 ml (30.0 mmol)) was added dropwise. The resulting mixture was further stirred under cooling with ice for 30 minutes and at room temperature for 30 minutes, and then concentrated under reduced pressure. Water was added to the residue and the mixture was extracted with diethyl ether. The extract was washed twice with water, dried over anhydrous magnesium sulfate and then concentrated under reduced pressure to give 4.73 g (100%) of 2-amino-5-methylthiobenzonitrile as yellow crystals.

mp: 50.0–54.0° C.; NMR (CDCl$_3$) δ:2.41 (3H, s),3.20–4.60 (2H, br), 6.70 (1H, ddd, J=9.1 & 2.2 & 1.1 Hz), 7.30–7.45 (2H, m).

(3) To a solution of 2-amino-5-methylthiobenzonitrile (4.60 g (28.0 mmol)) in pyridine (20.0 ml), p-toluenesulfonyl chloride (5.60 g (29.4 mmol)) was added under cooling with ice and with stirring. The mixture was further stirred for 30 minutes under cooling with ice and for one hour at room temperature. Water (200 ml) was then added to the reaction mixture and the mixture was stirred for 30 minutes to separate crystals. The crystals were filtered and washed with water to give 8.33 g (93%) of 2'-cyano-4'-thiomethyl-p-toluenesulfonanilide as pale yellow crystals.

mp: 170.0–173.0° C.; NMR (CDCl$_3$) δ: 2.40 (3H, s), 2.45 (3H, s), 7.20–7.35 (3H, m), 7.40 (1H, dd, J=8.9 & 2.3 Hz), 7.64 (1H, d, J=8.9 Hz),7.67 (2H, d, J=8.3 Hz).

(4) To a suspension of sodium hydride (60%, 0.27 g (6.75 mmol)) in 7.0 ml of DMF, 2'-cyano-4'-thiomethyl-p-toluenesulfonanilide (2.00 g (6.28 mmol)) was added with stirring at room temperature. To the resulting mixture, after 15 minutes' stirring at room temperature, dimethyl sulfate (0.70 ml (7.38 mmol)) was added dropwise and the mixture was stirred at room temperature for 18 hours. Then, the reaction mixture was poured into water and extracted with ethyl acetate. The extract was washed with water and a saturated aqueous solution of sodium chloride, dried over anhydrous magnesium sulfate, and concentrated under reduced pressure. The resulting residue was then subjected to silica gel column chromatography with chloroform as eluent to give 1.63 g (78%) of the title compound as white crystals.

mp: 139.0–140.0° C.; NMR (CDCl$_3$) δ: 2.45 (3H, s), 2.51 (3H, s), 3.22 (3H, s), 7.17 (1H, d, J=8.4 Hz), 7.25–7.45 (4H, m), 7.65 (2H, d, J=8.3 Hz).

Example 62

Synthesis of 2'-Cyano-N-ethyl-4'-methylthio-p-toluenesulfonanilide (Compound No. 100)

In a manner similar to that of Example 61-(4), but diethyl sulfate was used instead of dimethyl sulfate, and the reaction was carried out by heating at 100° C. for one hour with stirring, to give the title compound as white crystals in a yield of 43%.

mp: 136.0–137.0° C.; NMR (CDCl$_3$) δ: 1.10 (3H, t, J=7.2 Hz), 2.44 (3H, s), 2.51 (3H, s), 3.63 (2H, q, J=7.2 Hz), 7.12 (1H, d, J=8.5 Hz), 7.31 (2H, d, J=8.4 Hz), 7.38 (1H, dd, J=8.5 & 2.3 Hz), 7.44 (1H, d, J=2.3 Hz), 7.66 (2H, d, J=8.4 Hz).

Example 63

Synthesis of 2'-Cyano-4'-methanesulfonyl-N-methyl-p-toluenesulfonanilide (Compound No. 105)

To a solution of 2'-cyano-N-methyl-4'-methylthio-p-toluenesulfonanilide (0.29 g (0.87 mmol)) in chloroform (2.0 ml), 70% mCPBA (m-chloro-perbenzoic acid) (0.43 g (1.74 mmol) was added with stirring under cooling with ice. The mixture was stirred under cooling with ice for 30 minutes and at room temperature for 2 hours, diluted with chloroform, washed with aqueous sodium hydrogen sulfite solution, and 1% aqueous solution of sodium hydroxide, successively. The chloroform layer was dried with anhydrous magnesium sulfate and concentrated under reduced pressure to give 0.31 g (97.5%) of the title compound as white crystals.

mp: 179.0–180.5° C.; NMR (CDCl$_3$) δ:2.47 (3H, s), 3.12 (3H, s), 3.26 (3H, s), 7.36 (2H, d, J=8.3 Hz), 7.56 (1H, d, J=8.5 Hz), 7.67 (2H, d, J=8.3 Hz), 8.13 (1H, dd, J=8.5 & 2.2 Hz), 8.23 (1H, d, J=2.2 Hz).

Example 64

Synthesis of N-methoxy-4'-nitro-2',3,4-trichlorobenzenesulfonanilide (Compound No. 527)

(1) To a suspension of methoxylamine hydrochloride (0.93 g (11.1 mmol)) in pyridine (5.0 ml), 3,4-dichlorobenzenesulfonyl chloride (2.73 g (11.1 mmol)) was added with stirring under cooling with ice and the resulting mixture was stirred for one hour under cooling with ice, and at room temperature for 18 hours. Water (50.0 ml) was then added to the reaction mixture to bring about separation of crystals. The crystals were filtered and washed with water to give 2.69 g (95%) of 3,4-dichloro-N-methoxybenzenesulfonamide as pale yellow crystals.

mp: 146.0–147.0° C.; NMR (CDCl$_3$) δ:3.82 (3H, s), 7.63 (1H, dd, J=8.4 & 0.3 Hz), 7.76 (1H, dd, J=8.4 & 2.1 Hz), 7.86 (1H, s), 8.02 (1H, dd, J=2.1 & 0.3 Hz).

(2) To a suspension of sodium hydride (60%, 0.09 g (2.25 mmol)) in 3.0 ml of DMF, 3,4-dichloro-N-methoxybenzenesulfonamide (0.56 g (2.19 mmol)) was added with stirring under cooling with ice. To the resulting mixture, after 15 minutes' stirring under cooling with ice, 3-chloro-4-fluoronitrobenzene (0.35 ml (1.99 mmol)) was added and the mixture was stirred for one hour under cooling with ice and 3 hours at room temperature. Then, water was added to the reaction mixture and the resulting mixture was extracted with diethyl ether. The extract was washed twice with water and the ether layer was dried over anhydrous magnesium sulfate, and concentrated under reduced pressure to give 0.56 g (68%) of the title compound as pale yellow-white crystals.

mp: 132.0–133.0° C.; NMR (CDCl$_3$) δ: 3.87 (3H, s), 6.95 (1H, d, J=8.8 Hz), 7.53 (1H, dd, J=8.4 & 2.1 Hz), 7.64 (1H, dd, J=8.4 & 0.3 Hz), 7.88 (1H, dd, J=2.1 & 0.3 Hz), 8.03 (1H, dd, J=8.8 & 2.5 Hz), 8.39 (1H, d, J=2.5 Hz).

Example 65

Synthesis of N-Methoxy-4'-nitro-2,2',5-trichlorobenzenesulfonanilide (Compound No. 528)

(1) In a manner similar to that of Example 64-(1), but 2,5-dichlorobenzenesulfonyl chloride was used instead of 3,4-dichlorobenzenesulfonyl chloride to give 2,5-dichloro-N-methoxybenzenesulfonamide as pale yellow crystals in a yield of 93%.

mp: 127.0–128.5° C.; NMR (CDCl$_3$) δ: 3.80 (3H, s), 7.48 (1H, dd, J=8.5 & 0.4 Hz), 7.55 (1H, dd, J=8.5 & 2.3 Hz), 8.14 (1H, dd, J=2.3 & 0.4 Hz), 8.14 (1H, s).

(2) In a manner similar to that of Example 64-(2), but 2,5-dichloro-N-methoxybenzenesulfonamide was used instead of 3,4-dichloro-N-methoxybenzenesulfonamide to give the title compound as pale yellow-white crystals in a yield of 68%.

mp: 132.0–133.0° C.; NMR (CDCl$_3$) δ: 3.83 (3H, s), 7.23 (1H, d, J=9.0 Hz), 7.50 (1H, dd, J=8.6 & 0.3 Hz), 7.59 (1H, dd, J=8.6 & 2.4 Hz), 7.96 (1H, dd, J=2.4 & 0.3 Hz), 8.06 (1H, dd, J=9.0 & 2.5 Hz), 8.37 (1H, d, J=2.5 Hz).

Example 66

Synthesis of 2'-Chloro-N-methoxy-4'-nitro-3-trifluoromethylbenzenesulfonanilide (Compound No. 529)

(1) In a manner similar to that of Example 64-(1), but 3-trifluoromethylbenzenesulfonyl chloride was used instead of 3,4-dichlorobenzenesulfonyl chloride to give N-methoxy-3-trifluoromethylbenzenesulfonamide as pale yellow crystals in a yield of 97%.

mp: 78.0–81.0° C.; NMR (CDCl$_3$) δ: 3.83 (3H, s), 7.27 (1H, s), 7.72 (1H, t, J=7.8 Hz), 7.92 (1H, dt, J=7.8 & 0.6 Hz), 8.13 (1H, dt, J=7.8 & 0.6 Hz), 8.20 (1H, t, J=0.6 Hz).

(2) In a manner similar to that of Example 64-(2), but N-methoxy-3-trifluoromethylbenzenesulfonamide was used instead of 3,4-dichloro-N-methoxybenzenesulfonamide to give the title compound as white crystals in a yield of 57%.

mp: 95.5–96.5° C.; NMR (CDCl$_3$) δ: 3.86 (3H, s), 6.86 (1H, d, J=9.0 Hz), 7.73 (1H, t, J=7.9 Hz), 7.90–8.10 (4H, m), 8.39 (1H, d, J=2.5 Hz).

Example 67

Synthesis of 2'-Chloro-3,4'-dinitro-N-methoxybenzenesulfonanilide (Compound No. 530)

(1) In a manner similar to that of Example 64-(1), but 3-nitrobenzenesulfonyl chloride was used instead of 3,4-dichlorobenzenesulfonyl chloride to give N-methoxy-3-nitrobenzenesulfonamide as pale yellow crystals in a yield of 85%.

mp: 111.0–113.0° C.; NMR (CDCl$_3$) δ: 3.86 (3H, s), 7.28 (1H, s), 7.80 (1H, t, J=8.3 Hz), 8.26 (1H, ddd, J=8.3 & 1.8 & 1.1 Hz), 8.52 (1H, ddd, J=8.3 & 2.2 & 1.1 Hz), 8.77 (1H, dd, J=2.2 & 1.8 Hz).

(2) In a manner similar to that of Example 64-(2), but N-methoxy-3-nitrobenzenesulfonamide was used instead of 3,4-dichloro-N-methoxybenzenesulfonamide to give the title compound as pale yellow crystals in a yield of 80%.

mp: 167.5–169.0° C.; NMR (CDCl$_3$) δ: 3.89 (3H, s), 6.90 (1H, d, J=8.8 Hz), 7.80 (1H, t, J=8.2 Hz), 7.95–8.10 (2H, m), 8.40 (1H, d, J=2.5 Hz), 8.55–8.70 (2H, m).

Example 68

Synthesis of 2',4-Dichloro-3,4'-dinitro-N-methoxybenzenesulfonanilide (Compound No. 531)

(1) Methoxylamine hydrochloride(0.90 g (10.8 mmol) was suspended in pyridine (3.0 ml). To this, under cooling with ice and with stirring, 4-chloro-3-nitrobenzenesulfonylchloride (2.56 g (10.8 mmol)) was added and the mixture was stirred under cooling with ice for one hour and at room temperature for 3 hours. Water (50.0 ml) was added to the reaction mixture and the mixture was extracted with ethyl acetate. The extract was washed with dilute hydrochloric acid and water successively, dried over anhydrous magnesium sulfate and concentrated under reduced pressure to give 2.02 g (76%) of 4-chloro-N-methoxy-3-nitrobenzenesulfonamide as pale yellow-white crystals.

mp: 69.5–71.0° C.; NMR (CDCl$_3$) δ: 3.86 (3H, s), 7.29 (1H, s), 7.77 (1H, d, J=8.4 Hz), 8.05 (1H, dd, J=8.4 & 2.1 Hz), 8.41(1H, d, J=2.1 Hz).

(2) To a solution of 4-chloro-N-methoxy-3-nitrobenzenesulfonamide (0.53 g (1.99 mmol)) and 3-chloro-4-fluoronitrobenzene (1.05 g (5.98 mmol) in 5.0 ml of DMF, sodium hydride (60%, 0.09 g (2.25 mmol)) was added bit by bit with stirring under cooling with ice, and the mixture was stirred under cooling with ice for one hour and at room temperature for 2 hours. Water and diethyl ether were added to the resulting mixture and insolubles were removed by filtration. The filtrate was allowed to stand somewhile and then, the organic layer was separated and washed with water, dried over anhydrous magnesium sulfate and concentrated under reduced pressure The residue was subjected to silica gel column chromatography with ethyl acetate-hexane (1:5) as eluent to give 0.10 g (12%) of the title compound as pale yellow-white crystals.

mp: 138.0–139.0° C.; NMR (CDCl$_3$) δ: 3.89 (3H, s), 6.96 (1H, d, J=8.9 Hz), 7.70–7.90 (2H, m), 8.05 (1H, dd, J=8.9 & 2.5 Hz), 8.26 (1H, d, J=1.5 Hz), 8.40 (1H, d, J=2.5 Hz).

Example 69

Synthesis of 4-Chloro-2'-fluoro-N-methoxy-4'-nitro-3-(trifluoromethyl)benzenesulfonanilide (Compound No. 524)

(1) In a manner similar to that of Example 68-(1), but 4-chloro-3-(trifluoromethyl) benzenesulfonyl chloride was used instead of 4-chloro-3-nitrobenzenesulfonyl chloride to give 4-chloro-N-methoxy-3-(trifluoromethyl) benzenesulfonamide as white crystals in a yield of 92%.

mp: 88.0–90.5° C.; NMR (CDCl$_3$) δ: 3.84 (3H, s), 7.20 (1H, s), 7.72 (1H, d, J=8.4 Hz), 8.03 (1H, dd, J=8.4 & 2.2 Hz), 8.23 (1H, d, J=2.2 Hz).

(2) To a solution of 4-chloro-N-methoxy-3-(trifluoromethyl)benzenesulfonamide(0.58 g (2.00 mmol)) and 3,4-difluoronitrobenzene (0.66 ml (5.96 mmol)) in 5.0 ml of DMF, sodium hydride (60%, 0.09 g (2.25 mmol)) was added bit by bit with stirring under cooling with ice. The resulting mixture was stirred under cooling with ice for one hour and allowed to warm-up to room temperature. Water was added to the reaction mixture and the resulting mixture was extracted with diethyl ether. The extract was washed with water, and dried over anhydrous magnesium sulfate and concentrated under reduced pressure to give 0.32 g (37%) of the title compound as pale yellow crystals.

mp: 104.5–105.5° C.; NMR (CDCl$_3$) δ: 3.92 (3H, s), 7.03 (1H, dd, J=9.0 Hz, $J_{HF}$=7.0 Hz), 7.60–7.85 (2H, m), 7.90–8.15 (3H, m).

Example 70

Synthesis of 4-Chloro-2'-cyano-N-methoxy-4'-nitro-3-(trifluoromethyl)benzenesulfonanilide (Compound No. 536)

(1) In a manner similar to that of Example 69-(2), but 2-chloro-5-nitrobenzonitrile was used instead of 3,4-difluoronitrobenzene to give the title compound as pale yellow-white crystals in a yield of 38%.

mp: 140.5–142.0° C.; NMR (CDCl$_3$) δ: 3.88 (3H, s), 7.36 (1H, d, J=9.0 Hz), 7.72 (1H, d, J=8.4 Hz), 7.82 (1H, dd, J=8.4 & 2.1 Hz), 8.07 (1H, d, J=2.1 Hz), 8.39 (1H, dd, J=9.0 & 2.5 Hz), 8.58 (1H, d, J=2.5 Hz).

Example 71

Synthesis of 5-Chloro-1,3-dimethyl-N-(2,4-dinitrophenyl)-N-methoxy-4-pyrazolesulfonamide (Compound No. 552)

(1) Methoxylamine hydrochloride (0.90 g (10.8 mmol)) was suspended in pyridine (2.0 ml). To this, under cooling with ice and with stirring, a solution of 5-chloro-1,3-dimethyl-4-pyrazolesulfonyl chloride (2.29 g (10.0 mmol)) in acetonitrile (2.0 ml) was added dropwise, and the mixture was stirred under cooling with ice for one hour and at room temperature for one hour. Water (50.0 ml) was added to bring about separation of crystals. The crystals were filtered and washed with water, dried, and subjected to silica gel column chromatography with ethyl acetate-hexane (1:1) as eluent to give 1.72 g (72%) of 5-chloro-1,3-dimethyl-N-methoxy-4-pyrazolesulfonamide as white crystals.

mp: 120.0–122.5° C.; NMR (CDCl$_3$) δ: 2.43 (3H, s), 3.82 (3H, s), 3.83 (3H, s), 7.09 (1H, s).

(2) To a solution of 5-chloro-1,3-dimethyl-N-methoxy-4-pyrazolesulfonamide (0.48 g (2.00 mmol)) and 2,4-dinitrochlorobenzene (0.49 g (2.42 mmol)) in DMF (3.0 ml), sodium hydride (60%, 0.09 g (2.25 mmol)) was added dropwise under cooling with ice and with stirring and the mixture was stirred under cooling with ice for one hour and at room temperature for one hour. Water was added to the reaction mixture and the resulting mixture was extracted with ethyl acetate. The extract was washed with water, dried over anhydrous magnesium sulfate, and then concentrated under reduced pressure. The residue was subjected to silica gel column chromatography with chloroform-hexane (10:1) as eluent to give 0.65 g (87%) of the title compound as pale yellow crystals.

mp: 189.0–191.0° C. (dec.); NMR (CDCl$_3$) δ: 2.14 (3H, s), 3.81 (3H, s), 3.99 (3H, s), 7.59 (1H, d, J=9.0 Hz), 8.35 (1H, dd, J=9.0 & 2.5 Hz), 8.67 (1H, d, J=2.5 Hz).

Example 72

Synthesis of 5-Chloro-N-(2-cyano-4-nitrophenyl)-N-methoxy-2-thiophenesulfonamide (Compound No. 537)

(1) In a manner similar to that of Example 71-(1), but 5-chloro-2-thiophenesulfonyl chloride was used instead of 5-chloro-1,3-dimethyl-4-pyrazolesulfonyl chloride to give 5-chloro-N-methoxy-2-thiophenesulfonamide as white crystals in a yield of 69%.

mp: 65.5–66.5° C.; NMR (CDCl$_3$) δ: 3.86 (3H, s), 6.99 (1H, d, J=4.1 Hz), 7.08 (1H, s), 7.53 (1H, d, J=4.1 Hz).

(2) To a solution of 5-chloro-N-methoxy-2-thiophenesulfonamide (0.46 g (2.02 mmol)) and 2-chloro-5-nitrobenzonitrile (0.45 g (2.46 mol)) in DMF (3.0 ml), sodium hydride (60%, 0.09 g (2.25 mmol)) was added bit by bit under cooling with ice and with stirring and the mixture was stirred under cooling with ice for one hour and at room temperature for one hour. Water was added to the reaction mixture and the resulting mixture was extracted with ethyl acetate. The extract was washed with water, dried over anhydrous magnesium sulfate, and then concentrated under reduced pressure. The residue was subjected to silica gel chromatography with ethyl acetate-hexane (1:3) as eluent to give 0.41 g (54%) of the title compound as pale yellow crystals.

mp: 144.0–146.0° C.; NMR (CDCl$_3$) δ: 3.99 (3H, s), 7.03 (1H, d, J=4.1 Hz), 7.29 (1H, d, J=4.1 Hz), 7.37 (1H, d, J=9.0 Hz), 8.37 (1H, dd, J=9.0 & 2.5 Hz), 8.57 (1H, d, J=2.5 Hz).

Example 73

Synthesis of 2'-Chloro-4'-cyano-N-methoxy-p-toluenesulfonanilide (Compound No. 566)

To a suspension of sodium hydride (60%, 0.09 g (2.25 mmol)) in DMF (3.0 ml), N-methoxy-p-toluenesulfonamide (0.45 g (2.20 mmol)) was added with stirring under cooling with ice. To the resulting mixture, after 15 minutes' stirring under cooling with ice, 3-chloro-4-fluorobenzonitrile (0.31 g (1.99 mmol)) was added. The resulting mixture was then stirred under cooling with ice for one hour and at 50° C. for 18 hours.

Water was added to the reaction mixture and extracted with diethyl ether. The extract was washed with water and a saturated aqueous solution of sodium chloride, successively, dried over anhydrous magnesium sulfate, and then concentrated under reduced pressure, to give 0.54 g (81%) of the title compound as white crystals.

mp: 145.0–147.0° C.; NMR (CDCl$_3$) δ: 2.49 (3H, s), 3.81 (3H, s), 6.82 (1H, d, J=8.3 Hz), 7.34 (2H, d, J=8.3 Hz), 7.39 (1H, dd, J=8.3 & 1.8 Hz), 7.63 (2H, d, J=8.3 Hz), 7.77 (1H, d, J=1.8 Hz).

Example 74

Synthesis of 2-Chloro-2',4'-dinitro-N-methoxybenzenesulfonanilide (Compound No. 563)

(1) Methoxylamine hydrochloride (0.95 g (11.4 mmol)) was suspended in pyridine (4.0 ml). To this, under cooling with ice and with stirring, 2-chlorobenzenesulfonyl chloride (2.11 g (10.0 mmol)) was added and the mixture was stirred under cooling with ice for one hour and at room temperature for one hour. Water (50.0 ml) was added to the reaction mixture and the resulting mixture was extracted with ethyl acetate. The extract was washed with water, dilute hydrochloric acid and a saturated aqueous solution of sodium chloride, successively, dried over anhydrous magnesium sulfate and concentrated under reduced pressure to give 1.41 g (64%) of 2-chloro-N-methoxybenzenesulfonamide as pale yellow crystals.

mp: 92.5–94.0° C.; NMR (CDCl$_3$) δ: 3.80 (3H, s), 7.40–7.70 (3H, m), 7.86 (1H, s), 8.17 (1H, ddd, J=7.7 & 1.6 & 0.8 Hz).

(2) To a suspension of sodium hydride (60%, 0.09 g (2.25 mmol)) in DMF (3.0 ml), 2-chloro-N-methoxybenzenesulfonamide (0.48 g (2.17 mmol)) was added with stirring under cooling with ice. To the resulting mixture, after 15 minutes' stirring under cooling with ice, 2,4-dinitrochlorobenzene (0.41 g (2.02 mmol)) was added. The resulting mixture was then stirred under cooling with ice for one hour and at room temperature for one hour. Water was added to the reaction mixture and the resulting mixture was extracted with diethyl ether. The extract was washed with water, dilute hydrochloric acid and a saturated aqueous solution of sodium chloride, successively, dried over anhydrous magnesium sulfate, and then concentrated under reduced pressure, to give 0.49 g (62%) of the title compound as pale yellow crystals.

mp: 112.5–114.0° C.; NMR (CDCl$_3$) δ: 3.93 (3H, s), 7.40–7.70 (4H, m), 7.96 (1H, dd, J=7.9 & 1.7 Hz), 8.34 (1H, dd, J=8.9 & 2.5 Hz), 8.67 (1H, d, J=2.5 Hz).

Example 75

Synthesis of 3-Chloro-2',4'-dinitro-N-methoxybenzenesulfonanilide (Compound No. 564)

(1) In a manner similar to that of Example 74-(1), but 3-chlorobenzenesulfonyl chloride was used instead of 2-chlorobenzenesulfonyl chloride to give 3-chloro-N-methoxybenzenesulfonamide as pale yellow crystals in a yield of 38%.

mp: 72.0–74.5° C.; NMR (CDCl$_3$) δ: 3.83 (3H, s), 7.10 (1H, s), 7.50 (1H, dd, J=8.0 & 7.7 Hz), 7.63 (1H, ddd, J=8.0 & 2.0 & 1.2 Hz), 7.82 (1H, ddd, J=7.7 & 1.7 & 1.2 Hz), 7.92 (1H, dd, J=2.0 & 1.7 Hz).

(2) In a manner similar to that of Example 74-(2), but 3-chloro-N-methoxybenzenesulfonamide was used instead of 2-chloro-N-methoxybenzenesulfonamide to give the title compound as pale yellow crystals in a yield of 76%.

mp: 157.0–159.0° C.; NMR (CDCl$_3$) δ: 3.94 (3H, s), 7.35 (1H, d, J=8.9 Hz), 7.45–7.55 (2H, m), 7.65–7.75 (2H, m), 8.32 (1H, dd, J=8.9 & 2.7 Hz), 8.73 (1H, d, J=2.7 Hz).

Example 76

Synthesis of 2'-Cyano-N-methoxy-4'-nitro-4-(trifluoromethyl)-Benzenesulfonanilide (Compound No. 565)

(1) In a manner similar to that of Example 74-(1), but 4-(trifluoromethyl)benzenesulfonyl chloride was used instead of 2-chlorobenzenesulfonyl chloride to give N-methoxy-4-(trifluoromethyl)benzenesulfonamide as pale yellow-white crystals in a yield of 22%.

mp: 96.0–97.0° C.; NMR (CDCl$_3$) δ: 3.84 (3H, s), 7.15 (1H, s), 7.83 (2H, d, J=8.2 Hz), 8.07 (2H, d, J=8.2 Hz).

(2) To a suspension of sodium hydride (60%, 0.09 g (2.25 mmol)) in DMF (4.0 ml), N-methoxy-4-(trifluoromethyl) benzenesulfonamide (0.55 g (2.16 mmol)) was added with stirring under cooling with ice. To the resulting mixture, after 15 minutes' stirring under cooling with ice, 2-chloro-5-nitrobenzonitrile (0.37 g (2.03 mmol)) was added. The resulting mixture was then stirred under cooling with ice for one hour and at room temperature for one hour. Water was added to the reaction mixture and the resulting mixture was extracted with diethyl ether. The extract was washed with water, dilute hydrochloric acid and a saturated aqueous solution of sodium chloride, dried over anhydrous magnesium sulfate, and then concentrated under reduced pressure. The residue was subjected to silica gel column chromatography with ethyl acetate-hexane (1:4) as eluent to give 0.51 g (63%) of the title compound as white crystals.

mp: 133.5–135.0° C.; NMR (CDCl$_3$) δ: 3.87 (3H, s), 7.34 (1H, d, J=9.0 Hz), 7.84 (2H, d, J=8.6 Hz), 7.91 (2H, d, J=8.6 Hz), 8.37 (1H, dd, J=9.0 & 2.7 Hz), 8.57 (1H, d, J=2.7 Hz).

Example 77

Synthesis of 2',4'-Dinitro-N-methoxy-3-methylbenzenesulfonanilide (Compound No. 562)

(1) In a manner similar to that of Example 74-(1), but 3-methylbenzenesulfonyl chloride was used instead of 2-chlorobenzenesulfonyl chloride to give N-methoxy-3-methylbenzenesulfonamide as pale yellow crystals in a yield of 53%.

mp: 90.0–92.0° C.; NMR (CDCl$_3$) δ: 2.45 (3H, s), 3.80 (3H, s), 7.05 (1H, s), 7.40–7.55 (2H, m), 7.70–7.80 (2H, m).

(2) In a manner similar to that of Example 74-(2), but N-methoxy-3-methylbenzenesulfonamide was used instead of 2-chloro-N-methoxybenzenesulfonamide to give the title compound as pale yellow crystals in a yield of 77%.

mp: 147.5–149.5° C.; NMR (CDCl$_3$) δ: 2.42 (3H, s), 3.90 (3H, s), 7.32 (1H, d, J=9.0 Hz), 7.35–7.45 (2H, m), 7.45–7.60 (2H, m), 8.29 (1H, dd, J=9.0 & 2.5 Hz), 8.72 (1H, d, J=2.5 Hz).

Example 78

Synthesis of N-Methoxy-4'-methylthio-2'-nitro-p-toluene sulfonanilide (Compound No. 572)

(1) To a suspension of dry potassium fluoride (0.57 g (9.79 mmol) in dimethylsulfoxide (10.0 ml), 2-chloro-5-(methylthio)nitrobenzene (1.88 g (9.23 mmol)) was added and the mixture was stirred at 170° C. for 3 hours. As the reaction had not yet completed, dry potassium fluoride (0.68 g (11.7 mmol)) was added further and the mixture was stirred at 170° C. for another 3 hours. The reaction mixture was poured into water and extracted with diethyl ether. The extract was washed with water, dried over anhydrous magnesium sulfate and concentrated under reduced pressure. The residue was then distilled by means of a glass tube oven under reduced pressure, and a fraction which boiled at 110–160° C./0.8 mmHg was collcted to give 1.39 g of a 3:2 mixture of 2-fluoro-5-(methylthio)nitrobenzene and 2-chloro-5-(methylthio)nitrobenzene as yellow oil.

(2) To a suspension of sodium hydride (60%, 0.33 g (8.17 mmol)) in DMF (10.0 ml), N-methoxy-p-toluenesulfonamide (1.63 g (8.17 mmol)) was added with stirring under cooling with ice. To the resulting mixture, after 15 minutes' stirring at room temperature, a 3:2 mixture of 2-fluoro-5-(methylthio)nitrobenzene and 2-chloro-5-(methylthio)nitrobenzene (1.39 g) was added. The mixture was stirred overnight at room temperature, poured into water and extracted with diethyl ether. The extract was washed with water, dried over anhydrous magnesium sulfate, and then concentrated under reduced pressure. The residue was subjected to silica gel column chromatography with ethyl acetate-hexane (1:6 to 1:4) as eluent. The eluted substance was recrystallized from ethyl acetate-hexane to give 0.60 g of the title compound as yellow crystals.

mp: 110.3–110.8° C.; NMR (CDCl$_3$) δ: 2.46 (3H, s), 2.52 (3H, s), 3.82 (3H, s), 6.89 (1H, d, J=8.6 Hz), 7.23 (1H, dd, J=8.6 & 2.2 Hz), 7.30 (2H, d, J=8.0 Hz), 7.50–7.70 (3H, m).

Example 79

Synthesis of 2'-Cyano-N-methoxy-4'-methylthio-p-toluenesulfonylanilide (Compound No. 571)

(1) To a solution of 2-amino-5-(thiocyanato)benzonitrile (2.00 g (11.4 mmol)) and 42% borofluoric acid (7.16 g (34.2 mmol)) in ethanol (10.0 ml), a solution of sodium nitrite (0.87 g (12.6 mmol)) in water (1.2 ml), was added dropwise under cooling with ice. The mixture was stirred under cooling with ice for 2 hours and crystals separated were filtered. The solid was washed with water, methanol and then ether, successively, and dried under reduced pressure to give 2.98 g (95%) of 2-cyano-4-(thiocyanato) benzenediazonium fluoroborate as white crystals.

mp: 191° C. (dec.); NMR (DMSO-d$_6$) δ: 8.47 (1H, dd, J=8.9 & 2.1 Hz), 8.82 (1H, d, J=2.1 Hz), 9.01 (1H, d, J=8.9 Hz).

(2) 2-Cyano-4-(thiocyanato)benzenediazonium fluoroborate (2.98 g (10.9 mmol)) was decomposed by first heating with a heat-gun until until the whole mass became black and then by heating to 200° C. in an oil bath for 30 minutes. After cooling, water was added and the resulting mixture was extracted with ethyl acetate. The extract was washed with a saturated aqueous solution of sodium chloride, dried over anhydrous magnesium sulfate and concentrated under reduced pressure. The residue was then distilled by means of a glass tube oven under reduced pressure, and a fraction which boiled at 180–240 ° C./0.2 mmHg was collected to give 0.29 g (15%) of 2-fluoro-5-(thiocyanato)benzonitrile as a pale yellow-white crystals.

mp: 39.0–41.0° C.; NMR (CDCl$_3$) δ: 8.36 (1H, ddd, J=9.4 & 8.1 & 1.2 Hz), 7.7–7.9 (2H, m), 7.67 (1H, d, J=2.2 Hz).

(3) To a suspension of sodium borohydride (90%, 0.41 g (9.76 mmol)) in ethanol (10 ml), 2-fluoro-5-(thiocyanato) benzonitrile (0.29 g (1.63 mmol)) was added with stirring under cooling with ice. To the resulting mixture, after one hour's stirring at room temperature, methyl iodide (0.11 ml (1.71 mmol)) was added and the resulting mixture was stirred overnight at room temperature. Then, the reaction mixture was poured into water and the resulting mixture was extracted with ethyl acetate. The extract was washed with a saturated aqueous solution of sodium chloride, dried over anhydrous magnesium sulfate, and concentrated under reduced pressure. The residue was subjected to silica gel column chromatography with ethyl acetate-hexane (3:7) as eluent, to give 0.25 g (92%) of 2-fluoro-5-(methylthio) benzonitrile as pale yellow-white crystals.

mp: 61.7–62.7° C.; NMR (CDCl$_3$) δ: 2.50 (3H, s), 7.05–7.2 (1H, m), 7.4–7.55 (2H, m).

(4) To a suspension of sodium hydride (60%, 0.07 g (1.64 mmol)) in DMF (5.0 ml), N-methoxy-p-toluenesulfonamide (0.33 g (1.64 mmol)) was added with stirring under cooling with ice. To the resulting mixture, after 15 minutes' stirring at room temperature, 2-fluoro-5-(methylthio)benzonitrile (0.25 g (1.50 mmol)) was added and the mixture was stirred overnight at room temperature, without any progress of reaction. So, the mixture was further heated at 50° C. for 3 days and then allowed to cool. The reaction mixture was poured into water and the resulting mixture was extracted with diethyl ether. The extract was washed with water, dried over anhydrous magnesium sulfate, and then concentrated under reduced pressure. The residue was subjected to silica gel column chromatography with ethyl acetate-hexane (1:4) as eluent. The eluate was then purified by recrystallization from ethyl acetate-hexane, giving 0.34 g (65%) of the title compound as white crystals.

mp: 146.8–147.6° C.; NMR (CDCl$_3$) δ: 2.47 (3H, s),2.51 (3H, s), 3.76 (3H, s),6.96 (1H, d, J=8.7 Hz), 7.2–7.4 (3H, m), 7.44 (1H, d, J=2.2 Hz), 7.66 (2H, d, J=8.3 Hz).

Example 80

Synthesis of N-(4-Cyano-3-methoxy-5-isothiazolyl)-N-methoxy-p-toluenesulfon anilide (Compound No. 560)

To a suspension of sodium hydride (60%, 0.09 g (2.25 mmol)) in DMF (3.0 ml), N-methoxy-p-toluenesulfonamide (0.45 g (2.20 mmol)) was added with stirring under cooling with ice. To the resulting mixture, after 15 minutes' stirring under cooling with ice, 4-cyano-5-methanesulfonyl-3-methoxyisothiazole (0.44 ml (2.02 mmol)) was added. After being stirred for 30 minutes under cooling with ice and at room temperature for 30 minutes. Water was added to the reaction mixture and the resulting mixture was extracted with ethyl acetate. The extract was washed with water and a saturated aqueous solution of sodium chloride, dried over anhydrous magnesium sulfate, and then concentrated under reduced pressure. The residue was subjected to silica gel column chromatography with ethyl acetate-hexane (1:3) as eluent, giving 0.44 g (64%) of the title compound as white crystals.

mp: 115.5–118.0° C.; NMR (CDCl$_3$) δ: 2.46 (3H, s), 4.00 (3H, s), 4.14 (3H, s), 7.35 (2H, d, J=8.3 Hz), 7.77 (2H, d, J=8.3 Hz).

Example 81

Synthesis of 4'-Chloro-4-ethyl-N-isopropyl-2'-nitrobenzenesulfonanilide (Compound No. 328)

(1) To a solution of 4-ethylbenzenesulfonyl chloride (90%, 4.25 g (20.8 mmol)) in pyridine (10 ml), 4-chloroaniline (2.55 g (20.0 mmol)) was added with stirring at room temperature. After 18 hours' stirring at room temperature, water (100.0 ml) was added to the reaction mixture and the mixture was extracted with ethyl acetate. The extract was washed with dilute hydrochloric acid, water and a saturated aqueous solution of sodium chloride successively, dried over anhydrous magnesium sulfate, and then concentrated under reduced pressure to give 5.26 g (89%) of 4'-chloro-4-ethylbenzenesulfonanilide as white crystals.

mp: 119.5–121.5° C.; NMR (CDCl$_3$) δ: 1.23 (3H, t, J=7.6 Hz), 2.68(2H, q, J=7.6 Hz), 6.90 (1H, s), 7.02 (2H, d, J=8.8 Hz), 7.20 (2H, d, J=8.8 Hz), 7.26 (2H, d, J=8.4 Hz), 7.68 (2H, d, J=8.4 Hz).

(2) To a suspension of 4'-chloro-4-ethylbenzenesulfonanilide (4.70 g (15.9 mmol)) in 15 ml of acetic acid, 97% fuming nitric acid (0.69 ml (16.1 mmol)) was added dropwise with stirring at room temperature. The resulting mixture was stirred at 50° C. for 30 minutes and then allowed to cool to room temperature. Water (100.0 ml) was added to the reaction mixture and the resulting crystals were filtered and washed with waterto give 5.35 g (99%) of 4'-chloro-4-ethyl-2'-nitrobenzenesulfonanilide as pale yellow crystals.

mp: 104.5–105.5° C.; NMR (CDCl$_3$) δ: 1.23 (3H, t, J=7.6 Hz), 2.69 (2H, q, J=7.6 Hz), 7.30 (2H, d, J=8.4 Hz), 7.54 (1H, dd, J=9.0 & 2.5 Hz), 7.74 (2H, d, J=8.4 Hz), 7.84 (1H, d, J=9.0 Hz), 8.10 (1H, d, J=2.5 Hz), 9.73 (1H, brs).

(3) To a suspension of sodium hydride (60%, 0.12 g (3.00 mmol)) in DMF (7.0 ml), 4'-chloro-4-ethyl-2'-nitrobenzenesulfonanilide (1.00 g (2.93 mmol)) was added with stirring at room temperature. To the resulting mixture, after 15 minutes' stirring at room temperature, isopropyl iodide (0.70 ml (7.01 mmol)) was added dropwise and heated at 130° C. for 2 hours with stirring. After being allowed to cool to room temperature, water was added to the reaction mixture and the resulting mixture was extracted with diethyl ether. The extract was washed with 1% aqueous solution of sodium hydroxide and a saturated aqueous solution of sodium chloride, dried over anhydrous magnesium sulfate, and then concentrated under reduced pressure. The residue was subjected to silica gel column chromatography with ethyl acetate-hexane (1:3) as eluent to give 0.41 g (37%) of the title compound as pale red crystals.

mp: 117.0–118.5° C.; NMR (CDCl$_3$) δ: 1.06 (3H, d, J=6.7 Hz), 1.13 (3H, d, J=6.7 Hz), 1.27 (3H, t, J=7.6 Hz), 2.74 (2H, q, J=7.6 Hz), 4.37 (1H, septet, J=6.7 Hz), 7.23 (1H, d, J=8.6 Hz), 7.32 (2H, d, J=8.4 Hz), 7.55 (1H, dd, J=8.6 & 2.5 Hz), 7.69 (2H, d, J=8.4 Hz), 7.89 (1H, d, J=2.5 Hz).

Example 82

Synthesis of 4,4'-Dichloro-N-ethyl-2'-nitrobenzenesulfonanilide (Compound No. 338)

(1) In a manner similar to that of Example 81-(1), but 4-chlorobenzenesulfonyl chloride was used instead of 4-ethylbenzenesulfonyl chloride to give 4,4'-dichlorobenzenesulfonanilide as pale red crystals in a yield of 86%.

mp: 144.5–145.5° C.; NMR (CDCl$_3$) δ: 6.71 (1H, s), 7.01 (2H, d, J=8.9 Hz), 7.23 (2H, d, J=8.9 Hz), 7.43 (2H, d, J=8.8 Hz), 7.68 (2H, d, J=8.8 Hz).

(2) In a manner similar to that of Example 81-(2), but 4,4'-dichlorobenzenesulfonanilide was used instead of 4'-chloro-4-ethylbenzenesulfonanilide to give 4,4'-dichloro-2'-nitrobenzenesulfonanilide in a yield of 96%.

mp: 122.0–123.0° C.; NMR (CDCl$_3$) δ: 7.46 (2H, d, J=8.8 Hz), 7.57 (1H, dd, J=9.0 & 2.5 Hz), 7.77 (2H, d, J=8.8 Hz), 7.83 (1H, d, J=9.0 Hz), 8.12 (1H, d, J=2.5 Hz), 9.74 (1H, s).

(3) To a suspension of sodium hydride (60%, 0.13 g (3.25 mmol)) in DMF (7.0 ml), 4',4'-dichloro-2'-nitrobenzenesulfonanilide (1.00 g (2.88 mmol)) was added with stirring at room temperature. To the resulting mixture, after 15 minutes' stirring at room temperature, diethyl sulfate (0.45 ml (3.44 mmol)) was added dropwise and the mixture was heated at 100° C. for 2 hours with stirring. The reaction mixture was allowed to cool to room temperature, poured into water and extracted with diethyl ether. The extract was washed with 1% aqueous sodium hydroxide and saturated aqueous solution of sodium chloride, dried over anhydrous magnesium sulfate, and then concentrated under reduced pressure to give 0.51 g (47%) of the title compound as pale yellow crystals.

mp: 121.5–123.0° C.; NMR (CDCl$_3$) δ: 1.20 (3H, t, J=7.2 Hz), 3.68 (2H, q, J=7.2 Hz), 7.09 (1H, d, J=8.6 Hz), 7.47 (2H, d, J=8.7 Hz), 7.54 (1H, dd, J=8.6 & 2.5 Hz), 7.60 (2H, d, J=8.7 Hz), 7.88 (1H, d, J=2.5 Hz).

Example 83

Synthesis of 4'-Chloro-2'-hydroxymethyl-N-methyl-p-toluenesulfonanilide (Compound No. 65)

To a solution of 5-chloro-N-methyl-N-(p-toluenesulfonyl) anthranilic acid (5.20 g (15.3 mmol)) in chloroform (20.0 ml), thionyl chloride (2.00 g (27.4 mmol)) was added with stirring at room temperature. The resulting mixture was heated at 50° C. for 2 hours with stirring and then concentrated under reduced pressure. The residue was dissolved in acetonitrile (20.0 ml) and added dropwise to a solution of sodium borohydride (90%, 1.30 g (30.9 mmol)) in water (20.0 ml) under cooling with ice. After one hour's stirring at room temperature, water (100.0 ml) was added to the reaction mixture and the resulting mixture was extracted with ethyl acetate. The extract was washed with dilute hydrochloric acid, dried over anhydrous magnesium sulfate and concentrated under reduced pressure to give 4.40 g (88%) of the title compound as white crystals.

mp: 130.0–132.0° C.; NMR (CDCl$_3$) δ: 2.47 (3H, s), 2.70–3.20 (1H, br), 3.12 (3H, s), 4.61 (1H, brs), 4.94 (1H, brs), 6.37 (1H, d, J=8.5 Hz), 7.10 (1H, dd, J=8.5 & 2.5 Hz), 7.32 (2H, d, J=8.3 Hz), 7.54 (2H, d, J=8.3 Hz), 7.60 (1H, d, J=2.5 Hz).

Example 84

Synthesis of 5-Chloro-2-(N-methyl-N-p-toluenesulfonyl)aminobenzaldehyde (Compound No. 66)

A mixture of 4'-chloro-2'-hydroxymethyl-N-methyl-p-toluenesulfonanilide (3.83 g (11.8 mmol)), manganese dioxide (5.11 g (58.8 mmol) and acetonitrile (30.0 ml) was stirred at room temperature for 3 hours. Then, manganese dioxide (5.11 g (58.8 mmol)) was further added and the mixture was stirred for 20 hours further. The insolubles were filtered off, and the filtrate was concentrated under reduced pressure. The residue was subjected to silica gel column chromatography with chloroform-ethanol (100:1) as eluent to give 2.33 g (61%) of the title compound as white crystals.

mp: 123.0–124.0° C.; NMR (CDCl$_3$) δ: 2.46 (3H, s), 3.22 (3H, s), 6.64 (1H, d, J=8.6 Hz), 7.30 (2H, d, J=8.4 Hz), 7.41 (1H, dd, J=8.6 & 2.6 Hz), 7.44 (2H, d, J=8.4 Hz), 7.97 (1H, d, J=2.6 Hz), 10.39 (1H, s).

Example 85

Synthesis of 5-Chloro-2-(N-methyl-N-p-toluenesulfonyl)aminobenzaldehyde Methoxime (Compound No. 68)

A mixture of 5-chloro-2-(N-methyl-N-p-toluenesulfonyl) aminobenzaldehyde (0.30 g (0.93 mmol)), methoxylamine hydrochloride (0.10 g (1.20 mmol) and pyridine (0.50 ml) was stirred at room temperature for 18 hours. The reaction mixture was concentrated under reduced pressure and the residue was dissolved in diethyl ether, followed by washing with water. The organic layer was separated, dried over anhydrous magnesium sulfate and concentrated under reduced pressure to give 0.30 g (92%) of the title compound as white crystals.

mp: 123.5–124.5° C.; NMR (CDCl$_3$) δ: 2.45 (3H, s), 3.11 (3H, s), 3.99 (3H, s), 6.56 (1H, d, J=8.6 Hz), 7.18 (1H, dd, J=8.6 & 2.5 Hz), 7.31 (2H, d, J=8.4 Hz), 7.54 (2H, d, J=8.4 Hz), 7.96 (1H, d, J=2.5 Hz), 8.38 (1H, s).

Example 86

Synthesis of 2'-Amino-4'-chloro-N-methyl-p-toluenesulfonanilide (Compound No. 61)

A mixture of 4'-chloro-N-methyl-2'-nitro-p-toluenesulfonanilide (7.11 g (20.9 mmol)), stannous chloride (14.7 g (62.6 mmol)) and ethanol (100.0 ml) was stirred at room temperature for 45 minutes, and at 50° C. for 16 hours. After being allowed to cool to room temperature, the reaction mixture was neutralized with a saturated aqueous solution of sodium bicarbonate and the insolubles were removed by filtration. The filtrate was extracted with ethyl acetate and the extract was dried over anhydrous magnesium sulfate and concentrated under reduced pressure. The residue was subjected to silica gel column chromatography with acetone-chloroform-hexane (1:3:5) as eluent to give 5.22 g (81%) of the title compound as white crystals.

mp: 101.5–102.5° C.; NMR (CDCl$_3$) δ: 2.46 (3H, s), 3.10 (3H, s), 3.65 (2H, brs), 6.21 (1H, d, J=8.5 Hz), 6.50 (1H, dd, J=8.5 & 2.3 Hz), 6.81 (1H, d, J=2.3 Hz), 7.31 (2H, d, J=8.3 Hz), 7.58 (2H, d, J=8.3 Hz).

Example 87

Synthesis of 4'-Chloro-N-methyl-2'-nitroso-p-toluenesulfonanilide (Compound No. 284)

To a solution of 2'-amino-4'-chloro-N-methyl-p-toluenesulfonanilide (1.50 g (4.83 mmol)) in chloroform (20.0 ml), 70% mCPBA (m-chloro-perbenzoic acid) (2.38 g) was added with stirring at room temperature. After being stirred for 3 days at room temperature, saturated aqueous solution of sodium bicarbonate was added to the reaction mixture and the resulting mixture was extracted with chloroform. The extract was dried over anhydrous magnesium sulfate and concentrated under reduced pressure. The residue was subjected to silica gel column chromatography with ethyl acetate-hexane (1:6) as eluent to give 1.15 g (73%) of the title compound as blue-green crystals.

mp: 113.0–114.5° C.; NMR (CDCl$_3$) δ: 2.40 (3H, s), 3.63 (3H, s), 6.09 (1H, dd, J=1.8 & 1.1 Hz), 7.17 (2H, m), 7.45 (2H, d, J=8.3 Hz), 7.66 (1H, d, J=1.8 Hz), 7.66 (1H, d, J=1.1 Hz).

Example 88

Synthesis of 2'-Azoxycyano-4'-chloro-N-methyl-p-toluenesulfonanilide (Compound No. 393)

To a solution of 4'-chloro-N-methyl-2'-nitroso-p-toluenesulfonanilide (0.50 g (1.54 mmol)) in DMF (6.0 ml), NBS (N-bromosuccinimide) (0.28 g (1.54 mmol)) was added with stirring at room temperature. To the resulting mixture, after 20 minutes' stirring at room temperature, a solution of cyanamide (0.10 g (2.31 mmol)) in water (1.0 ml) was added dropwise and the mixture was stirred at room temperature for 2 days. Water was added to the reaction mixture and the mixture was extracted with ethyl acetate. The extract was dried over anhydrous magnesium sulfate and concentrated under reduced pressure. The residue was subjected to silica gel column chromatography with acetone-chloroform-hexane (1:3:8) as eluent to give 0.32 g (57%) of the title compound as pale yellow-white crystals.

mp: 140.0–142.0° C.; NMR (CDCl$_3$) δ: 2.46 (3H, s), 3.24 (3H, s), 7.11 (1H, d, J=8.6 Hz), 7.31 (2H, d, J=8.4 Hz), 7.52 (2H, d, J=8.4 Hz), 7.57 (1H, d, J=8.6 Hz), 7.84 (1H, d, J=2.5 Hz).

Example 89

Synthesis of 4'-Cyano-N-ethyl-p-toluenesulfonanilide (Compound No. 29)

To a suspension of sodium hydride (65%, 3.39 g (91.8 mmol)) in DMF (60.0 ml), 4'-cyano-p-toluenesulfonanilide (10.0 g (36.7 mmol)) was added with stirring at room temperature. To the resulting mixture, after stirring for an hour at room temperature, diethyl sulfate (12.0 ml (91.8 mmol)) was added dropwise, and the resulting mixture was heated with stirring at 75° C. for 4 hours. Then, the reaction mixture was allowed to cool to room temperature, poured into water and extracted with ethyl acetate. The extract was washed with dilute hydrochloric acid and a saturated aqueous solution of sodium chloride, dried over anhydrous magnesium sulfate, and concentrated under reduced pressure. The residue was subjected to silica gel column chromatography with chloroform as eluent, to give 9.8 g (89%) of the title compound as white crystals.

mp: 85.4–86.6° C.; NMR (CDCl$_3$) δ: 1.08 (3H, t, J=7.1 Hz), 2.43 (3H, s), 3.63 (2H, q, J=7.1 Hz), 7.15–7.30 (4H, m), 7.44 (2H, dt, J=8.4 & 2.0 Hz), 7.62 (2H, dt, J=8.4 & 2.0 Hz).

Example 90

Synthesis of 5-Chloro-N-(4-cyano-2-nitrophenyl)-N-ethyl-2-thiophenesulfonamide (Compound No. 415)

(1) 4'-Cyano-N-ethyl-p-toluenesulfonanilide (6.95 g (23.1 mmol) was dissolved in concentrated sulfuric acid (20.0 ml) under cooling with ice. To this, 97% fuming nitric acid (1.00 ml (23.4 mmol)) was added dropwise and the mixture was stirred for 30 minutes under cooling with ice. The resulting mixture was poured into ice-water, followed by extraction with ethyl acetate. The extract was washed with water, dried over anhydrous magnesium sulfate and concentrated under reduced pressure. The residue was subjected to silica gel column chromatography with ethyl acetate-hexane (1:3) as eluent, to give 1.25 g (28%) of 4-cyano-N-ethyl-2-nitroaniline as yellow crystals.

mp: 130.0–131.5° C.; NMR (CDCl$_3$) δ: 1.41 (3H, t, J=7.2 Hz), 3.42 (2H, dq, J=5.1 & 7.2 Hz), 6.91 (1H, d, J=9.0 Hz), 7.61 (1H, dd, J=9.0 & 2.0 Hz), 8.33 (1H, br), 8.52 (1H, d, J=2.0 Hz).

(2) To a suspension of sodium hydride (60%, 0.10 g (2.50 mmol)) in tetrahydrofuran (THF) (3.0 ml), 4-cyano-N-ethyl-2-nitroaniline (0.38 g (1.99 mmol)) was added with stirring at room temperature. To the mixture, upon stirring for 15 minutes at room temperature and after the solution had turned deep purple, 5-chloro-2-thiophenesulfonyl chloride (0.55 g (2.53 mmol)) was added and the resulting mixture was stirred at room temperature for 18 hours. The reaction mixture was poured into water and the resulting mixture was extracted with ethyl acetate. The extract was washed with a saturated aqueous solution of sodium chloride, dried over anhydrous magnesium sulfate and concentrated under reduced pressure. The residue was subjected to silica gel column chromatography with ethyl acetate-hexane (1:3) as eluent, to give 0.22 g (30%) of the title compound as yellow crystals.

mp: 101.5–103.0° C.; NMR (CDCl$_3$) δ: 1.24 (3H, t, J=7.2 Hz), 3.75 (2H, q, J=7.2 Hz), 6.96 (1H, d, J=4.1 Hz), 7.25 (1H, d, J=4.1 Hz), 7.36 (1H, d, J=8.3 Hz), 7.88 (1H, dd, J=8.3 & 1.9 Hz), 8.22 (1H, d, J=1.9 Hz).

Example 91

Synthesis of 5-Chloro-N-(4-chloro-2-nitrophenyl)-N,1,3-trimethyl-4-pyrazolesulfonanilide (Compound No. 377)

To a suspension of sodium hydride (65%, 0.14 g (3.86 mmol) in DMF (5.0 ml), 4-chloro-N-methyl-2-nitroaniline (0.48 g (2.57 mmol)) was added with stirring at room temperature. To the mixture, upon stirring for one hour at room temperature and after the solution had turned deep purple, 5-chloro-1,3-dimethyl-4-pyrazolesulfonyl chloride (0.70 g (3.06 mmol)) was added and the resulting mixture was stirred at room temperature for 16 hours. Upon addition of water to the reaction mixture, a solid separated. The solid was filtered and, after washing with water and drying, subjected to silica gel column chromatography with acetone-chloroform-hexane (1:3:8 to 1:0:5) as eluent, to give 0.55 g (56%) of the title compound as white crystals.

mp: 102.0–103.0° C. NMR(CDCl$_3$) δ: 2.14 (3H, s), 3.33 (3H, s), 3.81 (3H, s), 7.41 (1H, d, J=8.6 Hz), 7.57 (1H, dd, J=8.6 & 2.4 Hz), 7.82 (1H, d, J=2.4 Hz).

Example 92

Synthesis of N-(4-Chloro-2-nitrophenyl)-N,3,5-trimethyl-4-isoxazolesulfonamide (Compound No. 376)

(1) To a suspension of potassium carbonate (0.18 g (1.28 mmol)) in acetonitrile (5.0 ml), 4-chloroaniline (0.33 g (2.56 mmol)), 3,5-dimethyl-4-isoxazolesulfonyl chloride (0.50 g (2.56 mmol)), 18-crown-6 (0.20 g (0.77 mmol)), were added with stirring at room temperature and the resulting mixture was stirred for 16 hours at the same temperature. Then, water (15.0 ml) was added to the reaction mixture and the resulting mixture was extracted with ethyl acetate. The extract was dried over anhydrous magnesium sulfate and concentrated under reduced pressure. The residue was subjected to silica gel column chromatography with chloroform as eluent, to give 0.68 g (92%) of N-(4-chlorophenyl)-3,5-dimethyl-4-isoxazolesulfonamide.

mp: 143.5–144.3° C. NMR(CDCl$_3$) δ: 2.31 (3H, s), 3.46 (3H, s), 6.92 (1H, brs), 7.04. (2H, d, J=8.8 Hz), 7.29 (2H, d, J=8.8 Hz).

(2) To a solution of N-(4-Chlorophenyl)-3,5-dimethyl-4-isoxazolesulfonamide (1.10 g (3.84 mmol)) in acetic acid (4.0 ml), fuming nitric acid (0.20 ml (4.68 mmol)) was added dropwise with stirring at room temperature, and the mixture was heated at 50° C. for one hour with stirring. Water (20.0 ml) was added to the reaction mixture and the resulting mixture was extracted with ethyl acetate. The extract was washed with aqueous sodium hydroxide solution and a saturated aqueous solution of sodium chloride, dried over anhydrous magnesium sulfate and concentrated under reduced pressure. The residue was subjected to silica gel column chromatography with acetone-chloroform-hexane (1:3:8) as eluent, to give 0.82 g (64%) of N-(4-chloro-2-nitrophenyl)-3,5 dimethyl-4-isoxazolesulfonamide as yellow crystals.

mp: 129.5–130.7° C. NMR(CDCl$_3$) δ: 2.18 (3H, s), 2.35 (3H, s), 7.44 (1H, d, J=8.7 Hz), 7.81 (1H, dd, J=8.7 & 2.5 Hz), 8.10 (1H, d, J=2.5 Hz), 10.70 (1H, brs).

(3) To a suspension of sodium hydride (65%, 0.05 g (1.36 mmol)) in DMF (3.0 ml), N-(4-chloro-2-nitrophenyl)-3,5-dimethyl-4-isoxazolesulfonamide (0.30 g (0.90 mmol)) was added with stirring at room temperature. To the mixture, after stirring for one hour at room temperature, dimethyl sulfate (0.13 ml (1.36 mmol)) was added dropwise, and the mixture was stirred for 16 hours. Water (20.0 ml) was added to the reaction mixture and the resulting mixture was extracted with ethyl acetate. The extract was dried over anhydrous magnesium sulfate and concentrated under reduced pressure. The residue was subjected to silica gel column chromatography with acetone-hexane (1:4) as eluent, to give 0.11 g (35%) of the title compound as white crystals.

mp: 99.0–101.0° C. NMR(CDCl$_3$) δ: 2.21 (3H, s), 2.40 (3H, s), 3.33 (3H, s), 7.40 (1H, d, J=8.6 Hz), 7.61 (1H, dd, J=8.6 & 2.4 Hz), 7.86 (1H, d, J=2.4 Hz).

Example 93

Synthesis of 4'-Chloro-4-cyano-N-ethyl-2'-nitrobenzenesulfonanilide (Compound No. 356)

To a suspension of sodium hydride (60%, 0.10 g (2.50 mmol)) in tetrahydrofuran (THF)(3.0 ml), 4-chloro-N-ethyl-2-nitroaniline (0.40 g (1.99 mmol)) was added with stirring at room temperature. To the mixture, after stirring for 30 minutes at room temperature, 4-cyanobenzenesulfonyl chloride (0.50 g (2.48 mmol)) was added and the resulting mixture was stirred at room temperature for 3 hours. The reaction mixture was poured into water and the resulting mixture was extracted with ethyl acetate. The extract was washed with a saturated aqueous solution of sodium chloride, dried over anhydrous magnesium sulfate and concentrated under reduced pressure. The residue was subjected to silica gel column chromatography with ethyl acetate-hexane (1:2) as eluent, to give 0.47 g (64%) of the title compound as pale yellow crystals.

mp: 146.0–148.0° C. NMR(CDCl$_3$) δ: 1.22 (3H, t, J=7.2 Hz), 3.71 (2H, q, J=7.2 Hz), 7.16 (1H, d, J=8.5 Hz), 7.58 (1H, dd, J=8.5 & 2.5 Hz), 7.78 (4H, s), 7.89 (1H, d, J=2.5 Hz).

Table 1 shows the compound (I$^0$) which can be prepared by the methods similar to those in Examples 1 to 93 or based upon them (for example according to the methods of reaction equations from (A) to (D) and synthetic methods form (D) to (T)).

Abbreviations used in the Table have the meanings which follow: Me: methyl group, Et: ethyl group, n—Pr: n-propyl group, i—Pr: isopropyl group, c—Pr: cyclopropyl group, n—Bu: n-butyl group, i—Bu: isobutyl group, s—Bu: s-butyl group, t—Bu: t-butyl group, Ph: phenyl group, Ac: acetyl group.

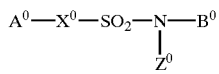

TABLE 1

| Compound No. | A⁰ | X⁰ | Z⁰ | B⁰ | Melting point (° C.) |
|---|---|---|---|---|---|
| 1 | 4-Me—Ph | — | Me | 4-Me—Ph | |
| 2 | 4-Me—Ph | — | Me | 4-Et-Ph | an oil[1] |
| 3 | 4-Me—Ph | — | Me | 4-(n-Pr)—Ph | |
| 4 | 4-Me—Ph | — | Me | 4-(i-Pr)—Ph | 92.5–93.5 |
| 5 | 4-Me—Ph | — | Me | 4-(n-Bu)—Ph | |
| 6 | 4-Me—Ph | — | Me | 2-F—Ph | |
| 7 | 4-Me—Ph | — | Me | 3-F—Ph | |
| 8 | 4-Me—Ph | — | Me | 4-F—Ph | 92.0–94.5 |
| 9 | 4-Me—Ph | — | Me | 2-Cl—Ph | 98.0–99.0 |
| 10 | 4-Me—Ph | — | Me | 3-Cl—Ph | |
| 11 | 4-Me—Ph | — | Me | 4-Cl—Ph | |
| 12 | 4-NH$_2$—Ph | — | Me | 4-Cl—Ph | 170.0–174.0 |
| 13 | 4-AcNH—Ph | — | Me | 4-Cl—Ph | 195.0–199.0 |
| 14 | 4-NO$_2$—Ph | — | Me | 4-Cl—Ph | 183.0–184.0 |
| 15 | 3,5-Me$_2$-4-isoxazolyl | — | Me | 4-Cl—Ph | 109.0–112.0 |
| 16 | 4-Me—Ph | — | Et | 4-Cl—Ph | |
| 17 | 4-Me—Ph | — | Me | 2-Br—Ph | |
| 18 | 4-Me—Ph | — | Me | 3-Br—Ph | |
| 19 | 4-Me—Ph | — | Me | 4-Br—Ph | 82.5–83.5 |
| 20 | 4-Me—Ph | — | Me | 2-SMe—Ph | 120.0–122.0 |
| 21 | 4-Me—Ph | — | Me | 2-SOMe—Ph | |
| 22 | 4-Me—Ph | — | Me | 2-SO$_2$Me—Ph | 191.0–194.0 |
| 23 | 4-Me—Ph | — | Me | 2-COOMe—Ph | 91.0–94.0 |
| 24 | 4-Me—Ph | — | Me | 2-COOH—Ph | 161.0–166.0 |
| 25 | 4-Me—Ph | — | Me | 2-CN—Ph | 138.5–140.0 |
| 26 | 4-Me—Ph | — | SO$_2$-(4-Me—Ph) | 2-CN—Ph | 179.5–181.0 |
| 27 | 4-Me—Ph | — | Me | 3-CN—Ph | 112.0–114.5 |
| 28 | 4-Me—Ph | — | Me | 4-CN—Ph | 117.0–120.0 |
| 29 | 4-Me—Ph | — | Et | 4-CN—Ph | 85.4–86.6 |
| 30 | 4-Me—Ph | — | Me | 2-CF$_3$—Ph | 122.5–124.0 |
| 31 | 4-Me—Ph | — | SO$_2$-(4-Me—Ph) | 2-CF$_3$—Ph | 176.0–177.5 |
| 32 | 4-Me—Ph | — | Me | 3-CF$_3$—Ph | 100.0–102.0 |
| 33 | 4-Me—Ph | — | Me | 4-CF$_3$—Ph | 75.0–76.0 |
| 34 | 4-Me—Ph | — | Me | 2-OCF$_3$—Ph | |
| 35 | 4-Me—Ph | — | Me | 3-OCF$_3$—Ph | |
| 36 | 4-Me—Ph | — | Me | 4-OCF$_3$—Ph | 61.5–63.0 |
| 37 | Ph | — | Me | 2-NO$_2$—Ph | |
| 38 | 4-Me—Ph | — | Me | 2-NO$_2$—Ph | 131.5–132.5 |
| 39 | 4-Me—Ph | — | SO$_2$-(4-Me—Ph) | 2-NO$_2$—Ph | 184.5–186.5 |
| 40 | 4-Me—Ph | — | Me | 3-NO$_2$—Ph | 108.0–109.0 |
| 41 | 4-Me—Ph | — | Me | 4-NO$_2$—Ph | 179.0–181.0 |
| 42 | 4-Me—Ph | — | Me | 3,4-(OMe)$_2$—Ph | 108.5–109.5 |
| 43 | 4-Me—Ph | — | Me | 3.4-(OCH$_2$O)—Ph | 124.0–125.0 |
| 44 | 4-Me—Ph | — | Me | 3,4-(OCF$_2$O)—Ph | |
| 45 | 4-Me—Ph | — | Me | 2-F-4-Cl—Ph | |
| 46 | 4-Me—Ph | — | Et | 2-F-4-Cl—Ph | |
| 47 | 4-Me—Ph | — | n-Pr | 2-F-4-Cl—Ph | |
| 48 | 4-Me—Ph | — | Me | 2,4-F$_2$—Ph | |
| 49 | 4-Me—Ph | — | Et | 2,4-F$_2$—Ph | |
| 50 | 4-Me—Ph | — | n-Pr | 2,4-F$_2$—Ph | |
| 51 | 4-Me—Ph | — | Me | 2,4-Cl$_2$—Ph | 86.0–87.0 |
| 52 | 4-Me—Ph | — | Et | 2,4-Cl$_2$—Ph | |
| 53 | 4-Me—Ph | — | n-Pr | 2,4-Cl$_2$—Ph | |
| 54 | 4-Me—Ph | — | Me | 2,6-Cl$_2$—Ph | |
| 55 | 4-Me—Ph | — | Et | 2,6-Cl$_2$—Ph | |
| 56 | 4-Me—Ph | — | n-Pr | 2,6-Cl$_2$—Ph | |
| 57 | 4-Me—Ph | — | Me | 3,4-Cl$_2$—Ph | 85.0–86.0 |
| 58 | 4-Me—Ph | — | Et | 3,4-Cl$_2$—Ph | |
| 59 | 4-Me—Ph | — | Me | 3,5-Cl$_2$—Ph | |
| 60 | 4-Me—Ph | — | Et | 3,5-Cl$_2$—Ph | |
| 61 | 4-Me—Ph | — | Me | 2-NH$_2$-4-Cl—Ph | 101.5–102.5 |
| 62 | 4-Me—Ph | — | Me | 4-Cl-2-SMe—Ph | 84.5–86.0 |
| 63 | 4-Me—Ph | — | Me | 4-Cl-2-SOMe—Ph | 142.0–143.5 |
| 64 | 4-Me—Ph | — | Me | 4-Cl-2-SO$_2$Me—Ph | 189.5–191.0 |
| 65 | 4-Me—Ph | — | Me | 4-Cl-2-CH$_2$OH—Ph | 130.0–132.0 |
| 66 | 4-Me—Ph | — | Me | 4-Cl-2-CHO—Ph | 123.0–124.0 |
| 67 | 4-Me—Ph | — | Me | 4-Cl-2-CH═NOH)—Ph | 160.5–162.0 |
| 68 | 4-Me—Ph | — | Me | 4-Cl-2-(CH═NOMe)—Ph | 123.5–124.5 |
| 69 | 4-Me—Ph | — | Me | 4-Cl-2-(CH═N—NH$_2$)—Ph | 107.5–109.5 |
| 70 | 4-Me—Ph | — | Me | 4-Cl-2-(CH═N—NMe$_2$)—Ph | 114.0–115.5 |
| 71 | 4-Me—Ph | — | Me | 4-Cl-2-COOH—Ph | 175.0–177.0 |
| 72 | 4-Me—Ph | — | Et | 4-CH$_2$—COOH—Ph | 163.0–165.0 |
| 73 | 4-Me—Ph | — | i-Pr | 4-Cl-2-COOH—Ph | 175.0–176.5 |
| 74 | 4-Me—Ph | — | Me | 2-Cl-4-COOMe—Ph | |
| 75 | 4-Me—Ph | — | Me | 4-Cl-2-COOMe—Ph | 65.5–67.0 |
| 76 | 4-Me—Ph | — | Et | 4-Cl-2-COOMe—Ph | 105.0–107.0 |
| 77 | 4-Me—Ph | — | i-Pr | 4-Cl-2-COOMe—Ph | 113.5–115.5 |

TABLE 1-continued

| Compound No. | A⁰ | X⁰ | Z⁰ | B⁰ | Melting point (° C.) |
|---|---|---|---|---|---|
| 78 | 4-Me—Ph | — | Me | 2-Cl-4-CONH₂—Ph | |
| 79 | 4-Me—Ph | — | Me | 4-Cl-2-CONH₂—Ph | 176.5–178.0 |
| 80 | 4-Me—Ph | — | Et | 4-Cl-2-CONH₂—Ph | 148.5–150.0 |
| 81 | 4-Me—Ph | — | i-Pr | 4-Cl-2-CONH₂—Ph | 177.0–178.5 |
| 82 | 4-Me—Ph | — | Me | 2-Cl-4-CSNH₂—Ph | |
| 83 | 4-Me—Ph | — | Me | 4-Cl-2-CSNH₂—Ph | 180.5–182.5 |
| 84 | 4-Me—Ph | — | Et | 4-Cl-2-CSNH₂—Ph | 180.0–182.0 |
| 85 | 4-Me—Ph | — | i-Pr | 4-Cl-2-CSNH₂—Ph | 189.0–191.0 |
| 86 | 4-Me—Ph | — | Me | 4-Cl-2-[C(SMe)=NH]—Ph (*) | amorphous[2] |
| 87 | 4-Me—Ph | — | Et | 4-Cl-2-[C(SMe)=NH]—Ph (*) | or >160 (dec.) |
| 88 | 4-Me—Ph | — | Et | 4-Cl-2-[C(SEt)=NH]—Ph (*) | or >161 (dec.) |
| 89 | 4-Me—Ph | — | Et | 4-Cl-2-[C(S(i-Pr))=NH]—Ph (*) | or >155 (dec.) |
| 90 | 4-Me—Ph | — | Me | 4-Cl-2-CONMe₂—Ph | an oil[3] |
| 91 | 4-Me—Ph | — | Me | 2-Cl-4-CN—Ph | |
| 92 | 4-Me—Ph | — | Et | 2-Cl-4-CN—Ph | |
| 93 | 4-Me—Ph | — | i-Pr | 2-Cl-4-CN—Ph | |
| 94 | 4-Me—Ph | — | Me | 4-Cl-2-CN—Ph | 145.0–147.0 |
| 95 | 4-Me—Ph | — | Et | 4-Cl-2-CN—Ph | 138.5–140.5 |
| 96 | 4-Me—Ph | — | n-Pr | 4-Cl-2-CN—Ph | |
| 97 | 4-Me—Ph | — | i-Pr | 4-Cl-2-CN—Ph | 129.5–130.5 |
| 98 | 4-Me—Ph | — | c-Pr | 4-Cl-2-CN—Ph | |
| 99 | 4-Me—Ph | — | Me | 2-CN-4-SMe—Ph | 139.0–140.0 |
| 100 | 4-Me—Ph | — | Et | 2-CN-4-SMe—Ph | 136.0–137.0 |
| 101 | 4-Me—Ph | — | i-Pr | 2-CN-4-SMe—Ph | 134.0–136.0 |
| 102 | 4-Me—Ph | — | Me | 2-CN-4-SOMe—Ph | |
| 103 | 4-Me—Ph | — | Et | 2-CN-4-SOMe—Ph | |
| 104 | 4-Me—Ph | — | i-Pr | 2-CN-4-SOMe—Ph | |
| 105 | 4-Me—Ph | — | Me | 2-CN-4-SO₂Me—Ph | 179.0–180.5 |
| 106 | 4-Me—Ph | — | Et | 2-CN-4-SO₂Me—Ph | 154.5–156.0 |
| 107 | 4-Me—Ph | — | i-Pr | 2-CN-4-SO₂Me—Ph | 184.0–186.0 |
| 108 | 4-Me—Ph | — | Et | 2-CN-4-COOH—Ph | 178.5–181.5 |
| 109 | 4-Me—Ph | — | Et | 2-CN-4-COOMe—Ph | 135.6–136.8 |
| 110 | 4-Me—Ph | — | SO₂-(4-Me—Ph) | 2-CN-4-COOMe—Ph | 166.5–167.5 |
| 111 | 4-Me—Ph | — | Et | 2-CN-4-CONH₂—Ph | 163.5–165.0 |
| 112 | 4-Me—Ph | — | Me | 2,4-(CN)₂—Ph | 146.0–147.3 |
| 113 | 4-Me—Ph | — | Et | 2,4-(CN)₂—Ph | 184.5–185.5 |
| 114 | 4-Me—Ph | — | i-Pr | 2,4-(CN)₂—Ph | 157.2–157.7 |
| 115 | 4-Me—Ph | — | SO₂-(4-Me—Ph) | 2,4-(CN)₂—Ph | 195.0–196.5 |
| 116 | 4-Me—Ph | — | Me | 4-Cl-2-CF₃—Ph | 143.0–144.5 |
| 117 | 4-Me—Ph | — | Et | 4-Cl-2-CF₃—Ph | |
| 118 | 4-Me—Ph | — | Me | 3,5-(CF₃)₂—Ph | 110.5–113.0 |
| 119 | 4-Me—Ph | — | Me | 4-Me-2-NO₂—Ph | 123.0–124.0 |
| 120 | 4-Me—Ph | — | Et | 4-Me-2-NO₂—Ph | |
| 121 | 4-Me—Ph | — | n-Pr | 4-Me-2-NO₂—Ph | |
| 122 | 4-Me—Ph | — | i-Pr | 4-Me-2-NO₂—Ph | |
| 123 | 4-Me—Ph | — | c-Pr | 4-Me-2-NO₂—Ph | |
| 124 | 4-Me—Ph | — | n-Bu | 4-Me-2-NO₂—Ph | |
| 125 | 4-Me—Ph | — | Me | 2-Me-4-NO₂—Ph | 103.0–104.0 |
| 126 | 4-Me—Ph | — | Me | 4-Me-3-NO₂—Ph | 103.5–106.0 |
| 127 | 4-Me—Ph | — | Me | 4-Et-2-NO₂—Ph | 137.0–139.0 |
| 128 | 4-Me—Ph | — | Me | 4-(i-Pr)-2-NO₂—Ph | 135.0–136.0 |
| 129 | 4-Me—Ph | — | Me | 4-C≡CH-2-NO₂—Ph | |
| 130 | 4-Me—Ph | — | Et | 4-C≡CH-2-NO₂—Ph | |
| 131 | 4-Me—Ph | — | n-Pr | 4-C≡CH-2-NO₂—Ph | |
| 132 | 4-Me—Ph | — | Me | 4-CHO-2-NO₂—Ph | |
| 133 | 4-Me—Ph | — | Et | 4-CHO-2-NO₂—Ph | |
| 134 | 4-Me—Ph | — | n-Pr | 4-CHO-2-NO₂—Ph | |
| 135 | 4-Me—Ph | — | Me | 4-CH=NOMe-2-NO₂—Ph | |
| 136 | 4-Me—Ph | — | Et | 4-CH=NOMe-2-NO₂—Ph | |
| 137 | 4-Me—Ph | — | n-Pr | 4-CH=NOMe-2-NO₂—Ph | |
| 138 | 4-Me—Ph | — | Me | 4-COOMe-2-NO₂—Ph | |
| 139 | 4-Me—Ph | — | Et | 4-COOMe-2-NO₂—Ph | |
| 140 | 4-Me—Ph | — | n-Pr | 4-COOMe-2-NO₂—Ph | |
| 141 | 4-Me—Ph | — | i-Pr | 4-COOMe-2-NO₂—Ph | |
| 142 | 4-Me—Ph | — | c-Pr | 4-COOMe-2-NO₂—Ph | |
| 143 | 4-Me—Ph | — | n-Bu | 4-COOMe-2-NO₂—Ph | |
| 144 | 4-Me—Ph | — | Me | 4-CONH₂-2-NO₂—Ph | |
| 145 | 4-Me—Ph | — | Et | 4-CONH₂-2-NO₂—Ph | |
| 146 | 4-Me—Ph | — | n-Pr | 4-CONH₂-2-NO₂—Ph | |
| 147 | 4-Me—Ph | — | i-Pr | 4-CONH₂-2-NO₂—Ph | |
| 148 | 4-Me—Ph | — | c-Pr | 4-CONH₂-2-NO₂—Ph | |
| 149 | 4-Me—Ph | — | n-Bu | 4-CONH₂-2-NO₂—Ph | |
| 150 | 4-Me—Ph | — | Me | 4-CSNH₂-2-NO₂—Ph | |
| 151 | 4-Me—Ph | — | Et | 4-CSNH₂-2-NO₂—Ph | |
| 152 | 4-Me—Ph | — | n-Pr | 4-CSNH₂-2-NO₂—Ph | |
| 153 | 4-Me—Ph | — | i-Pr | 4-CSNH₂-2-NO₂—Ph | |
| 154 | 4-Me—Ph | — | c-Pr | 4-CSNH₂-2-NO₂—Ph | |

TABLE 1-continued

| Compound No. | $A^0$ | $X^0$ | $Z^0$ | $B^0$ | Melting point (° C.) |
|---|---|---|---|---|---|
| 155 | 4-Me—Ph | — | n-Bu | 4-CSNH$_2$-2-NO$_2$—Ph | |
| 156 | 4-Me—Ph | — | Me | 4-OH-2-NO$_2$—Ph | 173.0–174.0 |
| 157 | 4-Me—Ph | — | Me | 2-OMe-4-NO$_2$—Ph | |
| 158 | 4-Me—Ph | — | Et | 2-OMe-4-NO$_2$—Ph | |
| 159 | 4-Me—Ph | — | n-Pr | 2-OMe-4-NO$_2$—Ph | |
| 160 | 4-Me—Ph | — | i-Pr | 2-OMe-4-NO$_2$—Ph | |
| 161 | 4-Me—Ph | — | c-Pr | 2-OMe-4-NO$_2$—Ph | |
| 162 | 4-Me—Ph | — | n-Bu | 2-OMe-4-NO$_2$—Ph | |
| 163 | Ph | — | Me | 4-OMe-2-NO$_2$—Ph | 90.0–91.5 |
| 164 | Ph | — | Et | 4-OMe-2-NO$_2$—Ph | |
| 165 | Ph | — | n-Pr | 4-OMe-2-NO$_2$—Ph | |
| 166 | Ph | — | i-Pr | 4-OMe-2-NO$_2$—Ph | |
| 167 | Ph | — | c-Pr | 4-OMe-2-NO$_2$—Ph | |
| 168 | Ph | — | n-Bu | 4-OMe-2-NO$_2$—Ph | |
| 169 | 2-Me—Ph | — | Me | 4-OMe-2-NO$_2$—Ph | an oil[4] |
| 170 | 3-Me—Ph | — | Me | 4-OMe-2-NO$_2$—Ph | |
| 171 | 4-Me—Ph | — | Me | 4-OMe-2-NO$_2$—Ph | 123.0–124.0 |
| 172 | 2,4,6-Me$_3$—Ph | — | Me | 4-OMe-2-NO$_2$—Ph | 161.0–163.0 |
| 173 | 3-OMe—Ph | — | Me | 4-OMe-2-NO$_2$—Ph | |
| 174 | 4-OMe—Ph | — | Me | 4-OMe-2-NO$_2$—Ph | 146.0–147.0 |
| 175 | 2-Cl—Ph | — | Me | 4-OMe-2-NO$_2$—Ph | |
| 176 | 3-Cl—Ph | — | Me | 4-OMe-2-NO$_2$—Ph | |
| 177 | 4-Cl—Ph | — | Me | 4-OMe-2-NO$_2$—Ph | 162.5–163.5 |
| 178 | 4-Cl—Ph | — | Et | 4-OMe-2-NO$_2$—Ph | |
| 179 | 4-Cl—Ph | — | n-Pr | 4-OMe-2-NO$_2$—Ph | |
| 180 | 4-Cl—Ph | — | i-Pr | 4-OMe-2-NO$_2$—Ph | |
| 181 | 4-Cl—Ph | — | c-Pr | 4-OMe-2-NO$_2$—Ph | |
| 182 | 4-Cl—Ph | — | n-Bu | 4-OMe-2-NO$_2$—Ph | |
| 183 | 4-Br—Ph | — | Me | 4-OMe-2-NO$_2$—Ph | |
| 184 | 2,5-Cl$_2$—Ph | — | Me | 4-OMe-2-NO$_2$—Ph | 113.0–115.0 |
| 185 | 2-COOMe—Ph | — | Me | 4-OMe-2-NO$_2$—Ph | |
| 186 | 3-COOMe—Ph | — | Me | 4-OMe-2-NO$_2$—Ph | |
| 187 | 4-COOMe—Ph | — | Me | 4-OMe-2-NO$_2$—Ph | |
| 188 | 2-CN—Ph | — | Me | 4-OMe-2-NO$_2$—Ph | |
| 189 | 3-CN—Ph | — | Me | 4-OMe-2-NO$_2$—Ph | |
| 190 | 4-CN—Ph | — | Me | 4-OMe-2-NO$_2$—Ph | |
| 191 | 2-CF$_3$—Ph | — | Me | 4-CMe-2-NO$_2$—Ph | |
| 192 | 3-CF$_3$—Ph | — | Me | 4-OMe-2-NO$_2$—Ph | |
| 193 | 4-CF$_3$—Ph | — | Me | 4-OMe-2-NO$_2$—Ph | |
| 194 | 2-NO$_2$—Ph | — | Me | 4-OMe-2-NO$_2$—Ph | 136.5–138.5 |
| 195 | 3-NO$_2$—Ph | — | Me | 4-OMe-2-NO$_2$—Ph | 123.5–125.0 |
| 196 | 4-NO$_2$—Ph | — | Me | 4-OMe-2-NO$_2$—Ph | 157.5–158.5 |
| 197 | 4-NO$_2$—Ph | — | Et | 4-OMe-2-NO$_2$—Ph | |
| 198 | 4-NO$_2$—Ph | — | n-Pr | 4-OMe-2-NO$_2$—Ph | |
| 199 | 4-NO$_2$—Ph | — | i-Pr | 4-OMe-2-NO$_2$—Ph | |
| 200 | 1-CONEt$_2$-triazol-3-yl | — | Me | 4-OMe-2-NO$_2$—Ph | 119.5–120.5 |
| 201 | 1-naphthyl | — | Me | 4-OMe-2-NO$_2$—Ph | 123.0–124.0 |
| 202 | 2-naphthyl | — | Me | 4-OMe-2-NO$_2$—Ph | 180.0–182.0 |
| 203 | 2-pyridyl | — | Me | 4-OMe-2-NO$_2$—Ph | 100.0–101.0 |
| 204 | 8-quinolyl | — | Me | 4-OMe-2-NO$_2$—Ph | 166.0–170.0 |
| 205 | 4-Me—Ph | — | Et | 4-OMe-2-NO$_2$—Ph | 91.0–92.0 |
| 206 | 4-Me—Ph | — | n-Pr | 4-OMe-2-NO$_2$—Ph | 85.0–86.0 |
| 207 | 4-Me—Ph | — | i-Pr | 4-OMe-2-NO$_2$—Ph | 148.0–149.5 |
| 208 | 4-Me—Ph | — | c-Pr | 4-OMe-2-NO$_2$—Ph | |
| 209 | 4-Me—Ph | — | n-Bu | 4-OMe-2-NO$_2$—Ph | an oil[5] |
| 210 | 4-Me—Ph | — | CH$_2$CH=CH$_2$ | 4-OMe-2-NO$_2$—Ph | 116.5–117.5 |
| 211 | 4-Me—Ph | — | CH$_2$CH≡CH | 4-OMe-2-NO$_2$—Ph | 84.0–85.0 |
| 212 | 4-Me—Ph | — | CH$_2$CH≡C-I | 4-OMe-2-NO$_2$—Ph | -,— |
| 213 | 4-Me—Ph | — | Ac | 4-OMe-2-NO$_2$—Ph | 172.5–174.0 |
| 214 | 4-Me—Ph | — | SO$_2$-(4-Me-Ph) | 4-OMe-2-NO$_2$—Ph | 180.5–182.0 |
| 215 | 4-Me—Ph | — | Me | 4-OEt-2-NO$_2$—Ph | 116.0–117.5 |
| 216 | 4-Me—Ph | — | Me | 4-O(n-Pr)$_2$—NO$_2$—Ph | 93.0–94.0 |
| 217 | 4-Me—Ph | — | Me | 4-O(i-Pr)$_2$—NO$_2$—Ph | 119.5–120.5 |
| 218 | 4-Me—Ph | — | Me | 4-OAc-2-NO$_2$—Ph | 122.5–123.5 |
| 219 | 4-Me—Ph | — | Me | 4-(OCH$_2$OCH$_3$)-2-NO$_2$—Ph | 110.5–112.0 |
| 220 | Ph | — | Me | 4-SMe-2-NO$_2$—Ph | |
| 221 | Ph | — | Et | 4-SMe-2-NO$_2$—Ph | |
| 222 | Ph | — | n-Pr | 4-SMe-2-NO$_2$—Ph | |
| 223 | Ph | — | i-Pr | 4-SMe-2-NO$_2$—Ph | |
| 224 | Ph | — | c-Pr | 4-SMe-2-NO$_2$—Ph | |
| 225 | Ph | — | n-Bu | 4-SMe-2-NO$_2$—Ph | |
| 226 | 4-Me—Ph | — | Me | 4-SMe-2-NO$_2$—Ph | 130.0–131.0 |
| 227 | 4-Me—Ph | — | Et | 4-SMe-2-NO$_2$—Ph | 135.0–136.0 |
| 228 | 4-Me—Ph | — | n-Pr | 4-SMe-2-NO$_2$—Ph | |
| 229 | 4-Me—Ph | — | i-Pr | 4-SMe-2-NO$_2$—Ph | 124.5–126.0 |
| 230 | 4-Me—Ph | — | c-Pr | 4-SMe-2-NO$_2$—Ph | |
| 231 | 4-Me—Ph | — | n-Bu | 4-SMe-2-NO$_2$—Ph | |

TABLE 1-continued

| Compound No. | A⁰ | X⁰ | Z⁰ | B⁰ | Melting point (° C.) |
|---|---|---|---|---|---|
| 232 | 4-Me—Ph | — | Me | 4-SOMe-2-NO₂—Ph | 168.5–170.5 |
| 233 | 4-Me—Ph | — | Et | 4-SOMe-2-NO₂—Ph | 115.0–117.0 |
| 234 | 4-Me—Ph | — | n-Pr | 4-SOMe-2-NO₂—Ph | |
| 235 | 4-Me—Ph | — | i-Pr | 4-SOMe-2-NO₂—Ph | 157.5–158.5 |
| 236 | 4-Me—Ph | — | c-Pr | 4-SOMe-2-NO₂—Ph | |
| 237 | 4-Me—Ph | — | n-Bu | 4-SOMe-2-NO₂—Ph | |
| 238 | 4-Me—Ph | — | Me | 4-SO₂Me-2-NO₂—Ph | 147.0–148.0 |
| 239 | 4-Me—Ph | — | Et | 4-SO₂Me-2-NO₂—Ph | 184.0–184.5 |
| 240 | 4-Me—Ph | — | n-Pr | 4-SO₂Me-2-NO₂—Ph | |
| 241 | 4-Me—Ph | — | i-Pr | 4-SO₂Me-2-NO₂—Ph | 178.7–179.3 |
| 242 | 4-Me—Ph | — | c-Pr | 4-SO₂Me-2-NO₂—Ph | |
| 243 | 4-Me—Ph | — | n-Bu | 4-SO₂Me-2-NO₂—Ph | |
| 244 | 4-Me—Ph | — | Me | 4-SO₂NMe₂-2-NO₂—Ph | |
| 245 | 4-Me—Ph | — | Et | 4-SO₂NMe₂-2-NO₂—Ph | |
| 246 | 4-Me—Ph | — | n-Pr | 4-SO₂NMe₂-2-NO₂—Ph | |
| 247 | 4-Me—Ph | — | i-Pr | 4-SO₂NMe₂-2-NO₂—Ph | |
| 248 | 4-Me—Ph | — | c-Pr | 4-SO₂NMe₂-2-NO₂—Ph | |
| 249 | 4-Me—Ph | — | n-Bu | 4-SO₂NMe₂-2-NO₂—Ph | |
| 250 | 4-Me—Ph | — | Me | 4-SCN-2-NO₂—Ph | |
| 251 | 4-Me—Ph | — | Et | 4-SCN-2-NO₂—Ph | |
| 252 | 4-Me—Ph | — | n-Pr | 4-SCN-2-NO₂—Ph | |
| 253 | 4-Me—Ph | — | i-Pr | 4-SCN-2-NO₂—Ph | |
| 254 | 4-Me—Ph | — | c-Pr | 4-SCN-2-NO₂—Ph | |
| 255 | 4-Me—Ph | — | n-Bu | 4-SCN-2-NO₂—Ph | |
| 256 | Ph | — | Me | 4-F-2-NO₂—Ph | |
| 257 | Ph | — | Et | 4-F-2-NO₂—Ph | |
| 258 | Ph | — | n-Pr | 4-F-2-NO₂—Ph | |
| 259 | Ph | — | i-Pr | 4-F-2-NO₂—Ph | |
| 260 | Ph | — | c-Pr | 4-F-2-NO₂—Ph | |
| 261 | Ph | — | n-Bu | 4-F-2-NO₂—Ph | |
| 262 | 4-Me—Ph | — | Me | 4-F-2-NO₂—Ph | 93.5–94.5 |
| 263 | 4-Me—Ph | — | Et | 4-F-2-NO₂—Ph | 93.0–94.5 |
| 264 | 4-Me—Ph | — | n-Pr | 4-F-2-NO₂—Ph | 96.0–98.0 |
| 265 | 4-Me—Ph | — | i-Pr | 4-F-2-NO₂—Ph | 129.0–130.0 |
| 266 | 4-Me—Ph | — | CH₂CH=CH₂ | 4-F-2-NO₂—Ph | 76.0–77.0 |
| 267 | 4-Cl—Ph | — | Me | 4-F-2-NO₂—Ph | |
| 268 | 4-Cl—Ph | — | Et | 4-F-2-NO₂—Ph | |
| 269 | 4-Cl—Ph | — | n-Pr | 4-F-2-NO₂—Ph | |
| 270 | 4-Cl—Ph | — | i-Pr | 4-F-2-NO₂—Ph | |
| 271 | 4-Cl—Ph | — | c-Pr | 4-F-2-NO₂—Ph | |
| 272 | 4-Me—Ph | — | i-Pr | 2-Cl-4-NO₂—Ph | 154.0–157.0 |
| 273 | 4-Me—Ph | — | Me | 4-F-3-NO₂—Ph | 119.0–121.0 |
| 274 | 4-Me—Ph | — | Me | 2-Cl-4-NO₂—Ph | 122.0–123.0 |
| 275 | 4-Me—Ph | — | Et | 2-Cl-4-NO₂—Ph | |
| 276 | Ph | — | Me | 4-Cl-2-NO₂—Ph | 102.5–103.5 |
| 277 | Ph | — | Et | 4-Cl-2-NO₂—Ph | 108.0–109.0 |
| 278 | Ph | — | n-Pr | 4-Cl-2-NO₂—Ph | |
| 279 | Ph | — | i-Pr | 4-Cl-2-NO₂—Ph | 129.0–130.5 |
| 280 | Ph | CH₂ | Me | 4-Cl-2-NO₂—Ph | 153.5–155.0 |
| 281 | Ph | CHMe | Me | 4-Cl-2-NO₂—Ph | |
| 282 | Ph | CH=CH | Me | 4-Cl-2-NO₂—Ph | 162.0–164.0 |
| 283 | 4-Me—Ph | CMe=CH | Me | 4-Cl-2-NO₂—Ph | |
| 284 | 4-Me—Ph | — | Me | 4-Cl-2-NO—Ph | 113.0–114.5 |
| 285 | 4-Me—Ph | — | Et | 4-Cl-2-NO—Ph | |
| 286 | 4-Me—Ph | — | i-Pr | 4-Cl-2-NO—Ph | |
| 287 | 3-Me—Ph | — | Me | 4-Cl-2-NO₂—Ph | 115.5–117.0 |
| 288 | 4-Me—Ph | — | Me | 4-Cl-2-NO₂—Ph | 97.5–99.0 |
| 289 | 4-Me—Ph | — | Et | 4-Cl-2-NO₂—Ph | 132.5–134.0 |
| 290 | 4-Me—Ph | — | n-Pr | 4-Cl-2-NO₂—Ph | 88.0–89.5 |
| 291 | 4-Me—Ph | — | i-Pr | 4-Cl-2-NO₂—Ph | 112.0–114.0 |
| 292 | 4-Me—Ph | — | c-Pr | 4-Cl-2-NO₂—Ph | 98.5–100.0 |
| 293 | 4-Me—Ph | — | n-Bu | 4-Cl-2-NO₂—Ph | |
| 294 | 4-Me—Ph | — | s-Bu | 4-Cl-2-NO₂—Ph | |
| 295 | 4-Me—Ph | — | i-Bu | 4-Cl-2-NO₂—Ph | 127.5–130.0 |
| 296 | 4-Me—Ph | — | t-Bu | 4-Cl-2-NO₂—Ph | |
| 297 | 4-Me—Ph | — | CH=C=CH₂ | 4-Cl-2-NO₂—Ph | |
| 298 | 4-Me—Ph | — | CH=CH₂ | 4-Cl-2-NO₂—Ph | >108 (dec.) |
| 299 | 4-Me—Ph | — | CH₂CH=CH₂ | 4-Cl-2-NO₂—Ph | 77.0–78.0 |
| 300 | 4-Me—Ph | — | CH₂CH≡CH | 4-Cl-2-NO₂—Ph | 122.0–124.5 |
| 301 | 4-Me—Ph | — | CH₂CH≡C—I | 4-Cl-2-NO₂—Ph | |
| 302 | 4-Me—Ph | — | CH₂NMe₂ | 4-Cl-2-NO₂—Ph | |
| 303 | 4-Me—Ph | — | CH₂CH₂OH | 4-Cl-2-NO₂—Ph | 102.0–103.5 |
| 304 | 4-Me—Ph | — | CH₂CH₂F | 4-Cl-2-NO₂—Ph | |
| 305 | 4-Me—Ph | — | CH₂CH₂Br | 4-Cl-2-NO₂—Ph | 70.0–72.0 |
| 306 | 4-Me—Ph | — | CH₂CH₂NMe₂ | 4-Cl-2-NO₂—Ph | 108.0–109.0 |
| 307 | 4-Me—Ph | — | CH₂CH₂SMe | 4-Cl-2-NO₂—Ph | 94.5–95.5 |
| 308 | 4-Me—Ph | — | CH₂OCH₃ | 4-Cl-2-NO₂—Ph | 61.0–62.0 |

TABLE 1-continued

| Compound No. | A⁰ | X⁰ | Z⁰ | B⁰ | Melting point (° C.) |
|---|---|---|---|---|---|
| 309 | 4-Me—Ph | — | CH₂COOMe | 4-Cl-2-NO₂—Ph | an oil[6] |
| 310 | 4-Me—Ph | — | CH₂CN | 4-Cl-2-NO₂—Ph | |
| 311 | 4-Me—Ph | — | Ac | 4-Cl-2-NO₂—Ph | 173.0–175.0 |
| 312 | 4-Me—Ph | — | COCH₂Cl | 4-Cl-2-NO₂—Ph | 195.0–199.0 |
| 313 | 4-Me—Ph | — | COCF₃ | 4-Cl-2-NO₂—Ph | |
| 314 | 4-Me—Ph | — | NMe₂ | 4-Cl-2-NO₂—Ph | |
| 315 | 4-Me—Ph | — | NHAc | 4-Cl-2-NO₂—Ph | |
| 316 | 4-Me—Ph | — | NHCOOMe | 4-Cl-2-NO₂—Ph | |
| 317 | 4-Me—Ph | — | N=CMe₂ | 4-Cl-2-NO₂—Ph | |
| 318 | 4-Me—Ph | — | SCCl₂F | 4-Cl-2-NO₂—Ph | |
| 319 | 4-Me—Ph | — | SCF₃ | 4-Cl-2-NO₂—Ph | |
| 320 | 4-Me—Ph | — | SCCl₃ | 4-Cl-2-NO₂—Ph | |
| 321 | 4-Me—Ph | — | SOCF₃ | 4-Cl-2-NO₂—Ph | |
| 322 | 4-Me—Ph | — | SO₂Me | 4-Cl-2-NO₂—Ph | 163.5–165.5 |
| 323 | 4-Me—Ph | — | SO₂-(4-Me—Ph) | 4-Cl-2-NO₂—Ph | 205.0–206.5 |
| 324 | 4-Me—Ph | — | Ph | 4-Cl-2-NO₂—Ph | 157.0–159.0 |
| 325 | 4-Et-Ph | — | Me | 4-Cl-2-NO₂—Ph | 100.0–101.5 |
| 326 | 4-Et-Ph | — | Et | 4-Cl-2-NO₂—Ph | 123.0–125.0 |
| 327 | 4-Et-Ph | — | n-Pr | 4-Cl-2-NO₂—Ph | |
| 328 | 4-Et-Ph | — | i-Pr | 4-Cl-2-NO₂—Ph | 117.0–118.5 |
| 329 | 4-F—Ph | — | Me | 4-Cl-2-NO₂—Ph | 140.5–141.5 |
| 330 | 4-F—Ph | — | Et | 4-Cl-2-NO₂—Ph | 155.5–156.5 |
| 331 | 4-F—Ph | — | n-Pr | 4-Cl-2-NO₂—Ph | |
| 332 | 4-F—Ph | — | i-Pr | 4-Cl-2-NO₂—Ph | 122.0–123.0 |
| 333 | 4-F—Ph | — | c-Pr | 4-Cl-2-NO₂—Ph | |
| 334 | 4-F—Ph | — | n-Bu | 4-Cl-2-NO₂—Ph | |
| 335 | 2-Cl—Ph | — | Me | 4-Cl-2-NO₂—Ph | 116.0–117.0 |
| 336 | 3-Cl—Ph | — | Me | 4-Cl-2-NO₂—Ph | 136.5–138.5 |
| 337 | 4-Cl—Ph | — | Me | 4-Cl-2-NO₂—Ph | 158.5–160.5 |
| 338 | 4-Cl—Ph | — | Et | 4-Cl-2-NO₂—Ph | 121.5–123.0 |
| 339 | 4-Cl—Ph | — | n-Pr | 4-Cl-2-NO₂—Ph | |
| 340 | 4-Cl—Ph | — | i-Pr | 4-Cl-2-NO₂—Ph | 99.5–100.5 |
| 341 | 4-Cl—Ph | — | c-Pr | 4-Cl-2-NO₂—Ph | |
| 342 | 4-Cl—Ph | — | n-Bu | 4-Cl-2-NO₂—Ph | |
| 343 | 4-Cl—Ph | — | CH₂CH=CH₂ | 4-Cl-2-NO₂—Ph | |
| 344 | 4-Cl—Ph | — | CH₂C≡CH | 4-Cl-2-NO₂—Ph | |
| 345 | 4-Cl—Ph | — | CH₂C≡C—I | 4-Cl-2-NO₂—Ph | |
| 346 | 4-Cl—Ph | — | Ph | 4-Cl-2-NO₂—Ph | |
| 347 | 3,4-Cl₂—Ph | — | Me | 4-Cl-2-NO₂—Ph | 140.5–142.0 |
| 348 | 4-Br—Ph | — | Me | 4-Cl-2-NO₂—Ph | 155.5–157.5 |
| 349 | 4-Br—Ph | — | Et | 4-Cl-2-NO₂—Ph | |
| 350 | 4-Br—Ph | — | n-Pr | 4-Cl-2-NO₂—Ph | |
| 351 | 4-Br—Ph | — | i-Pr | 4-Cl-2-NO₂—Ph | |
| 352 | 4-Br—Ph | — | c-Pr | 4-Cl-2-NO₂—Ph | |
| 353 | 4-Br—Ph | — | n-Bu | 4-Cl-2-NO₂—Ph | |
| 354 | 3-CN—Ph | — | Et | 4-Cl-2-NO₂—Ph | 165.0–166.5 |
| 355 | 4-CN—Ph | — | Me | 4-Cl-2-NO₂—Ph | |
| 356 | 4-CN—Ph | — | Et | 4-Cl-2-NO₂—Ph | 146.0–148.0 |
| 357 | 4-CN—Ph | — | n-Pr | 4-Cl-2-NO₂—Ph | |
| 358 | 4-CN—Ph | — | i-Pr | 4-Cl-2-NO₂—Ph | |
| 359 | 4-CN—Ph | — | c-Pr | 4-Cl-2-NO₂—Ph | |
| 360 | 4-CN—Ph | — | n-Bu | 4-Cl-2-NO₂—Ph | |
| 361 | 3-CF₃—Ph | — | Me | 4-Cl-2-NO₂—Ph | 120.5–122.0 |
| 362 | 4-CF₃—Ph | — | Et | 4-Cl-2-NO₂—Ph | 105.0–106.0 |
| 363 | 4-OCF₃—Ph | — | Me | 4-Cl-2-NO₂—Ph | 117.0–118.0 |
| 364 | 5-Me-2-thienyl | — | Me | 4-Cl-2-NO₂—Ph | |
| 365 | 5-Me-2-thienyl | — | Et | 4-Cl-2-NO₂—Ph | |
| 366 | 5-Me-2-thienyl | — | n-Pr | 4-Cl-2-NO₂—Ph | |
| 367 | 5-Me-2-thienyl | — | i-Pr | 4-Cl-2-NO₂—Ph | |
| 368 | 5-Me-2-thienyl | — | c-Pr | 4-Cl-2-NO₂—Ph | |
| 369 | 5-Me-2-thienyl | — | n-Bu | 4-Cl-2-NO₂—Ph | |
| 370 | 5-Cl-2-thienyl | — | Me | 4-Cl-2-NO₂—Ph | 85.0–86.0 |
| 371 | 5-Cl-2-thienyl | — | Et | 4-Cl-2-NO₂—Ph | 95.0–96.0 |
| 372 | 5-Cl-2-thienyl | — | n-Pr | 4-Cl-2-NO₂—Ph | |
| 373 | 5-Cl-2-thienyl | — | i-Pr | 4-Cl-2-NO₂—Ph | |
| 374 | 5-Cl-2-thienyl | — | c-Pr | 4-Cl-2-NO₂—Ph | |
| 375 | 5-Cl-2-thienyl | — | n-Bu | 4-Cl-2-NO₂—Ph | |
| 376 | 3,5-Me₂-4-isoxazolyl | — | Me | 4-Cl-2-NO₂—Ph | 99.0–101.0 |
| 377 | 5-Cl-1,3-Me₂-4-pyrazolyl | — | Me | 4-Cl-2-NO₂—Ph | 102.0–103.0 |
| 378 | 1-Me-4-COOMe-5-pyrazolyl | — | Me | 4-Cl-2-NO₂—Ph | |
| 379 | 1,3-Me₂-4-COOMe-5-pyrazolyl | — | Me | 4-Cl-2-NO₂—Ph | 236.5–237.5 |
| 380 | 1,3-Me₂-4-COOH-5-pyrazolyl | — | Me | 4-Cl-2-NO₂—Ph | 129.0–130.5 |
| 381 | 1,3-Me₂-4-CONH₂-5-pyrazolyl | — | Me | 4-Cl-2-NO₂—Ph | 164.0–164.5 |
| 382 | 1,3-Me₂-4-CN-5-pyrazolyl | — | Me | 4-Cl-2-NO₂—Ph | 109.0–110.5 |
| 383 | 3-Cl-1-Me-4-COOMe-5-pyrazolyl | — | Me | 4-Cl-2-NO₂—Ph | |
| 384 | 1-Me-4-imidazolyl | — | Me | 4-Cl-2-NO₂—Ph | 199.0–201.5 |
| 385 | 1,2,4-triazol-3-yl | — | Me | 4-Cl-2-NO₂—Ph | 219.5–220.0 |

TABLE 1-continued

| Compound No. | A⁰ | X⁰ | Z⁰ | B⁰ | Melting point (° C.) |
|---|---|---|---|---|---|
| 386 | 2-pyridyl | — | Me | 4-Cl-2-NO₂—Ph | 127.0–128.0 |
| 387 | 3-pyridyl | — | Me | 4-Cl-2-NO₂—Ph | 125.5–127.5 |
| 388 | 2,1,3-benzothiadiazol-4-yl | — | Me | 4-Cl-2-NO₂—Ph | 124.5–126.5 |
| 389 | 2-Cl-imidazo[1,2-a]pyridin-3-yl | — | Me | 4-Cl-2-NO₂—Ph | |
| 390 | 2-SO₂Rt-imidazo[1,2-a]pyridin-3-yl | — | Me | 4-Cl-2-NO₂—Ph | |
| 391 | 2-Cl-imidazo[2,1-b]thiazol-5-yl | — | Me | 4-Cl-2-NO₂—Ph | 168.0–172.0 |
| 392 | 8-quinolyl | — | Me | 4-Cl-2-NO₂—Ph | 177.0–178.5 |
| 393 | 4-Me—Ph | — | Me | 4-Cl-2-(NO=N—CN)—Ph | 140.0–142.0 |
| 394 | 4-Me—Ph | — | Et | 4-Cl-2-(NO=N—CN)—Ph | |
| 395 | 4-Me—Ph | — | i-Pr | 4-Cl-2-(NO=N—CN)—Ph | |
| 396 | 4-Me—Ph | — | Me | 4-Cl-3-NO₂—Ph | 106.0–107.0 |
| 397 | 4-Me—Ph | — | Me | 5-Cl-2-NO₂—Ph | 118.0–120.0 |
| 398 | 4-Me—Ph | — | Me | 4-Br-2-NO₂—Ph | 108.0–110.5 |
| 399 | 4-Me—Ph | — | Et | 4-Br-2-NO₂—Ph | |
| 400 | 4-Me—Ph | — | n-Pr | 4-Br-2-NO₂—Ph | |
| 401 | 4-Me—Ph | — | i-Pr | 4-Br-2-NO₂—Ph | |
| 402 | 4-Me—Ph | — | c-Pr | 4-Br-2-NO₂—Ph | |
| 403 | 4-Me—Ph | — | n-Bu | 4-Br-2-NO₂—Ph | |
| 404 | 4-Me—Ph | — | Me | 4-Br-3-NO₂—Ph | 93.0–94.5 |
| 405 | 4-Me—Ph | — | Me | 4-I-2-NO₂—Ph | |
| 406 | 4-Me—Ph | — | Me | 4-CN-2-NO₂—Ph | 123.0–124.5 |
| 407 | 4-Me—Ph | — | Et | 4-CN-2-NO₂—Ph | 158.0–160.0 |
| 408 | 4-Me—Ph | — | n-Pr | 4-CN-2-NO₂—Ph | |
| 409 | 4-Me—Ph | — | i-Pr | 4-CN-2-NO₂—Ph | 125.0–126.0 |
| 410 | 4-Me—Ph | — | c-Pr | 4-CN-2-NO₂—Ph | |
| 411 | 4-Cl—Ph | — | Me | 4-CN-2-NO₂—Ph | 159.5–160.5 |
| 412 | 4-Cl—Ph | — | Et | 4-CN-2-NO₂—Ph | 172.5–174.5 |
| 413 | 4-Cl—Ph | — | i-Pr | 4-CN-2-NO₂—Ph | 167.5–168.5 |
| 414 | 4-CN—Ph | — | Et | 4-CN-2-NO₂—Ph | 171.0–172.0 |
| 415 | 5-Cl-2-thienyl | — | Et | 4-CN-2-NO₂—Ph | 101.5–103.0 |
| 416 | Ph | — | Me | 2-CN-4-NO₂—Ph | |
| 417 | Ph | — | Et | 2-CN-4-NO₂—Ph | |
| 418 | Ph | — | i-Pr | 2-CN-4-NO₂—Ph | |
| 419 | 4-Me—Ph | — | Me | 2-CN-4-NO₂—Ph | 165.0–167.0 |
| 420 | 4-Me—Ph | — | Et | 2-CN-4-NO₂—Ph | 135.0–136.5 |
| 421 | 4-Me—Ph | — | i-Pr | 2-CN-4-NO₂—Ph | 140.5–142.5 |
| 422 | 4-Me—Ph | — | Me | 2-NO₂-4-OCF₃—Ph | 91.0–92.0 |
| 423 | 4-Me—Ph | — | Me | 2-NO₂-4-CF₃—Ph | 145.5–147.0 |
| 424 | 4-Me—Ph | — | Et | 2-NO₂-4-CF₃—Ph | |
| 425 | Ph | — | Me | 2,4-(NO₂)₂—Ph | 151.5–153.0 |
| 426 | Ph | — | Et | 2,4-(NO₂)₂—Ph | 129.5–131.0 |
| 427 | Ph | — | n-Pr | 2,4-(NO₂)₂—Ph | |
| 428 | Ph | — | i-Pr | 2,4-(NO₂)₂—Ph | |
| 429 | Ph | — | c-Pr | 2,4-(NO₂)₂—Ph | 166.0–168.0 |
| 430 | Ph | — | n-Bu | 2,4-(NO₂)₂—Ph | |
| 431 | Ph | — | CH₂CH=CH₂ | 2,4-(NO₂)₂—Ph | |
| 432 | Ph | — | Ph | 2,4-(NO₂)₂—Ph | |
| 433 | Ph | — | NMe₂ | 2,4-(NO₂)₂—Ph | |
| 434 | 4-Me—Ph | — | Me | 2,4-(NO₂)₂—Ph | 130.5–133.0 |
| 435 | 4-Me—Ph | — | Et | 2,4-(NO₂)₂—Ph | 135.0–136.5 |
| 436 | 4-Me—Ph | — | n-Pr | 2,4-(NO₂)₂—Ph | |
| 437 | 4-Me—Ph | — | i-Pr | 2,4-(NO₂)₂—Ph | 141.5–142.5 |
| 438 | 4-Me—Ph | — | c-Pr | 2,4-(NO₂)₂—Ph | 113.0–114.5 |
| 439 | 4-Me—Ph | — | n-Bu | 2,4-(NO₂)₂—Ph | |
| 440 | 4-Me—Ph | — | s-Bu | 2,4-(NO₂)₂—Ph | |
| 441 | 4-Me—Ph | — | i-Bu | 2,4-(NO₂)₂—Ph | |
| 442 | 4-Me—Ph | — | t-Bu | 2,4-(NO₂)₂—Ph | |
| 443 | 4-Me—Ph | — | CH₂CH=CH₂ | 2,4-(NO₂)₂—Ph | |
| 444 | 4-Me—Ph | — | CH₂C≡CH | 2,4-(NO₂)₂—Ph | |
| 445 | 4-Me—Ph | — | CH₂C≡C—I | 2,4-(NO₂)₂—Ph | |
| 446 | 4-Me—Ph | — | NMe₂ | 2,4-(NO₂)₂—Ph | |
| 447 | 4-Me—Ph | — | N=CMe₂ | 2,4-(NO₂)₂—Ph | >175 (dec) |
| 448 | 4-F—Ph | — | Me | 2,4-(NO₂)₂—Ph | 172.0–173.5 |
| 449 | 4-Cl—Ph | — | Me | 2,4-(NO₂)₂—Ph | 135.0–137.0 |
| 450 | 4-Cl—Ph | — | Et | 2,4-(NO₂)₂—Ph | |
| 451 | 4-Cl—Ph | — | n-Pr | 2,4-(NO₂)₂—Ph | |
| 452 | 4-Cl—Ph | — | i-Pr | 2,4-(NO₂)₂—Ph | |
| 453 | 4-Cl—Ph | — | c-Pr | 2,4-(NO₂)₂—Ph | |
| 454 | 4-Cl—Ph | — | n-Bu | 2,4-(NO₂)₂—Ph | |
| 455 | 4-CN—Ph | — | Et | 2,4-(NO₂)₂—Ph | 150.5–152.0 |
| 456 | 5-Cl-2-thienyl | — | Me | 2,4-(NO₂)₂—Ph | 156.0–157.5 |
| 457 | 5-Cl-2-thienyl | — | Et | 2,4-(NO₂)₂—Ph | 109.0–111.0 |
| 458 | 5-Cl-2-thienyl | — | n-Pr | 2,4-(NO₂)₂—Ph | |
| 459 | 5-Cl-2-thienyl | — | i-Pr | 2,4-(NO₂)₂—Ph | |
| 460 | 5-Cl-2-thienyl | — | n-Bu | 2,4-(NO₂)₂—Ph | |
| 461 | 4-Me—Ph | — | Me | 4,5-(OMe)₂-2-NO₂—Ph | 179.0–181.0 |
| 462 | 4-Me—Ph | — | Me | 4,5-(OCH₂O)-2-NO₂—Ph | 181.0–182.0 |

TABLE 1-continued

| Compound No. | A⁰ | X⁰ | Z⁰ | B⁰ | Melting point (° C.) |
|---|---|---|---|---|---|
| 463 | 4-Me—Ph | — | Me | 4,5-(OCF₂O)-2-NO₂—Ph | |
| 464 | 4-Me—Ph | — | Me | 4,5-Cl₂-2-NO₂—Ph | 185.0–187.0 |
| 465 | 4-Me—Ph | — | Me | 4-Cl-2,6-(NO₂)₂—Ph | 168.5–169.5 |
| 466 | 4-Me—Ph | — | Et | 4-Cl-2,6-(NO₂)₂—Ph | |
| 467 | 4-Me—Ph | — | n-Pr | 4-Cl-2,6-(NO₂)₂—Ph | |
| 468 | 4-Me—Ph | — | i-Pr | 4-Cl-2,6-(NO₂)₂—Ph | |
| 469 | 4-Me—Ph | — | c-Pr | 4-Cl-2,6-(NO₂)₂—Ph | |
| 470 | 4-Me—Ph | — | Me | 2,6-(NO₂)₂-4-CF₃—Ph | 176.5–177.5 |
| 471 | 4-Me—Ph | — | Me | 2-NO₂-1-naphthyl | |
| 472 | 4-Me—Ph | — | Me | 1-NO₂-2-naphthyl | |
| 473 | 4-Me—Ph | — | Me | 3,5-Cl₂-2-thienyl | |
| 474 | 4-Me—Ph | — | Et | 3,5-Cl₂-2-thienyl | |
| 475 | 4-Me—Ph | — | i-Pr | 3,5-Cl₂-2-thienyl | |
| 476 | 4-Me—Ph | — | Me | 5-Cl-3-NO₂-2-thienyl | |
| 477 | 4-Me—Ph | — | Et | 5-Cl-3-NO₂-2-thienyl | |
| 478 | 4-Me—Ph | — | i-Pr | 5-Cl-3-NO₂-2-thienyl | |
| 479 | 4-Me—Ph | — | Me | 1-Me-4-CN-5-pyrazolyl | |
| 480 | 4-Me—Ph | — | Me | 1,3-Me₂-4-NO₂-5-pyrazolyl | |
| 481 | 4-Me—Ph | — | Me | 1-Me-5-NO₂-4-imidazolyl | |
| 482 | 4-Me—Ph | — | Me | 2-Me-5-CN-4-thiazolyl | |
| 483 | 4-Me—Ph | — | Me | 2-SMe-5-CN-4-thiazolyl | |
| 484 | 4-Me—Ph | — | Me | 2-Cl-5-CN-4-thiazolyl | |
| 485 | 4-Me—Ph | — | Me | 2-Me-5-CF₃-4-thiazolyl | |
| 486 | 4-Me—Ph | — | Me | 2-Me-5-NO₂-4-thiazolyl | |
| 487 | 4-Me—Ph | — | Me | 2-Cl-5-NO₂-4-thiazolyl | |
| 488 | 4-Me—Ph | — | Me | 3-OMe-4-CF₃-5-isothiazolyl | |
| 489 | 4-Me—Ph | — | Me | 3-Me-4-CN-5-isothiazolyl | |
| 490 | 4-Me—Ph | — | Me | 3-Me-4-NO₂-5-isothiazolyl | |
| 491 | 4-Me—Ph | — | Me | 5-Cl-2-pyridyl | 74.0–75.0 |
| 492 | 4-Me—Ph | — | Me | 6-Cl-3-pyridyl | |
| 493 | 4-Me—Ph | — | Me | 3-NO₂-2-pyridyl | 118.5–119.5 |
| 494 | 4-Me—Ph | — | Me | 5-Cl-3-NO₂-2-pyridyl | 141.0–143.0 |
| 495 | 4-Me—Ph | — | Et | 5-Cl-3-NO₂-2-pyridyl | |
| 496 | 4-Me—Ph | — | n-Pr | 5-Cl-3-NO₂-2-pyridyl | |
| 497 | 4-Me—Ph | — | i-Pr | 5-Cl-3-NO₂-2-pyridyl | |
| 498 | 4-Me—Ph | — | c-Pr | 5-Cl-3-NO₂-2-pyridyl | |
| 499 | 4-Me—Ph | — | n-Bu | 5-Cl-3-NO₂-2-pyridyl | |
| 500 | 4-Me—Ph | — | Me | 6-Me-4-NO₂-2-pyridyl | |
| 501 | 4-Me—Ph | — | Me | 6-OMe-4-NO₂-2-pyridyl | |
| 502 | 4-Me—Ph | — | Me | 6-Cl-4-NO₂-2-pyridyl | |
| 503 | 4-Me—Ph | — | Me | 3,5-(NO₂)2-2-pyridyl | amorphous[7] |
| 504 | 4-Me—Ph | — | Me | 6-Cl-3-pyridazinyl | 80.0–81.0 |
| 505 | 4-Me—Ph | — | Et | 6-Cl-3-pyridazinyl | |
| 506 | 4-Me—Ph | — | n-Pr | 6-Cl-3-pyridazinyl | |
| 507 | 4-Me—Ph | — | i-Pr | 6-Cl-3-pyridazinyl | |
| 508 | 4-Me—Ph | — | c-Pr | 6-Cl-3-pyridazinyl | |
| 509 | 4-Me—Ph | — | n-Bu | 6-Cl-3-pyridazinyl | |
| 510 | 1-Me-4-imidazolyl | — | Me | 6-Cl-3-pyridazinyl | 183.5–184.5 |
| 511 | 4-Me—Ph | — | Me | 5-Cl-2-pyrimidinyl | 136.0–139.0 |
| 512 | 4-Me—Ph | — | Et | 5-Cl-2-pyrimidinyl | |
| 513 | 4-Me—Ph | — | n-Pr | 5-Cl-2-pyrimidinyl | |
| 514 | 4-Me—Ph | — | i-Pr | 5-Cl-2-pyrimidinyl | |
| 515 | 4-Me—Ph | — | c-Pr | 5-Cl-2-pyrimidinyl | |
| 516 | 4-Me—Ph | — | n-Bu | 5-Cl-2-pyrimidinyl | |
| 517 | 4-Me—Ph | — | Me | 6-Cl-4-pyrimidinyl | 99.5–100.5 |
| 518 | 4-Me—Ph | — | Me | 5-Cl-6-Me-4-pyrimidinyl | 162.0–164.0 |
| 519 | 4-Me—Ph | — | Me | 3-NO₂-2-imidazo[1,2-a]pyridyl | 169.5–171.0 |
| 520 | 4-Me—Ph | — | Et | 3-NO₂-2-imidazo[1,2-a]pyridyl | |
| 521 | 4-Me—Ph | — | OMe | 4-NO₂—Ph | 142.5–144.5 |
| 522 | 4-Me—Ph | — | OMe | 2-Me-4-NO₂—Ph | 118.0–119.0 |
| 523 | 4-Me—Ph | — | OMe | 2-F-4-NO₂—Ph | 154.0–155.5 |
| 524 | 4-Cl-3-CF₃—Ph | — | OMe | 2-F-4-NO₂—Ph | 104.5–105.5 |
| 525 | 4-Me—Ph | — | OMe | 2-Cl-4-NO₂—Ph | 128.0–127.5 |
| 526 | 4-Cl—Ph | — | OMe | 2-Cl-4-NO₂—Ph | 150.0–151.0 |
| 527 | 3,4-Cl₂—Ph | — | OMe | 2-Cl-4-NO₂—Ph | 132.0–133.0 |
| 528 | 2,5-Cl₂—Ph | — | OMe | 2-Cl-4-NO₂—Ph | 136.0–138.0 |
| 529 | 3-CF₃—Ph | — | OMe | 2-Cl-4-NO₂—Ph | 95.5–96.5 |
| 530 | 3-NO₂—Ph | — | OMe | 2-Cl-4-NO₂—Ph | 167.5–169.0 |
| 531 | 4-Cl-3-NO₂—Ph | — | OMe | 2-Cl-4-NO₂—Ph | 138.0–139.0 |
| 532 | 4-Cl-3-CF₃—Ph | — | OMe | 2-Cl-4-NO₂—Ph | 111.5–113.0 |
| 533 | 4-Me—Ph | — | OEt | 2-Cl-4-NO₂—Ph | 133.5–135.0 |
| 534 | 4-Me—Ph | — | O(i-Pr) | 2-Cl-4-NO₂—Ph | 160.5–162.0 |
| 535 | 4-Me—Ph | — | OMe | 2-CN-4-NO₂—Ph | 148.0–149.5 |
| 536 | 4-Cl-3-CF₃—Ph | — | OMe | 2-CN-4-NO₂—Ph | 140.5–142.0 |
| 537 | 5-Cl-2-thienyl | — | OMe | 2-CN-4-NO₂—Ph | 144.0–146.0 |
| 538 | 4-Me—Ph | — | OMe | 2-CF₃-4-NO₂—Ph | 123.0–124.5 |
| 539 | 4-Me—Ph | — | OMe | 2-NO₂—Ph | 104.5–105.5 |

TABLE 1-continued

| Compound No. | A⁰ | X⁰ | Z⁰ | B⁰ | Melting point (° C.) |
|---|---|---|---|---|---|
| 540 | 4-Me—Ph | — | OMe | 4-Cl-2-NO₂—Ph | 114.0–115.0 |
| 541 | 2,5-Cl₂—Ph | — | OMe | 4-Cl-2-NO₂—Ph | >180 (dec.) |
| 542 | 3-CF₃—Ph | — | OMe | 4-Cl-2-NO₂—Ph | 84.5–85.5 |
| 543 | 4-Cl-3-CF₃—Ph | — | OMe | 4-Cl-2-NO₂—Ph | 108.0–109.0 |
| 544 | 4-Me—Ph | — | OMe | 2-Cl-4-CF₃—Ph | 131.0–132.5 |
| 545 | 4-Me—Ph | — | OMe | 2,4-(NO₂)₂—Ph | 146.0–148.0 |
| 546 | 4-Me—Ph | — | OEt | 2,4-(NO₂)₂—Ph | |
| 547 | 4-Me—Ph | — | OAc | 2,4-(NO₂)₂—Ph | |
| 548 | 4-Cl—Ph | — | OMe | 2,4-(NO₂)₂—Ph | |
| 549 | 2,5-Cl₂—Ph | — | OMe | 2,4-(NO₂)₂—Ph | 153.0–155.0 |
| 550 | 3-CF₃—Ph | — | OMe | 2,4-(NO₂)₂—Ph | 130.5–132.0 |
| 551 | 4-Cl-3-CF₃—Ph | — | OMe | 2,4-(NO₂)₂—Ph | 108.0–109.5 |
| 552 | 5-Cl-1,3-Me₂-4-pyrazolyl | — | OMe | 2,4-(NO₂)₂—Ph | 189.0–191.0 |
| 553 | 4-Me—Ph | — | OMe | 3-Cl-5-CF₃-2-pyridyl | 99.0–100.0 |
| 554 | 4-Me—Ph | — | OMe | 5-NO₂-2-pyridyl | 96.0–97.0 |
| 555 | 4-Me—Ph | — | OMe | 6-Cl-3-pyridazinyl | 91.5–92.5 |
| 556 | 4-Me—Ph | — | OMe | 6-CN-3-pyridazinyl | 112.0–113.0 |
| 557 | 4-Me—Ph | — | OMe | 5-NO₂-2-thiazolyl | 135.0–138.5 |
| 558 | 4-Me—Ph | — | OMe | 4-CF₃-2-thiazolyl | 107.0–108.5 |
| 559 | 4-Me—Ph | — | OMe | 5-CF₃-1,3,4-thiadiazol-2-yl | 84.0–85.5 |
| 560 | 4-Me—Ph | — | OMe | 4-CN-3-OMe-5-isothiazolyl | 115.5–118.0 |
| 561 | Ph | — | OMe | 2,4-(NO₂)₂—Ph | 161.0–163.5 |
| 562 | 3-Me—Ph | — | OMe | 2,4-(NO₂)₂—Ph | 147.5–149.5 |
| 563 | 2-Cl—Ph | — | OMe | 2,4-(NO₂)₂—Ph | 112.5–114.0 |
| 564 | 3-Cl—Ph | — | OMe | 2,4-(NO₂)₂—Ph | 157.0–159.0 |
| 565 | 4-CF₃—Ph | — | OMe | 2-CN-4-NO₂—Ph | 133.5–135.0 |
| 566 | 4-Me—Ph | — | OMe | 2-Cl-4-CN—Ph | 145.0–147.0 |
| 567 | 4-F—Ph | — | OMe | 2,4-(NO₂)₂—Ph | 118.0–119.5 |
| 568 | 4-Et-Ph | — | OMe | 2,4-(NO₂)₂—Ph | 90.0–92.0 |
| 569 | 4-Me—Ph | — | OMe | 4-CN-2-NO₂—Ph | 126.0–128.0 |
| 570 | 4-NO₂—Ph | — | OMe | 2,4-(NO₂)₂—Ph | 117.0–119.0 |
| 571 | 4-Me—Ph | — | OMe | 2-CN-4-SMe—Ph | 146.8–147.6 |
| 572 | 4-Me—Ph | — | OMe | 4-SMe-2-NO₂—Ph | 110.3–110.8 |

[1] NMR(CDCL₃)δ: 1.22(3H, t, J=7.6Hz), 2.42(3H, s), 2.63(2H, q, J=7.6Hz), 3.14(3H, s), 6.99(2H, d, J=8.6 & 2.3Hz), 7.12(2H, d, J=8.6 & 2.3Hz), 7.24 (2H, d, J=8.3Hz), 7.45(2H, d, J=8.3Hz).
[2] NMR(CDCl₃)δ: 2.46(3H, s), 3.17(3H, s), 3.27(3H, s), 6.68(1H, d, J=8.7Hz), 7.34(2H, d, J=8.3Hz), 7.43(1H, dd, J=8.7 & 2.4Hz), 7.51(2H, d, J=8.3Hz), 7.77(1H, d, J=2.4Hz), 11.00–12.00(2H, br).
[3] NMR(CDCl₃)δ: 2.46(3H, s), 3.01(3H, s), 3.14(6H, s), 6.80(1H, d, J=8.9Hz), 7.20–7.35(2H, m), 7.34(2H, d, J=8.3Hz), 7.66(2H, d, J=8.3Hz).
(*) Isolated as hydroiodide and measured the melting point
[4] NMR(CDCl₃)δ: 2.47(3H, s), 3.35(3H, s), 3.85(3H, s), 7.06(1H, dd, Jz =8.9 & 3.0Hz), 7.10–7.35(3H, m), 7.34(1H, dt, J=8.9Hz), 7.45(1H, dt, J=1.4 & 7.9Hz), 7.69(1H, dd, J=7.9 & 1.4Hz).
[5] NMR(CDCl₃)δ: 0.87(3H, t, J=7.2Hz), 1.30(2H, brq, J=7.2Hz), 1.40–1.70(2H, br), 2.43(3H, s), 3.45–3.70(2H.br), 3.87(3H, s), 6.90–7.10(2H, m), 7.26 (2H, d, J=8.3Hz), 7.34(1H, d, J=2.2Hz), 7.5 1(2H, d, J=8.3Hz).
[6] NMR(CDCl₃)δ: 2.43(3H, s), 3.74(3H, s), 4.59(2H, brs), 7.24(2H, d, J=8.4Hz), 7.40–7.60(3H, m), 7.71(1H, d, J=8.6Hz), 7.83(1H, d, J=2.3Hz).
[7] NMR(CDCl₃)δ: 2.45(3H, s), 3.28(3H, s), 7.32(2H, d, J=8.3Hz), 7.48(2H, d, J=8.3Hz), 9.06(1H, d, J=2.5Hz), 9.33(1H, d, J=2.5Hz).

Formulation Example 1

Compound No. 171 (20 wt %), xylene (75 wt %) and polyoxyethyleneglycol ether (NONIPOL 85™) (5 wt %) were mixed intimately to produce an emulsion.

Formulation Example 2

Compound No. 226 (30 wt %), sodium ligninsulfonate (5 wt %), polyoxyethyleneglycol ether (NONIPOL 85™) (5 wt %). white carbon (30 wt %) and clay (30 wt %) were mixed intimately to produce a wettable powder.

Formulation Example 3

Compound No. 263 (3 wt %), white carbon (3 wt %) and clay (94 wt %) were mixed intimately to produce a powder.

Formulation Example 4

Compound No. 291 (10 wt %), sodium ligninsulfonate (5 wt %) and clay (85 wt %) were crushed finely, mixed intimately, then kneaded with addition of water, granulated and dried to produce a granule.

Formulation Example 5

Compound No. 289 (11 wt %), ethylene glycol (12 wt %). Antifoam E20 (0.2 wt %), Butylparaben (0.1 wt %), NOI-GEN EA-177 (2 wt %), NEW KALGEN FS-7 (2 wt %), Kunipia F (1 wt %), polyvinyl alcohol 224 (1 wt %) and water (70.7 wt %) were mixed intimately and then wet ground using Dynomill KDL to produce a homogeneous suspension (a flowable).

Formulation Example 6

Compound No. 409 (11 wt %), ethylene glycol (12 wt %), Antifoam E20 (0.2 wt %), Butylparaben (0.1 wt %), NOI-GEN EA-177 (2 wt %), NEW KALGEN FS-7 (2 wt %), Kunipia F (1 wt %), CELLOGEN 7A(1.5 wt %) and water (70.2 wt %) were mixed intimately and then wet ground using Dynomill KDL to produce a homogeneous suspension (a flowable).

Formulation Example 7

Compound No. 292 (2 wt %), ferimzone (2 wt %), white carbon (3 wt %), and clay (93 wt %) were mixed intimately to produce a mixed powder.

Formulation Example 8

Compound No. 289 (11 parts), ferimzone (20 parts), ethylene glycol (12 parts), Antifoam E20 (0.2 part), Butylparaben (0.1 part), NOIGEN EA-177 (2 parts), NEW KAL- GEN FS-7 (2 parts), Kunipia F (1 part), polyvinyl alcohol (1 part), and water (50.7 parts) were mixed and wet ground using Dynomill KDL to produce a homogeneous suspension (a flowable).

Formulation Example 9

Compound No. 289 (11 parts), azoxystrobin (2 parts), ethylene glycol (12 parts), Antifoam E20 (0.2 part), Butylparaben (0.1 part), NOIGEN EA-177 (2 parts), NEW KALGEN FS-7 (2 parts), Kunipia F (1 part), polyvinyl alcohol (1 part), water (68.7 parts) were mixed and wet ground using Dynomill KDL to give a homogeneous suspension (a flowable).

Formulation Example 10

Compound No. 289 (4 parts), ValidamycinA (0.3 part), ferimzone (2 parts), fthalide (1.5 parts), IP solvent (0.2 part), NEW KALGEN EP-60P (2 parts), white carbon (1.5 parts), Butylparaben (0.05 part), NEW KALGEN D-1504 (3 parts), Hertall fatty acids (0.25 part) and calcium carbonate (85.2 parts) were mixed homogeneously and then ground to produce a DL powder.

Formulation Example 11

Compound No. 421 (15 parts), chlorothalonil (15 parts), sodium ligninsulfonate (5 parts), polyoxyethyleneglycol ether (NONIPOL 85™)(5 parts), white carbon (30 parts) and clay (30 parts) were blended intimately to produce a wettable powder.

Formulation Example 12

Compound No. 289 (17 parts), clothianidin (8 parts), xylene (70 parts) and, polyoxyethyleneglycol ether (Nonipol 85™)(5 parts) were mixed intimately to produce an emulsion.

Formulation Example 13

Compound No. 289 (17 parts), clothianidin(8 parts), NOIGEN EA-177 (0.5 part), NEW KALGEN FS-4 (2 parts), Gosenol GH-17 (2 parts), Butylparaben(0.1 part) and water (70.4 parts) were mixed and suspended well using a high-speed stirrer, and then wet ground using Dynomill(Shinmaru enterprises Corporation, 1.0 mm glass beads, ratio of filling 80%, rotation speed 15 m/s) to produce a homogeneous suspension (a flowable).

Formulation Example 14

Compound No. 437 (5 parts), clothianidin (1 part), NEW-POL PE-64 (0.5 parts), dextrin NDS (4 parts) and clay (89.5 parts) were mixed homogeneously, kneaded with water (5–10 parts) and then granulated by extruding through a screen of 0.8 mmφ. The granules obtained were dried at 60° C. for 1 hour to produce a granule.

Formulation Example 15

A solution of Nitenpyram (20 parts) and TOYODELINE P (80 parts) in water (400 parts) was spray-died to give the cyclodextrin inclusion compound of nitenpyram (cyclodextrin inclusion compound A). Compound No. 274 (1 parts), cyclodextrin inclusion compound A (5 parts), NEW KALGEN EP-70P(2 parts), dextrin NDS (10 parts) and clay (82 parts) were mixed homogeneously, kneaded with water (5–10 parts), and then granulated by extruding through a screen of 0.8 mmφ. The granules obtained were dried at 60° C. for 1 hour to produce a granule.

Formulation Example 16

Compound No. 545 (4 parts), clothianidin (0.15 part), NEW KALGEN EP-70P (2 parts), IP solvent (0.2 part), white carbon (1 part) and clay (92.65 parts) were mixed and kneaded homogeneously and then ground to produce a DL powder.

Formulation Example 17

Compound No. 409 (4 parts), cyclodextrin inclusion compound A(1.25 parts), NEW KALGEN EP-70P(2 parts), IP solvent (0.2 part), white carbon (1.5 parts) and clay (91.05 parts) were mixed and kneaded homogeneously and then ground to produce a DL powder.

Formulation Example 18

Compound No. 545 (4 parts), cartap hydrochloride (2 parts), Hertallfatty acids(1 part), IP solvent (0.2 part), white carbon (1.5 parts) and clay (91.3 parts) were mixed and kneaded homogeneously and then ground to produce a DL powder.

Formulation Example 19

Compound No. 525 (60 parts), clothianidin (15 parts), HITENOL NE-15 (5 parts), VANILEX-N (10 parts), white carbon CARPLEX #80D (10 parts) were mixed and ground homogeneously, and then stirred, mixed and kneaded with smallamount of water, and granulated by using a granulater of an extruder type. The granules obtained were then dried to produce a wettable granule (a dry flowable).

Test Examples

Test Example 1

Protective effects against rice blast (*Pyricularia oryzae*) Each test compound (denoted by the compound No. in Table 1 above) was dissolved in dimethylformamide (final concentration was 1 wt %) Xylene (final concentration was 0.02 wt %) and Tween 20 (Trade Name) (final concentration was 0.02 wt %) were added to the solution. The resulting mixture was diluted with water to give a test solution which contained the effective constituent in a given concentration (200 ppm). A spreader adjuvant SINDAIN (Trade name, Manufactured by Takeda Chemical Industries, Ltd, and containing 20 wt % of polyoxyethylene nonylphenyl ether and 12 wt % of calcium ligninsulfonate) was added to this solution in the final concentration of 0.05 wt % to give a spray agent. The spray solution was sprayed in an amount of 10 ml/pot on young rice plants (cultural variety: Asahi No. 4) which were cultivated for 2 to 3 weeks in a greenhouse. After drying up in a romm, the treated rice plants were inoculated with placing infected rice plants beside the treated ones on the condition of natural inoculation. After 24 hours, the infected plants were removed and the treated rice plants were cultivated for a week in a greenhouse kept at 25–35° C. (in humidity of more than 70%). Then, the ratio of the lesion area on the treated rice plants to that on untreated plants was investigated, and the protective effect of the compound was evaluated as a protection score as follows.

Protection score 3: the lesion area ratio on the treated plants relative to that on the untreated plants is less than 14%

Protection score 2: the ratio is from 15 to 29%

Protection score 1: the ratio is from 30 to 55%

Protection score 0: the ratio is more than 56%

Test Results: Compounds of the compound No. 43, 174, 201, 262, 305, 519, 276, 361, 362, 393, 538 showed the protection score 3.

Test Example 2

Protective Effects Against Rice Leaf Spot (*Cochliobolus miyabeanus*)

Each spray solution was prepared in a manner similar to that in the Test Example 1, and sprayed in an amount of 10 ml/pot on young rice plants (cultural variety: Nihonbare or Asahi No.4) cultivated for 3 to 4 weeks in a greenhouse. After drying up in a room, the treated rice plants were inoculated with Cochliobolus miyabeanus spores by spraying suspension of 3 to $5 \times 10^5$ spores/ml, and had been kept in a high-humidity-room at 28° C. for 2 days. After cultivation for 5 days further in a greenhouse, the ratio of the lesion area on the treated rice plants to that on untreated plants as investigated and the preventive effect of the compound was evaluated as a protection score as follows.

Protection score 3: the lesion area ratio on the treated plants relative to that on the untreated plants is less than 10%

Protection score 2: the ratio is from 11 to 20%

Protection score 1: the ratio is from 21 to 50%

Protection score 0: the ratio is more than 51%

Test Results: Compounds of the compound No. 171, 207, 262, 288, 289, 292 showed the protection score 3.

Test Example 3

Protective Effects Against Apple Alternaria Leaf Blotch(*Alternaria mali*)

Each spray solution was prepared in a manner similar to that in the Test Example 1, and sprayed in an amount of 10 ml/pot on apple seedlings (cultural variety: Starking-Delicious) cultivated for 3 to 4 weeks in a greenhouse. On the next day of the treatment, the treated apple plants were inoculated with spraying a suspension which contains 1% yeast extract, 1% sacchalose and $5 \times 10^5$ spores/ml of the Alternaria mali spores in an amount of 1 ml/pot. After inoculation, the treated plants were kept in a high-humidity box maintained at 28° C. for 4 days. The ratio of the lesion area on the treated leaves relative to that on untreated ones was investigated and the protective effect of the compound was evaluated as a protection score as follows.

Protection score 3: the lesioned area ratio is less than 10%

Protection score 2: the ratio is from 11 to 20%

Protection score 1: the ratio is from 21 to 50%

Protection score 0: the ratio is more than 51%

Test Results: Compounds of the compound No. 12, 23,25, 30, 40, 51, 84, 94, 116, 118, 119, 125, 126, 127, 163, 171, 172, 177, 194, 195, 205, 206, 207, 209, 210, 211, 213, 214, 216, 218, 219, 226, 262, 263, 264, 265, 266, 273, 274, 276, 277, 279, 282, 288, 289, 290, 291, 292, 295, 298, 299, 300, 305, 307, 308, 309, 311, 322, 324, 326, 332, 337, 338, 340, 370, 387, 396. 398, 404, 406, 407, 409, 411, 412, 413, 423, 425, 426, 429, 434, 435, 438, 545, 448, 449, 450, 456, 464, 494, 503, 504, 511, 517, 26, 61, 65, 67, 69, 80, 83, 85, 86, 87, 88, 89, 95, 97, 99, 100, 101, 105, 111, 112, 113, 114, 227, 229, 348, 354, 356, 414, 415, 419, 420, 421, 437, 455, 457, 522, 523, 525, 533, 535, 538, 539, 540, 554, 563, 565, 566, 567, 571, 572 showed protection score 3.

Test Example 4

Preventive Effects Against Club Root (*Plasmodiophora brassicae*) of *Brassica campestris* L. subsp. napus Hook. f. et Thoms, var. komatsuna Makino Each test compound (denoted by the compound No. in Table 1 above) was dissolved in dimethylformamide (final concentration was 1 wt %). The resulting solution was admixed with xylene (final concentration was 0.02 wt %), Tween20 (Trade Name)(final concentration was 0.02 wt %) and diluted with water further. This solution was irrigated onto soil infected with club root disease in an amount of 353.7 mg compound/$m^2$, followed by a thorough mixing the soil. Then, seeds of Chinese cabbage (cv. Komatsuna) were sown in the soil and cultivated in a greenhouse for 4–6 weeks. The roots of the plants were rinsed out and the degree of disease development was investigated. The test results were shown in the protection score as follows, Protection score 3: degree of disease development is less than 25%

Protection score 2: the degree is from 26 to 50%

Protection score 1: the degree is from 51 to 75%

Protection score 0: the degree is more than 76%

Test Results: Compounds of the compound No. 115, 312, 525, 528, 529, 535, 536, 537, 545, 552, 560 showed the protection score 3.

Hereunder, in the Test Examples 5 to 9, the evaluation of each fungicide was carried out by converting the ratio into a protection value after measuring the lesion area ratio (in percentage). The protection value was calculated by means of the equation as follows. protection value=(1−(lesion area in the division treated with fungicide)/lesion area in the division not treated with fungicide))×100

An estimated protection value of a mixture of active ingredients was calculated according to the Colby's formula [R. S. Colby, Weeds 15, 20–22 (1967)] and compared with the experimental protection value.

Colby's Equation:

$$E=x+y-xy/100$$

[wherein, E is the estimated protection value (additive effect) which will be obtained when the active ingredients A and B are used in a mixture in concentrations a and b, respectively x is the protection value obtained when the active igredient A is used in a concentration a, and y is the protection value obtained when the active ingredient B is used in a concentration b. When an experimental protection value is greater than the expected value E, it shows the presence of synergism (potentiation). A protection value equal 0 means that the lesion area ratio of the plants in the test group is as large as that of the plants in the untreated control group. A protection value equals 100 means that the plants in the test group are free from the disease.

Test Example 5

Protective Effects Against Apple Alternaria Leaf Blotch (*Alternaria mali*)

The test compounds (denoted by the compound No. in Table 1 above), chlorothalonil, hexaconazole and azoxystrobin, individually or in combination, were dissolved in dimethylformamide (final concentration was 1 wt %). Xylene (final concentration was 0.02 wt %) and Tween 20 (Trade Name) (final concentration was 0.02 wt %) were added to the solution. The resulting mixture was diluted with water to give a test solution which contains the active ingredient in a given concentration (ppm). A spreader adjuvant SINDAIN (Trade name, Manufactured by Takeda Chemical Industries, Ltd, and comprises 20 wt % of polyoxyethylene nonylphenyl ether and 12 wt % of calcium ligninsulfonate) was added to this solution in the final concentration of 0.05 wt % to give a spray agent. Each solution was then sprayed in an amount of 10 ml/pot on the apple seedlings (cultural variety: Starking-Delicious) cultivated for 3 to 4 weeks in a greenhouse. After one day, the treated apple plants were inoculated with spraying in an amount of 1 ml/pot suspension which contain 1% yeast extract, 1% sacchalose and 5×10$^5$ spores/ml of the Alternaria mali spores. After inoculation, the treated plants were kept in a high-humidity box maintained at 28° C. for 4 days, and then, the lesion area ratio on the treated leaves was investigated and the protective effect of the compound was evaluated as a protection score mentioned above. The results are shown in Table 2.

Compounds No. 289 and No. 421 showed a higher protection effect when used in combination with chlorothalonil, hexaconazole and azoxystrobin than the estimated protection effect which was obtained when each compound was used individually, thus Synergy effects were shown by the results.

TABLE 2

| Test substances | Concentration of the active ingredient (ppm) | Lesion area ratio (%) | Protection value | E value |
|---|---|---|---|---|
| Compound No. 289 | 25 | 4.3 | 93 | — |
|  | 6.3 | 3.8 | 94 | — |
|  | 1.6 | 20.8 | 65 | — |
|  | 0.4 | 36.9 | 38 | — |
| Compound No. 421 | 25 | 0.3 | 99 | — |
|  | 6.3 | 2.3 | 96 | — |
|  | 1.6 | 20.0 | 66 | — |
|  | 0.4 | 24.7 | 58 | — |
| Chlorothalonil | 100 | 16.8 | 72 | — |
|  | 25 | 60.0 | 0 | — |
|  | 6.3 | 43.5 | 27 | — |
| Azoxystrobin | 25 | 25.0 | 58 | — |
|  | 6.3 | 25.8 | 56 | — |
| Hexaconazole | 6.3 | 21.7 | 63 | — |
|  | 1.6 | 66.7 | 0 | — |
|  | 0.4 | 70.0 | 0 | — |
| Compound No. 421 + Chlorothalonil | 1.6 + 6.3 | 2.2 | 96 | 75 |
|  | 1.6 + 25 | 1.5 | 97 | 66 |
| Compound No. 421 + Azoxystrobin | 1.6 + 6.3 | 1.5 | 97 | 91 |
| Compound No. 289 + Azoxystrobin | 0.4 + 6.3 | 10.7 | 82 | 73 |
| Compound No. 289 + Hexaconazole | 0.4 + 0.4 | 31.0 | 48 | 38 |
|  | 1.6 + 0.4 | 16.5 | 72 | 65 |
|  | 0.4 + 1.6 | 31.7 | 47 | 38 |
| Untreated plot | — | 59.3 | — | — |

Test Example 6

Protective Effects Against Apple Alternaria Leaf Blotch (*Alternaria mali*)

The test compounds (denoted by the compound No. in Table 1 above), iminoctadine, mepanipyrim and kresoxim-methyl, individually or in combination, were tested by similar way to test example 4. The lesion area ratios on the treated leaves were investigated and the results are shown as protection value above. Table 3 shows the results.

Compounds No. 289 and No. 97 showed a higher protection effect when used in combination with mepanipyrim and iminoctadine, respectively, than the estimated protection effect which was obtainable when each compound was used individually, thus Synergy effects were shown by the results.

TABLE 3

| Test substances | Concentration of the active ingredient (ppm) | Lesion area ratio (%) | Protection value | E value |
|---|---|---|---|---|
| Compound No. 289 | 6.3 | 9.3 | 87 | — |
|  | 1.6 | 13.7 | 81 | — |
|  | 0.4 | 18.3 | 74 | — |
| Compound No. 97 | 6.3 | 8.0 | 89 | — |
|  | 1.6 | 19.2 | 73 | — |
|  | 0.4 | 25.0 | 65 | — |
| Iminoctadine | 6.3 | 35.0 | 51 | — |
|  | 1.6 | 33.8 | 52 | — |
|  | 0.4 | 66.7 | 6 | — |
| Mepanipyrim | 6.3 | 19.3 | 73 | — |
|  | 1.6 | 73.3 | 0 | — |
|  | 0.4 | 68.3 | 4 | — |
| Compound No. 97 + Iminoctadine | 0.4 + 0.4 | 16.3 | 77 | 67 |
| Compound No. 289 + Mepanipyrim | 1.6 + 0.4 | 5.3 | 93 | 82 |
|  | 1.6 + 1.6 | 4.3 | 94 | 81 |
| Untreated plot | — | 70.8 | — | — |

Test Example 7

Protective Effect Against Rice Blast (*Pyricularia oryzae*)

The test compound (denoted by the compound No. in Table 1 above) and azoxystrobin, individually or in combination, were dissolved in dimethylformamide (final concentration was 1 wt %). Xylene (final concentration was 0.02 wt %) and Tween 20 (Trade Name) (final concentration was 0.02 wt %) were added to the solution. The resulting mixture was diluted with water to give a test solution which contains (contained a given concentration (ppm) of) the active ingredient in a given concentration (ppm). A spreader adjuvant SINDAIN(Trade name, Manufactured by Takeda Chemical Industries, Ltd, and comprises 20 wt % of polyoxyethylene nonylphenyl ether and 12 wt % of calcium ligninsulfonate) was added to this solution in the final concentration of 0.05 wt % to give a spray agent. The spray agent above was sprayed in an amount of 10 ml/pot on rice plants (cultural variety: Asahi No.4) cultivated for 2 to 3 weeks in a greenhouse. After drying up in a room, the treated rice plants were inoculated with placing infected rice plants beside the treated ones on the condition of natural inoculation. After 24 hours, the infected plants were removed and the treated rice plants were cultivated for a week in a greenhouse kept at 25–35° C. (in humidity more than 70%). Then, the ratio of the lesion area on the rice plants treated with the sulfonamide (test compounds) and that on the plants treated with another substance to that on untreated plants was investigated and the results are shown as protection value above. Table 4 shows the results.

Compounds No. 289 showed a higher protection effect when used in combination with azoxystrobin than the estimated protection effect which was obtainable when each compound was used individually, thus Synergy effects were shown by the results.

TABLE 4

| Test substances | Concentration of the active ingredient (ppm) | Lesion area ratio (%) | Protection value | E value |
|---|---|---|---|---|
| Compound No. 289 | 200 | 25.0 | 0 | — |
| | 100 | 25.0 | 0 | — |
| Azoxystrobin | 0.5 | 5.0 | 80 | — |
| | 0.1 | 11.0 | 56 | — |
| Compound No. 289 + Azoxystrobin | 200 + 0.5 | 0.8 | 97 | 80 |
| | 200 + 0.1 | 3.5 | 86 | 56 |
| | 100 + 0.5 | 0.8 | 97 | 80 |
| | 100 + 0.1 | 5.0 | 80 | 56 |
| Untreated plot | — | 25.0 | — | — |

Test Example 8

Protective Effect Against Rice Helminthosporium Leaf Spot (*Cochliobolus miyabeanus*)

The test compound (denoted by the compound No. in Table 1 above) and ferimzone, individually or in combination, were dissolved in dimethylformamide (final concentration was 1 wt %). Xylene (final concentration was 0.02 wt %) and Tween 20 (Trade Name) (final concentration was 0.02 wt %) were added to the solution. The resulting mixture was diluted with water to give a test solution which contained a given concentration (ppm) of the active ingredient. A spreader adjuvant SINDAIN(Trade Name, Manufactured by Takeda Chemical Industries, Ltd, and comprises 20 wt % of polyoxyethylene nonylphenyl ether and 12 wt % of calcium ligninsulfonate) was added to this solution in the final concentration of 0.05 wt % to give a spray agent.

This spray agent was sprayed in an amount of 10 ml/pot on young rice plants (cultural variety: Nihonbare or Asahi No.4) cultivated for 3 to 4 weeks in a greenhouse. After drying up in a room, the treated rice plants were inoculated with Cochliobolus miyabeanus spores by spraying suspension of 3 to 5×10$^5$ spores/ml, and had been kept in a high-humidity room at 28° C. for 2 days. After cultivation for 5 days further in a greenhouse, the ratio of the lesion area on the plants treated with the test compound and that on the plants treated with another test substance to that on untreated plants was investigated. The results are shown as protection value above. Table 5 shows the results.

Compounds No. 289 showed a higher protection effect when used in combination with ferimzone than the estimated protective effect which was obtainable when each compound was used individually, thus Synergy effects were shown by the results.

TABLE 5

| Test substances | Concentration of the active ingredient (ppm) | Lesion area ratio (%) | Protection value | E value |
|---|---|---|---|---|
| Compound No. 289 | 100 | 4.5 | 74.3 | — |
| | 25 | 5.0 | 71.4 | — |
| Ferimzone | 100 | 0.4 | 98.0 | — |
| | 25 | 1.5 | 91.4 | — |
| Compound No. 289 + Ferimzone | 100 + 25 | 0.2 | 98.9 | 97.8 |
| | 25 + 25 | 0.3 | 98.6 | 97.6 |
| Untreated plot | — | 25.0 | — | — |

Test Example 9

Protective Effect Against Cucumber Gray Mold (*Botrytis cinerea*)

The test compound (denoted by the compound No. in Table 1 above), azoxystrobin, mepanipyrim and iprodione, individually or in combination, were dissolved in dimethylformamide (final concentration was 1 wt %). Xylene (final concentration was 0.02 wt %) and Tween 20 (Trade Name) (final concentration was 0.02 wt %) were added to the solution. The resulting mixture was diluted with water to give a test solution which contained a given concentration (ppm) of the active ingredient. A spreader adjuvant SINDAIN (Trade Name, Manufactured by Takeda Chemical Industries, Ltd, and comprises 20 wt % of polyoxyethylene nonylphenyl ether and 12 wt % of calcium ligninsulfonate) was added to this solution in the final concentration of 0.05 wt % to give a spray agent.

The spray agent was sprayed in an amount of 10 ml/pot on young cucumber (cultural variety: Yotsuba) cultivated for 3 to 4 weeks in a greenhouse. After drying up in a room, the treated cucumbers were inoculated with pathogenic fangi on the leaves by placing the mycelial disks which were cut out from a PSA medium grown with Botrytis cinerea and then kept in a greenhouse at 28° C. for 3 days. Then, the ratio of the lesion area on the plants treated with the test compound and that on the plants treated with another substances to that on untreated plants was investigated. The results are shown as protection value above. Table 6 shows the results.

Compounds No. 289 showed a higher protection effect when used in combination with azoxystrobin, mepanipyrim and iprodione than the estimated protection effect which was obtainable when each compound was used individually, thus Synergy effects were shown by the results.

TABLE 6

| Test substances | Concentration of the active ingredient (ppm) | Lesion area ratio (%) | Protection value | E value |
|---|---|---|---|---|
| Compound No. 289 | 100 | 13.2 | 0.0 | — |
| Azoxystrobin | 10 | 3.9 | 69.8 | — |
| Mepanipyrim | 10 | 6.0 | 53.8 | — |
| Iprodione | 10 | 3.7 | 71.3 | — |
| Compound No. 289 + Azoxystrobin | 100 + 10 | 1.9 | 85.4 | 69.3 |
| Compound No. 289 + Mepanipyrim | 100 + 10 | 5.3 | 59.2 | 53.0 |
| Compound No. 289 + Iprodione | 100 + 10 | 2.9 | 77.2 | 70.8 |
| Untreated plot | — | 25.0 | — | — |

INDUSTRIAL APPLICABILITY

Compound (I°) or salts thereof, more specifically compound(I) to (V) or salts thereof are useful as excellent agricultural or horticultural microbicides, because they are sulfonamide derivatives, are safe to use because they have little influence on human and animals, natural enemies and the environment, and show an excellent preventive effect even on drug-resistant microbes. They have especially effective as protective against blast, Helminthosporium leaf spot and fusarium leaf spot of rice plant, leaf spot, yellow mottle leaf and net blotch of barley, yellow nottle leaf and leaf blotch of wheat, southern leaf blight of corn, early blight of potato, Alternaria sooty spot, ring spot and black rot of tomato, black rot of Chinese cabbage, black rot of pear, and Alternaria leaf blotch of apple, and so on.

What is claimed is:

1. A compound of Formula (VI):

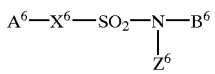

or salt thereof, wherein $A^6$ is a phenyl group which may be substituted with a substituent or substituents selected from $C_{1-4}$ alkyl, halogens and cyano, $X^6$ is a chemical bond, $B^6$ is a 2-nitrophenyl group or 2-cyanophenyl group which may be substituted with a substituent or substituents selected from halogens, nitro and cyano, $Z^6$ is ethyl, isopropyl, cyclopropyl, methoxy, ethoxy or isopropoxy group.

2. A compound or a salt thereof as claimed in claim 1, wherein $A^6$ is a phenyl group which may be substituted with a substituent or substituents selected from $C_{1-4}$ alkyl, halogens and cyano, $X^6$ is a chemical bond, $B^6$ is a 2-nitrophenyl group which is substituted with a substituent or substituents selected from halogens, nitro and cyano, $Z^6$ is ethyl, isopropyl, or cyclopropyl group.

3. A compound or a salt thereof as claimed in claim 1, the compound is 4'-chloro-N-ethyl-2'-nitro-p-toluenesulfonanilide, 2',4'-dinitro-N-ethyl-p-toluenesulfonanilide, 2',4'-dicyano-N-ethyl-p-toluenesulfonanilide, 4'-chloro-N-isopropyl-2'-nitro-p-toluenesulfonanilide, 4'-fluoro-N-isopropyl-2'-nitro-p-toluenesulfonanilide, 4'-cyano-N-isopropyl-2'-nitro-p-toluenesulfonanilide, 4'-chloro-N-isopropyl-2'-cyano-p-toluenesulfonanilide, 2',4'-dinitro-N-isopropyl-p-toluenesulfonanilide, 4'-nitro-N-isopropyl-2'-cyano-p-toluenesulfonanilide, 2'-cyano-N-methoxy-4'-nitro-p-toluenesulfonanilide or 2',4'-dinitro-N-methoxy-p-toluenesulfonanilide or a salt thereof.

4. A microbicidal composition comprising the compound according to claim 1, or a salt thereof, together with a liquid carrier or a solid carrier.

5. A method of treating a plant microbial disease, which comprises applying an effective amount of the compound according to claim 1, or a salt thereof, on the plant.

6. A method for manufacturing the compound according to claim 1, or a salt thereof, which comprises:

(1) reacting a compound represented by the formula:

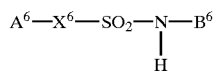

or a salt thereof, wherein $A^6$, $X^6$ and $B^6$ have the same meaning as defined in claim 1, with an electrophile represented by the formula $Z^6$–L", wherein L" is a leaving group, and $Z^6$ has the same meaning as defined in claim 1, or, (2) reacting a compound represented by the formula:

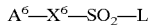

or a salt thereof, wherein L is a leaving group, and $A^6$ and $X^6$ have the same meanings as defined in claim 1, with an amine or a salt thereof represented by the formula $Z^6HN$-$B^6$, wherein $X^6$ and $B^6$ have the same meanings as defined in claim 1, or, (3) reacting a compound represented by the formula:

or a salt thereof, wherein $A^6$, $X^6$ and $Z^6$ have the same meanings as described in claim 1, with a compound or a salt thereof represented by the formula L'–$B^6$, wherein L' is a leaving group, and $B^6$ has the same meaning as defined in claim 1, or, (4) nitrating a compound represented by the formula:

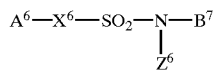

or a salt thereof, wherein $A^6$, $X^6$ and $Z^6$ have the same meanings as defined in claim 1, and $B^7$ is a phenyl group which is substituted with a substituent or substituents selected from halogen, nitro and cyano, provided that both 2- and 6-positions are not substituted at the same time, to obtain the compound according to claim 1.

* * * * *